US012788215B2

(12) United States Patent
Tilson et al.

(10) Patent No.: US 12,788,215 B2
(45) Date of Patent: Nov. 10, 2026

(54) BODY LUMEN MAPPING WITH A NESTED RIGIDIZING SYSTEM

(71) Applicant: Neptune Medical Inc., Burlingame, CA (US)

(72) Inventors: Alexander Q. Tilson, Burlingame, CA (US); Christopher J. Hasser, Lotus, CA (US); Avinash Siravuru, San Jose, CA (US); Dwight Meglan, Needham, MA (US); Mingyen Ho, Burlingame, CA (US); Timothy Budding, Burlingame, CA (US)

(73) Assignee: Neptune Medical Inc., Burlingame, CA (US)

( * ) Notice: Subject to any disclaimer, the term of this patent is extended or adjusted under 35 U.S.C. 154(b) by 0 days.

(21) Appl. No.: 19/340,856

(22) Filed: Sep. 25, 2025

(65) Prior Publication Data

US 2026/0083303 A1 Mar. 26, 2026

Related U.S. Application Data

(60) Provisional application No. 63/859,865, filed on Aug. 7, 2025, provisional application No. 63/859,851, filed
(Continued)

(51) Int. Cl.
*A61B 1/00* (2006.01)
*A61B 1/005* (2006.01)
(Continued)

(52) U.S. Cl.
CPC ...... *A61B 1/00078* (2013.01); *A61B 1/00045* (2013.01); *A61B 1/00154* (2013.01);
(Continued)

(58) Field of Classification Search
CPC ............ A61B 1/00078; A61B 1/00082; A61B 1/00135; A61B 1/00142; A61B 1/00154;
(Continued)

(56) References Cited

U.S. PATENT DOCUMENTS 2,268,321 A 12/1941 Flynn
2,767,705 A 10/1956 Moore
(Continued)

FOREIGN PATENT DOCUMENTS

AU 2013207571 B2 8/2013
CN 2613655 Y 4/2004
(Continued)

OTHER PUBLICATIONS

Dow; Dow white paper: Can you estimate modulus from durometer hardness for silicones: Yes, but you only roughly and you must choose your modulus carefully!; 5 pages; retrieved from the internet (https://www.dow.com/content/dam/doc/documents/en-us/tech-art/11/11-37/11-3716-01-durometer-hardness-for-silicones.pdf) on Jan. 18, 2023.
(Continued)

*Primary Examiner* — Aaron B Fairchild
(74) *Attorney, Agent, or Firm* — Shay Glenn LLP

(57) ABSTRACT

Apparatuses and methods for mapping a body lumen, including but not limited to, a colon. These methods may include the robotic and/or automatic or semi-automatic use of one or more rigidizing member to create a stable foundation from which a second member (which is optionally rigidizing) may be advanced and/or withdrawn and/or rotated in order to take multiple images of the body lumen (e.g., of the walls of the body lumen) to create a coverage map of the body lumen. These methods may include controlling the first and/or second member to apply one or more techniques to ensure that the mapping is performed rapidly
(Continued)

while achieving full or nearly full coverage of the body lumen over the full extent of the lumen or a selected sub-region.

22 Claims, 38 Drawing Sheets

Related U.S. Application Data on Aug. 7, 2025, provisional application No. 63/699,151, filed on Sep. 25, 2024.

(51) Int. Cl.
*A61B 34/00* (2016.01)
*A61B 34/10* (2016.01)
*A61B 34/30* (2016.01)
*A61B 90/00* (2016.01)

(52) U.S. Cl.
CPC ...... *A61B 1/00172* (2013.01); *A61B 1/00177* (2013.01); *A61B 1/00181* (2013.01); *A61B 1/00183* (2013.01); *A61B 1/0051* (2013.01); *A61B 2034/107* (2016.02); *A61B 2034/254* (2016.02); *A61B 2034/301* (2016.02); *A61B 90/361* (2016.02)

(58) Field of Classification Search
CPC .............. A61B 1/00172; A61B 1/0183; A61B 1/0051–53; A61B 1/0055–58; A61B 1/0125; A61B 1/00045; A61B 1/00177; A61B 1/00181
See application file for complete search history.

(56) References Cited

U.S. PATENT DOCUMENTS 3,459,229 A 8/1969 Croft
3,466,220 A 9/1969 Allinikov et al.
3,859,986 A 1/1975 Okada et al.
3,998,216 A 12/1976 Hosono
4,066,071 A 1/1978 Nagel
4,141,364 A 2/1979 Schultze
4,151,800 A 5/1979 Dotts et al.
4,160,451 A 7/1979 Chittenden
4,176,662 A 12/1979 Frazer
4,425,919 A 1/1984 Alston, Jr.
4,551,140 A 11/1985 Shinohara
4,676,229 A 6/1987 Krasnicki et al.
4,690,131 A 9/1987 Lyddy, Jr. et al.
4,696,544 A 9/1987 Costella
4,717,379 A 1/1988 Ekholmer
4,794,412 A 12/1988 Casey et al.
4,794,912 A 1/1989 Lia
4,815,450 A 3/1989 Patel
4,817,613 A 4/1989 Jaraczewski et al.
4,890,602 A 1/1990 Hake
4,893,613 A 1/1990 Hake
4,913,369 A 4/1990 Lia et al.
4,959,058 A 9/1990 Michelson
4,961,738 A 10/1990 Mackin
4,967,732 A 11/1990 Inoue
5,018,436 A 5/1991 Evangelista et al.
5,019,121 A 5/1991 Krauter
5,025,778 A 6/1991 Silverstein et al.
5,037,386 A 8/1991 Marcus et al.
5,037,404 A 8/1991 Gold et al.
5,050,585 A 9/1991 Takahashi
5,105,819 A 4/1992 Wollschlager et al.
5,123,421 A 6/1992 Sinofsky
5,125,143 A 6/1992 Takahashi
5,174,276 A 12/1992 Crockard
5,183,471 A 2/1993 Wilk
5,188,595 A 2/1993 Jacobi
5,193,525 A 3/1993 Silverstein et al.
5,201,908 A 4/1993 Jones
5,217,001 A 6/1993 Nakao et al.
5,251,611 A 10/1993 Zehel et al.
5,254,107 A 10/1993 Soltesz
5,337,733 A 8/1994 Bauerfeind et al.
5,342,299 A 8/1994 Snoke et al.
5,360,440 A 11/1994 Andersen
5,447,148 A 9/1995 Oneda et al.
5,470,322 A 11/1995 Horzewski et al.
5,483,951 A 1/1996 Frassica et al.
5,496,292 A 3/1996 Burnham
5,503,616 A 4/1996 Jones
5,531,685 A 7/1996 Hemmer et al.
5,531,719 A 7/1996 Takahashi
5,547,455 A * 8/1996 McKenna .......... A61B 1/00181 600/113
5,549,542 A 8/1996 Kovalcheck
5,577,992 A 11/1996 Chiba et al.
5,591,137 A 1/1997 Stevens
5,601,588 A 2/1997 Tonomura et al.
5,603,991 A 2/1997 Kupiecki et al.
5,607,435 A 3/1997 Sachdeva et al.
5,624,381 A 4/1997 Kieturakis
5,632,734 A 5/1997 Galel et al.
5,637,075 A 6/1997 Kikawada
5,662,587 A 9/1997 Grundfest et al.
5,662,621 A 9/1997 Lafontaine
5,746,692 A 5/1998 Bacich et al.
5,746,694 A 5/1998 Wilk et al.
5,749,828 A 5/1998 Solomon et al.
5,749,889 A 5/1998 Bacich et al.
5,759,151 A 6/1998 Sturges
5,779,624 A 7/1998 Chang
5,782,811 A 7/1998 Samson et al.
5,823,961 A 10/1998 Fields et al.
5,882,345 A 3/1999 Yoon
5,882,347 A 3/1999 Mouris Laan et al.
5,891,112 A 4/1999 Samson
5,891,114 A 4/1999 Chin et al.
5,906,591 A 5/1999 Dario et al.
5,916,145 A 6/1999 Chu et al.
5,916,147 A 6/1999 Boury
5,921,968 A 7/1999 Lampropoulos et al.
5,941,499 A 8/1999 De Chant
5,951,539 A 9/1999 Nita et al.
5,961,526 A 10/1999 Chu et al.
5,976,074 A 11/1999 Moriyama
6,090,099 A 7/2000 Samson et al.
6,159,187 A 12/2000 Park et al.
6,162,171 A 12/2000 Ng et al.
6,165,123 A 12/2000 Thompson
6,179,776 B1 1/2001 Adams et al.
6,190,357 B1 2/2001 Ferrari et al.
6,203,493 B1 3/2001 Ben-Hain
6,217,565 B1 4/2001 Cohen
6,217,566 B1 4/2001 Ju et al.
6,276,661 B1 8/2001 Laird
6,296,644 B1 10/2001 Surat et al.
6,309,346 B1 10/2001 Farhadi
6,352,503 B1 3/2002 Matsu et al.
6,364,878 B1 4/2002 Hall
6,368,315 B1 4/2002 Gillis et al.
6,408,682 B2 6/2002 Greszler
6,468,203 B2 10/2002 Belson
6,485,409 B1 11/2002 Voloshin et al.
6,503,225 B1 1/2003 Kirsch et al.
6,517,477 B1 2/2003 Wendlandt
6,547,724 B1 4/2003 Soble et al.
6,572,538 B2 6/2003 Takase
6,572,590 B1 6/2003 Stevens et al.
6,579,277 B1 6/2003 Rabiner et al.
6,610,007 B2 8/2003 Belson et al.
6,612,982 B1 9/2003 Ouchi
6,616,628 B2 9/2003 Hayzelden
6,620,126 B2 9/2003 Unsworth et al.
6,623,424 B2 9/2003 Hayakawa et al.
6,709,429 B1 3/2004 Schaefer et al.
6,712,832 B2 3/2004 Shah

(56) References Cited

U.S. PATENT DOCUMENTS 6,726,677 B1 4/2004 Flaherty et al.
6,730,020 B2 5/2004 Peng et al.
6,740,030 B2 5/2004 Martone et al.
6,780,151 B2 8/2004 Grabover et al.
6,783,491 B2 8/2004 Saadat et al.
6,790,173 B2 9/2004 Saadat et al.
6,793,621 B2 9/2004 Butler et al.
6,793,661 B2 9/2004 Hamilton et al.
6,800,056 B2 10/2004 Tartaglia et al.
6,869,393 B2 3/2005 Butler
6,899,673 B2 5/2005 Ogura et al.
6,911,004 B2 6/2005 Kim et al.
6,923,754 B2 8/2005 Lubock
6,960,162 B2 11/2005 Saadat et al.
6,974,411 B2 12/2005 Belson
6,984,203 B2 1/2006 Tartaglia et al.
7,060,199 B2 6/2006 Woydt et al.
7,172,552 B2 2/2007 Wendlandt
7,214,230 B2 5/2007 Brock et al.
7,273,469 B1 9/2007 Chan et al.
7,288,101 B2 10/2007 Deem et al.
7,291,127 B2 11/2007 Eidenschink
7,354,427 B2 4/2008 Fangrow
7,365,509 B2 4/2008 Park et al.
7,438,712 B2 10/2008 Chouinard
7,511,733 B2 3/2009 Takizawa et al.
7,537,562 B2 5/2009 Takano
7,559,916 B2 7/2009 Smith et al.
7,591,782 B2 9/2009 Fujikura
7,594,888 B2 9/2009 Raymond et al.
7,598,652 B2 10/2009 Kornbluh et al.
7,658,738 B2 2/2010 Nobis et al.
7,695,428 B2 4/2010 Machida
7,699,864 B2 4/2010 Kick et al.
7,736,323 B2 6/2010 Von Weymarn-Scharli
7,749,196 B2 7/2010 Osborne et al.
7,758,501 B2 7/2010 Frasier et al.
7,780,692 B2 8/2010 Nance et al.
7,837,615 B2 11/2010 Le et al.
7,850,725 B2 12/2010 Vardi et al.
7,901,347 B2 3/2011 Sekiguchi et al.
7,909,755 B2 3/2011 Itoi
7,918,819 B2 4/2011 Karmarkar et al.
7,918,845 B2 4/2011 Saadat et al.
7,931,661 B2 4/2011 Saadat et al.
7,935,047 B2 5/2011 Yoshida et al.
7,947,000 B2 5/2011 Vargas et al.
7,957,790 B2 6/2011 Kleen
7,970,455 B2 6/2011 Zilberstein et al.
7,988,621 B2 8/2011 Smith et al.
8,047,236 B2 11/2011 Perry
8,075,476 B2 12/2011 Vargas
8,092,374 B2 1/2012 Smith et al.
8,109,953 B1 2/2012 King, III et al.
8,123,739 B2 2/2012 McQueen et al.
8,125,755 B2 2/2012 Garcia et al.
8,192,422 B2 6/2012 Zubiate et al.
8,206,287 B2 6/2012 Matsuo
8,226,548 B2 7/2012 Kucklick
8,241,299 B2 8/2012 Hibner
8,246,575 B2 8/2012 Viola
8,257,257 B2 9/2012 Takizawa et al.
8,262,677 B2 9/2012 Goto
8,298,161 B2 10/2012 Vargas
8,313,014 B2 11/2012 Bettuchi
8,361,090 B2 1/2013 Belson
8,366,606 B2 2/2013 Watanabe et al.
8,388,519 B2 3/2013 Garcia et al.
8,425,602 B2 4/2013 Guyer et al.
8,439,825 B2 5/2013 Sekiguchi
8,460,179 B2 6/2013 Ikeda et al.
8,480,576 B2 7/2013 Sandhu
8,485,968 B2 7/2013 Weimer et al.
8,496,648 B2 7/2013 Rogers
8,506,479 B2 8/2013 Piskun et al.
8,517,923 B2 8/2013 Belson et al.
8,545,491 B2 10/2013 Abboud et al.
8,550,989 B2 10/2013 Dohi et al.
8,556,804 B2 10/2013 Smith et al.
8,652,033 B2 2/2014 Berci et al.
8,663,096 B2 3/2014 Viola
8,663,196 B2 3/2014 Kassab et al.
8,708,894 B2 4/2014 Smith et al.
8,721,530 B2 5/2014 Ohline et al.
8,753,312 B2 6/2014 Bowe et al.
8,758,231 B2 6/2014 Bunch et al.
8,777,844 B1 7/2014 Sadanand
8,808,169 B2 8/2014 Macnamara et al.
8,920,369 B2 12/2014 Salahieh et al.
8,969,639 B2 3/2015 Xu et al.
8,992,420 B2 3/2015 Maahs et al.
9,011,318 B2 4/2015 Choset et al.
9,066,655 B2 6/2015 Stefanchik et al.
9,114,228 B2 8/2015 Zook et al.
9,125,653 B2 9/2015 Kovach
9,155,451 B2 10/2015 Smith et al.
9,192,284 B2 11/2015 Hirsch et al.
9,192,288 B2 11/2015 Okaniwa
9,211,140 B2 12/2015 Lauryssen et al.
9,220,398 B2 12/2015 Woodley et al.
9,226,825 B2 1/2016 Starksen et al.
9,241,611 B2 1/2016 Konno
9,254,123 B2 2/2016 Alvarez et al.
9,282,993 B1 3/2016 Cohen et al.
9,295,511 B2 3/2016 Smith et al.
9,320,508 B2 4/2016 Carroux
9,333,287 B2 5/2016 Nitsan et al.
9,358,073 B2 6/2016 Piligian et al.
9,364,955 B2 6/2016 Oyola et al.
9,386,910 B2 7/2016 West
RE46,134 E 9/2016 Smith et al.
9,498,108 B1 11/2016 Lombardi
9,498,198 B2 11/2016 Hu et al.
9,505,125 B2 11/2016 Zubiate et al.
9,585,546 B2 3/2017 Surti et al.
9,610,068 B2 4/2017 Kappel et al.
9,649,473 B2 5/2017 Gregorich et al.
9,763,562 B2 9/2017 Avitsian et al.
9,795,771 B2 10/2017 Trieu et al.
9,814,372 B2 11/2017 Smith et al.
9,913,570 B2 3/2018 Kucharski et al.
9,937,324 B2 4/2018 Kim et al.
9,980,744 B2 5/2018 Corbin et al.
9,993,142 B2 6/2018 Salman et al.
10,092,291 B2 10/2018 Voegele et al.
10,307,042 B2 6/2019 Lombardi
10,448,811 B2 10/2019 London Brown et al.
10,463,495 B2 11/2019 Rogers et al.
10,555,782 B2 2/2020 Morard et al.
10,582,834 B2 3/2020 Hastings
10,625,413 B1 4/2020 McPherson
10,682,108 B1 6/2020 Ma et al.
10,702,305 B2 7/2020 Garofalo et al.
10,716,461 B2 7/2020 Jenkins
10,828,120 B2 11/2020 Kostrzewski et al.
10,959,607 B2 3/2021 Rogers et al.
11,006,975 B1 5/2021 Cohen et al.
11,020,214 B2 6/2021 Gupta et al.
11,122,971 B2 9/2021 Tilson et al.
11,135,398 B2 10/2021 Tilson et al.
11,219,351 B2 1/2022 Tilson et al.
11,478,608 B2 10/2022 Tilson et al.
11,554,248 B1 1/2023 Tilson et al.
11,724,065 B2 8/2023 Tilson et al.
11,744,443 B2 9/2023 Lopez et al.
11,793,392 B2 10/2023 Tilson et al.
11,903,669 B2 2/2024 Cope et al.
11,937,778 B2 3/2024 Tilson et al.
11,944,277 B2 4/2024 Tilson et al.
12,059,128 B2 8/2024 Tilson et al.
12,082,776 B2 9/2024 Tilson et al.
12,102,289 B2 10/2024 Tilson et al.
12,121,677 B2 10/2024 Gomes et al.
12,193,637 B2 1/2025 Tilson et al.

(56) References Cited

U.S. PATENT DOCUMENTS 12,285,571 B2 4/2025 Tilson et al.
12,295,550 B2 5/2025 Tilson et al.
12,311,122 B2 5/2025 Tilson et al.
12,324,565 B2 6/2025 Tilson et al.
12,329,473 B2 6/2025 Tilson et al.
12,330,292 B2 6/2025 Devengenzo et al.
12,336,695 B2 6/2025 Tilson et al.
2001/0041881 A1 11/2001 Sarge et al.
2002/0049423 A1 4/2002 Howell et al.
2002/0080359 A1* 6/2002 Denk .................. G02B 21/002 356/446
2002/0107478 A1 8/2002 Wendlandt
2002/0161355 A1 10/2002 Wollschlager
2003/0023259 A1 1/2003 Dubrul et al.
2003/0035048 A1 2/2003 Shipp
2003/0036748 A1 2/2003 Cooper et al.
2003/0083546 A1 5/2003 Butler et al.
2003/0122374 A1 7/2003 Ouchi et al.
2003/0153866 A1 8/2003 Long et al.
2003/0208220 A1 11/2003 Worley et al.
2003/0216681 A1 11/2003 Zhang et al.
2003/0216691 A1 11/2003 Jacobson
2003/0225379 A1 12/2003 Schaffer et al.
2004/0019252 A1 1/2004 Hirata
2004/0044350 A1 3/2004 Martin et al.
2004/0092960 A1 5/2004 Abrams et al.
2004/0186349 A1 9/2004 Ewers et al.
2004/0186350 A1 9/2004 Brenneman et al.
2004/0242958 A1 12/2004 Fujikawa et al.
2004/0243227 A1 12/2004 Starksen et al.
2004/0260236 A1 12/2004 Manning et al.
2005/0005363 A1 1/2005 Giori et al.
2005/0010237 A1 1/2005 Niazi
2005/0085829 A1 4/2005 Kraemer et al.
2005/0113643 A1* 5/2005 Hale .................. A61B 1/00045 600/109
2005/0154258 A1 7/2005 Tartaglia et al.
2005/0165275 A1 7/2005 Von Felten et al.
2005/0165366 A1 7/2005 Brustad et al.
2005/0203340 A1 9/2005 Butler et al.
2005/0261581 A1 11/2005 Hughes et al.
2005/0272974 A1 12/2005 Iddan
2005/0277966 A1 12/2005 Ewers et al.
2006/0015010 A1 1/2006 Jaffe et al.
2006/0041188 A1 2/2006 Dirusso et al.
2006/0047183 A1 3/2006 Park
2006/0058582 A1 3/2006 Maahs et al.
2006/0063973 A1 3/2006 Makower et al.
2006/0089530 A1 4/2006 Tartaglia
2006/0106285 A1 5/2006 Boulais et al.
2006/0129130 A1 6/2006 Tal et al.
2006/0178560 A1 8/2006 Saadat et al.
2006/0192465 A1 8/2006 Kornbluh et al.
2006/0195017 A1 8/2006 Shluzas et al.
2006/0199999 A1 9/2006 Ikeda et al.
2006/0200023 A1 9/2006 Melkent et al.
2006/0235457 A1 10/2006 Belson
2006/0235458 A1 10/2006 Belson
2006/0258906 A1 11/2006 Binmoeller
2006/0264707 A1 11/2006 Kinney
2006/0264821 A1 11/2006 Vo et al.
2006/0276692 A1 12/2006 Kucklick
2006/0287666 A1 12/2006 Saadat et al.
2007/0015965 A1 1/2007 Cox et al.
2007/0038025 A1 2/2007 Yoshida
2007/0045504 A1 3/2007 Wollschlager
2007/0088367 A1 4/2007 Von Weymarn-Scharli
2007/0100414 A1 5/2007 Licata et al.
2007/0106302 A1 5/2007 Ortiz
2007/0118015 A1 5/2007 Wendlandt
2007/0135803 A1 6/2007 Belson
2007/0156018 A1 7/2007 Krauter et al.
2007/0219411 A1 9/2007 Dejima et al.
2007/0239252 A1 10/2007 Hopkins et al.
2007/0250113 A1 10/2007 Hegeman et al.
2007/0250149 A1 10/2007 Oepen et al.
2007/0255101 A1 11/2007 Bar Or
2007/0260121 A1 11/2007 Bakos et al.
2007/0282358 A1 12/2007 Remiszewski et al.
2008/0009669 A1* 1/2008 Ozawa ............... A61B 1/00045 600/101
2008/0051635 A1 2/2008 Tanaka et al.
2008/0058595 A1 3/2008 Snoke et al.
2008/0058722 A1 3/2008 Oepen et al.
2008/0091073 A1 4/2008 Park
2008/0103440 A1 5/2008 Ferren et al.
2008/0139887 A1 6/2008 Fitzpatrick
2008/0172037 A1 7/2008 Huang et al.
2008/0188928 A1 8/2008 Salahieh et al.
2008/0200762 A1 8/2008 Stokes et al.
2008/0214893 A1 9/2008 Tartaglia et al.
2008/0234546 A1 9/2008 Kawano et al.
2008/0242928 A1 10/2008 Kawano et al.
2008/0249362 A1 10/2008 Jiang et al.
2008/0262300 A1 10/2008 Ewers et al.
2008/0262301 A1 10/2008 Gibbons et al.
2008/0275299 A1 11/2008 Park
2008/0318456 A1 12/2008 Yow et al.
2008/0319266 A1 12/2008 Poll et al.
2009/0023983 A1 1/2009 Stefanchik
2009/0048483 A1 2/2009 Yamamoto
2009/0062611 A1 3/2009 Toyama
2009/0062837 A1 3/2009 Gasche et al.
2009/0062872 A1 3/2009 Chin et al.
2009/0104250 A1 4/2009 Boyden et al.
2009/0112063 A1 4/2009 Bakos et al.
2009/0112064 A1 4/2009 Levey et al.
2009/0131752 A1 5/2009 Park
2009/0157068 A1 6/2009 Kallel et al.
2009/0187163 A1 7/2009 Uihlein
2009/0240202 A1 9/2009 Drasler et al.
2009/0248041 A1 10/2009 Williams et al.
2009/0259200 A1 10/2009 Lampropoulos et al.
2009/0264704 A1 10/2009 Shtul
2009/0287049 A1 11/2009 Jones et al.
2010/0010308 A1 1/2010 Braun et al.
2010/0010437 A1 1/2010 Miles et al.
2010/0010504 A1 1/2010 Simaan et al.
2010/0016663 A1 1/2010 Maisch et al.
2010/0036363 A1 2/2010 Watanabe et al.
2010/0063358 A1 3/2010 Kessler
2010/0069712 A1 3/2010 Yamaya
2010/0069716 A1 3/2010 Chin et al.
2010/0076451 A1 3/2010 Zwolinski et al.
2010/0087711 A1 4/2010 Edwards
2010/0137686 A1 6/2010 Meron et al.
2010/0145151 A1 6/2010 Fukunaga et al.
2010/0160735 A1 6/2010 Bakos
2010/0185172 A1 7/2010 Fabro
2010/0204546 A1 8/2010 Hassidov et al.
2010/0268025 A1 10/2010 Belson
2010/0331625 A1 12/2010 Rosemurgy et al.
2010/0331820 A1 12/2010 Prisco et al.
2011/0015729 A1 1/2011 Jimenez et al.
2011/0023888 A1 2/2011 Vazales et al.
2011/0040282 A1 2/2011 Uihlein
2011/0046442 A1 2/2011 Matsushita
2011/0049282 A1 3/2011 Danielsson
2011/0054253 A1 3/2011 Jordá Albiñana et al.
2011/0065985 A1 3/2011 Wehrheim
2011/0087070 A1 4/2011 Tilson et al.
2011/0137127 A1 6/2011 Schwartz et al.
2011/0196392 A1 8/2011 Saadat et al.
2011/0237888 A1 9/2011 Matsushita
2011/0245611 A1 10/2011 Yeh et al.
2011/0245858 A1 10/2011 Milsorn et al.
2011/0263938 A1* 10/2011 Levy .................. A61B 1/00181 600/109
2011/0282149 A1 11/2011 Vargas et al.
2011/0288553 A1 11/2011 Jansen et al.
2011/0301414 A1 12/2011 Hotto et al.
2011/0306950 A1 12/2011 Cucin
2011/0319714 A1 12/2011 Roelle et al.
2012/0004676 A1 1/2012 Vargas

(56) References Cited

U.S. PATENT DOCUMENTS

2012/0022329 A1 1/2012 Wagh et al.
2012/0029296 A1 2/2012 Mishra et al.
2012/0041291 A1 2/2012 Ferren et al.
2012/0095548 A1 4/2012 Gregorich et al.
2012/0108902 A1 5/2012 Frassica et al.
2012/0130173 A1 5/2012 Lutze et al.
2012/0143005 A1 6/2012 Yeh et al.
2012/0143006 A1 6/2012 Avitsian et al.
2012/0165607 A1 6/2012 Ashida et al.
2012/0165792 A1 6/2012 Ortiz et al.
2012/0172651 A1 7/2012 Cutrer
2012/0209062 A1 8/2012 Qiao
2012/0209292 A1 8/2012 Devengenzo et al.
2012/0259177 A1 10/2012 Fiorella
2012/0277528 A1 11/2012 Qiao
2012/0277729 A1 11/2012 Melsheimer
2013/0023920 A1 1/2013 Terliuc et al.
2013/0131641 A1 5/2013 Jimenez et al.
2013/0190565 A1 7/2013 Gora et al.
2013/0274553 A1 10/2013 Piskun
2013/0304179 A1 11/2013 Bialas et al.
2013/0333472 A1 12/2013 Georgeson
2013/0338440 A1 12/2013 Sinal et al.
2014/0005683 A1 1/2014 Stand et al.
2014/0073853 A1 3/2014 Swisher et al.
2014/0074170 A1 3/2014 Mertens et al.
2014/0081169 A1 3/2014 Gerding et al.
2014/0088459 A1 3/2014 Roush et al.
2014/0142393 A1 5/2014 Piskun et al.
2014/0155702 A1 6/2014 Tilson et al.
2014/0155783 A1 6/2014 Starksen et al.
2014/0171736 A1 6/2014 Stigall et al.
2014/0172029 A1 6/2014 Guyer et al.
2014/0188054 A1 7/2014 Iijima et al.
2014/0207083 A1 7/2014 Pessin
2014/0234600 A1 8/2014 Wang et al.
2014/0243796 A1 8/2014 Tegg et al.
2014/0243873 A1 8/2014 Franklin
2014/0275860 A1 9/2014 Rottenberg et al.
2014/0276601 A1 9/2014 Edward
2014/0276642 A1 9/2014 Cully et al.
2014/0309587 A1 10/2014 Kim et al.
2014/0309661 A1 10/2014 Sheps et al.
2014/0343358 A1 11/2014 Hameed et al.
2014/0371718 A1 12/2014 Alvarez et al.
2014/0371764 A1 12/2014 Oyola et al.
2015/0018616 A1 1/2015 Kumoyama
2015/0038919 A1 2/2015 Bramwell et al.
2015/0073216 A1 3/2015 Papay
2015/0073342 A1 3/2015 Pacheco et al.
2015/0073409 A1 3/2015 Watson et al.
2015/0094656 A1 4/2015 Salahieh et al.
2015/0119640 A1 4/2015 Reydel
2015/0126814 A1 5/2015 Mesallum et al.
2015/0133729 A1 5/2015 Reydel
2015/0142013 A1 5/2015 Tanner et al.
2015/0148602 A1 5/2015 Hill et al.
2015/0148606 A1 5/2015 Rottenberg et al.
2015/0164314 A1 6/2015 Peterson
2015/0216589 A1 8/2015 Wittenberger et al.
2015/0276097 A1 10/2015 Carlson et al.
2015/0313445 A1 11/2015 Davidson et al.
2015/0335387 A1 11/2015 Atzinger et al.
2015/0342608 A1 12/2015 Hernandez
2015/0369325 A1 12/2015 Bureau et al.
2016/0007832 A1 1/2016 Shimada
2016/0015259 A1 1/2016 Mody et al.
2016/0058268 A1 3/2016 Salman et al.
2016/0066773 A1 3/2016 Cooper et al.
2016/0096004 A1 4/2016 Gerrans et al.
2016/0100747 A1 4/2016 Nitsan et al.
2016/0129547 A1 5/2016 Duescher et al.
2016/0136393 A1 5/2016 Tsai et al.
2016/0174829 A1 6/2016 Reydel
2016/0198935 A1 7/2016 Choi et al.
2016/0206425 A1 7/2016 Madrid et al.
2016/0270865 A1 9/2016 Landey et al.
2016/0270870 A1 9/2016 Kowshik
2016/0279388 A1 9/2016 Barrish et al.
2016/0287059 A1 10/2016 Ha et al.
2016/0302818 A1 10/2016 Weisenburgh et al.
2016/0309989 A1 10/2016 Sato et al.
2016/0324412 A1 11/2016 Hassidov et al.
2017/0023154 A1 1/2017 Jaeker et al.
2017/0156567 A1 6/2017 Kaneko
2017/0157363 A1 6/2017 Barrish et al.
2017/0312920 A1 11/2017 Yip et al.
2017/0340862 A1 11/2017 Calabrese et al.
2017/0360281 A1 12/2017 Ponsky
2018/0001062 A1 1/2018 O'Carrol et al.
2018/0015257 A1 1/2018 Krolik et al.
2018/0043134 A1 2/2018 Alvarez et al.
2018/0064366 A1 3/2018 Sweeney et al.
2018/0078282 A1 3/2018 Takemoto
2018/0085559 A1 3/2018 Laby et al.
2018/0126144 A1 5/2018 Furnish et al.
2018/0132705 A1 5/2018 Higuchi
2018/0160893 A1 6/2018 Truckai et al.
2018/0184885 A1 7/2018 St. George
2018/0249893 A1 9/2018 Yeung et al.
2018/0256876 A1 9/2018 Furnish et al.
2018/0263469 A1 9/2018 Okaniwa et al.
2018/0264239 A1 9/2018 Piskun
2018/0289925 A1 10/2018 Palmer et al.
2018/0326144 A1 11/2018 Truckai
2018/0326197 A1 11/2018 McArthur et al.
2018/0338673 A1 11/2018 Krimsky et al.
2018/0361116 A1 12/2018 Quick et al.
2018/0374603 A1 12/2018 Greenwood
2019/0046012 A1 2/2019 Ikeda
2019/0104932 A1 4/2019 Truckai et al.
2019/0175799 A1 6/2019 Hsu et al.
2019/0226447 A1 7/2019 Stecher et al.
2019/0247050 A1 8/2019 Goldsmith
2019/0282072 A1 9/2019 Katballe et al.
2019/0282073 A1 9/2019 Truckai
2019/0380715 A1 12/2019 Goldin et al.
2020/0022712 A1 1/2020 Deville et al.
2020/0030575 A1 1/2020 Bogusky et al.
2020/0100653 A1 4/2020 Nakamura
2020/0138271 A1 5/2020 Toth et al.
2020/0171276 A1 6/2020 Onozuka
2020/0187751 A1 6/2020 Zheng et al.
2020/0230808 A1 7/2020 Simaan et al.
2020/0315429 A1 10/2020 Russo et al.
2020/0315433 A1 10/2020 Axon et al.
2020/0315440 A1 10/2020 Basadonna et al.
2020/0329953 A1 10/2020 Truckai
2020/0383677 A1 12/2020 Piligian et al.
2020/0391002 A1 12/2020 Hilton et al.
2020/0407149 A1 12/2020 Pherson et al.
2021/0000505 A1 1/2021 Lenker et al.
2021/0030260 A1 2/2021 Julian et al.
2021/0045626 A1 2/2021 Hsu et al.
2021/0114507 A1 4/2021 Alexander et al.
2021/0138187 A1* 5/2021 Tilson ................. A61M 25/005
2021/0146111 A1 5/2021 Modlish et al.
2021/0197684 A1 7/2021 Graham et al.
2021/0228973 A1 7/2021 Conte
2021/0280312 A1 9/2021 Freedman et al.
2021/0323767 A1 10/2021 Liu et al.
2021/0330938 A1 10/2021 Kendrick et al.
2021/0361895 A1 11/2021 Nekhendzy et al.
2022/0000346 A1 1/2022 Switzer
2022/0347430 A1 11/2022 Pedersen
2022/0369903 A1 11/2022 Schneider et al.
2022/0414880 A1 12/2022 Inoue et al.
2023/0017488 A1 1/2023 Somasundaram et al.
2023/0062769 A1 3/2023 Lichtenstein
2023/0070264 A1 3/2023 Leuthardt et al.
2023/0121021 A1 4/2023 Sinay et al.
2023/0138203 A1 5/2023 Bazdanes et al.
2023/0210351 A1 7/2023 Scheeff et al.
2023/0338702 A1 10/2023 Tilson et al.

(56) References Cited

U.S. PATENT DOCUMENTS

| | | | |
|---|---|---|---|
| 2023/0346204 | A1 | 11/2023 | Tilson et al. |
| 2023/0346205 | A1 | 11/2023 | Tilson et al. |
| 2023/0346399 | A1 | 11/2023 | Schaller et al. |
| 2023/0353879 | A1 | 11/2023 | Nishide et al. |
| 2023/0380662 | A1 | 11/2023 | Slawinski et al. |
| 2023/0404486 | A1 | 12/2023 | Carreel et al. |
| 2024/0016638 | A1 | 1/2024 | McGowan et al. |
| 2024/0016639 | A1 | 1/2024 | McGowan et al. |
| 2024/0024640 | A1 | 1/2024 | Gomes et al. |
| 2024/0082557 | A1 | 3/2024 | Tilson et al. |
| 2024/0090744 | A1 | 3/2024 | Lopez et al. |
| 2024/0165833 | A1 | 5/2024 | Tanner et al. |
| 2024/0293003 | A1 | 9/2024 | Tilson et al. |
| 2024/0339112 | A1 | 10/2024 | Rabinovich et al. |
| 2024/0350768 | A1 | 10/2024 | Tilson et al. |
| 2024/0358232 | A1 | 10/2024 | Joseph et al. |
| 2025/0031949 | A1 | 1/2025 | Tilson et al. |
| 2025/0065078 | A1 | 2/2025 | Morris et al. |
| 2025/0082178 | A1 | 3/2025 | Witte et al. |
| 2025/0089992 | A1 | 3/2025 | Tilson et al. |
| 2025/0090801 | A1 | 3/2025 | Zayed et al. |
| 2025/0107697 | A1 | 4/2025 | Tilson et al. |
| 2025/0107812 | A1 | 4/2025 | Eisler et al. |
| 2025/0134352 | A1 | 5/2025 | Tilson et al. |
| 2025/0135159 | A1 | 5/2025 | Gomes et al. |
| 2025/0160620 | A1 | 5/2025 | Lopez et al. |
| 2025/0160891 | A1 | 5/2025 | Gomes et al. |
| 2025/0169678 | A1 | 5/2025 | Tilson et al. |
| 2025/0194904 | A1 | 6/2025 | Tilson et al. |
| 2025/0262407 | A1 | 8/2025 | Tilson et al. |
| 2025/0275672 | A1 | 9/2025 | Tilson et al. |
| 2025/0276456 | A1 | 9/2025 | Devengenzo et al. |
| 2025/0281718 | A1 | 9/2025 | Tilson et al. |
| 2026/0007482 | A1 | 1/2026 | Tilson et al. |
| 2026/0033702 | A1 | 2/2026 | Witte et al. |
| 2026/0041308 | A1 | 2/2026 | Tilson et al. |
| 2026/0145345 | A1 | 5/2026 | Tanner et al. |

FOREIGN PATENT DOCUMENTS

| | | | |
|---|---|---|---|
| CN | 1706349 | A | 12/2005 |
| CN | 1732855 | A | 2/2006 |
| CN | 1764800 | A | 4/2006 |
| CN | 1806770 | A | 7/2006 |
| CN | 1861011 | A | 11/2006 |
| CN | 101119765 | A | 2/2008 |
| CN | 101129255 | A | 2/2008 |
| CN | 101888872 | A | 11/2010 |
| CN | 102137628 | A | 7/2011 |
| CN | 201899767 | U | 7/2011 |
| CN | 102711585 | A | 10/2012 |
| CN | 102872519 | A | 1/2013 |
| CN | 103384500 | A | 11/2013 |
| CN | 104168860 | A | 11/2014 |
| CN | 104287684 | B | 3/2016 |
| CN | 105759418 | A | 7/2016 |
| CN | 105813536 | A | 7/2016 |
| CN | 105832279 | A | 8/2016 |
| CN | 106137397 | A | 11/2016 |
| CN | 106455929 | A | 2/2017 |
| CN | 106488744 | A | 3/2017 |
| CN | 106659367 | A | 5/2017 |
| CN | 106823102 | A | 6/2017 |
| CN | 107296584 | A | 10/2017 |
| CN | 107697631 | A | 2/2018 |
| CN | 207979960 | U | 10/2018 |
| CN | 109883620 | A | 6/2019 |
| CN | 110077771 | A | 8/2019 |
| CN | 110403651 | A | 11/2019 |
| CN | 110582324 | A | 12/2019 |
| CN | 210161176 | U | 3/2020 |
| CN | 111465420 | A | 7/2020 |
| CN | 112218595 | A | 1/2021 |
| CN | 212558299 | U | 2/2021 |
| DE | 102005039601 | A1 | 2/2007 |
| DE | 102017219621 | A1 | 3/2019 |
| EP | 401129 | A1 | 12/1990 |
| EP | 0941743 | A2 | 9/1999 |
| EP | 1662972 | A2 | 6/2006 |
| EP | 1695657 | A1 | 8/2006 |
| EP | 1578255 | B1 | 9/2006 |
| EP | 1487318 | B1 | 3/2008 |
| EP | 2016914 | A2 | 1/2009 |
| EP | 1499227 | B1 | 10/2010 |
| EP | 2258322 | A2 | 12/2010 |
| EP | 2364637 | A1 | 9/2011 |
| EP | 2368481 | A1 | 9/2011 |
| EP | 2368483 | A1 | 9/2011 |
| EP | 3256052 | A1 | 12/2017 |
| EP | 2604175 | B1 | 11/2019 |
| GB | 2482355 | A | 10/2010 |
| GB | 2497544 | A | 6/2013 |
| JP | S6289014 | A | 4/1987 |
| JP | H0471524 | A | 3/1992 |
| JP | H05220102 | A | 8/1993 |
| JP | H05293077 | A | 11/1993 |
| JP | H0644503 | U | 6/1994 |
| JP | 2002125921 | A | 5/2002 |
| JP | 2003501197 | A | 1/2003 |
| JP | 2003508133 | A | 3/2003 |
| JP | 2005152300 | A | 6/2005 |
| JP | 2005323778 | A | 11/2005 |
| JP | 2006068449 | A | 3/2006 |
| JP | 2006511291 | A | 4/2006 |
| JP | 03965108 | B2 | 8/2007 |
| JP | 2009506839 | A | 2/2009 |
| JP | 2009507617 | A | 2/2009 |
| JP | 2009061173 | A | 3/2009 |
| JP | 2010000360 | A | 1/2010 |
| JP | 2010279795 | A | 12/2010 |
| JP | 2011194126 | A | 10/2011 |
| JP | 2012183232 | A | 9/2012 |
| JP | 2013514150 | A | 4/2013 |
| JP | 2013176465 | A | 9/2013 |
| JP | 2014124475 | A | 7/2014 |
| JP | 2014176713 | A | 9/2014 |
| JP | 2015525609 | A | 9/2015 |
| JP | 2017506129 | A | 3/2017 |
| JP | 2018500054 | A | 1/2018 |
| JP | 2018514350 | A | 6/2018 |
| JP | 2018525197 | A | 9/2018 |
| JP | 2018537229 | A | 12/2018 |
| JP | 2021175686 | A | 11/2021 |
| KR | 10-2015-0131502 | A | 11/2015 |
| KR | 20180053852 | A | 5/2018 |
| KR | 101908933 | B1 | 10/2018 |
| TW | 201438661 | A | 10/2014 |
| WO | WO97/43941 | A1 | 11/1997 |
| WO | WO99/053827 | A1 | 10/1999 |
| WO | WO03/013348 | A1 | 2/2003 |
| WO | WO2005/110199 | A1 | 11/2005 |
| WO | WO2005/110200 | A1 | 11/2005 |
| WO | WO2007/035931 | A2 | 3/2007 |
| WO | WO2008/041809 | A1 | 4/2008 |
| WO | WO2008/122969 | A1 | 10/2008 |
| WO | WO2008/122997 | A1 | 10/2008 |
| WO | WO2009/154192 | A1 | 12/2009 |
| WO | WO2011/018147 | A1 | 2/2011 |
| WO | WO2011/018157 | A1 | 2/2011 |
| WO | WO2011/148172 | A2 | 12/2011 |
| WO | WO2012/054480 | A2 | 4/2012 |
| WO | WO2012/080947 | A1 | 6/2012 |
| WO | WO2012/122288 | A2 | 9/2012 |
| WO | WO2013/132992 | A1 | 9/2013 |
| WO | WO2014/081892 | A1 | 5/2014 |
| WO | WO2016/034598 | A1 | 3/2016 |
| WO | WO2016/190324 | A1 | 12/2016 |
| WO | WO2017/041052 | A1 | 3/2017 |
| WO | WO2018/035452 | A1 | 8/2017 |
| WO | WO2019/054867 | A1 | 3/2019 |
| WO | WO2019/160865 | A1 | 8/2019 |
| WO | WO2019/211457 | A1 | 11/2019 |
| WO | WO2019/234734 | A1 | 12/2019 |
| WO | WO2020/018934 | A1 | 1/2020 |

(56) References Cited

FOREIGN PATENT DOCUMENTS

| | | | |
|---|---|---|---|
| WO | WO2020/128072 | A1 | 6/2020 |
| WO | WO2020/214221 | A1 | 10/2020 |
| WO | WO2020/237426 | A1 | 12/2020 |
| WO | WO2021/202336 | A1 | 10/2021 |
| WO | WO2021/242884 | A1 | 12/2021 |
| WO | WO2022/051682 | A1 | 3/2022 |
| WO | WO2022/087093 | A1 | 4/2022 |
| WO | WO2022/146939 | A1 | 7/2022 |
| WO | WO2022/159861 | A1 | 7/2022 |
| WO | WO2023/122667 | A1 | 6/2023 |
| WO | WO2023/122767 | A2 | 6/2023 |
| WO | WO2023/133403 | A1 | 7/2023 |
| WO | WO2023/154743 | A2 | 8/2023 |
| WO | WO2023/183952 | A2 | 9/2023 |
| WO | WO2023/212641 | A2 | 11/2023 |
| WO | WO2023/225520 | A2 | 11/2023 |
| WO | WO2013/184192 | A2 | 12/2023 |
| WO | WO2024/233497 | A1 | 11/2024 |
| WO | WO2025/129198 | A1 | 6/2025 |
| WO | WO2025/171405 | A1 | 8/2025 |
| WO | WO2025/199177 | A1 | 9/2025 |
| WO | WO2026/025118 | A1 | 1/2026 |
| WO | WO2026/064742 | A2 | 3/2026 |
| WO | WO2026/072879 | A1 | 4/2026 |
| WO | WO2026/090198 | A1 | 4/2026 |
| WO | WO2026/112621 | A1 | 5/2026 |

OTHER PUBLICATIONS

Bearing Works; PTFE Datasheet; 2 pages; Jan. 21, 2021 retrieved from the internet (https://www.bearingworks.com/uploaded-assets/pdfs/retainers/ptfe-datasheet.pdf) on Nov. 10, 2023.

Entrada® colonic overtube product brochure downloaded from internet http://www usendoscopy.com/~/media/Files/Documents/Spec-Sheet-International/760358c_entrada_intl_ss_web.pdf Accessed Date: Jun. 5, 2017 (the year of publication is sufficiently earlier than the effective U.S. filing date and any foreign priority date so that the particular month of publication is not in issue) 2009.

Filip et al.; Design, Implementation, and Testing of a miniature self-stabilizing capsule endoscope with wireless image transmission capabilities; Intl. Journal "Information Technologies & Knowledge"; 5(1); downloaded from http://www.foibg.com/ijitk/ijitk-vol05/ijitk05-1-p01.pdf on Jul. 28, 2016; (the year of publication is sufficiently earlier than the effective U.S. filing date and any foreign priority date so that the particular month of publication is not in issue) 2011.

Loeve et al.; Endoscope Shaft-Rigidity Control Mechanism: "Forguide"; IEEE Trans. On Biomed. Eng.; 59(2); pp. 542-551; Feb. 2012.

Loeve et al.; Vacuum packed particles as flexible endoscope guides with controllable rigidity; Granular Matter; 12(6); pp. 543-554; Jun. 24, 2010.

Mayinger et al.; Disposable-sheath, flexible gastroscope system versus standard gastroscopes: a prospective, randomized trial; Gastrointestinal Endoscopy; 50(4); pp. 461-467; Oct. 1999.

Mayinger et al.; Disposable protection for flexible gastroenterologic endoscopy: prospective comparative evaluation of a new gastroscopy system (Endosheath) compared to the standard fiberglass gastroscope; (English Abstract Only); Zeitschrift Fur Gastrenterologia; 36(6); pp. 501-507; Jun. 1998 (Eng Abs only).

Ofstead et al.; A systematic review of disposable sheath use during flexible endoscopy; AORN Journal; 109(6); pp. 757-771; Jun. 2019.

Rothstein et al.; Disposable, sheathed, flexible sigmoidoscopy: a prospective, multicenter, randomized trial; Gastrointestinal Endoscopy; 41(6); pp. 566-572; Jun. 1995.

Sardinha et al.; Efficiency and productivity of a sheathed fiberoptic sigmoidoscope compared with a conventional sigmoidoscope; Diseases of the Colon and Rectum; 40(10); pp. 1248-1253; Oct. 1997.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

Ferrante et al.; U.S. Appl. No. 18/851,053 entitled "Methods and apparatuses for navigating using a pair of rigidizing devices," filed Sep. 25, 2024.

Tilson et al.; U.S. Appl. No. 19/100,929 entitled "Dynamic rigidization methods and apparatuses," filed Feb. 3, 2025.

Tilson et al.; U.S. Appl. No. 19/223,003 entitled "Devices and methods for enhanced visualization of body lumen," filed Feb. 3, 2025.

Tilson et al.; U.S. Appl. No. 19/344,491 entitled "Methods of performing vascular procedures using a rigidizing device," filed Sep. 29, 2025.

Tilson et al.; U.S. Appl. No. 19/344,510 entitled "Methods of performing vascular procedures using a rigidizing device," filed Sep. 29, 2025.

Kuperij et al.; Design of a user interface for intuitive colonoscope control; In2011 IEEE/RSJ International Conference on Intelligent Robots and Systems; pp. 937-942; Sep. 25, 2011.

Smooth-On; Durometer Shore Hardness Scale; smooth-on.com; retrieved from the internet (https://www.smooth-on.com/page/durometer-shore-hardness-scale/); 2 pages; 2026.

Koch et al.; U.S. Appl. No. 19/481,880 entitled "Large bore suction overtube," filed Nov. 5, 2025.

Tilson et al.; U.S. Appl. No. 19/544,566, entitled "Methods of attaching a rigidizing sheath to an endoscope," filed Feb. 19, 2026.

* cited by examiner

Real image plane

Band image

BODY LUMEN MAPPING WITH A NESTED RIGIDIZING SYSTEM

CLAIM OF PRIORITY

This patent application claims priority to U.S. provisional patent application No. 63/699,151, filed on Sep. 25, 2024, titled "BODY LUMEN MAPPING WITH A NESTED RIGIDIZING SYSTEM," and U.S. provisional patent application No. 63/859,865, filed on Aug. 7, 2025, titled "ENDOSCOPIC INTERROGATION," and U.S. provisional patent application No. 63/859,851, filed Aug. 7, 2025 and titled, "AUTONOMOUS CONTROL OF NESTED RIGIDIZING ROBOT," each of which is herein incorporated by reference in its entirety.

BACKGROUND

Imaging ('mapping') a luminal wall during a colonoscopy is important for diagnosing and managing colorectal diseases, especially for cancer screening, surveillance of inflammatory bowel diseases (IBD), and identifying abnormal growths like polyps. Disease cannot be diagnosed when it is missed or not imaged and seen, and the literature is clear that current manual methods miss a notable portion of the luminal wall. Mapping may help in pinpointing the exact location of any abnormal findings, such as polyps, tumors, and/or inflammation. The colon is a long, looping organ, and being able to accurately document where a lesion is found is vital for treatment planning and future surveillance. The colon may be divided into segments (rectum, sigmoid colon, descending colon, transverse colon, ascending colon, and cecum), and mapping allows physicians to record the lesion's location within these segments. In cases where surgical or other therapeutic interventions are required (e.g., polypectomy, resection of a tumor), mapping ensures that surgeons and gastroenterologists can precisely target the affected area. Mapping the entire surface is a critical part of a diagnosis-missed wall is potentially a missed diagnosis.

In addition, for individuals at risk of colorectal cancer, particularly those with a family history or conditions like Lynch syndrome, mapping aids in tracking changes over time. Accurate mapping allows for monitoring whether previously identified polyps have grown or changed, ensuring timely intervention. In conditions like Crohn's disease and ulcerative colitis, mapping inflammation patterns is essential for long-term management. For example, it helps identify areas of inflammation or precancerous changes, such as dysplasia, and can guide biopsies from specific regions.

While mapping the colon during a colonoscopy can aid in accurate diagnosis and treatment, several challenges and problems can arise. The colon is a long, looping organ with multiple folds and turns, making it difficult to navigate during a colonoscopy. The colon's structure can vary between individuals, and the colon shifts as the procedure progresses due to patient movement, endoscope motion, or the introduction of air to inflate the colon. This makes precise localization challenging. While some parts of the colon, like the cecum, rectum, or ileocecal valve, have distinct features, the majority of the colon lacks consistent landmarks. This can make it difficult to map the exact position of polyps, lesions, or areas of inflammation, especially when documenting subtle or smaller abnormalities. In addition, during the procedure, the colonoscope may cause loops to form within the colon. These loops distort the colon's position and make it harder to estimate the exact location of any findings. Even experienced gastroenterologists may struggle to maintain an accurate sense of orientation, particularly in long, tortuous colons. In some cases, endoscopic tattooing or clipping is used to mark locations of interest for future procedures, like surgery or follow-up colonoscopies. However, this can be imprecise or difficult in certain areas of the colon. The ink from a tattoo may spread, leading to ambiguous markings, or clips may move or dislodge over time. In addition, there is no universal system for mapping the colon that all gastroenterologists follow. While the colon is divided into broad sections (rectum, sigmoid, descending, transverse, ascending, and cecum), the detailed mapping and description of findings can vary widely. This lack of standardization can lead to confusion and communication issues when sharing reports between healthcare providers. Further, in patients with multiple polyps or widespread disease, accurately mapping each lesion can be difficult. Keeping track of numerous lesions and precisely documenting their size, shape, and position is time-consuming and can lead to errors if the documentation is not meticulous.

The kinematics of colonoscopy are very challenging. When a scope is placed, a clinician moving the shaft forward often does not see a commensurate and definitive movement of the endoscope tip, as the scope sometimes moves backwards ('paradoxical motion'), does nothing (as the scope stretches or distends the organ), or erratically jumps forward. 'Looping' kinematically obfuscates the goal of precise advancement. Looping additionally causes significant patient discomfort and is the driver of the need for patient sedation.

When a clinician wants to withdraw a scope, a 'reduction' typically occurs, as the colon is straightened (and its length is reduced). Again, precise kinematic control is poor: For a given clinician scope withdraw, sometimes the scope tip does nothing, sometimes it withdraws, and sometimes it actually moves forward. When a colonoscope is in a looped configuration and a clinician wants to torque the shaft, the torquing moves the scope off its central axis, and typically whips it either forward or backward, which is very disorienting and creates difficulties with regard to the goal of careful and methodical luminal interrogation. Manual colonoscopy does not allow precise motion, e.g., advancement, withdrawal, or rotational, when deeply positioned. These kinematic truths make the precise interrogation of a region kinematically, which can require repeated and methodically motion back and forth, very challenging if not outright impossible.

Interrogating a full colon wall requires significant kinematic challenges for the clinician. ERI (Endoscopy Related Injuries) are pervasive, as the user manipulates the scope handle, torques the knobs, and advances and rotates the shaft. Traditional scope interfaces are poorly designed with regard to the repeated use, resulting in high stresses on the user when used for a high volume of daily cases, for long cases (ESD cases can extend for hours), and these issues are compounded with more a diverse and gender-equivalent workforce. It would be useful to have a system that simultaneously improved mapping and reduced the physical burden of colonoscopy.

Although most colonoscopies rely on visual inspection and manual recording, and while technology has improved, real-time mapping tools are still limited. Innovations like advanced imaging techniques and computer-aided detection (CAD) are promising but are still in development and are either minimally or not yet commercialized. Without advanced guidance systems, mapping continues to depend largely on the skill and experience of the endoscopist. Thus, mapping the colon accurately during a colonoscopy faces challenges related to the colon's anatomy, looping, subjective interpretation, and lack of consistent landmarks. These problems can affect the precision and reproducibility of the procedure, but advancements in imaging technologies and standardization efforts are gradually helping to mitigate these issues. What is needed are methods and apparatuses that may more completely, accurately, safely, reliably, ergonomically, and quickly map a colon during a colonoscopy. Described herein are methods and apparatuses that may address these needs.

SUMMARY OF THE DISCLOSURE

Described herein are apparatuses (devices and systems, including hardware, software and firmware) and methods for mapping a body lumen, including but not limited to, a colon. These methods may include the robotic and/or automatic or semi-automatic use of one or more rigidizing member to create a stable foundation from which a second member (which in optionally rigidizing) may be advanced and/or withdrawn and/or rotated in order to take multiple images of the body lumen (e.g., of the walls of the body lumen) and stitching these images together to create a coverage map of the body lumen. The map may be an arrayed series of planar images, or it may include topological features, including such that it could be used to create images that are displayed as part of a full 3D model. The second member may be advanced and/or withdrawn and/or rotated to generate this coverage mapping without substantially moving the stable foundation within the body lumen. In particular, these methods may include controlling the first and/or second member to apply one or more techniques to ensure that the mapping is performed rapidly while achieving full or nearly full coverage of the body lumen over the full extent of the lumen or a selected sub-region. Optionally, the first member may also carry imaging or other sensors and be moved along the second member, especially while it is rigid, in order to gather mapping information for the lumen.

As used herein, mapping may include constructing a 2D or 3D representation of the interior surface of the body lumen, e.g., colon, when performing a procedure such as a colonoscopy.

In general, these methods and apparatuses may include topological features, including such that they could be used to create images that are displayed as part of a full 3D model.

In general, these methods and apparatuses may provide coverage mapping that may be used to create an arrayed set of images that are "unwrapped" to show a mapping representation (e.g., image) of the colon which may extend virtually the entire length of the colon, e.g., from the anal region to the cecum.

These methods have significant advantages over prior art methods suggested for mapping, including speed, completeness, precise and repeated motion, and ergonomics, as well as automation, and include features that are specifically adapted in order to accomplish these advantages.

For example, these methods and apparatuses are configured to ensure complete or nearly complete (e.g., >80%, >85%, >90%, >95%, >99%, etc., or any other mapping completion threshold) mapping of the body lumen. It is known that existing and currently proposed colonoscopy systems (including mapping systems), typically miss more than 25% (with some studies showing up to 35%) of neoplastic lesions. Further, it is known that there is an enormous variation in wall coverage percentage amongst different clinician groups, resulting in highly inconsistent procedural quality, significantly compromising procedural efficacy. Described herein are apparatuses, including software/firmware/hardware that track and may automatically or semi-automatically scan a body region (e.g., colon) to a desired threshold of completeness, even where the body lumen may be irregular, including having folds/protrusions and tortuosity that may occlude regions of the wall and potentially mask lesions.

The methods and apparatuses are configured to systematically and in a highly controlled manner map subregions of the lumen in order to construct a map, e.g., a coverage model or a coverage map, of the lumen. In some examples the apparatus and method may do this by positioning a first (rigidizing) member in position within the lumen, rigidizing the first member to provide a stable and fixed platform from which the second member, which in some cases may be nested with the first member, may be extended and may move in one or more degrees of freedom relative to the rigid first member to scan a subregion of the lumen. Scanning may be performed using one or more cameras on the second member. Scanning may include dithering, e.g., repeatedly and methodically moving back and forth relative to the rigid first member, such as moving axially back and forth. Scanning may include bending/articulating, and/or rotating/torquing the device relative to the second device (e.g., in some cases rotating within the lumen of the first member). Scanning (including dithering) may be continued multiple times until the subregion has been completed to a desired percentage of completeness, based on the controller, which may monitor and track the mapping, including identifying unmapped regions, particularly regions obscured by folds, protrusions, etc. The controller may include control logic for identifying features and mapping completeness. In some cases the controller may cause one or more expandable and/or collapsable spreaders (e.g., balloons, cage, frame, shell, probes, arms, etc.) and/or irrigation and/or insufflation, etc., when the controller determines that one or more regions are occluded. Alternately or additionally the controller may identify one or more features of interests (e.g., polyps) and may take additional or enhanced imaging of this region. In some cases the controller may control the position and/or rigidity of the first and/or second elongate members (e.g., overtube and/or endoscope) in order to map the region more fully. In some cases the subregion may be passively mapped as the user is navigating through the body lumen; the apparatus or method may track the percentage of mapping and may guide or instruct (or control) the apparatus to fill in the unmapped or inadequately mapped regions later. Alternatively in some cases the apparatus may control (robotically control) the mapping. Once the mapping of the subregion is completed, the apparatus or method may advance to the next (e.g., an adjacent) subregion to continue mapping of the overall lumen. The first member may also carry imaging or other sensors and move with respect to the second member in a complementary manner to all of the situations described above.

The method and apparatuses described herein may identify gaps or regions that are not mapped or not fully and/or satisfactorily mapped. The controller (including one or more processors) may be configured to build a coverage map and determine, in real time and/or as the scanning is being performed, that the coverage of the body lumen and/or a subset of the body lumen is tracking and/or covering the amount (e.g., percent) of the body wall(s). The system may show the user this coverage in real time, e.g., in a display. The system may automatically or semi-automatically control the robotic apparatus to scan (or re-scan) region that are less well covered or that have not yet been covered. In some variations, the apparatus may control the operation of the paired (e.g. nested) system of rigidizing members that may systematically control mapping of the body lumen during advancing and/or retracting of the rigidizing members through the body lumen.

In general, any of these apparatuses may include one or more cameras for collecting images of the body lumen. In some cases the system may include a forward facing camera, or cameras that are forward facing but at offset skew angles, and/or or one or more side or distal (back) facing cameras. The camera may be on a first elongate member (e.g., an inner nested member, such as an endoscope or cover/shield for an endoscope) and/or on an outer member (e.g., an overtube). The cameras may be configured to image one or more wavelengths or range of wavelengths. In some cases the cameras may be configured to image white light images. In some cases the cameras may be configured to image infrared (e.g., near-infrared). In some cases the cameras may be configured to image narrow band wavelengths. Narrow band imaging (NBI, also referred to as virtual chromoendoscopy) techniques may use a narrow range of light wavelengths to improve image contrast and visibility. For example, any of these apparatuses and methods may use a narrow band light illumination and detection, such as two wavelengths, e.g., 415 nanometers (nm) of blue light and/or 540 nm of green light. NBI may be used for mapping (e.g., tracking vascular landmarks, such as blood vessels in/on the walls, detecting lesions/polyps, etc. In some cases NBI may be used to help classify polyps (e.g., based on their pit patterns). NBI may be used to differentiate tissue (e.g., normal vs. dysplastic tissue in the colon), detection of adenoma, etc. Other wavelengths, including white light, near-infrared, etc. may also or alternatively be used for mapping and/or detection.

These methods and apparatuses may generate a map of the colon that may be formed by combining, e.g., image stitching, images of one or more wavelength to form an image that may be stored, transmitted and/or manipulated. The map may be referred to as a coverage map and may include a full circumferential view of the lumen as it extends through the body lumen. The coverage map may be configured to show folds and protrusion as images or consensus images taken as described herein. The map may be displayed statically (e.g., printed) as an "unrolled" map representative of the body lumen. Alternatively, in some examples the coverage map may be dynamic, including different/alternative views of the lumen, particularly in regions having high tortiously and/or complexity, e.g., folds. The map may include a surface that is part of a 3-D model. Such region may include representations of multiple 'sides' of the region (e.g., fold). In some cases the coverage map may include multiple layers of image that form the map, including images of the same region taken from different perspectives, or from different manipulations (e.g., expanded/relaxed, etc.). The coverage mapping may be representative of a defined or user-adjustable perspective, such as a midline (e.g., middle of the lumen) perspective. The coverage mapping may be synthesized from multiple overlapping and/or adjacent images of the body lumen; as described in greater detail here, the coverage map may be formed (built, assembled, constructed, etc.) in real time and displayed. Alternatively or additionally, the coverage mapping may be constructed or modified after the scanning is complete.

The apparatuses and methods described herein may automatically or semi-automatically modify the body lumen, at least locally (e.g., in the sub-region being mapped), by expanding it, e.g., by applying pressure (e.g., insufflation) and/or mechanical manipulation (e.g., expandable and/or collapsable spreaders) or other manipulator) against the wall(s) of the lumen. For example, the first or second (e.g., inner and/or outer) elongate members may include a mechanical spreader configured as a balloon, and in particular, a transparent balloon through which imaging may be performed, to expand or smooth the wall of the lumen. Other manipulators may include fingers or other manipulators to contact and expose or expand a region to allow better mapping. As mentioned, this mechanical or pressure-based manipulation may be coordinated by the controller, which may determine if additional manipulation of the lumen is helpful or necessary, and may deploy such manipulator device, either via an algorithm or as a result of a user interface, including from a prompt.

In general, these methods and apparatuses may annotate, automatically and/or manually, the coverage maps generated herein. For example, the methods or apparatuses described herein may identify one or more regions of interests (e.g., lesions, polyps, etc.) and may annotate the coverage map accordingly. The apparatus and/or method may be configured to receive and processes user input to allow the user to manually annotate the coverage map. Annotations may be part of the coverage map or included (e.g., as a layer, metadata, etc.) with the coverage map In general, the methods and apparatuses described herein may be used for mapping, and in particular for generating a coverage map for the lumen. In particular, these methods and apparatuses may be used for generating a visual map of a patient's colon. These methods and apparatuses may perform passive and/or active mapping. Passive mapping may be performed as the user (e.g., doctor, technician, nurse, or other clinician) is driving the apparatus, such as a nested robotic dual-rigidizing apparatus, through the body, including but not limited to the colon. One or more cameras on the apparatus may continuously or periodically image the walls of the colon and combine these images to form a coverage map. The system may display a forward-facing image while the user is operating the device and may optionally and/or additionally show peripheral images, e.g., taken from one or more side-facing and/or rear-facing images. Under passive mapping, the map may be constructed and regions that are not covered (or that are not sufficiently covered) may be tracked by the apparatus for later scanning in additional detail. Optionally the apparatus or method may monitor all or some of the camera images and may automatically (e.g., using a trained machine learning agent) identify one or more regions of interest such as a polyp, occlusion, lesion, plaque, diseased region, etc.; when the apparatus identifies (e.g., in any of these views, including a peripheral view) a region of interest, it may alert the user, and may provide the user an option to automatically or semi-automatically navigate to the region of interest, including scanning the region in greater detail. For example the user may be shown a forward-facing image but may be presented with an alert that a potential polyp was identified in a peripheral view. The user may select an input so that the apparatus automatically controls the rigidizing state and/or steering to navigate to the identified potential polyp. At any point, including after traversing the full colon to the cecum, the user may switch between manual and automatic mapping (or vice versa). For example, the user may switch via a user input, from manual to automatic allowing the apparatus to automatically and systemically traverse the lumen (e.g., of the colon) to image the colon walls. In cases in which the partial mapping (e.g., partial coverage map) has been formed already, the apparatus may focus on imaging regions not yet fully or sufficiently scanned. The coverage may may be formed by stitching together one or more images (which may be averaged, added, subtracted, or otherwise combined). To facilitate the capabilities above, where the first member or second member have more than one camera, all cameras on one member can be calibrated with respect to each other ("extrinsic calibration") so that where there is overlap and an object appears in more than one camera view, a prediction can be made about where in one camera view the object will appear in the other camera view. Where there is no overlap, a prediction can be made about how to move the first or second member in order to bring the object into view in the second camera. For example, artificial intelligence-based polyp detection software may detect a polyp in a side view camera, and with or without operator command, then move the primary front-facing camera to "look" at the polyp.

For example, a method of mapping a body lumen (such as but not limited to a colon) may include: rigidizing a first member of a nested, rigidizing apparatus within the body lumen; axially and/or rotationally manipulating a second member extending distally relative to the rigidized first nested member to scan a subregion of the body lumen by imaging walls of the body lumen; combining the images of the walls of the body lumen into a coverage map of the body lumen; repositioning the nested, rigidizing apparatus within the lumen by shape copying; and repeating the steps of rigidizing, manipulating, scanning, combining and repositioning over a plurality of continuous subregions to map body lumen. Maintaining one member rigid while the other moves may minimize motion of the anatomy, allowing for stable creation of a local map. Movements of the members can be coordinated so that local maps overlap each other substantially, allowing for "stitching" of the local maps together to assure continuous mapping coverage of the inner lumen. The local maps "stitched" together could be image arrays, 2D models, or 3D models.

As mentioned, the apparatus may include one or more cameras, including cameras oriented to face distally, at a skew axial to straight ahead, and/or one or more cameras oriented to face laterally and/or proximally.

In general, axially and/or rotationally manipulating the second member may include steering the second member in any manner while maintaining the first member rigid, to act as a stable base. The steering may be performed to scan the lumen and may be guided by the controller, which may continuously or semi-continuously combine the scanned images into the coverage map. The coverage map may therefore be formed by combining one or more images, including overlapping images, and may include multiple/alternative views of the same region. Axially and/or rotationally manipulating the second member may include using one or more cameras on a distal end region of the second member of the nested, rigidizing apparatus to scan the subregion. For example, axially and/or rotationally manipulating the second member may comprise retracting and/or extending a distal end region of the second member within a first distance relative to a distal end of the first member. In some cases axially and/or rotationally manipulating the second member comprises retracting and/or extending a distal end region of the second member within a first distance relative to a distal end of the first member of between about 1 mm and about 300 mm (e.g., 1 mm and 250 mm, 1 mm and 200 mm, 1 mm and 175 mm, 1 mm and 150 mm, 1 mm, and 125 mm, 1 mm and 100 mm, etc.).

In any of these methods and apparatuses, axially and/or rotationally manipulating the second member comprises dithering the distal end region of the second member by scanning as a distal end region of the second member is repeatedly extended and retracted along a first distance to scan the subregion. Dithering may be particularly helpful for providing multiple, potentially overlapping scans of the lumen wall(s), and these multiple images may be used to form the coverage mapping. In some cases a consensus image or images may be generated from the multiple images.

Any appropriate imaging speed may be used, such as imaging at relatively high frequency (e.g., x frames per second, such as between 5 frames per second and 200 frames per second, e.g., 10 frames per second or faster, 15 frames per second or faster, 20 frames per second or faster, 25 frames per second or faster, 30 frames per second or faster, etc.). The apparatus may illuminate the lumen with one or more wavelengths (e.g., white light, infrared/near-infrared, narrow bandwidth, etc.). A higher speed of image capture provides more images with more overlap, to better create a fully contiguous image set.

In any of these apparatuses and methods, rigidizing the first member within the body lumen may comprise rigidizing the first member within the colon. Imaging walls of the body lumen may comprise imaging using one or more distal-facing camera and one or more side and/or rear facing cameras.

In general, the second member may be scanned while the first member is rigid. The first member may be rigidized. For example, axially and/or rotationally manipulating the second member may comprise maintaining the first member in a rigid configuration. Alternatively, where there is a camera on the first member, the second member may be rigid.

Any of these apparatuses and methods may include receiving one or more user inputs for controlling the apparatus, including receiving a user input (e.g., command) to map all or a region of the body lumen.

The methods and apparatuses may be configured to axially and/or rotationally manipulate the second member by rotating the second member relative to the first member. In some cases these methods and apparatuses may be configured to axially and/or rotationally manipulate the second member by articulating a distal end region of the second member.

As mentioned, in general, these methods may include combining the images by stitching the images into the coverage map. The apparatus and method may identify 'new' (e.g. unmapped region) or new and/or alternatively views of regions already mapped. In some cases the images may be averaged, smoothed, filtered, combined, enhanced, etc. prior to stitching into the coverage map. In some cases all or some of the images may be stored, e.g., as part of a data structure with or instead of the coverage map.

The method or apparatus may be configured to fully or partially map the body lumen or a region of the body lumen; in general, these methods and apparatuses (e.g., controller) may be configured to determine or estimate the extent of coverage. In some cases axially and/or rotationally manipulating the second member may comprises continuing scanning until the subregion of the body lumen has been mapped to a preset or user-defined mapping completion threshold (e.g., 80% coverage or more, 85% or more, 90% or more, 95% or more, 98% or more, 99% or more, etc.).

As described herein, repositioning may comprise advancing or withdrawing between about 1 mm and about 300 mm (e.g., between about 1 mm and 250 mm, 1 mm and 200 mm, 1 mm and 175 mm, 1 mm and 150 mm, 1 mm and 125 mm, 1 mm and 100 mm, etc.) to an adjacent subregion. In any of these methods and apparatuses the lumen may be divided up into subregions that extend a predetermined or adjustable length (e.g. between 1 mm and 150 mm, between 2 mm and 130 mm, between 1 mm and 100 mm, etc.). Thus, the apparatus or method may be configured to methodically scan each sub-region to a predetermined threshold of completion (e.g., x % complete, such as 80%, 85%, 90%, 95%, etc.) before moving on. Completion may be determined using one or more algorithms to identify structures (folds, protrusions, etc.) and confirm regions around/behind these structures have been fully scanned. The controller may further determine that the scanning is adequate, e.g., based on the imaging angle with the lumen wall (e.g., the imaging angle must be greater than a threshold (e.g., 30 degrees, 35 degrees, 40 degrees, 45 degrees, 50 degrees, 55 degrees, 60 degrees, 65 degrees, 70 degrees, 75 degrees, etc.).

These steps (e.g., rigidizing the first member and scanning with the second member) may be repeated until the target mapping (full mapping) has been achieved, such as repeating until a mapping of the body lumen has been mapped to a completion threshold is reached or exceeded (e.g., at least 80%, 85%, 90%, 95%, 99%, etc.).

Any of these method may include monitoring, while scanning, to detect one or more regions of interest and alerting a user if one or more regions of interest is detected. As mentioned, the apparatus or method may use an algorithm, such as but not limited to a machine learning agent, to identify one or more regions of interest from the collected images. For example, any of these methods may include stopping or pausing the method if one or more regions of interest is detected, and/or presenting the user with the option of immediately or later returning to the region of interest to further examine and/or scan it. The methods and apparatuses may annotate the map and/or keep a separate list referencing these regions.

Any of these methods may also include manipulating the walls of the lumen while scanning by one or more of: applying additional insufflation and/or contacting the walls with a probe. For example, these methods and apparatuses may be configured to identify when the wall(s) of the lumen are collapsed or insufficiently expanded and may automatically or semi-automatically, the system to expand the region, e.g., by further insufflation, rinsing, and/or mechanical manipulation (including but not limited to balloon inflation). Because features such as vasculature near the surface of the lumen walls may change depending on the amount of insufflation in the lumen, the system may use pressure sensors to measure lumen pressure. When returning to a location previously imaged, the system may display for the operator the current pressure and the pressure measured during creation of the map, to allow the operator to adjust insufflation pressure to match or may automatically adjust insufflation pressure to be at the level it was when the map was obtained.

As mentioned, any of these methods may include repositioning the nested, rigidizing apparatus within the lumen by shape copying. For example, shape copying may be performed by coordinating the first and second (e.g., outer and inner) rigidizing members so that they alternately rigidize and de-rigidize so that the rigid member may be held stationary as the de-rigidized (e.g., flexible) member is advance and steered, or retracted, then re-rigidized so that the opposite member can be advanced and/or retracted over the now rigid member. Thus, shape copying may comprise positioning and then rigidizing the second member, de-rigidizing the first member, and advancing or withdrawing the first member relative to the second member within the body lumen while the second member remains rigid.

For example, a method of mapping a body lumen may include: rigidizing a first member of a nested, rigidizing apparatus within the body lumen; dithering a distal end region of a second member of the nested, rigidizing apparatus so that it extends and retracts a first distance range from a distal end of the first member; imaging the walls of the body lumen using one or more cameras on the distal end region of the second member while dithering; adding the images of the walls of the body lumen into a coverage map of the body lumen; rigidizing the second member and de-rigidizing the first member, and advancing or withdrawing the first member relative to the second member within the body lumen; and repeating the steps of rigidizing, dithering, imaging and adding the images to map the body lumen.

In some cases a method of mapping a long and tortuous body lumen may include: rigidizing a first member of a nested, flexible rigidizing apparatus within the body lumen; axially and/or rotationally manipulating a second member that is nested with the first member to methodically scan a subregion of the body lumen by imaging walls of the body lumen; combining the images of the walls of the body lumen into a coverage map of the body lumen; repositioning the nested, rigidizing apparatus within the lumen; and repeating the steps of rigidizing, manipulating, scanning, combining and repositioning to map body lumen.

In general, described herein are apparatuses (e.g., systems, devices, etc.) configured to perform any of these methods. For example, described herein are nested, rigidizing apparatuses for mapping a body lumen, the apparatus comprising: a first rigidizing member, wherein the first rigidizing member is configured to be converted from a flexible configuration to a rigid configuration; a second rigidizing member, wherein the second rigidizing member is configured to be converted from a flexible configuration to a rigidizing configuration and is nested within the first rigidizing member; one or more cameras on a distal end region of the second member; and one or more processors running software configured to control the first rigidizing device and the second rigidizing device to perform a method comprising: rigidizing the first member within a body lumen; scanning a subregion of the body lumen by imaging walls of the body lumen using the one or more cameras on the distal end region of the second member as the second member is retracted and/or extended within a first distance relative to a distal end of the first member; combining the images of the walls of the body lumen into a coverage map of the body lumen; repositioning the nested, rigidizing apparatus within the lumen by rigidizing the second member and de-rigidizing the first member, and advancing or withdrawing the first member relative to the second member within the body lumen while the second member remains rigid; and repeating the steps of rigidizing, scanning, combining and repositioning to map body lumen.

A nested, rigidizing apparatus for mapping a body lumen may comprise: a first elongate member; a second elongate member, wherein the second elongate member is configured to rigidize; wherein the first elongate member is configured to advance relative to the second elongate member and to capture images; and a controller configured to stitch together the captured images to create a coverage map of the body lumen.

The first elongate member may be configured to advance relative to the second elongate member without colon looping. In any of these examples, the first elongate member may be covered by a removable shield having a camera window through which the captured images are captured. The first elongate member may be configured to advance relative to the second elongate member by sliding within a lumen of the second elongate member. The controller may be configured to store the coverage map in a patient's medical record so that it may be compared to a second coverage map taken at a different time.

Any of these apparatuses may include one or more cameras on the second elongate member configured to capture additional images, wherein the controller is configured to stitch together the captured images and the captured additional images to create the coverage map of the body lumen. The second elongate member may be configured to rigidize in a coordinated manner to create a stable foundation enabling the first elongate member to be advanced and/or withdrawn and/or rotated without substantially moving the stable foundation within the body lumen.

In general, a controller may include circuitry, memory and one or more processors configured (including by storing one or more sets of instructions) to coordinate the actions described herein. For example, a controller may be configured to control rigidization of the second elongate member and movement of the first elongate member to methodically capture images of the body lumen that are stitched together to create the coverage map.

Any of these apparatuses may include one or more cameras on the first and/or second elongate members that are configured to capture multi-band images for the captured images. Any of these apparatuses may include one or more cameras configured to receive infrared (e.g., near-IR) images. Any of these apparatuses may include one or more cameras and may be configured to include white light.

As mentioned above, any of these apparatuses may include an expandable spreader configured to expand the lumina wall to assist in capturing images, wherein the expandable spreader is on either the first or second elongate member. For example, the expandable spreader may comprise a transparent balloon. In general, the controller may be configured to control deployment of the expandable spreader based on the captured images, to enhance expansion and visibility of the body lumen. In any of these apparatuses the controller may be configured to control the application of insufflation into the body lumen based on the captured images, to enhance expansion and visibility of the body lumen. In some cases the controller may be configured to control the application of fluid (e.g., saline) and aspiration of fluid (e.g., wash) to assist in cleaning the camera lens and/or in rinsing the colon to improve imaging and therefore mapping.

In general, the first elongate member may be configured to rotate relative to the second elongate member without whip or axial displacement of the first elongate member. For example the first elongate member may be configured to rotate within the second member in a flexible configuration and may be smoothly bendable, including at the distal tip region.

In any of these apparatuses and methods, the controller may be configured to stitch together the captured images to create the coverage map of the body lumen comprising a bowel preparation adequacy rate.

The first and second elongate members may be configured to sequentially rigidize to create repeatable axial and rotation motions, wherein the controller is further configured to control the repeatable axial and rotation motions to automate interrogation of the body lumen.

As mentioned, also described herein are methods and apparatuses for automatically driving the apparatus to view a region of interest, e.g., a lesion, polyp, etc. The region of interested may be manually or automatically identified. In some cases the user may identify, from the map (e.g., the coverage map) a region of interest and may enter this region into the apparatus so that the apparatus may automatically drive the apparatus to that region during or after the mapping region. Thus, the apparatus or method may include automatically controlling the nested rigidizing apparatus to alternate between rigidizing and de-rigidizing a first rigidizing device and a second rigidizing device to advance and/or to retract by shape copying so that a distal end of the first rigidizing device is adjacent to the one or more features of interest. In some cases the apparatus or method may at least partially encircle the region of interest so that is image from multiple directions (e.g., angles).

In some cases a region of interest may be identified by the system. For example, a method of automatically or semi-automatically viewing or imaging a region of interest may include: advancing a nested, rigidizing apparatus in a body lumen while displaying to a user a forward-facing video image, further wherein the apparatus automatically monitors one or more (e.g., a plurality of) side-facing or distal and side-facing video image to identify one or more features of interest; presenting an alert if one or more features are identified; receiving a user command to automatically direct the apparatus to the identified one or more identified features; and automatically controlling the nested rigidizing apparatus to alternate between rigidizing and de-rigidizing a first rigidizing device and a second rigidizing device to advance and/or to retract by shape copying so that a distal end of the first rigidizing device is adjacent to the one or more features of interest.

Any of these methods may include manually inserting the apparatus into the body lumen. The one or more features of interest may include a polyp, lesion, etc. In any of these methods, presenting the alert may comprise displaying a notification that one or more features of interested have been identified and requesting the user command to automatically direct the apparatus to the identified one or more identified features.

Any of these methods may include display, on the user interface, analytic information about the one or more features of interest. The analytic information may comprise one or more of: circumference, diameter, and/or height. In some cases the analytic information comprises a diagnostic output (e.g., an indicator of likelihood that the polyp is villous or tubulovillous, etc.). The analytic information may be based on a trained machine learning agent. This anatomical information has a variety of uses: for example, based upon a lesion's size, a next-scheduled colonoscopy time period is modulated.

Any of these methods may include storing the analytic information in a digital patient record. In general, automatically controlling the nested rigidizing apparatus may further comprise steering a distal end region of the first rigidizing device so that the one or more features of interest is displayed in the forward-facing video image. Automatically controlling the nested rigidizing apparatus may further comprise rolling the first rigidizing device to reposition a distal end of the first rigidizing device relative to the one or more features of interest. In some cases automatically controlling comprises controlling the nested rigidizing apparatus so that the distal end of the first rigidizing device at least partially circumnavigates the one or more features of interest.

Any of these methods may include receiving a user command to deploy a tool to the identified one or more features of interest. The methods described herein may include automatically deploying a tool to the identified one or more features of interest. The methods and apparatuses described herein may include presenting a user command input to automatically deploy the tool. For example, the user commend input may include one or more of: contacting the one or more features of interest with the tool, capturing the one or more features with the tool, and/or retrieving the one or more features with the tool.

Any of these methods may include continuing the steps of advance the nested, rigidizing apparatus in the body lumen, presenting the alert, receiving the user command and automatically controlling the nested, rigidizing apparatus, until a landmark is reached. For example, the landmark may be the cecum.

Any of these methods may include alerting the user that the landmark has been reached. Any of these methods may include automatically withdrawing the nested, rigidizing apparatus out of the body lumen. For example, these methods may include controlling the automatic withdrawal so that it is completed in less than a prescribed time, for example, 6 minutes, 7 minutes, 8 minutes, 9 minutes, 10 minutes, 12 minutes, 15 minutes, etc.

Also described herein are methods comprising: advancing a nested, rigidizing apparatus in a colon while displaying to a user substantially distally facing video image, further wherein the apparatus automatically monitors a plurality of side-facing or distal and side-facing video image to identify one or more features of interest; presenting an alert if one or more features are identified; receiving a user command to automatically direct the apparatus to the identified one or more identified features; and automatically controlling the nested rigidizing apparatus to alternate between rigidizing and de-rigidizing a first rigidizing device and a second rigidizing device to advance and/or to retract by shape copying so that a distal end of the first rigidizing device is adjacent to the one or more features of interest and/or steering a distal end region of the first rigidizing device so that the one or more features of interest is displayed in the forward-facing video image.

Also described herein are apparatuses for performing any of these methods. For example, a nested, rigidizing apparatus for mapping a body lumen may include: a first rigidizing member, wherein the first rigidizing member that is configured to be converted from a flexible configuration to a rigid configuration; a second rigidizing member, wherein the second rigidizing member is configured to be converted from a flexible configuration to a rigidizing configuration and is nested within the first rigidizing member; one or more forward-facing cameras and one or more side-facing or distal-facing cameras on a distal end region of the second member; and one or more processors running software configured to control the first rigidizing device and the second rigidizing device to perform a method comprising: advancing the nested, rigidizing apparatus in a body lumen while displaying to a user a forward-facing video image, and while automatically monitoring a plurality of side-facing or distal and side-facing video images to identify one or more features of interest; presenting an alert if one or more features are identified; receiving a user command to automatically direct the nested, rigidizing apparatus to the identified one or more identified features; and automatically controlling the nested, rigidizing apparatus to alternate between rigidizing and de-rigidizing the first rigidizing member and the second rigidizing member to advance and/or to retract by shape copying so that a distal end of the first rigidizing member is adjacent to the one or more features of interest.

In general, the apparatuses described herein may include apparatuses (e.g., systems) for full mapping that uses coupled (e.g., nested) rigidizing members that are specifically adapted to coordinate the movement of the rigidizing members to map and stitch together images to form the mapping. For example, described herein are methods and apparatuses including nested rigidizing robots with software to map and stitch together images. These methods and apparatuses may automatically control the nested rigidizing components to alternate between rigidizing and de-rigidizing and use shape copying so mapping may be performed quickly and more accurately that previously described.

For example, a robotic system for fully mapping a body lumen may include: a first rigidizing device that is configured to be converted from a flexible configuration to a more rigid configuration; a second rigidizing device nested within the first rigidizing device that is configured to be converted from a flexible configuration to a more rigid configuration, wherein a distal end region of the second rigidizing device is steerable; one or more processors running software configured to control the first rigidizing device and the second rigidizing device to rigidize the first rigidizing device while the second rigidizing device is flexible and is steered to image the body lumen to create a stitched image of the body lumen, and to alternate between rigidizing and de-rigidizing the first and second rigidizing devices to advance and/or to retract the first and second rigidizing devices traverse the body lumen to create a coverage map of the body lumen, wherein the software identifies one or more regions of the body lumen that have not been mapped and controls the first and second rigidizing devices to capture images of the identified regions and add them to the stitched image.

The software may include a kinematic algorithm that controls the first and second rigidizing devices to interrogate the anatomy to generate the stitched image to create a full coverage mapping of the body lumen. In some cases the software is configured to detect polyps, as described above. The software may be configured to control movement of the first and second rigidizing devices without the need for manual control. In some cases the software may be configured to assist manual control of the first and second rigidizing devices by flagging regions to be imaged.

The software may be configured to perform preprogrammed series of movements to robotically circumnavigate a selected region or polyp. In some cases the preprogrammed series of movements may include controlling rigidization, steering of endoscope and advancing/withdrawing the endoscope. The robotic system may be configured for mapping any appropriate body region, including, but not limited to, a colon.

As mentioned, in some cases the first rigidizing device comprises a rigidizing overtube. The first rigidizing device may be configured to rigidize by the application of pressure within a layered structure forming a wall of the first rigidizing device. The second rigidizing device may comprise an endoscope. The second rigidizing device may be configured to be converted from the flexible configuration to the more rigid configuration by the application of pressure within a layered structure forming a wall of the second rigidizing device.

Also described herein are methods for mapping a body lumen (e.g., within the GI tract, such as the within the colon). A method may include: advancing and/or retracting a nested apparatus within the body lumen, wherein the nested apparatus includes a first rigidizing device that is configured to be converted from a flexible configuration to a more rigid configuration and a second rigidizing device that is configured to be converted from a flexible configuration to a more rigid configuration, wherein the first second rigidizing device is nested in the second rigidizing device and wherein the nested apparatus is configured to be advance and/or retracted by alternately rigidizing and de-rigidizing the first rigidizing device and the second rigidizing device and advancing or retracting the rigidizing device that is in its flexible configuration; creating a coverage map of the body lumen as the nested apparatus is advanced and/or retracted by continuously stitching together images of the body lumen taken with one or more cameras on a distal end region of the second rigidizing device to form the coverage map; and automatically controlling the first and second rigidizing devices to rigidize the first rigidizing device while steering the distal end region of the second rigidizing device to capture images and updating the coverage map with the captured images.

Any of these methods may include automatically controlling by identifying regions of the body lumen that have not been mapped. The apparatus may track regions that have been mapped (or have been adequately mapped) and regions that have not been adequately mapped and may display this as a graphic/image and/or as data (percent, etc.).

These methods may include inserting the nested apparatus into the body lumen. As described herein, automatically capturing comprise retroflexing the second rigidizing map. Advancing and/or retracting the nested apparatus may comprise alternating between: advancing or retracting the first rigidizing member relative to the second rigidizing member, while the first rigidizing member is in the flexible configuration and the second rigidizing member is held in the more rigid configuration, and holding the first rigidizing member in the more rigid configuration while advancing the second rigidizing member over the first rigidizing member while the second rigidizing member is in the flexible configuration.

As mentioned any of the apparatuses described herein may include multiple cameras, and in particular, may include distal facing, side-facing cameras and/or rear-facing cameras. Thus, described herein are apparatuses for rigidizing devices with front-facing camera and lateral camera around periphery for simultaneous mapping lumen. Similar approaches may be extended for use with rear-facing cameras. Cameras may also face at an angle partially to the side and partially forward, or at an angle partially to the side and partially backward.

For example, a device (e.g., rigidizing endoscope and/or overtube) may include an elongate body configured to rigidize, the elongate body comprising a rigidizing layer, comprising, a support layer, and a bladder layer, wherein the bladder layer is configured to be driven against the bladder layer by the application of positive and/or negative pressure to rigidize elongate body; a distal tip at a distal end of the elongate body; a distal tip region comprising one or more cameras on or near a distal face of the distal tip; and a plurality of lateral cameras circumferentially arrange around the distal tip configured to image completely around the circumference. The apparatus may be configured to engage with a sheath or cover that may secure a cap over the distal end, including the multiple cameras in a manner to maintain the viewing capabilities of the camera.

In general, the methods and apparatuses described herein may be configured to provide multiple views from these multiple cameras (having different camera orientations) without overwhelming the user, including by displaying a distal-facing primary camera with peripheral images that are further processed, e.g., to de-emphasize and/or emphasize one or more features. The features may be identified by a trained machine learning agent. Thus, side and/or rear views may be modified (animated, compressed, dimmed, etc.) to prevent distracting the user, while allowing potentially important structures to be suggested so that the user may steer or command the apparatus to take a closer look. The views may be integrated into a distal-facing ('forward') view and one or more side/rear facing views that may be arranged at the periphery of the distal facing view (e.g. in a compressed format). The apparatus may fully monitor these side/distal-facing views and may use them for mapping (e.g., passive mapping, as described above) and/or for identifying one or more features of interest. For example, any of these apparatuses may include a controller configured to detect, from an image collected by the plurality of lateral cameras if at least one of the lateral cameras is obscured, and to automatically apply wash fluid to the at least one of the lateral cameras Also described herein are covers/shields that may be used to protect the elongate member (e.g., endoscope/colonoscope) and may engage with the scope without blocking, impinging or reducing the view from the additional (e.g., side) cameras. This may be particularly challenging as the optical properties of the cameras may be negatively impacted if the cap or cover at the distal end region of the cover/shield is not securely coupled at a constant separation. Thus, the distal cap or cover region of the cover/shield may be held in tension while secured in such a manner as to prevent changing the relative position of the cap to the cameras. These apparatuses may also include one or more regions for washing the side-viewing and/or rear-viewing cameras to keep them clear/clean. For example, any of these apparatuses may include one or more wash channels configured to apply wash fluid to the plurality of cameras. These apparatuses may also include illumination for illuminating the side/rear viewing regions for the cameras (including in white light and/or non-visible light such as infrared, and/or narrow bandwidth, etc.).

In general, any of these methods may include a user interface for displaying imaging and/or the map(s) and/or the progress of the mapping. In particular, any of these methods and apparatuses may be configured to display, in real time, the progress of mapping all or a region of the body lumen (e.g., colon). This may be shown graphically, using a black and white or preferably color image (e.g., outline, wireframe, etc.) showing the progress through the body lumen and indicating regions that have been mapped; in some cases regions that have not been mapped may be indicated (shown as different colors, shades, textures, etc.) and/or regions that have not fully been mapped.

For example, described herein are methods and apparatuses for real-time display of Extent of Mapping. These methods and apparatuses may indicate in real time what percentage of mapping completeness has been achieved. This may be shown as the apparatus is performing the mapping (and/or as a user is navigating the lumen), e.g., in real time or near-real time.

For example, a method of mapping a body lumen may include: advancing and/or retracting a nested, rigidizing apparatus through the body lumen by alternately rigidizing and de-rigidizing a first rigidizing member and a second rigidizing member to so that the first rigidizing member moves over the second rigidizing member when the first rigidizing member is in a flexible configuration and the second rigidizing member is in a rigid configuration and the second rigidizing member moves within the first rigidizing member when the second rigidizing member is in the flexible configuration and the first rigidizing member is in the rigid configuration; scanning using one or more cameras on a distal end region of the second rigidizing member to capture images of the walls of the body lumen when the second rigidizing member is in the flexile configuration; adding the images into a coverage map of the body lumen; and displaying, in real time or near-real time, an extent map comprising a model of the body lumen indicating regions that have been scanned.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 9B shows an end view of the distal end region of the catheter of FIG. 9A.

FIG. 14A is a depiction of a region of a lumen to be mapped. FIG. 14B illustrates the use of images from multiple perspectives and possibly multiple imaging devices to create a lumen map over time. FIG. 14C illustrates the use of one imaging device being moved in a somewhat spiral pattern to capture images during axial movement in one direction as the lumen wall is interrogated. FIG. 14D illustrates identifying an unimaged area in an existing lumen map and defining a pattern of endoscope movement to capture images that can be registered to the existing lumen map using common recognized features of the lumen and the existing lumen map.

As shown in FIG. 15B the tubular elongate body lumen mapping may be "unwrapped" or "unzipped" to form a 2D mapping representation as shown in FIG. 15C.

FIGS. 28A and B show distal end and slide views, respectively.

FIG. 28C show an "unrolled" view.

FIG. 29A shows an image into a body lumen (in this example, a colon). FIGS. 29B and 29C show distal end and slide views, respectively.

FIG. 30A shows an image into a body lumen (in this example, a colon). FIGS. 30B and 30C show distal end and slide views, respectively.

DETAILED DESCRIPTION

Figure 1A:
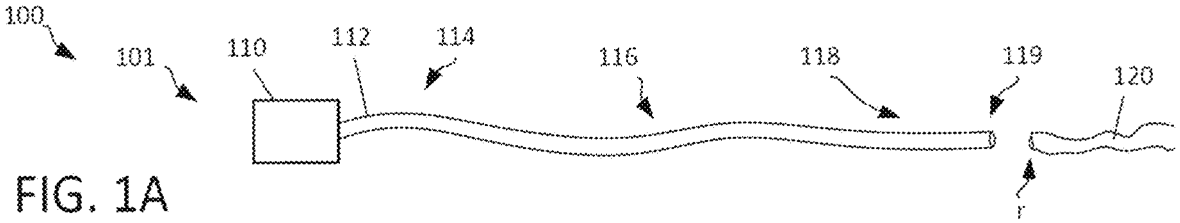
FIGS. 1A-1C schematically illustrate examples of endoscopes (e.g., a rigidizing endoscope) for use in a lumen of the body.

Devices are inserted into the body to diagnose and treat disease. Catheters and flexible endoscopes are particularly useful for endoluminal or endovascular anatomy. Exploring this anatomy becomes increasingly difficult as the lumen length increases, when the anatomy provides minimal support, as curvature or tortuosity increases, and as anatomy exhibits creases and folds. Imaging these lumens is difficult, such that regions are often missed, disease is not properly diagnosed, procedure time is increased, and procedural efficacy can be notably compromised.

The modern flexible gastroscope was introduced in 1950. Since then, there have been significant improvements in lighting and imaging. However, seventy-five years later, the kinematics of flexible endoscopy remain remarkably similar. Despite the advancement of robotics in many medical fields, and despite the advantages shown by Dynamically Rigidizing™ systems, full length flexible endoscopy remains the domain of manual approaches. Flexible endoscopy has a long learning curve, typically hundreds of cases. Flexible endoscopy causes Endoscopy Related Injuries (ERIs). Flexible endoscopy remains cumbersome for non-specialists attempting to do cross-over cases, including surgeons. Pushing a six-foot-long flexible scope through a thin-walled and poorly supported organ can be an exercise in futility, defining long cases, the need for staff support, poor control, compromised therapeutic results, and compromised patient outcomes. Looping, as the patient's colon is stretched to its limit and then as the mesentery is stretched to its limit before the colonoscope advances, causes significant pain, which creates complications that necessitates a range of countermeasures, including the need for anesthesia.

Procedural efficacy is critical, as the highest volume flexible endoscopic procedure, colonoscopy, is the gold standard for colon cancer prevention. Colorectal cancer is the second most common cause of cancer deaths when numbers for men and women are combined.

Software methodology, such as Simultaneous Localization and Mapping ("SLAM") has been created to 'unfold' or 'unfurl' the image of the colon as it is traversed. This software further assists in identifying unseen or missed areas. In general, SLAM may include feature extraction & visual odometry, local mapping and optimization and loop closure and global optimization. Different techniques may be used to perform these methods with the images and rigidizing apparatus described herein. For example, feature extraction may include identifying visual features (e.g., edges, corners, gradients, etc.), and one or more techniques may be used to do this, such as but not limited to FAST (Features from Accelerated Segment Test), Harris corner detector, etc. Feature detection may include blob detectors (e.g., Scale-Invariant Feature Transform (SIFT), Speeded-Up Robust Features (SURF), etc.), edge detectors (e.g., Canny edge detector, etc.); feature descriptors (e.g., Oriented FAST and Rotated BRIEF (ORB), Binary Robust Independent Elementary Features (BRIEF), Binary Robust Invariant Scalable Keypoints (BRISK), etc.). In some cases a deep learning agent may be used (e.g., convolutional neural networks (CNNs)) for feature detection and description.

Local Mapping may include the use of sparse maps or dense maps and may use 3D reconstruction techniques like Multi-View Stereo & Structure From Motion. Kalman Filters or Particle Filters may be used to predict and update the position of each feature in 3D and/or to predict and update the position of the camera in this 3D environment.

Maneuvering a colonoscope around complex anatomy, including haustral folds, is particularly difficult. It is generally recommended that withdraw time (withdrawing the scope from cecum to anus) should not be less than six minutes in most manual colonoscopies. However, there are many issues with this metric: During withdrawal, the scope can fall back or 'slip', such that a large amount of tissue or a significant amount of tissue length passes by quickly, without proper tissue interrogation. When someone withdraws too quickly but still attempts to meet the six-minute standard, they can perform what is cynically known as 'rectal parking', e.g., staying in one place (in this case, the rectum), merely to pass the time until the time standard is reached. The six-minute guideline implies that a longer withdraw time is more thorough. However, longer time does not inherently correlate to full polyp detection or full mucosal surface coverage. Recent guidelines recommend increasing the six minutes to eight minutes, and much of the data used for that decision actually supports an optimal withdrawal time of nine, ten, and even eleven minutes. Recent work has suggested that increasing the withdrawal time in manual endoscopies, e.g., up to 13 minutes, resulted in an increased adenoma detection rate. Keeping track of what portion of the mucosa has and has not been seen is complex and dis-orienting. Proximal fold imaging is notoriously difficult.

Traditional endoscopy, even robotically assisted endoscopy, has not yet been able to fully and effectively provide mapping of the colon or other both lumen, particularly in regions with soft, malleable and sometimes folded tissue. In colonoscopy, literature has shown that, even with highly experienced clinicians, areas that have not been uncovered or seen during colonoscopy (which leads directly to a 'diagnostic miss rate') is typically somewhere between 10% and 35%. This is a highly sub-optimal relative to the protective goal of the procedure. The detection rate is thought to be worse as distance and tortuosity increase (i.e., on the right side), highlighting that fact that a large portion of the performance gap is due to sub-optimal kinematic performance of current systems.

Manual systems, and even proposed robotically assisted systems, do not adequately track location, and are difficult to control. As a scope is inserted, it may not consistently move forward: the scope often buckles within the colon, or stretches the colon until the mesentery is stretched, and only then advances unreliably (often looping). When an endoscope is torqued so as to rotate the camera position, the scope rarely stays in the same location during rotation: it typically whips around and either moves forward or backward, while moving significantly off of its rotational axis. This is very disorienting and may make reviewing of the resulting images difficult and unreliable. As a scope is withdrawn, it withdraws most consistently when it is under tension, but with significant looping that occurred during insertion, a given clinician hand movement withdrawal distance does not inherently correspond to a consistent endoscope withdrawal distance. This effect, wherein the colon length is shortened as the scope is withdrawn, is known as a reduction. After withdrawal, a subsequent advancement is not predictable, as the scope must build up length and anatomical stretch before it advances.

Manually manipulating the endoscope involves significant movement of the endoscope shaft, knobs, and the operator's body. Having an automated process for this activity, both insertion and/or withdrawal, would prevent significant ergonomic issues and could be helpful towards reducing or eliminating Endoscope Related Injuries (ERIs).

The methods and apparatuses described herein may successfully resolve many or all of these kinematic issues, and may include the use of a nested, rigidizing (and/or dual rigidizing) robotic system. These robotic apparatuses may provide predictability, precision, stability and control necessary for methodically and efficiently completing the difficult clinical challenge of a full colon wall interrogation. The ability to provide 'deep stability' (e.g., rigidizing to provide stability deep in the body and in deeply tortuous anatomy) and predictable motion allow for timely and complete full- or nearly full-coverage mapping. Shape determination/shape copying, axial location, relative location, and rotational indexing elements are also advantageous elements. These methods and apparatuses may include other system elements to create full or nearly full coverage mapping and have the potential to dramatically reduced the diagnostic miss rate. These systems could create superior clinical results with a less skilled and less operationally engaged clinician, and they could do so in less time, and with less physical strain on the clinician.

Methods and apparatuses (e.g., systems and devices, including firmware, software and hardware) for mapping an internal lumen are described herein. These methods and apparatuses may include elongate rigidizing apparatuses that may be controlled to transition between a more flexible configuration and a more rigid configuration, including transitioning from a highly flexible configuration to a highly rigid, e.g., stiff, configuration. In some examples the methods and apparatuses described herein may include dual elongate member apparatus, including dual rigidizing apparatuses that may be operated in tandem including, but not limited to, nested, such as nested dual rigidizing apparatuses. These methods and apparatuses may use one rigidizing device to precisely control advancing/retracting with a body lumen to provide a stable platform that may allow mapping of the body lumen, e.g., the walls of the body lumen, while avoiding uncontrolled movements (e.g., lunging, jerking, catching) and movements that may undesirably deform the body lumen.

The methods and apparatuses described herein may be used, including used to map and/or navigate) any appropriate body lumen, including, but not limited to the colon. For example, these methods and apparatuses may be used with any portion of the gastrointestinal tract (mouth, esophagus, stomach, small intestines, large intestines, etc.) or region of the GI tract (e.g., upper GI, lower GI), airways (lungs, bronchi, trachea, etc.), biliary tract, urethra, ureters, circulatory system (e.g., arteries, veins, chambers of the heart, etc.).

In general, these methods and apparatuses may be used with any type of endoscope, including flexible endoscopes (including but not limited to gastroscope, colonoscope, bronchoscope, duodenoscope, enteroscope, nasopharyngoscope, etc.), rigid endoscopes (e.g., laparoscope, arthroscope, cystoscope, hysteroscope, proctoscope, etc.). For example, one of the two elongate members may be an endoscope. In an of these methods and apparatuses including an endoscope, the endoscope may be rigidizing, as described in greater detail below.

"Mapping" may generally refer to generating a representation (2D and/or 3D) of a body region. Mapping may include correlating a variety of different data (including but not limited to anatomic structures, textures, landmarks, etc.) to relative physical locations within the body region. The resulting map may provide a reference framework for analyzing, predicting and/or visualizing the body region and associated data. As described herein a map may refer to a two-dimensional (e.g., "flat") map, or a three-dimensional map (e.g., "model") of the body lumen. Any of these maps may be digital. Any of these maps may be labeled, including dynamic/interactive labels, manual annotations, etc. For example, any of the maps described herein may include automatic or manually added indicators (e.g., markers, labels, etc.) of one or more lesions, e.g., polyps (neoplastic, non-neoplastic), non-polypoid (flat, elevated, depressed, mixed), tumors, growths, inflammation, etc.

"Inspection" as used herein refers to an investigation of a site at a single position of an endoscope or a single position of an overtube.

"Interrogation" as used herein refers to an investigation of an area that includes multiple inspection sites. Interrogation may include mapping of the lumen.

"Endoscopy" or "endoscopic procedure" as used herein refers to any medical procedure which uses an endoscope of any kind. Examples include, without limitation, angioscopy, arthroscopy, bronchoscopy, colonoscopy, cystoscopy, duodenoscopy, enteroscopy, esophagogastroduodenoscopy, gastroscopy, hysteroscopy, laparoscopy, laryngoscopy, mediastinoscopy, sigmoidoscopy, thoracoscopy, and ureteroscopy. "Endoscopic system" as used herein refers to a system used to perform an endoscopic procedure.

Described herein are flexible endoscopic systems in which rigidization may be used to create the ability for nested members to repeatedly and reliably dither axially and/or to repeatedly and reliably dither rotationally about a centerline without undue displacement. Rigidization may be dynamically applied and removed by user input. "Dynamic Rigidization™" is the proprietary term coined by Neptune Medical Inc. to describe this user-controlled capability. Rigidization of the endoscope could be factory-installed or provided in a manner such that rigidization can be field installable by a user (e.g., by way of an installable rigidizing shield). Rigidization can be single device rigidization or dual device rigidization ("DDR"), for example a rigidizing outer member (e.g., overtube) and a rigidizing inner member (e.g., rigidizing endoscope, including endoscope with a rigidizing shield). Rigidization can occur along the entire length of a rigidizing device (e.g., overtube, endoscope, and/or shield) or along a portion or portions of the length of the rigidizing device. An example of rigidization along a portion of the length is rigidization along the length of an endoscope except for an articulating region. Rigidization values can be selectable at manufacture and/or selectable at use. For example, the amount of rigidization may be selectable at x, 2x, 5x, 10x, 15x, 50x, 100x, or other multiple of "x" where 'x' refers to rigidity of the rigidizing device at rest without rigidization being applied (e.g., in the more flexible configuration). In a DDR system, each rigidizing device may have different values of rigidity at rest as compared to the other rigidizing device, and each may have different capability for selectable and/or maximum rigidization values as compared to the other rigidizing device.

Rigidization can be achieved by many techniques, including using positive and/or negative pressure (e.g., positive pressure, negative pressure, or positive pressure and negative pressure together). Rigidization can be achieved with vacuum. Rigidization can be achieved by using fluid under pressure within the structure of the rigidizing device. Multiple fluids may be used in sequence or in conjunction. A fluid may be a liquid and/or a gas and/or other fluidic material. In an example, pressurized fluid may drive or pull a bladder layer against a structural layer (e.g., a rigidizing layer, such as layer of filament(s) or wire(s)) to limit or minimize movement of the structural layer. Rigidization can be achieved using other techniques, including by jamming particles, by phase change and/or shape memory alloys, by interlocking components (e.g., cables with discs or cones, etc.), electro-active polymers (EAP), or any other rigidizing mechanism.

Endoscopic devices may be manually or automatedly actuated. Endoscopic devices may be moved due to actuator-based motion. Actuators combined with device rigidization may be used to advance, withdraw, or rotate a device methodically to allow for an imaging device or multiple imaging devices to inspect or interrogate a surface. Such inspection or interrogation can be used, for example, to identify irregularities of the surface, to create an aggregated image from multiple images, or to create a map of the surface. Examples of methods for inspecting and interrogating a surface are provided below.

A "lumen" as used herein may be any channel or cavity. A "wall" of a lumen may be referred to as a lumen wall or a luminal wall.

A "body lumen" or "lumen of the body" as used herein refers to a blood vessel lumen, a lumen of the gastrointestinal (GI) tract (e.g., upper and/or lower GI), a lumen of the urology or gynecology tract, a lumen within a body cavity, or any other channel and/or cavity (for example, within the abdomen) formed by body structure.

"Proximal" and "distal" as used herein are used to indicate a relative position with respect to a user or controller, where proximal refers to nearer the user or controller and distal refers to farther from the user or controller.

Rigidization

Any of the methods and apparatuses described herein may be used with a rigidizing (e.g., dynamically rigidizing) apparatus or may be part of a rigidizing apparatus and/or method. FIGS. 1A-1G illustrate, by way of introduction, examples of endoscopic systems for use in a lumen such as a lumen of the body. Any of these apparatuses may be rigidizing as described herein. In some embodiments, a portion of the endoscopic system (e.g., endoscope and/or overtube) is advanced over a guidewire (not shown) that was previously positioned within the lumen. FIGS. 1A-1G each schematically illustrate examples of endoscopic systems including an endoscope 101. In each example the endoscope 101 includes a handle 110 and a tubular flexible shaft 112 fixedly or removably attached to the handle 110. The shaft 112 includes a proximal portion 114 adjacent to the handle 110, a mid-portion 116, a distal portion 118, and a distal end 119 of the distal portion 118.

Endoscopes (e.g., the endoscope 101) come in a variety of lengths, including the longest, an enteroscope that may be over two meters (m) long. Endoscopes come in a variety of diameters, such as an endoscope with diameter of a few mm to an endoscope with diameter of 13 mm. Endoscopes generally are provided with an indication of flexibility/rigidity of the endoscope. A flexible endoscope may have a consistent flexibility along its length, or an endoscope may be more flexible along one portion of its length and less flexible along another portion or portions of its length. In some cases, an endoscope may be hyper-flexible in a distal region. An endoscope may have an articulation region such as along a length of a distal end of the endoscope. The length, diameter, and flexibility of the endoscope may be selected for suitability to the intended procedure. FIGS. 1A-1G illustrate example of endoscopes and/or nested apparatuses including endoscopes that may be used or adapted for use, with any of the apparatuses described herein.

In FIG. 1A, the endoscope 101 is positioned to be advanced into a lumen 120 at an entry point 'r' to the lumen 120. The entry point 'r' may be, for example in a body lumen, a body sphincter (e.g., anus), a port positioned for access into the lumen 120, a natural body orifice (e.g., mouth), an incision, etc.

Figure 1B:
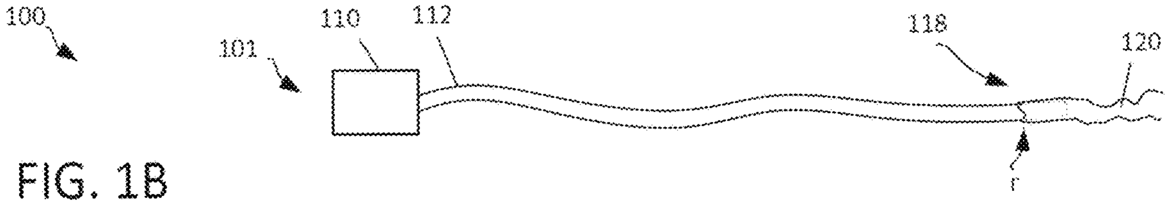
Figure 1C:
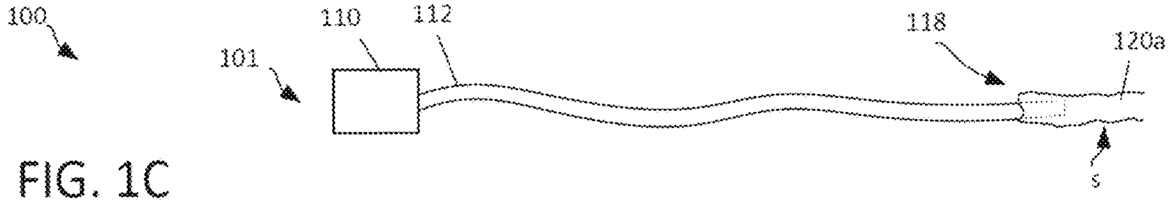

In FIG. 1B, the endoscope 101 is illustrated as being advanced somewhat into the lumen 120. The lumen 120 in the illustration of FIGS. 1A-1B is shown as being extensible such that it may have an inner diameter when relaxed, constricted, or peristaltic that is about equal to or less than an outer diameter of the endoscope 120 and may expand sufficiently for the endoscope 101 to be advanced into and within the lumen 120. In other embodiments, a lumen may have an inner diameter greater than, or substantially greater than, an outer diameter of the endoscope 120. In FIG. 1C, a lumen 120*a* is illustrated as having a larger inner diameter than the outer diameter of the endoscope 101 so that the endoscope 101 may be advanced without extending the lumen 120*a*. The lumen (e.g., 120, 120*a*) may be insufflated to increase the inner diameter of the lumen 120*a* around or ahead of the endoscope 101, such as, for example, by insufflating the section 's' of the lumen 120*a*.

It can be the case that it is difficult to advance an endoscope into a lumen or retract an endoscope from a lumen because the endoscope must be pushed or pulled through the lumen from a proximal end of a flexible endoscope (e.g., at or near the handle 110) and it may have a tendency to loop, buckle, kink, crumple, accordion, or fold. For example, it can be the case that the endoscope 101 can be difficult to push or pull through a lumen (e.g., 120, 120*a*, or other lumen) due to the strictures of the lumen, the flexibility of the endoscope 101, the anatomy, the resultant curvature of the endoscope, the length of the endoscope 101, and/or other aspects of the lumen and/or the endoscope 101.

It can be the case that an endoscope is difficult to roll by rotating the endoscope from a proximal end (e.g., at or near the handle 110, or on the shaft 112), and the torsional forces that propagate along the length of the endoscope in the confines of the lumen may act unpredictably so that movement of the endoscope in the lumen may at times be jerky. For example, it can be the case that it can be difficult to control a rolling motion of the endoscope 101 within a lumen (e.g., 120, 120*a*, or other lumen) due to the strictures of the lumen, the flexibility of the endoscope 101, the anatomy, the resultant curvature of the endoscope, the length of the endoscope 101, and/or other aspects of the lumen and/or the endoscope 101.

For these reasons and more, for a given user proximal input, responsive movement along the endoscope can be highly variable, inconsistent, and/or unpredictable.

A rigidizing, and in particular a nested and rigidizing endoscopic system as described herein may be configured to reduce or mitigate difficulties in pushing, pulling, or rolling an endoscope and thereby improve endoscopic procedures. The nested system may include an overtube and an endoscope. The overtube may be advanced over the endoscope or the endoscope may be advanced through the overtube. The overtube may provide a structure around the endoscope that allows the endoscope to be pushed, pulled, or rolled more easily and in a more controllable fashion.

Figure 1D:
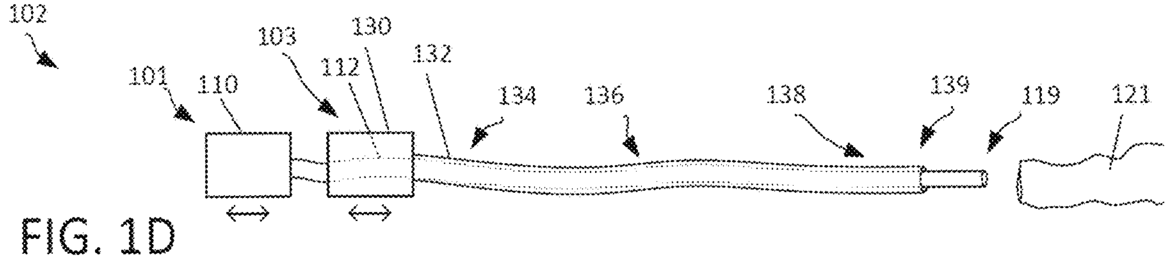
FIGS. 1D and 1E schematically illustrate examples of nested apparatuses including an endoscope with an overtube for use in a lumen of the body.

FIG. 1D illustrates an example of an endoscopic system 102 including the endoscope 101 and an overtube 103. The overtube 103 includes a handle 130 and a tubular flexible shaft 132 fixedly or removably attached to the handle 130. The shaft 132 includes a proximal portion 134, a mid-portion 136, a distal portion 138, and a distal end 139 of the distal portion 138. The endoscope 101 is movably positioned within the overtube 103 such that the endoscope may be fully retracted within the overtube 103 by the handle 110 of the endoscope 101 being moved away from the handle 130 of the overtube 103 (e.g., the handle 110 moved left in the illustration of FIG. 1D) or by the handle 130 of the overtube 103 being moved away from the handle 110 of the endoscope 101 (e.g., the handle 130 moved right in the illustration of FIG. 1D.) In an embodiment, the endoscope 101 passes through the handle 130. The shaft 112 of the endoscope 101 is longer than the shaft 132 of the overtube 103 so that when the shaft 112 is inserted through the shaft 132 of the overtube 103 (and the handle 130), the distal end 119 of the endoscope 101 can be extended beyond the distal end 139 of the overtube 130.

Figure 1E:
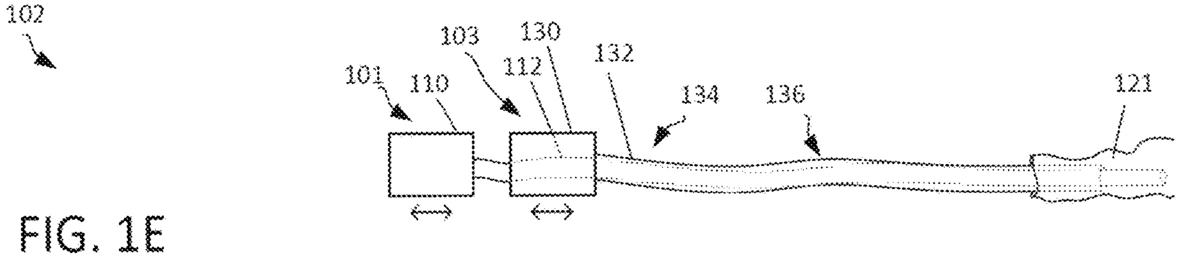

In the endoscopic system 102 of FIG. 1D, either the endoscope 101 or the overtube 103 may be advanced into and within a lumen 121, or both the endoscope 101 and the overtube 103 may be advanced together into and within the lumen 121. FIG. 1E illustrates an example in which both the endoscope 101 and the overtube 103 have been advanced within the lumen 121.

Advantages of a nested endoscopic system may be further enhanced using lubrication, low friction surfaces, lubricious coating, hydrophilic coating, or hydrophobic coating. The two devices can have a coating or surface condition on their adjacent surfaces so that friction between them is engineered to a minimum.

Any of the examples of endoscopes, and/or nested systems including endoscopes shown in FIGS. 1A-1G may be rigidizing. Specifically, the outer member (e.g., overtube) and/or the inner member (e.g., the endoscope) or preferably both, may be rigidizing as described herein. For example, the nested system, including an overtube (e.g., the overtube 103) and/or an endoscope (e.g., the endoscope 101) can be rigidizable, meaning that at least a portion of the overtube and/or endoscope can be changed from a first flexibility state to a second flexibility state and then to the first flexibility state or to another flexibility state. For example, the overtube (or the endoscope) may be changed from a relaxed (e.g., more flexible) state to a rigid (e.g., less flexible) state and then to a relaxed state or to a partially rigid state, or from a relaxed state to a partially rigid state and then to a relaxed state or to another partially rigid state. The outer and inner members may be rigidized by different techniques (e.g., the outer member may be rigidized by negative pressure and the inner member may be rigidized by positive pressure, or vice versa), and/or to different extents. For example, the inner member may be rigidized to a greater extent than the outer member, or vice versa. In some examples in which the nested system includes both a rigidizable overtube (e.g., the overtube 103) and a rigidizable endoscope (e.g., the endoscope 101) the nested overtube/endoscope system may be referred to as a DDR system. As mentioned, any of these DDR systems may be configured so that the overtube and the endoscope are configured to be separately controlled to change between flexibility states. In an example, consider a rigidizing endoscope nested within a rigidizing overtube; the endoscope in a flexible state can be advanced within a lumen to a desired location, the endoscope then rigidized, the overtube in a flexible state can be advanced over a portion of the rigidized endoscope and then the overtube can be rigidized, and the endoscope can be relaxed and then extended partially out of the rigidized overtube for an intended purpose, such as for examination or treatment. This procedure may also be referred to a "shape copying" as coordinating the transition between rigid and flexible states by the DDR may allow relatively complex shapes to be copied as the DDR system advances or withdraws within the body with minimal sliding or force applied against the tissue.

In some examples a rigidizing overtube may be advanced within a lumen to a desired location and then rigidized, and the endoscope can be extended through and partially out of the rigidized overtube for an intended purpose, such as for examination or treatment. A rigidized overtube may provide a stable structure through, against, and/or out of which the endoscope can be manipulated for improved control of the movements of the endoscope and the distal end of the endoscope.

Further, by advancing, retracting, and/or rolling the endoscope within the rigidized overtube, the portion of the endoscope within the overtube is not directly engaging the lumen of the body and friction between the endoscope and the lumen is significantly reduced as compared to traditional commercial manual endoscopes. This reduced interaction with the lumen reduces a possibility of damage to the lumen by the endoscope engaging against the lumen and may greatly enhance tracking within the lumen. As described in greater detail below, this may significantly enhance imaging when "dithering," e.g., moving the endoscope distally/proximally relative to the overtube and/or rotating (e.g., turning, rolling, etc.) the endoscope within the overtube to image the lumen.

Thus, the overtube and the endoscope may be alternately rigidized and relaxed so that, for example, the endoscope is rigidized, the overtube is advanced over the endoscope and rigidized to shape copy the endoscope, the endoscope is relaxed and extended out of the overtube to a new position and rigidized, shape copying the overtube to the extent that the overtube covers the endoscope, the overtube is relaxed and advanced over the endoscope and rigidized to shape copy the endoscope, and so forth. Such a repeated shape copy technique can serve to reduce trauma to the lumen during advancement, as well as provide a stable structure against which the endoscope can be manipulated (e.g., advanced, withdrawn, or rotated) at a desired location and along the length of the overtube to improve stability of the endoscope and reduce trauma at the location during manipulation. Shape copying may be used for advancement and/or withdrawal of the endoscopic system into/from the lumen. In some examples the endoscope may be configured to be rigidized by the use of a shield positioned over the endoscope; for example, the shield may be rigidizing and the endoscope may not be rigidizing on its own, such that the shape copy of the overtube as described above is performed by the shield rigidizing to shape copy the overtube rather than the endoscope itself rigidizing to shape copy the overtube. In an embodiment, a shield positioned over the endoscope is rigidizing and the endoscope is also rigidizing, such that the shape copy of the overtube as described above can be performed by the shield and/or endoscope rigidizing to shape copy the overtube. The shield may be configured as a single-use or limited-use shield (which may be rigidizing) covering a non-rigidizing and reusable endoscope.

As described herein, it should be understood that a rigidizing endoscope may refer to an endoscope assembly including the non-rigidizing endoscope and a rigidizing shield couple to the endoscope. It should also be understood that the methods and apparatuses described herein may be used with an outer endoscope and an inner rigidizing member (e.g., within a lumen of the endoscope). Thus, although the examples may illustrate a rigidizing overtube nested over a rigidizing endoscope (or endoscope assembly), it may instead and equivalently be performed with a rigidizing endoscope nested over a rigidizing inner member (e.g., rigidizing tube, rod, etc.).

The difficulty in pushing a traditional commercial manual endoscope through a lumen can also create looping of the endoscope in the lumen, and corresponding looping of the lumen, and the looping must then be overcome. Looping can cause discomfort and can increase a potential for complications due to the endoscopic procedure. Looping can be significantly reduced by the use of a rigidizing overtube or a DDR system as described herein.

An endoscopic system (e.g., the endoscopic system 100 or the endoscopic system 102) or portions thereof may be supported by a mechanical device before, during, or after an endoscopic procedure to aid the user in managing the endoscopic system.

Figure 1F:
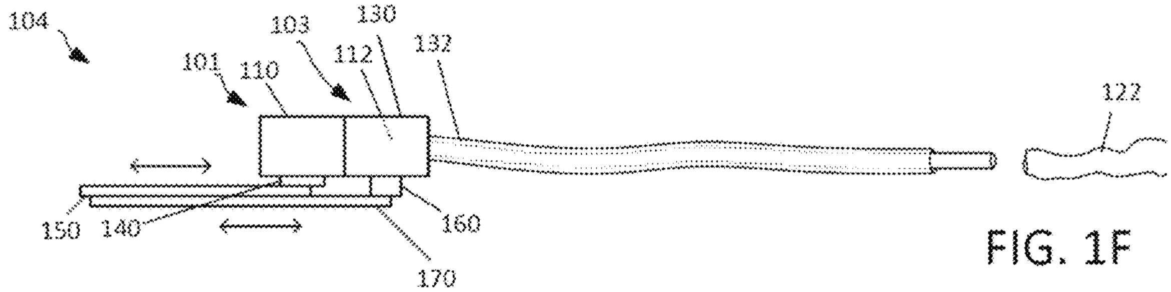
FIGS. 1F and 1G schematically illustrate examples of an endoscope and an overtube mounted on movable arms coupled to a base.

FIG. 1F illustrates an endoscopic system 104 including the endoscope 101 and the overtube 103. The handle 110 of the endoscope 101 is permanently or removably attached to a mount 140 which is in turn permanently or removably attached to a movable arm 150, which may be supported by a mechanical device (not shown) to aid the user. The handle 130 of the overtube 103 is attached to a mount 160 which is in turn permanently or removably attached to a movable arm 170, which may be supported by a mechanical device (not shown) to aid the user. The arms 150, 170 may be manipulated to advance the endoscope 101 and/or the overtube 103 into and within a lumen 122. A mount 140/160 may move its respective device 101/103 in multiple ways, including but not limited to axially or rotationally.

Thus, any of these apparatuses may include a robotic arm or arms that are configured to advance and/or withdraw the assembly of rigidizing members (e.g., the endoscope and/or overtube, DDR, etc.). The apparatus may be telescoping; in some examples, as shown in FIG. 1H below, a plurality of telescoping links may be included that may slide distally and/or proximally to advance and/or withdraw the assembly of rigidizing members. In some cases the telescoping member may be tubular telescoping arms or links. Alternatively or additionally the apparatus may include a more traditional robotic arm having multiple degrees-of-freedom linkages. Thus, any of these apparatuses may include a telescoping set of links, and in particular vertically-arranged links. For example, the apparatuses (device, systems, etc.) described herein may be configured as a portion of a robotic system for delivery of a pair of a nested endoscope device, including an inner endoscope and an outer overtube, that are each capable of relatively high and low levels of compliance. The apparatuses described herein may have a generally linear form factor and may therefore provide a linear kinematic system for delivery of devices. In some examples the primary linear axis that may position the apparatus (e.g., the overtube of the endoscope) into the patient includes a telescoping mechanism formed of a link assembly. The bidirectional telescoping action of this link assembly may allow the relatively long linear axis to be relatively short when its full extension is not needed, which addresses room size limitations in some facilities. In examples including flexible tubular member systems with both inner and outer members, the position of the inner endoscope relative to the outer overtube may be controlled by an independent linear axis. Although these apparatuses may be used with virtually any flexible tubular member, they may be particularly helpful when using a nested, and in particular rigidizing, endoscope, such as a dual rigidizing endoscope.

Figure 1G:
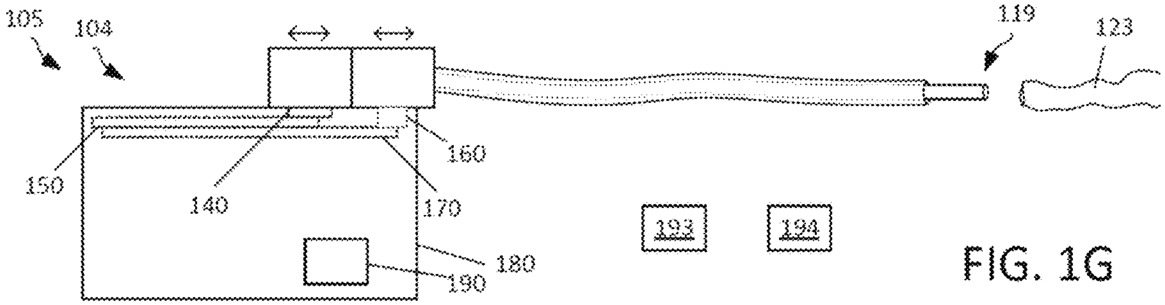
Figure 1H:
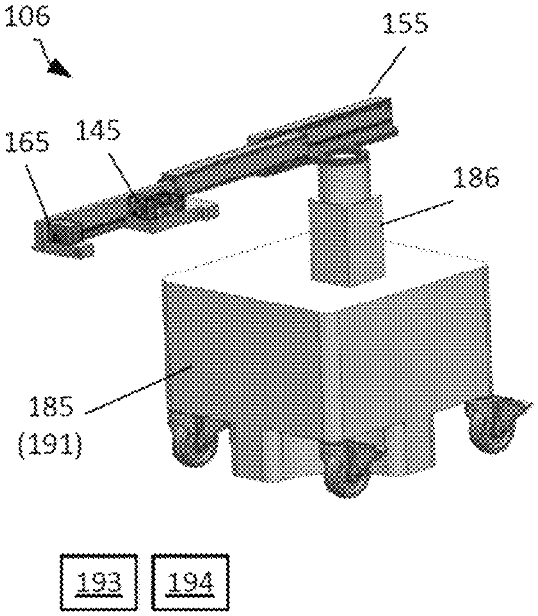
FIG. 1H schematically illustrates an example of a robotic apparatus including a base with movable arms.

FIG. 1G illustrates an embodiment of a robotic system 105 including the endoscopic system 104 and a base 180.

The arms 150, 170 are movably attached to the base 180, such as on rails, scissor-type extensible mechanisms, accordion-style extensible mechanisms, rotary-style mechanisms, or other types of mechanisms so that the arms 150, 170 are movable with respect to each other and with respect to the base 180. The base 180 supports the arms 150, 170 and thereby the handles 110, 130, respectively, to aid the user in manipulating the endoscope 101 and the overtube 103. The base 180 may further include one or more supports (not shown) that can be extended to support the endoscope 101 and the overtube 103 while out of the body and can be collapsed or otherwise moved out of the way as the endoscope 101 and the overtube 103 are advanced into and within the body.

FIG. 1H illustrates a robotic system 106 similar in concept to system 105, where system 106 includes a base 185 supporting a riser 186 which in turn supports mounts 145, 165 on telescoping arm system 155 (e.g., showing a plurality of links that are configured to slide relative to each other).

Figure 1I:
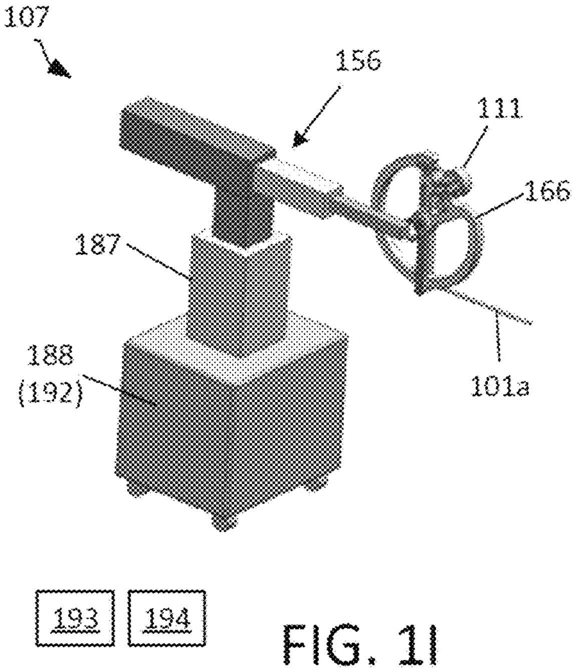
FIG. 1I schematically illustrates an example of a robotic apparatus a base with an endoscope mounted on a rotationally movable arm.

FIG. 1I illustrates an embodiment of an endoscopic system 107 in which a wheel-like rotation mount 166 provides for mounting an endoscope handle 111 of an endoscope **101*a* on an arm 156, which is coupled to a riser 187 coupled to a base 188. The endoscope is advanced through an overtube (not shown). The combination of the nested components (e.g., overtube and endoscope) and the mechanical system may be referred to as a robotic system. In any of these examples, the system (e.g., any of the endoscopic systems 100, 102, 104, 105, 106, or 107**) may be controlled at least in part by a mechanical or electromechanical system.

In an example, an endoscopic system (e.g., any of the endoscopic systems 100, 102, 104, 105, 106, or 107) may be manipulated manually.

FIG. 1G, FIG. 1H, FIG. 1I each further illustrates an optional electronic controller 190, 191, or 192 (or 190/191/192) located in or on the base 180, 185, or 188 (or 180/185/188), respectively. The controller 190/191/192 may control actuators that manipulate the movable portions of the respective endoscopic system and may control rigidization of the endoscope and/or the overtube. The controller 190/191/192 may further control other aspects of the endoscope and/or the overtube, such as the application of suction or insufflation, the delivery of fluid, imaging, shape sensing, or the use of tools passed through, adjacent to, incorporated into, or attached to the endoscope or the overtube. The controller 190/191/192 may be located apart from the base 180/185/188 and in communication with the actuators via a communication interface.

Any of the endoscopic systems described herein (e.g., any of the endoscopic systems 105, 106, or 107 (or 105/106/107)) may include a user interface 193 for displaying information regarding the endoscopic system and/or its environment, such as a displayed video feed representative of the surroundings of the distal end of the endoscope (e.g., a video representative of the view of an interior of a lumen as a distal end 119 of the endoscope 101 is moved within the lumen), sensor information regarding a shape of the shaft of the endoscope and/or the shaft of the overtube, sensor information regarding force applied against the lumen by the endoscope and/or the overtube, and/or other information that may be useful during an endoscopic procedure. The user interface 193 may be implemented across multiple devices, such as multiple displays.

The user interface 193 and/or a separate interface device 194 may also include a capability for a user to send a command to the controller (e.g., 190/191/192) such as to initiate a movement, turn on a light or other illumination source, provide insufflation, rigidize, de-rigidize, bend, straighten, shape copy, move forward, retract, capture an image, initiate or halt and automated process, etc. In an embodiment, the interface device 194 is a handheld device. In an embodiment, the interface device 194 is affixed (e.g., positioned temporarily or permanently on a stand or on a base (e.g., 180/185/188)) when in use. In an embodiment, the interface device 194 is implemented as multiple devices, each of which may be handheld or affixed when in use.

In an embodiment, the user interface 193 and/or the interface device 194 (any, a user access device) includes at least one physical input for activation by a hand or finger such as one or more keys, one or more buttons, one or more levers, one or more rollers, one or more trackballs, one or more switches, one or more touch sensors, one or more touch pads, and/or one or more other physical inputs. In an embodiment, a user access device includes audio inputs to detect voice commands and/or other audio commands. In an embodiment, a user access device includes motion inputs to detect finger, hand, arm, head, eye, foot, leg, and/or other body motions of the user which can be interpreted as commands. In an embodiment, a user access device includes a combination of input types, such as any combination of physical inputs, audio inputs, and/or motion inputs. In an embodiment, some or all commands may be input without user touch or words, thereby supporting inclusive use of the system by those with physical disabilities. In an embodiment, commands may be input by the user directly to the system through a brain wave interface.

The methods and apparatuses described herein may control the operation of a nested pair of rigidizing apparatuses, as shown in FIGS. 1J-1M. FIGS. 1J-1M illustrate one example of a dual rigidization (DDR) apparatus 1100 forming a nested robotic rigidizing system that may rigidize to form a stable platform within the body (e.g., within a natural or artificial body lumen, vessel, etc.) to be mapped. The methods for mapping described herein may be particularly well adapted for use with these systems but are not limited to such systems. Any of the methods and apparatuses described herein may equivalently be used with a rigidizing (or non-rigidizing in some examples) shield covering an endoscope, as discussed above.

Aspects of the present disclosure may be integrated into a robotically-enabled medical system capable of performing a variety of medical procedures, including both minimally invasive procedures, such as laparoscopy, and non-invasive procedures, such as endoscopy. Among endoscopy procedures, the system may be capable of performing colonoscopy, enteroscopy, bronchoscopy, ureteroscopy, gastroscopy, etc. Examples of endoscopes may include, but are not limited to colonoscopes, arthroscopes, bronchoscopes, cystoscopes, hysteroscope, enteroscopes, esophagogastroduodenoscopes, hysteroscopes, neuroendoscopes, sinuscopes, laparoscopes, laryngoscopes, mediastinoscopes, sigmoidoscopes, nasopharyngoscopes, thoracoscopes, ureteroscopes, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions.

Figure 1J:
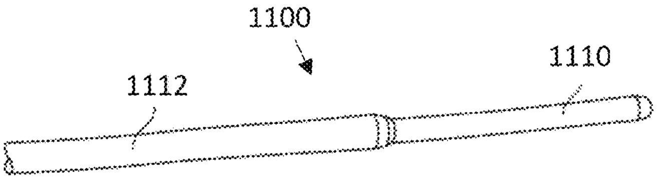
FIGS. 1J-1M illustrate one example of a nested robotic scope device that may be incorporated into any of the apparatuses and methods described herein, including but not limited to mapping. The elongate medical instrument in this example is an endoscope (e.g., in some examples, a colonoscope) having a nested inner member and an outer member that are both selectively rigidizing.
Figure 1K:
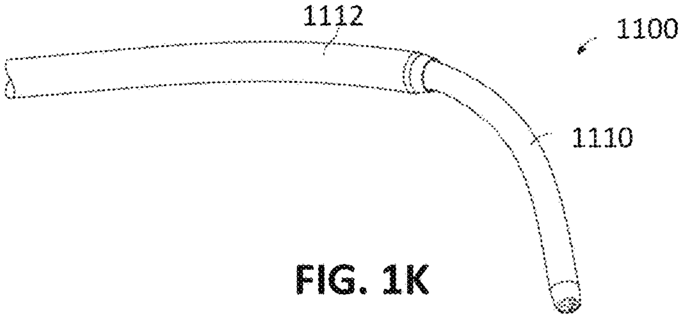
Figure 1L:
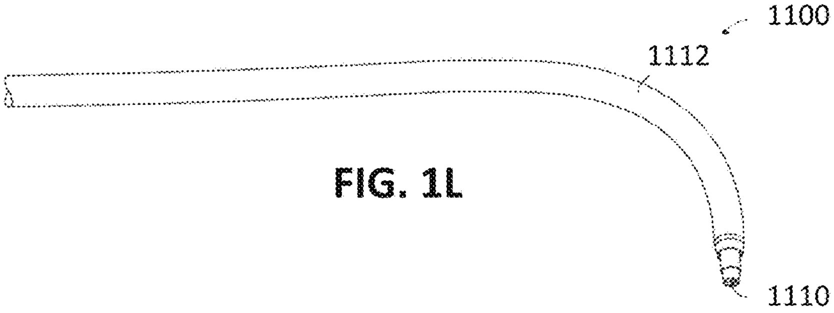
Figure 1M:
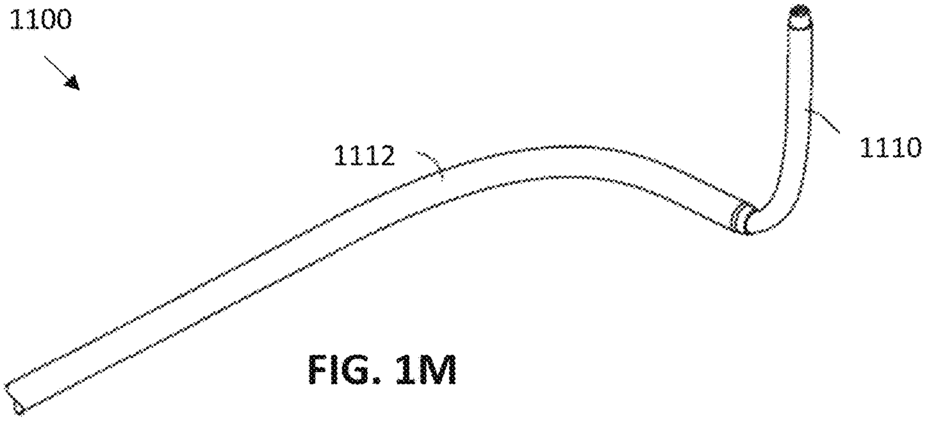

In FIGS. 1J-1M one example of a robotic scope configured as a dual rigidizing endoscope is illustrated. The dual rigidizing endoscope 1100 is configured as a nested system including a rigidizable (e.g., rigidizing) outer member 1112 and a rigidizable inner member 1110. In FIG. 1J, the steerable inner rigidizing member 1110 is positioned within the outer rigidizing member 1112 such that the distal end of the inner rigidizing member 1110 extends outside of the outer rigidizing member. In some cases the inner rigidizing member may be fully withdrawn and removed from the outer member. In some cases it may be subsequently re-inserted through the outer member, or another inner member may be inserted through the outer member. In some cases the inner rigidizing member 1110 may be fully retracted into the outer rigidizing member 1112. FIG. 1K shows the distal end of the inner rigidizing member 1112 is bent slightly in a desired direction/orientation (e.g., via steering cables or other steering mechanism) and then rigidized (e.g., using positive or negative pressure). 1112 may also be bent because it was in the flexible state as it followed the curvature of 1110, and then was subsequently rigidized. In FIG. 1L, the outer rigidizing member 1112 (in the flexible configuration) is advanced over the rigidized inner rigidizing member 1110 (including over the bending distal section). Once the distal end of the outer rigidizing member 1100 is sufficiently advanced over the distal end of the inner rigidizing member 1110, then the outer rigidizing member 1112 can be rigidized (e.g., using positive or negative pressure as described herein). In FIG. 1M, the inner rigidizing member 1110 can then be transitioned to the flexible state (e.g., by removing the positive or negative pressure in some examples, and by allowing the steering cables to go slack such that tip can move easily) and can be advanced and directed/oriented/steered as desired. Alternately, in FIG. 1M, the inner rigidizing member 1110 can be actively steered (either manually or via computational control) as it emerges such that is minimizes the load on the rigidized outer tube. Minimizing the load on the outer rigidizing member may make it easier for this tube to hold the rigidized shape. Once the inner rigidizing member 1110 is rigidized, the outer rigidizing member 1112 can be transitioned to the flexible state and advanced thereover. The process can then be repeated to navigate through even more tortious anatomies. However, it may be particularly difficult to coordinate the movement of the inner and outer members, including advancing/retracting and selectively rigidizing either the inner or outer or both, making a robotically controlled system particularly advantageous. The repeated process can result in shape copying, whereby the inner and outer rigidizing members, while in a flexible configuration, may continuously conform to (or copy) the shape of whichever member is in the rigid configuration.

The example of a robotic scope shown in FIGS. 1J-1M illustrate the operation of just one type of medical instrument that may be used with the methods and apparatuses described herein, including mapping. Furthermore, these apparatuses may be configured so as to function as endoscopes, including one or more of imaging, irrigation, lighting, steering channels for removing or applying materials, etc. For example, the robotic scope 1100 may include one or more cameras, lighting and a distal steering section. The device (e.g., scope or portion of a scope) may be well sealed such that it is easy to clean between procedures. In some examples it does not need to be cleaned because it is fully sheathed, including both on the outside and through the working channels, e.g. within a shield as described above. In some examples a second inner device may then be placed inside the rigidized outer member and advanced past the distal end of the outer member. The second inner member may be a "therapeutic" tube comprising such elements as a camera, lights, water, suction and various tools. The "therapeutic" device may not have a steering section or the ability to rigidize, thereby giving additional room in the body of the therapeutic tube for the inclusion of other features, for example, tools for performing therapies. Once in place, the tools on the "therapeutic" tube may be used to perform a therapy in the body, such as, for example, a mucosal resection or dissection in the human GI tract.

The rigidizing devices described herein (including the robotic, nested rigidizing devices as well as rigidizing version of any of the tools described herein) may be configured to rigidize using any appropriate structures. In some cases the rigidizing devices (e.g., shields, endoscopes, overtubes, etc.) may be configured to rigidize by the application of pressure, positive and/or negative pressure to compress one or more rigidizing layer. For example, any of these apparatuses may include an elongate rigidizing body formed of a plurality of different layers; pressure may be applied (either positive and/or negative pressure and/or both positive and negative pressure simultaneously or intermittently) to set the flexibly/rigidity of the elongate body. For example, that elongate body of the rigidizing apparatus may include a support layer (e.g., a cylindrical/tubular support layer that may be reinforced, e.g., by a wire coil or otherwise), a rigidizing layer (which may be formed of multiple lengths of overlapping strands, fibers, filaments, etc., e.g., a knitted, woven, braided, etc. cylindrical layer), and a compression layer (e.g., a bladder layer) that may be compressed by the application of positive and/or negative pressure against the rigidizing layer. In the more flexible configurations of the elongate body, the multiple lengths of strands of the rigidizing layer may slide against each other freely or with little friction. The compression layer may be driven against the lengths of strands of the rigidizing layer to restrict their relative movement (e.g., sliding) which results in an increase stiffness. In general, the greater the pressure applied by the compression layer, which may be function of the applied pressure, the greater the stiffness (e.g., the lower the flexibility) of the rigidizing layer, and therefore the elongate body. Examples of alternative configuration for rigidizing and controlling the stiffness/rigidity are provided below. Alternatively or additionally, in some examples the rigidizing layer may be formed of a plurality of elongate lengths of liner members (e.g., filaments, fibers, wires, etc.) that may be arranged along al or a portion of the length the rigidizing member.

The rigidizable apparatuses and methods described herein may be part of a medical access system (e.g., robot) for diagnosing and treating regions of the body that are otherwise hard to access and operate within, particularly during minimally or non-invasive procedures. In particular, these methods and apparatuses may be used in highly tortuous and/or unsupported regions of the body. These methods and apparatuses may be used in combination with, and/or may modify and improve the rigidizable devices and methods of using them described in U.S. Pat. No. 11,135,398 (titled "DYNAMICALLY RIGIDIZING COMPOSITE MEDICAL STRUCTURES"), U.S. patent application Ser. No. 17/604,203 (also titled "DYNAMICALLY RIGIDIZING COMPOSITE MEDICAL STRUCTURES"), PCTUS2021024582 (titled "LAYERED WALLS FOR RIGIDIZING DEVICES"), PCTUS2021034292 (titled "RIGIDIZING DEVICES"), PCTUS2022014497, titled "DEVICES AND METHODS TO PREVENT INADVERTENT MOTION OF DYNAMICALLY RIGIDIZING DEVICES," PCTUS2022019711, titled "CONTROL OF ROBOTIC DYNAMICALLY RIGIDIZING COMPOSITE MEDICAL STRUCTURES," U.S. provisional patent application 63/265,934, "METHODS AND APPARATUSES FOR REDUCING CURVATURE OF A COLON," U.S. provisional patent application 63/296,478, titled "RECONFIGURABLE STRUCTURES," U.S. provisional patent application 63/308,044, "DYNAMICALLY RIGIDIZING COMPOSITE MEDICAL STRUCTURES," U.S. provisional patent application 63/324,011, "METHODS AND APPARATUSES FOR NAVIGATING USING A PAIR OF RIGIDIZING DEVICES, U.S. provisional patent application 63/342,618, "EXTERNAL WORKING CHANNELS FOR ENDOSCOPIC DEVICES," U.S. provisional patent application 63/335,720, "HYGIENIC DRAPING FOR ROBOTIC ENDOSCOPY," and U.S. provisional patent application 63/332,686, "MANAGING AND MANIPULATING A LONG LENGTH ROBOTIC ENDOSCOPE," each of which is herein incorporated by reference in its entirety.

Rigidizing apparatuses as described herein may be configured to rigidize when negative pressure and/or positive pressure is applied. These rigidizing apparatuses as described herein may be used in conjunction with other rigidizing devices that rigidize with other methods, including those that do not rely upon the application of positive or negative pressure. For example, a rigidizing device may be configured to include multiple layers arranged into an elongate catheter-like body. The device may include a handle or other manipulator and may include a connection to one or more pressure sources. Applying pressure from the pressure source may be controlled by multiple methods, including operation of a handle or an electronically controlled device. Control may result in a pressure differential that causes the device to transition between a highly flexible configuration, allowing the tubular body to readily bend, when steered or otherwise guided (e.g., over a guidewire, etc.), and one or more (e.g., a continuum) of rigid configurations. In some examples, particularly (but not exclusively) in reference to apparatuses that rigidize based on the application of positive pressure, the rigidity of the elongate body is proportional to the applied pressure differential, so that the greater the pressure differential, the more rigid the device may become over at least a range of pressure differential values.

In general, these apparatuses may include multiple layers, including a rigidizing layer and at least one of an outer or inner layer. Many of these examples also include a compression layer that may engage with the rigidizing layer, and in some examples the apparatus may include a combined rigidizing layer/compression layer. Described herein are rigidizing layers that may be particularly well suited to rapid and precise actuation over a variety of pressures, including in particular negative pressure (vacuum, full vacuum, partial vacuum) or positive pressures (e.g., high positive pressures, i.e., atm of about 2 or more, 4 or more, 6 or more, 8 or more, 10 or more, 15 or more, 20 or more, 30 or more, etc.). Any of these apparatuses may also be configured so that at least some of the inner and/or outer layers making up the rigidizable device have different durometers on the inner and outer portion of either the inner or outer layers. Also described herein are apparatuses and methods including nested sets of rigidizable apparatuses, which may include any of these rigidizable devices. Any of these apparatuses may include one or more torsional enhancing layers for improving torsional control, particularly when included as part of a nested pair of rigidizable devices (e.g., as part of the inner, or child, device).

Figure 2A:
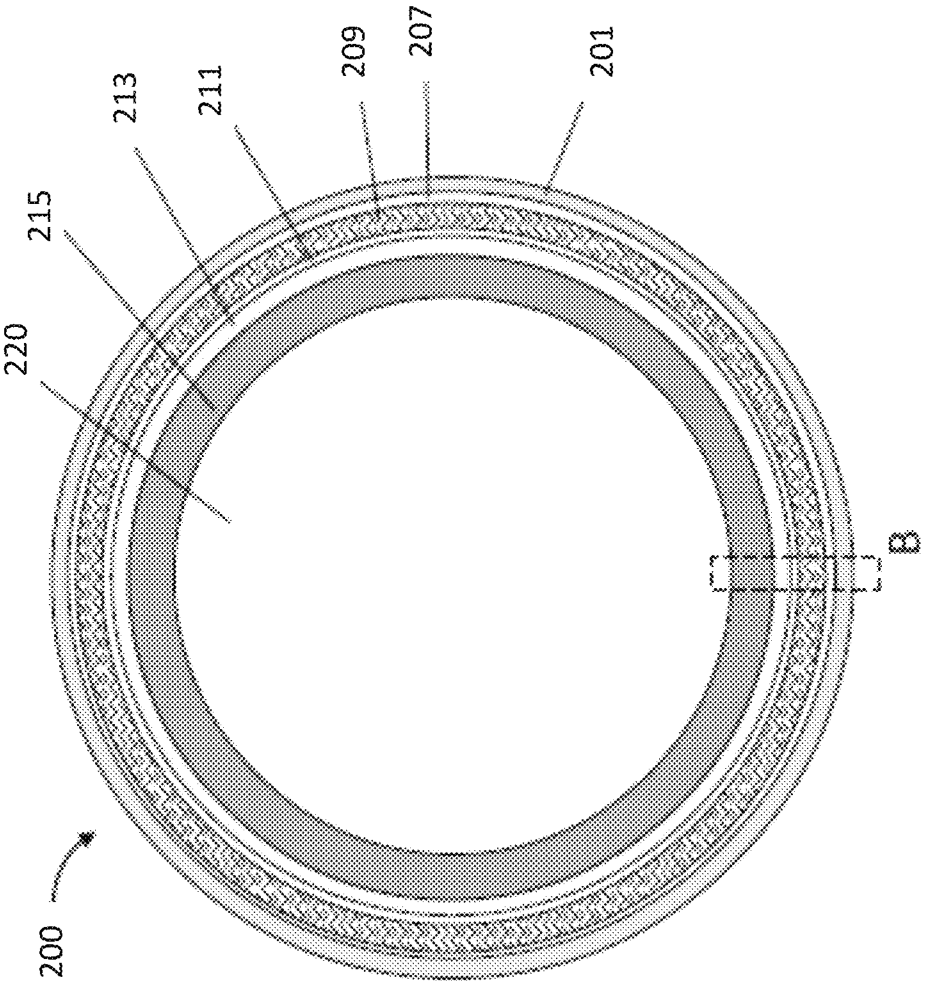
FIG. 2A is a section through an example of an elongate rigidizable device (e.g., rigidizing overtube) that may be rigidized by the application of negative pressure.
Figure 2B:
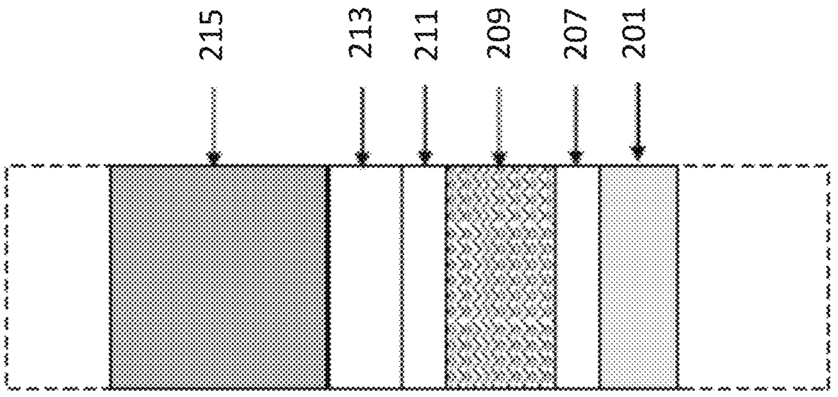
FIG. 2B is an enlarged view showing one example of the arrangement of layers within the elongate rigidizable device of FIG. 2A.

FIG. 2A illustrates an example of a transverse section through an elongate rigidizing device, showing the arrangements of the many layers that may be included. In this example the rigidizable device 200 is configured to be actuated by the application of a negative pressure (e.g., vacuum). The device 200 shown includes an inner layer (215) that may be reinforced (e.g., by including one or more reinforming members, such as a helically arranged strip, ribbon or wire), an optional slip layer (213), a gap (211), a rigidizing layer (209), configured in this example as a braid layer, a second gap (207) and an outer layer (201). In some examples a vacuum may be applied between the outer layer and the inner layer to rigidize. For example, a port configured to couple to the source of negative pressure may be located at the proximal end of the device and may be in fluid communication with the gap region 207 between the flexible outer layer 201 and the rigidizing layer 209, e.g., braided layer. Thus, in this example the outer layer may act as a compression layer. FIG. 2B shows a section through one wall region B of the cylindrical-shaped body of the device. Applying suction may allow the outer layer 201 to be drawn onto the rigidizing layer, causing it to rigidize, limiting or preventing bending of the device.

Figure 3B:
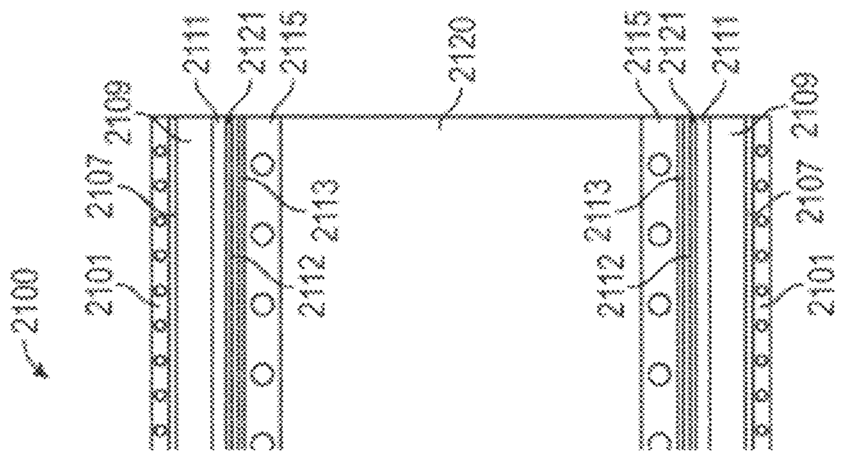
FIG. 3B is an alternative sectional view showing one example of the arrangement of layers within the elongate rigidizing device of FIG. 3A.
Figure 3A:
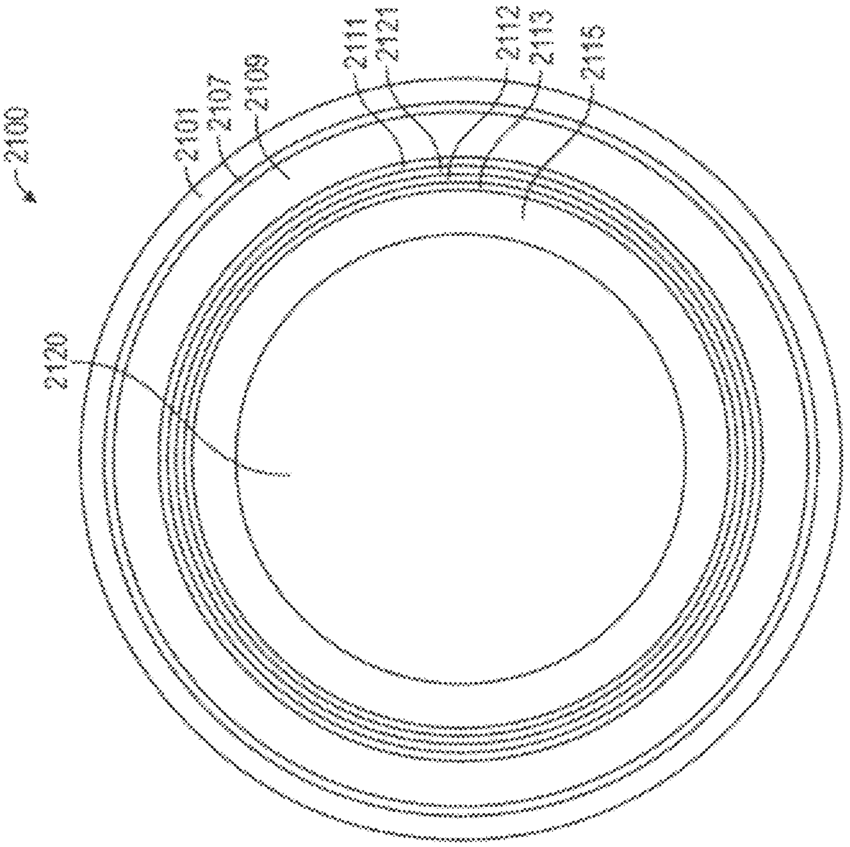
FIG. 3A is a section through an elongate rigidizable device (e.g., rigidizing overtube) that may be rigidized by the application of positive pressure.

Another example of a rigidizable device is shown in FIGS. 3A-3B. In this example the device may also be an elongate, e.g., catheter or tubular-shaped device similar to that in FIGS. 2A-2B but may be rigidized by the application of positive pressure. For example, FIG. 3A shows a section transverse to the long axis of an elongate rigidizable device. In this example, the layers forming the device are arranged so that an inner reinforced layer 2115 is the most radially-inward layer and may be reinforced, e.g., by a helically wound ribbon, strip, cable, etc. The device may also include an optional slip layer 2113 which may reduce the friction between the inner layer and the more radially-outward layers. The slip layer may be a powder, or it may be a lubricious layer or a layer of lubricious material. A first gap 2112 layer is shown separating the inner layer 2115 and/or the slip layer 2113 from a compression layer, configured in this example as a bladder layer 2121. A second (or intermediate) gap layer 2111 spaces the bladder layer from the rigidizing layer 2109, shown in this example as a braid layer. A third gap layer 2107 is positioned between the rigidizing layer and an outer layer 2101. The outer layer in this example (similar to the inner layer 2115) is reinforced, for example, by a helically wound filament, wire, fiber, band, etc. Although not shown, when actuated by the application of positive pressure between the compression (e.g., bladder) layer and the inner layer, the bladder layer may push the braid layer into the outer layer to rigidize the rigidizing layer.

Both examples of a devices shown in FIGS. 2A-2B and 3A-3B may include additional optional layers or components. Further, the compositions of the rigidizing layers may be modified in order to improve performance. In particular the rigidizing layer may be modified to include structures (e.g., knits, wovens, braids, scales, plates, arrays of filaments, granules, and combinations thereof, etc.) that may enhance or improve performance. Rigidizing elements may be used as one type alone, or in conjunction with other rigidizing elements. In some examples the inner and/or outer layers may be modified to enhance or improve performance, including the addition of torsional control components, and/or modulating the durometer of the inner and outer regions of these layers.

Further, any of the rigidizable devices described herein may be configured as nested apparatuses that may be nested to provide enhanced performance. For example, a nested apparatus (system) may include an outer rigidizable device (e.g., rigidizing overtube) and an inner rigidizable device (e.g., rigidizing endoscope). The inner rigidizing device (e.g., scope) can be, for example, configured to receive pressure (positive and/or negative pressure) to rigidize from a more flexible to a less flexible configuration. Any of these rigidizing devices may include an air/water channel and a working channel that can extend with the inner rigidizing device.

Figure 4A:
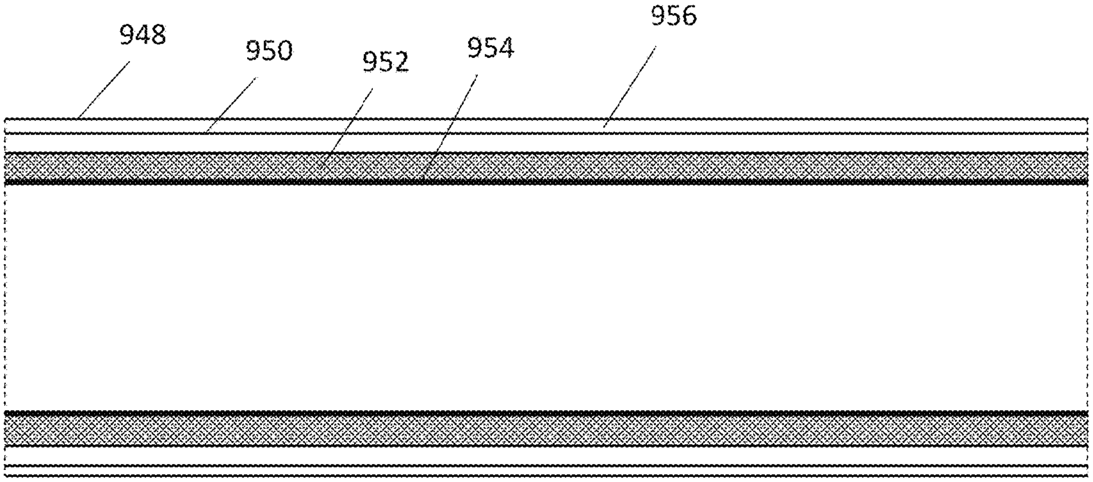
FIGS. 4A-4B schematically illustrate rigidizing of a pressure-actuated rigidizable device.

As mentioned above, in general, these apparatuses may be configured to be rigidized by the application of pressure. This is illustrated schematically in FIGS. 2A-3B and 4A-4B for a generic rigidizing layer. In these examples the device is shown in longitudinal cross-section through a portion of the length of the device. The layers forming the device are arranged as concentric tubes. In FIG. 4A the device is shown without the application of pressure, and includes an inner layer (tube) 954, an outer layer (tube) 948 and a compression layer (e.g., bladder) 950 and a rigidizing layer 952. The particular configuration shown illustrates the rigidizing layer 952 between the inner layer 954 and the compression layer 950. A first gap layer 956 is present between the outer layer 948 and the rigidizing layer 952. A port (not shown) may be present at an end (e.g., a proximal end region) of the device to couple to the source of pressure (e.g., positive pressure). A second gap layer may be present between the compression layer 950 and the rigidizing layer 952, and/or between the rigidizing layer 952 and the inner layer 954. In the configuration shown in FIG. 4A the device may be flexible as each of these layers may slide relative to each other when bending the device. In particular, the rigidizing layer may flex and slide relative to the inner layer 954 and the compression layer 950.

Figure 4B:
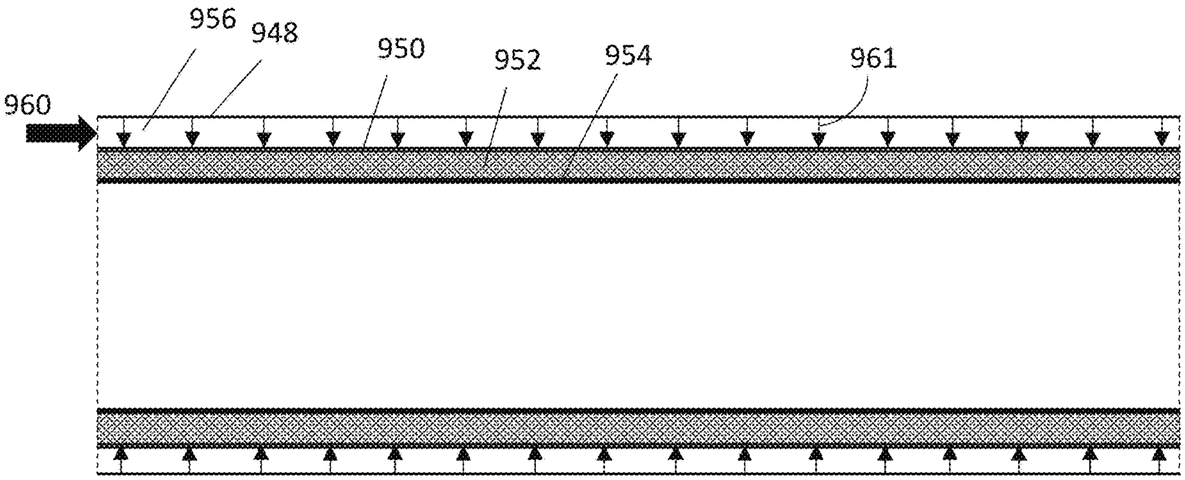

FIG. 4B illustrates the device of FIG. 4A when positive pressure 960 is applied between the outer layer 948 and the compression layer 950. Alternatively the compression layer may be a bladder into which the positive pressure is applied. In FIG. 4B, as positive pressure is applied the compression layer 950 is driven 961 against the rigidizing layer 952, so that is compressed between the compression layer 950 and the inner layer 954 (and/or any intervening layers). Compressing the rigidizing layer 952 rigidizes the device. Any bends or curves are preserved without changing the shape.

In the example shown in FIGS. 4A and 4B, any appropriate rigidizing layer 952 may be used, including knit compression layers, woven, braided, granules, scales, etc.

In some examples, particularly those having elastic (e.g., elastomeric) compression layers and rigidizing layers formed of filament lengths that cross over and under each other, the compression layer may deform into the rigidizing layer, which may enhance the rigidity of the device. For example, as pressure is applied, the compression layer (e.g., bladder) may apply force directly to the rigidizing layer. Depending on the bladder type, the bladder may deform, depress, or interdigitate into the space around and between the elements (e.g., filaments, wires, etc.) of the rigidizing layer. Conforming to the overlapping (over-and-under) fiber or filament lengths may help lock the rigidizing layer relative to the inner layer (or in some examples outer layer) to which it is being compressed. The application of positive pressure in this manner may therefore increase rigidization as positive pressure is increased even beyond what is otherwise expected. Thus a rigidizing layer comprising a plurality of filament lengths crossing over and under each may be generally configured so that, in the flexible configuration, the filament (e.g., fiber) lengths may shear relative to each other. However, when positive pressure is applied, the deformable compression layer may be pushed against the rigidizing layer so that the compression layer may conform to or deform into or between the plurality of filament lengths to prevent shear of the plurality of filament lengths relative to each other.

Robotic Apparatuses

Figure 5:
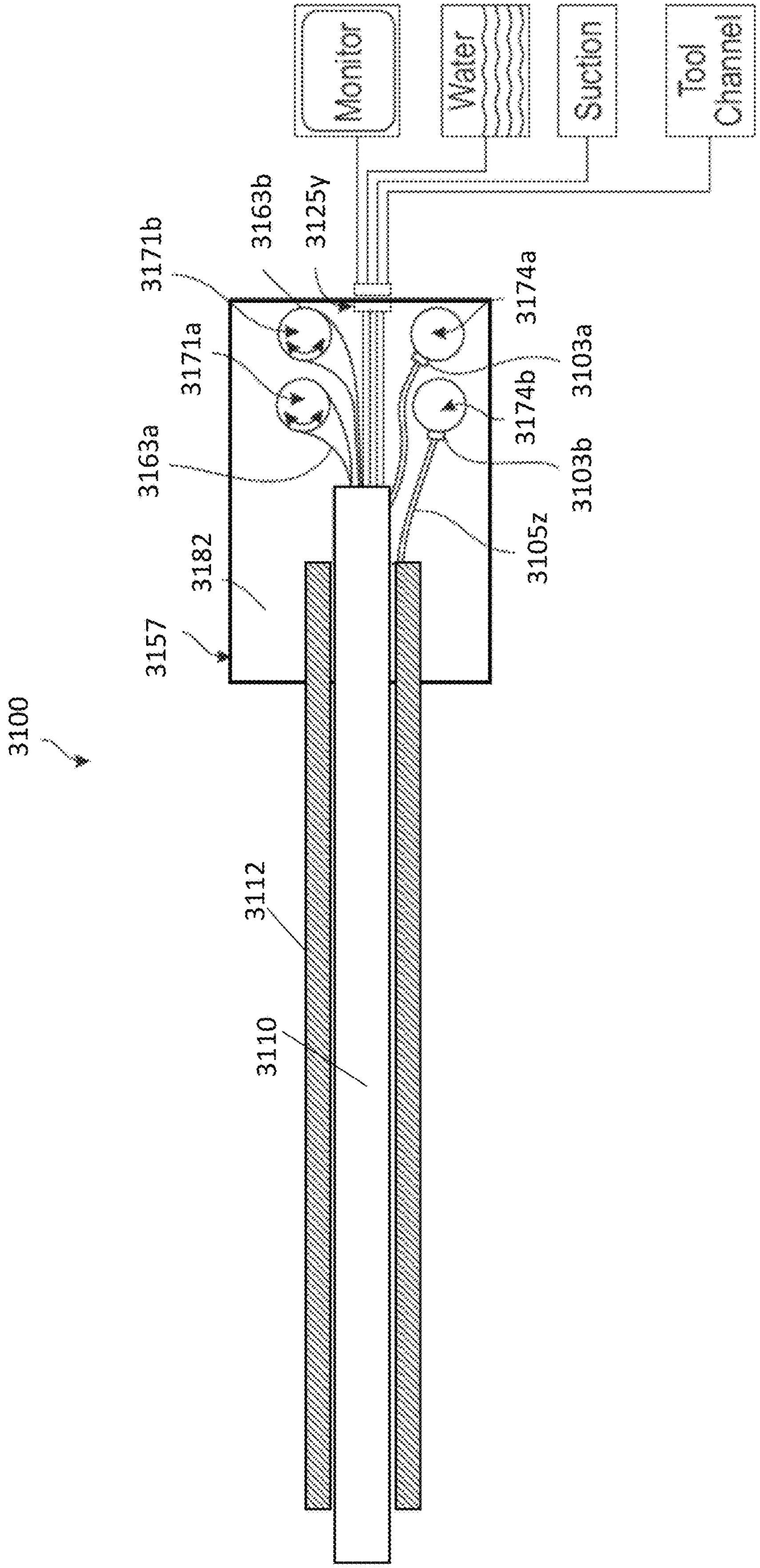
FIG. 5 schematically illustrates one example of a robotic system for performing any of the methods described herein, including mapping.

As mentioned above, any of the methods and apparatuses described herein may be part of a robotic method/system, as illustrated in FIGS. 1F-1I. For example, the rigidizing apparatuses (e.g., rigidizing overtube) described herein may be configured as part of a robotic system or for use with robotic apparatuses. In some cases the other components (e.g., steerable redirector, endoscope, etc.) may also or alternatively be part of the robotic system and the movements of these components may also be robotically controlled and/or implemented. Thus, any of these methods may be performed by a robotic apparatus. In some examples the rigidizing apparatus may be configured as an outer tubular member (overtube) that is robotically controlled, e.g., configured as a robotically controlled overtube and/or endoscope assembly. FIG. 5 shows an exemplary apparatus 3100, including a rigidizing device configured as an overtube 3112; the system may optionally include the steerable inner member (e.g., endoscope) 3110. The overtube and endoscope can be separately or collectively be robotically controlled or manipulated (e.g., steering, movement, rotation, etc. including in some examples, rigidizing). The overtube and inner endoscope may be configured as illustrated in any of the examples described above, and may have the same general construction, or may be of different constructions. As shown in FIG. 5, the rigidizing overtube 3112 and the endoscope 3110 may be terminated together into a common structure, such as a cassette 3157, or two separate cassettes may be used. In some cases a single controller may coordinate movement of the one or more cassettes. The rigidizing overtube 3100 can be movable (both axially and rotationally) with respect to the steerable endoscope 3110 by rotation of a driver mounted to the cassette 3157. The system may include actuators 3171*a*, 3171*b* that may connect to cables 3163*a,b* respectively, to steer (e.g., bend or deflect) the steerable region of the steerable endoscope 3110 (or in some examples, the rigidizing overtube 3112). Other steering mechanisms (e.g., pneumatics, hydraulics, shape memory alloys, EAP (electro-active polymers), or motors) are also possible. The cassette 3157 can further include a link to a pressure source or a pressure generator (e.g., bellows) 3103*a*, 3103*b* that may connect to the pressure inlet of the rigidizing overtube 3112, to drive fluid (e.g., air, $CO_2$, etc.) through pressure lines 3105*z*, in some variations for rigidizing the overtube and/or endoscope (or shield for an endoscope). As shown in this example, the cassette 3157 can include eccentric cams 3174*a,b* to control bellows 3103*a,b*. Alternatively, one or more linear actuators can be configured to actuate the bellows. As another alternative, the rigidizing overtube (and/or in some examples the steerable redirector) can be rigidized and de-rigidized through one or more pumps or pressure sources (e.g., via pressure line 3105*z*). The drive wheels shown (3171*a*, 3171*b*, 3174*a*, 3174*b*) can be used to articulate the bending section at the distal end of 3110.

In general, the mapping apparatuses described herein may be used to automatically and/or semi-automatically control operation, including steering, mapping, etc., of the robotic apparatus. In some cases the coverage map may be used for automatic deployment of the robotic apparatus, as one or more regions of interested on the map may be selected so that the apparatus may automatically drive the distal end (forward facing camera) to the one or more regions of interested. The apparatus may automatically provide an optimal view of the region of interest. Alternatively or additionally these apparatuses may at least partially automatically map the body lumen by tracking coverage, dividing the lumen into sub-regions and performing specific orchestrated steps to map each subregion. Thus, aspects of the present disclosure may be used with or integrated into a robotically enabled medical system capable of performing a variety of medical procedures, including both minimally invasive procedures-such as laparoscopy- and non-invasive procedures-such as endoscopy. Among endoscopy procedures, the robotic system may be capable of performing colonoscopy, enteroscopy, bronchoscopy, ureteroscopy and/or gastroscopy.

Figure 6B:
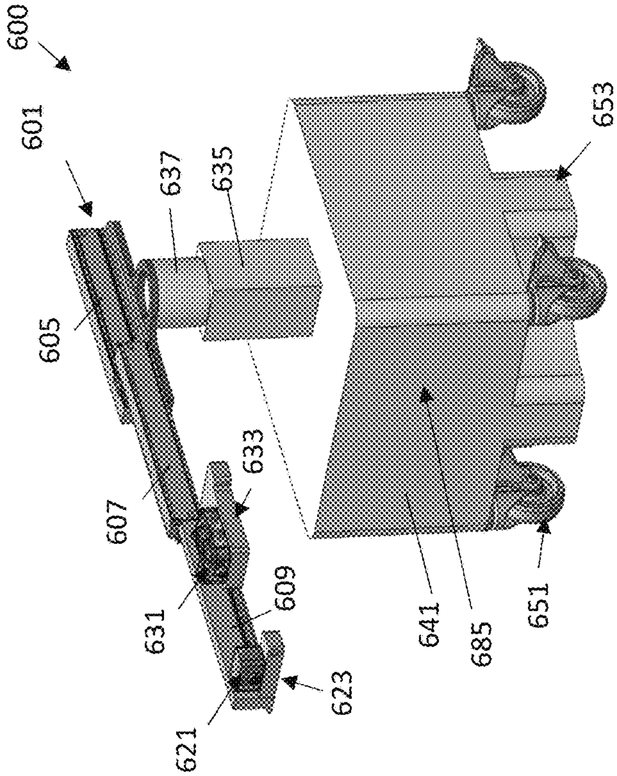
FIGS. 6A and 6B illustrate an example of a robotic apparatus that may be part of the apparatuses and methods described herein.
Figure 6A:
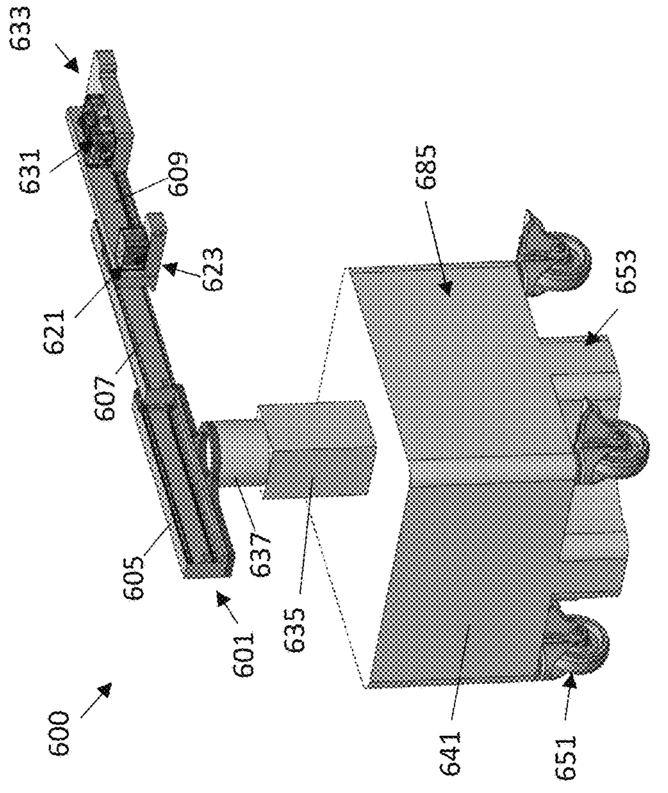

FIGS. 6A and 6B show an example of an apparatus (e.g., system) for dispensing and/or controlling a flexible tubular member that may be configured to generate a full- or nearly-full mapping of the body lumen, and in particular, the colon, similar to that shown in FIG. 1H, in greater detail. In FIGS. 6A and 6B, the apparatus is shown to be configured for use with a flexible tubular member configured as a nested endoscope that includes an outer tube (also referred to as an overtube) and an inner tube (also referred to as an inner tube) that may be moved proximally/distally relative to each other and may each be rigidized to guide and/or steer the device through the patient's body (as described above). However, it should be understood that these apparatuses may be used with any flexible tubular member, including those that are not nested and that do not rigidize (e.g., single-body endoscopes).

In FIGS. 6A and 6B, the system 600 shown includes a base 641 that may support the weight of the rest of the system, including any flexible tubular member attached to the system. The base 641 may be weighted so as to allow the telescoping link assembly and any attached flexible tubular member to cantilever distally or proximally away from the base, while remaining stable. The base 641 may house one or more additional components, including power source, power conditioners, motors, pressure source/pressure supplies, controllers, control circuitry, etc. The base 641 may include wheels 651 to allow the apparatus to be moved and positioned relative to a patient's bed. In some examples the base 641 may include an anchoring region 653 that may be lowered and/or raised to allow or prevent movement. The wheels 651 may be locking or lockable.

The system 600 includes a link assembly 601 configured as a vertically arranged link assembly including three links: a first link 605 (e.g., outer link), a second link 607 (e.g., an intermediate link) and a third link 609 (e.g., inner link). The first link 605 is coupled with yaw adjust arm 637 that is also configured as (or may be coupled to) a vertical lift arm 635 connecting the link assembly 601 to the baes 641. The system 600 shown includes a mount assembly that includes a pair of mounts 623, 633 that are coupled with the third link 609. In this example the first mount 623 is configured as an overtube mount for coupling with an overtube of an endoscope. The overtube mount is located at or near the distal end region of the third link and includes an overtube drive assembly (e.g., driver) 621 that may interface with the overtube of the endoscope. In some examples, the overtube drive assembly may include drive components for controlling roll, for steering (optionally, in examples in which the overtube may be steered at the distal end), and/or pressure inputs/outputs for rigidizing/de-rigidizing. The overtube mount 623 may be configured to secure to the overtube portion separately from the inner tube. In some examples the overtube mount 623 may secure by including a securing mechanism such as a clamp, clasp, latch, lock, etc.

The second mount 633 is configured as an inner tube mount and may also include an inner tube drive assembly (driver) 631. The inner tube drive assembly 631 may interface with the inner tube member and may include drive components, including steering components (e.g., for steering a distal end/tip region of a flexible tube member), roll control, pressure input/output (e.g., for rigidizing/de-rigidizing, etc.). The inner tube mount 631 may be configured to secure to the inner tube separately from the overtube, e.g., by including a securing mechanism such as a clamp, clasp, latch, lock, hook, bracket, grip, vice, etc.

In general, these apparatuses may include multiple (e.g., eight or more) degrees of freedom for the mount assembly and therefore the medical device (e.g., flexible tubular member). For example, the first 605, second 607 and third 609 links may be moved in a proximal to distal direction when extending and retracting. Insertion and retraction may be driven by an overtube insertion motor 615 (e.g., a linear drive, such as a ball screw/nut assembly). The overtube mount 623 also includes an overtube roll motor. The inner tube mount 633 includes an endoscope driver 631 including an endoscope roll motor and multiple steering motors. The link assembly is pivotally attached to a yaw adjustment arm 657 and a vertical lift arm 655.

In FIGS. 6A-6B the robotic apparatus may include a controller 685, e.g., within the housing or base 641, the controller having one or more processors and a memory storing instructions that, when executed, perform any of the methods described herein, including mapping. Thus, the robotic apparatuses described herein may be configured to deliver elongate medical instruments, such as endoscopes.

Any of the apparatuses described herein may have link assemblies including any number of links, e.g., two links, three links, four links, five links, six links, or more. The additional links may be configured and controlled as described herein.

Figure 7:
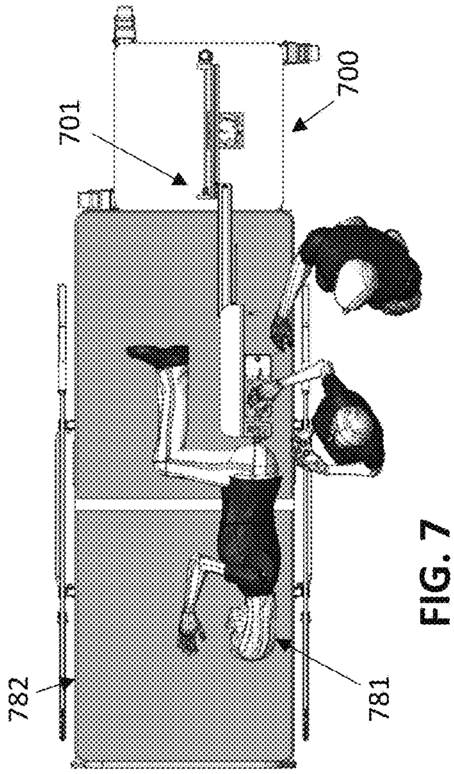
FIG. 7 shows an example of an overhead view of an apparatus for mapping a patient's colon as described herein.

As mentioned, these apparatuses may be used with a variety of procedures. For example, these systems may be used as part of lower or upper gastrointestinal (GI) procedures, as shown in the top view of FIG. 7. In these examples, a system 700, including a vertically arranged linear link assembly 701, may be used with a patient 781 in virtually any orientation on the bed/cart 782. The flexible tubular member is part of a system 700 and can be inserted and manipulated using a vertically arranged linear link assembly described herein. A position of the system 700 may be adjusted so that the flexible tubular member held by the link assembly may be used to insert, manipulate and retract the flexible tubular member into the patient's body 781. FIG. 7 shows an example colonoscopy procedure with the system 700 positioned on the foot of the patient's bed/cart 782.

In general, the methods and apparatuses described herein may include fully apparatuses including dual rigidizing apparatuses, such as those described above. These apparatuses may be fully flexible along the entire length (or most of the length, e.g., >80%, >85%, >90%, >95%, etc.) of the length of the elongate members. The dual members may be nested, as described above, and either one or both may be rigidizing. These apparatuses may be configured for robotic control, including robotically controlling relative movement of each relative to the other. In any of these examples one of the elongate members may be an endoscope (e.g., a colonoscope) as described above. Either or both elongate members may include a steerable distal end region. For example, the inner member may be rigidizing and steerable.

Figure 8A:
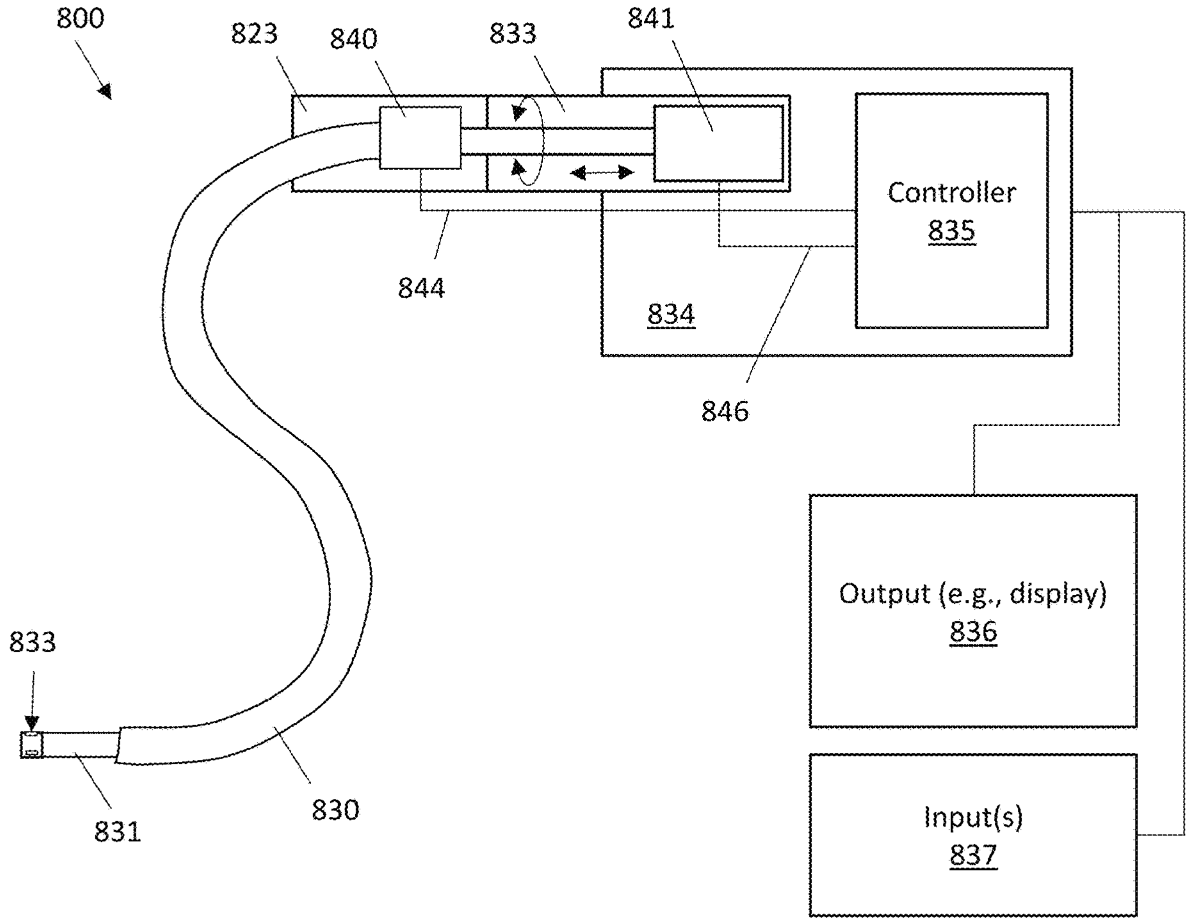
FIG. 8A schematically illustrates another example of an apparatus as described herein configured for mapping a body lumen.

FIG. 8A schematically illustrates an example of an apparatus as described herein. In FIG. 8A the apparatus 800 includes a first elongate member 830 configured as a rigidizing overtube and a second elongate member 831, configured as an endoscope including a plurality of cameras 833 at the distal end. The second elongate member 831 may also be rigidizing and is nested within the first rigidizing member 830. The proximal end of the first elongate member 830 is coupled to a cartridge 840 (or handle) that may interface with a pressure source (not shown) and/or controller via one or more control lines 844. The control lines may include pressure, power, and/or data lines. The first elongate member is also coupled to a motion-controlling telescoping link assembly 834 via a mount 823 that may be controlled by the controller to move axially (e.g., in/out). 830 may be axially moved or rotationally torqued.

Any of these apparatuses may include one or more sensor for providing input into the system, e.g., to the controller, in addition to input from the one or more cameras, and user input(s). For example, the apparatus may include one or more position sensors such as but not limited to sensors sensing the position of the proximal ends of the first and second elongate members (e.g., on the mount(s) 823, 833 or relative to the mount(s) and the links or base of the robotic driver. The apparatus may include shape sensors for sensing the shape of the first and/or second elongate members. The apparatus may include one or more position sensors for detecting position of the distal end regions of the first and/or second elongate members. The apparatus may include one or more rotational position sensors, for determining the rotational position of the inner and/or outer elongate members (such as an encoder on the mount and/or cartridge). In general any of these sensors may be used as feedback to control operation of the apparatus, including mapping and automatic movements of the apparatus.

The second elongate member 831 is also coupled at the proximal end to a cartridge or handle 841 and may be driven to move axially via a mount 833. Either the mount or the cartridge/handle may also be configured to drive rotation of the second elongate member, and steering (e.g., by actuating one or more cables/tendons to steer the distal end region of the second elongate member). The second elongate member and/or the mount 833 may also be connected to the controller 835 by one or more lines (e.g., data lines, pressure lines, control lines, etc.) 846. The apparatus may include an input 837 and an output 836; in some cases the output may also be an input, such as a touchscreen or the like. The output may include a connection to one or more video monitors (not shown) for displaying images from the one or more cameras and/or from the controller.

Figure 8B:
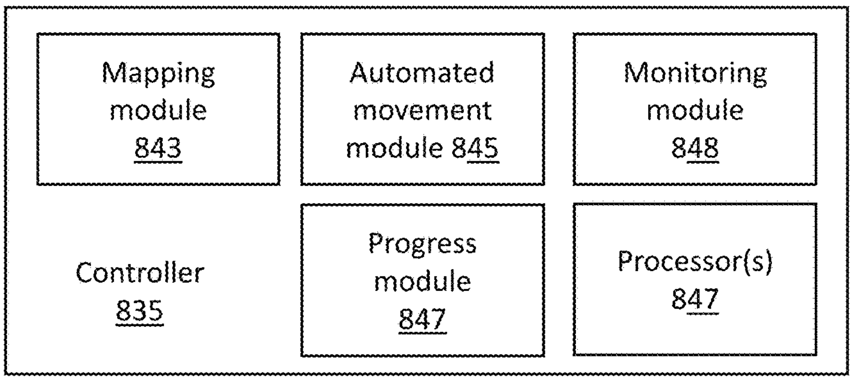
FIG. 8B schematically illustrates an example of a controller of FIG. 8A for coordinating the apparatus to perform any of the methods for mapping a body lumen as described herein. This shows that the endoscope can be moved back and forth and rotated, and that the entire platform (e.g., including the endoscope and overtube) can move back and forth. This example also illustrates that the overtube can roll.

The controller 835 may coordinate the operation of the apparatus to allow mapping as described herein. FIG. 8B schematically shows an example of a controller which may include one or more processors 847, memory, clock, and circuitry for controlling operation of the apparatus. The controller may be configured to operate completely locally (e.g., in the housing of the apparatus 800, e.g., the base as shown in FIGS. 6A-6B) or it may be at least partially remote, e.g., accessible by data connection (wired or wirelessly). The controller 835 may include software, hardware and/or firmware for receiving input (e.g., from the one or more cameras, from one or more sensors) processing images, generating the map, including the coverage map, for tracking the extend of the mapping progress, and for controlling movement both automatic and manual of the inner and/or outer elongate members, including controlling pressure (and therefore rigidity) of the inner and/or outer members.

As shown in FIG. 8B the controller may include one or more modules, including a mapping module 843, an automated movement module 845, a monitoring module 848 and a progress module 847. Each of these modules may be configured to coordinate and perform the methods described in greater detail below. For example, the mapping module 843 may be configured to generate the coverage map of the lumen, including controlling the cameras, collecting images, modifying/enhancing the images, stitching the images to form the coverage map, storing and/or transmitting the images, etc. The mapping module may also subdivide the lumen into a plurality of sub-regions, which may have a predetermined length. Any of these modules may communicate and cross-call each other. For example, the mapping module may also communicate with any of the other modules, including the automated movement module, that may be used to control first and second member in order to fully (or nearly fully) map the lumen in an automated and efficient (or semi-automated) manner as described below. The automated movement module may be used to automatically reposition the tip of the apparatus (the endoscope 831) so that it at least partially circumnavigates and ends up facing and displaying an area or interest (e.g., on the forward-facing camera). The automated movement module 845 may also be used to control movement of the first and second elongate members to map sub-regions of the lumen.

The progress module 847 may track progress of the mapping through the lumen and may output a tracking meter and/or display, including an animation of the extent of sufficient (or partial/incomplete and/or insufficient) mapping. The progress module may also be configured to receive input from the monitoring module 848, which may analyze the collected images and/or the coverage map, e.g., to identify regions of interest, to identify sufficient coverage (e.g., to determine missing or occluded regions, such as regions behind folds or protrusions within the lumen), which may be used by the progress module to update progress and/or may be used by the mapping module to automate control of mapping to get full/compete mapping and/or to deploy a technique to improve imaging of the vessel wall, such as a balloon (e.g., transparent balloon), one or more mechanical probes, insufflation, irrigation/suction, etc.

Any of these modules, including in particular the monitoring module, may include one or more trained machine learning agents that may be trained on a labeled dataset to identify regions of interest, including polyps, folds, etc. The monitoring module may be configured to identify occlusions/occluded regions from the collected images. The controller and any of the associated modules may be configured to operate in real time or near real time. As used herein real time may be concurrent within about 0.5 seconds, 1 second, 2 seconds, 3 seconds, 4 seconds, 5 seconds, 10 seconds, 15 seconds, 1 minute, etc.

In general, as described herein, the term machine learning and "machine learning agent" refers to a class of computational techniques that enable systems to learn patterns and make decisions or predictions based on data, without being explicitly programmed for each specific task. Machine learning involves the development of algorithms that can generalize from examples, adapt to new inputs, and improve performance over time. A machine learning agent is any system or component (e.g., subsystem) that employs such algorithms to perform tasks such as classification, regression, clustering, decision-making, or control. These machine learning agents may operate autonomously or as part of a larger system, and they can be implemented in software, hardware, firmware or a combination of any of these.

Machine learning encompasses a broad range of methodologies, which can be broadly categorized into supervised learning, unsupervised learning, semi-supervised learning, and reinforcement learning, any of which may be used by the machine learning agents described herein. In supervised learning, the agent is trained on labeled data, learning to map inputs to known outputs. Unsupervised learning involves discovering hidden patterns or structures in unlabeled data, such as clustering or dimensionality reduction. Semi-supervised learning combines both labeled and unlabeled data to improve learning efficiency. Reinforcement learning, on the other hand, involves an agent interacting with an environment and learning to make decisions by receiving feedback in the form of rewards or penalties.

Additionally, machine learning includes specialized subfields such as deep learning, which uses multi-layered neural networks to model complex relationships in data, and transfer learning, where knowledge gained from one task is applied to a different but related task. Other techniques include ensemble learning, which combines multiple models to improve predictive performance, and online learning, where models are updated continuously as new data arrives. These approaches may be used individually or in combination, depending on the requirements of the invention.

In the context of the methods and apparatuses described herein, the term “machine learning” and “machine learning agent” are intended to be interpreted broadly, encompassing any computational method or system that utilizes data-driven learning to perform tasks, adapt behavior, or improve outcomes. This includes but is not limited to neural networks, decision trees, support vector machines, probabilistic models, and evolutionary algorithms. The invention may incorporate one or more of these techniques to achieve its objectives, and the scope of the patent should be understood to include all such variations and implementations.

Figure 9A:
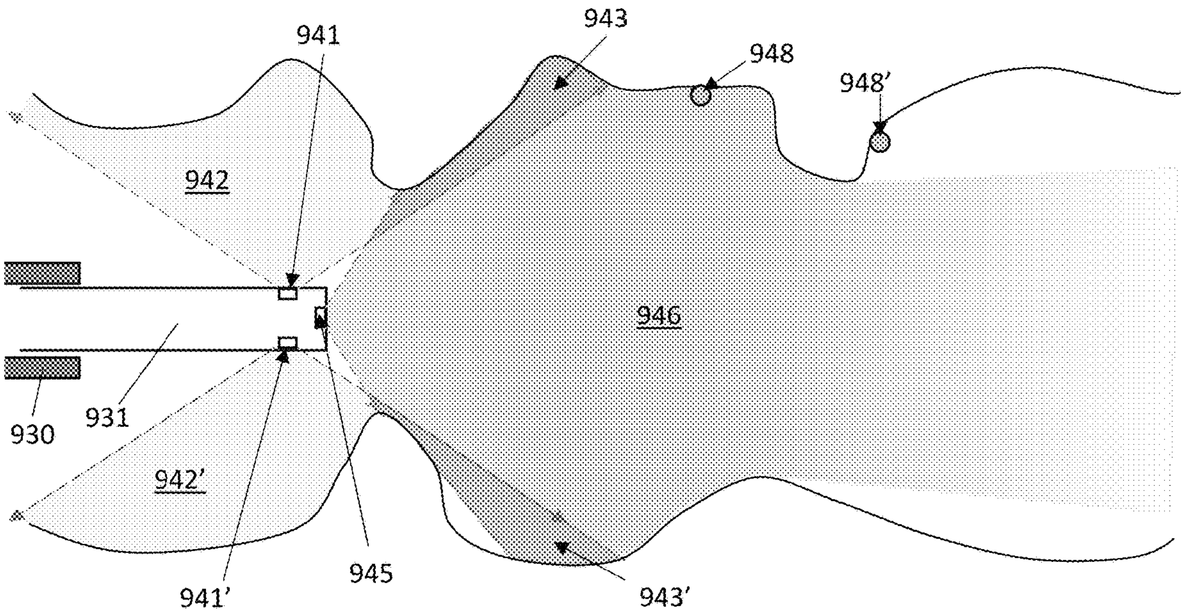
FIGS. 9A and 9B illustrate an example of a distal end region of an endoscope including a plurality of cameras (e.g., distal-facing camera, and side-facing cameras) showing examples of different fields of view within a body lumen (e.g., colon).
Figure 9B:
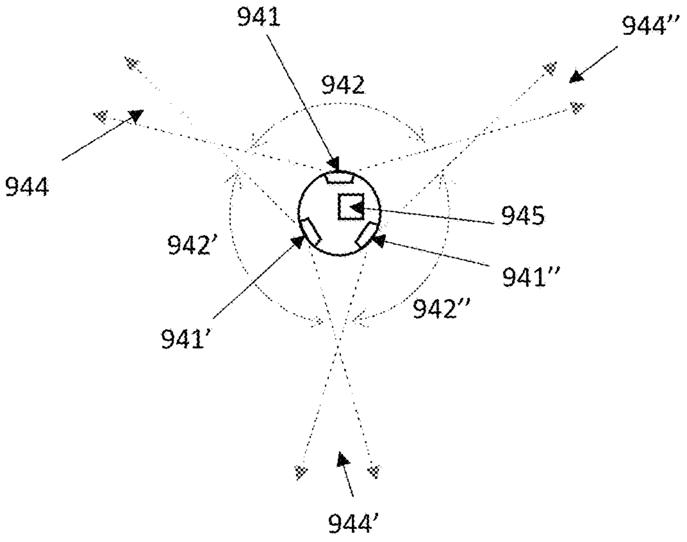

As mentioned, either the first (e.g., outer) or the second (e.g., inner) members may include one or more cameras 833. In some examples the apparatus may include a distal-facing camera and/or one or more side-facing cameras, as shown in FIGS. 9A-9B. In FIG. 9A the distal end region of a second elongate member 931 is shown, extending from an outer elongate member (e.g., overtube) 930. The distal end includes a distal-facing camera 945 and two or more (e.g., three, four, five, six, etc.) side-facing camera 941, 941', 941". In FIGS. 9A-9B three side-facing cameras are shown, each with a field of view 942, 942', 942" that extends greater than 160 degrees (e.g., approximately 170 degrees). The front-facing camera 145 may have a different size field of view 946. In FIGS. 9A-9B the fields of view of each of the side-facing cameras overlaps somewhat with each other 944, 944', 944" and with the front-facing camera 943, 943', in overlapping regions. These overlapping regions may provide some redundancy and may be helpful when stitching together the images from different cameras to form the coverage map (see, e.g., FIG. 13B).

Any number of cameras may be used, and the cameras may be specific to a particular wavelength of light or multiple wavelengths of light, including visible light (e.g., white light) narrow-band wavelengths (e.g., blue, green, red, etc.), non-visible light (e.g., Ultraviolet, infrared/near-infrared, etc.). These apparatuses may also include multiple sources of illumination, including LEDs, fiber optics, etc. for illuminating the lumen while taking images. The outer elongate member may also include one or more cameras (not shown) including side-facing cameras.

FIG. 9A also illustrates the detection of regions of interest, such as polyps in the field of view of the cameras. For example, in FIG. 9A a first polyp 948 is visible on the wall of the lumen by the forward-facing camera, however a second polyp 948' is not visible as it is positioned on the far side of the fold in the wall of the vessel even in an insufflated vessel. However, the side-facing camera 941 may image this second region of interest 948' when the distal end of the second elongate member is adjacent to this sub-region of the lumen, based on the field of view of the side-facing cameras. In general, the plurality of cameras may be arranged and configured so that their fields of view, orientation, and location permit both redundant image overlap and full coverage while navigating through the vessel, and in particular, while mapping. In some cases if side cameras ae not present the apparatus may be configured to schematically map each subregion by retroflexing to look “back” (proximally) during the mapping stage and optionally spin the tip while retroflexing in order to capture both potentially occluded regions. In some cases the apparatus (e.g., via the mapping module and/or automated movement module) may be configured to fully or partially automated this mapping to rigorously and rapidly examine both forward, side and/or retroflexed configurations.

The controller may therefore be configured to perform and coordinate a variety of movements of the inner and outer (e.g., second and first) elongate members. In some cases the apparatus may be configured to coordinate advancing, withdrawal, rotation (of the inner relative to the outer), bending/steering (of the inner relative to the outer), and dithering, e.g., oscillating back and forth either longitudinally (in/out), rotationally (clockwise/counterclockwise), or in bending (‘wagging’ left/right, up/down, etc.). The controller may also control lighting (e.g., turning on/off, specific wavelengths, intensity, etc.). The controller may also control washing/rinsing of the camera lenses.

Imaging devices such as discussed herein may be any type of device which can translate aspects of a sensed area into data that can be interpreted as a representation of an image. Such representation may be provided to a user on a display and/or provided to a system for evaluation or documentation and/or stored for later use. Detection and/or reflection of wavelengths or wavelength ranges of the electromagnetic spectrum is an example of data that an imaging device may collect. An imaging device may detect temperature gradations. An imaging device may detect multiple aspects of a sensed area. An imaging device may constitute a single device or multiple devices. An imaging device may have a capability to “zoom” in on an area under inspection. Output from an imaging device may be represented by analog or digital signals, or a combination thereof, and may be provided by way of a wired or wireless communication interface using a proprietary or standardized communication protocol.

Images may be of multiple types. Images may be captured using white light or other illumination types. For example, certain features may be more visible in an image captured using colored light (e.g., red, blue, green, yellow), or in an image captured using illumination in a frequency range or multiple frequency ranges that do not include visible light (e.g., infrared, microwave, ultrasound, etc.). More than one illumination type may be used to create more feature-rich images, which in turn can be used to make more feature-rich lumen maps. Feature-rich images also may allow for more accurate image stitching.

An imaging device may be poly-chromatic with a number of chromatic bandwidths each centered on a predefined wavelength and having a predefined bandwidth, and an image captured by the imaging device includes color information limited to the number of chromatic bandwidths. In an embodiment, the number of chromatic bandwidths is between three and six. In an embodiment, the number of chromatic bandwidths is less than ten. In an embodiment, the number of chromatic bandwidths is less than twenty. In an embodiment, none of the chromatic bandwidths overlap each other. In an embodiment, at least two of the chromatic bandwidths overlap each other.

In an embodiment, the imaging device detects wavelengths in an infrared wavelength range.

The system may include multiple imaging devices and at least one of the imaging devices has a different field of view and/or different orientation with respect to at least one of the other of the imaging devices.

An imaging device may be located adjacent to a side surface of the endoscope. A focal axis of the imaging device may be in a direction approximately perpendicular to the lengthwise axis of the endoscope or may be at an angle relative to the lengthwise axis of the endoscope. A focal axis of the imaging device may be tangential to the approximately tubular outer side surface of the endoscope.

An illumination source may be poly-chromatic with a number of chromatic bandwidths each centered on a predefined wavelength, and an image captured by the imaging device when the lumen is illuminated by the poly-chromatic illumination source includes color information limited to the number of chromatic bandwidths. In an embodiment, the number of chromatic bandwidths is between three and six. In an embodiment, the number of chromatic bandwidths is less than ten. In an embodiment, the number of chromatic bandwidths is less than twenty. In an embodiment, none of the chromatic bandwidths overlap each other. In an embodiment, at least two of the chromatic bandwidths overlap each other.

In an embodiment, the system includes an illumination source that emits light in an infrared wavelength range.

Figure 10A:
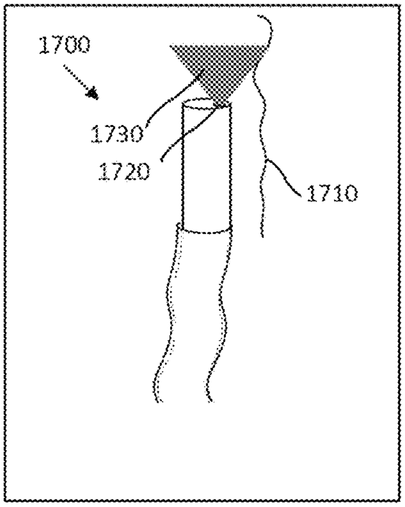
FIGS. 10A-10G each illustrate examples of placement and field of view of an imaging device or imaging devices.
Figure 10B:
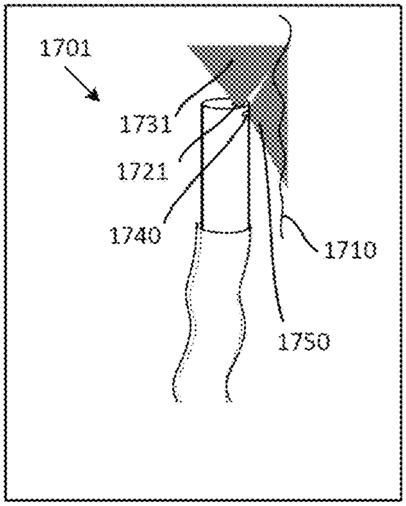
Figure 10C:
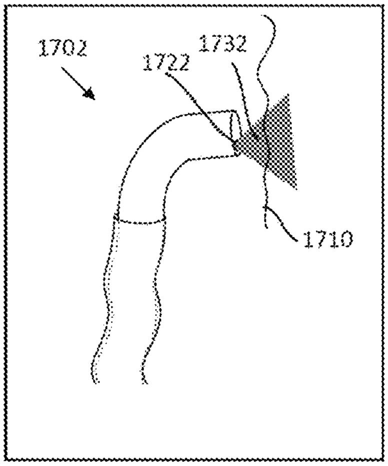
Figure 10D:
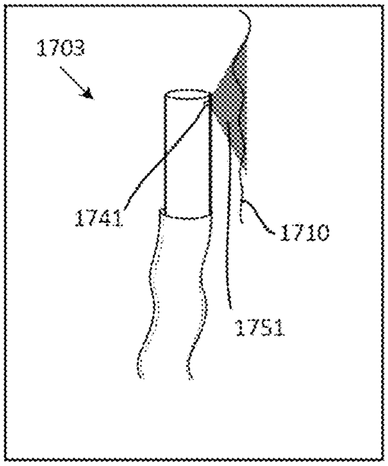
Figure 10E:
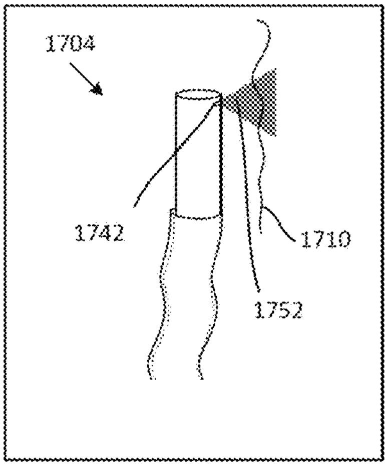
Figure 10F:
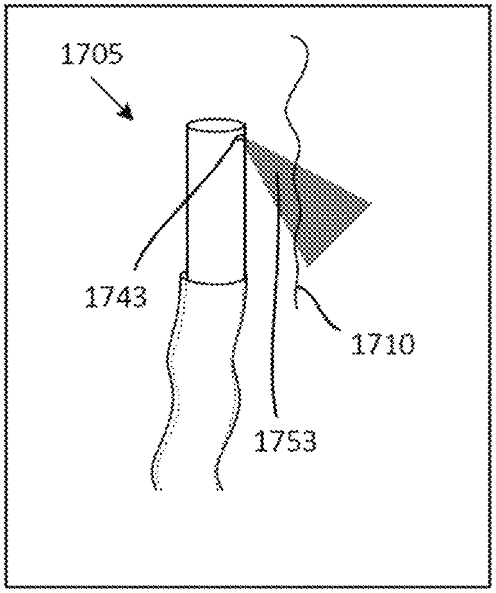
Figure 10G:
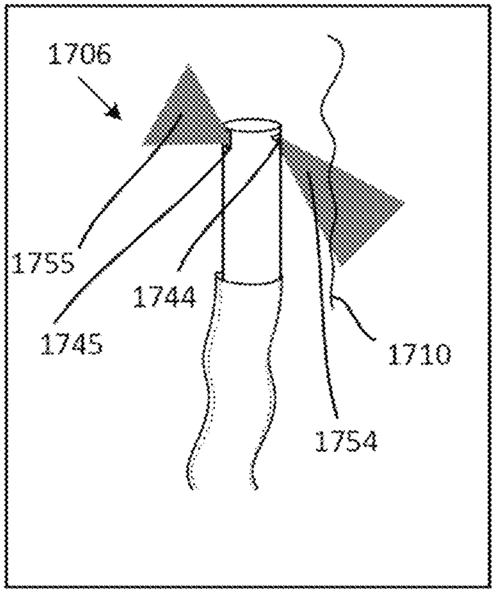

FIG. 10A, FIG. 10B, FIG. 10C, FIG. 10D, FIG. 10E, FIG. 10F, and FIG. 10G each illustrate an example of placement and field of view of an imaging device or imaging devices, shown with respect to an endoscope (which may be covered by a shield, or the imaging devices are on a shield) adjacent to a lumen wall 1710. FIG. 10A illustrates an endoscope 1700 having a forward-facing imaging device 1720 with a vertical field of view (FOV) 1730. FIG. 10B illustrates an endoscope 1701 having a forward-facing imaging device 1721 with vertical FOV 1731 and a side-facing imaging device 1740 having a vertical FOV 1750. FIG. 10C illustrates an endoscope having a forward-facing imaging device 1722 with vertical FOV 1732. FIG. 10D illustrates an endoscope 1703 having a side-facing imaging device 1741 with vertical FOV 1751. FIG. 10E illustrates an endoscope 1704 having a side-facing imaging device 1742 with vertical FOV 1752. FIG. 10F illustrates an endoscope 1705 having a side-facing imaging device 1743 facing at an angle with respect to the lengthwise axis of the shaft and with vertical FOV 1753. FIG. 10G illustrates an endoscope 1706 having a side-facing imaging device 1744 with vertical FOV 1754 and a side-facing imaging device 1745 with vertical FOV 1755, where each of device 1744 and 1745 have different vertical FOVs and different angles with respect to the lengthwise axis of the shaft. FIG. 10A-FIG. 10G illustrate just a few examples of the variety of devices and FOVs that may be used in embodiments of the present disclosure. Many other imaging device arrangements are possible and within the scope of this disclosure.

Figure 10H:
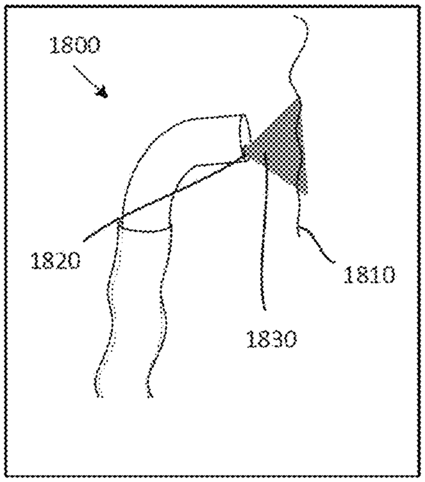
FIG. 10H illustrates an example of endoscope having a front-facing imaging device where the endoscope distal end is bent to image a lumen wall area.

FIG. 10H illustrates an example of endoscope 1800 having a front-facing imaging device 1820 with vertical FOV 1830, where the endoscope distal end is bent to image a lumen 1810 wall area.

Figure 10I:
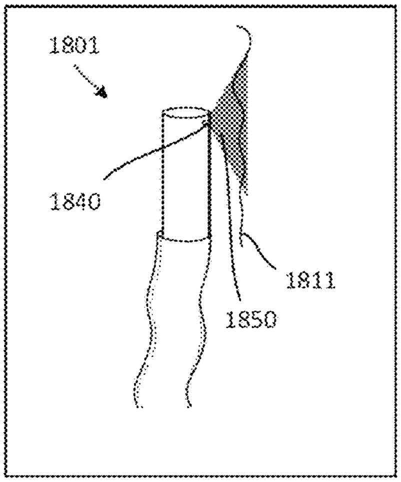
FIG. 10I illustrates an example of an endoscope having a side-facing imaging device to image a lumen wall area.

FIG. 10I illustrates an example of an endoscope 1801 having a side-facing imaging device 1840 having a vertical FOV 1850 to image a lumen 1811 wall area.

Figure 10J:
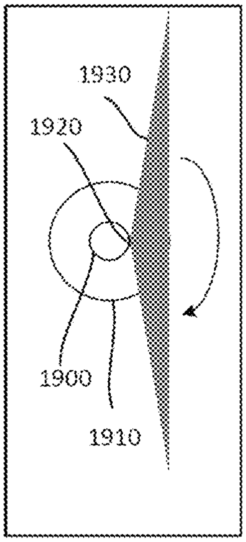
FIG. 10J, FIG. 10K, and FIG. 10L each illustrate examples of rotating either of the endoscopes illustrated in FIG. 10H or FIG. 10I to obtain a 360-degree view of a lumen wall.
Figure 10K:
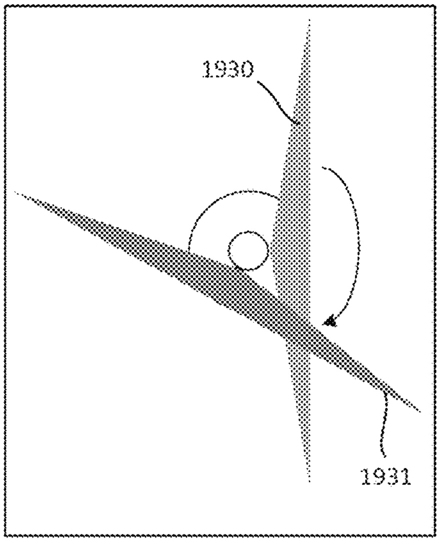
Figure 10L:
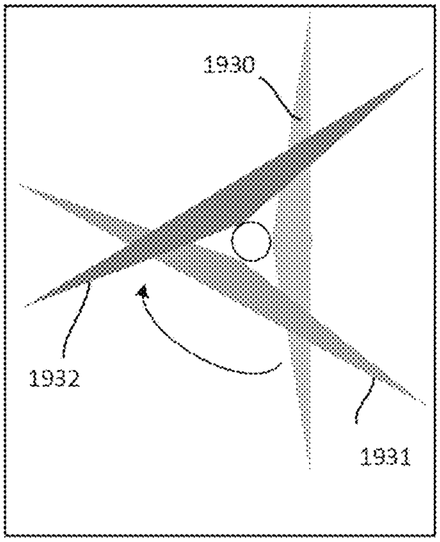

FIG. 10J, FIG. 10K, and FIG. 10L together illustrate twice rotating an endoscope 1900 having an imaging device 1920 with a 120-degree horizontal FOV, rotating each time by approximately 120 degrees, to obtain a 360-degree view of a lumen 1910 wall. For example, either of the endoscopes illustrated in FIG. 10H or FIG. 10I can have a 120-degree horizontal field of view in the respective stance illustrated. As can be seen by FIG. 10H-10L, vertical field of view is not necessarily equal to horizontal field of view.

Figure 10M:
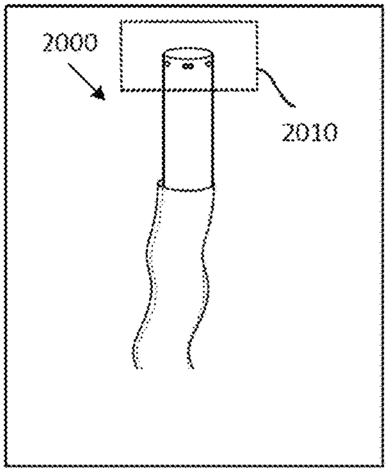
FIG. 10M illustrates an example of an endoscope having multiple imaging devices.

FIG. 10M illustrates an example of an endoscope 2000 having multiple imaging devices as shown in the dotted-line box 2010.

Figure 10N:
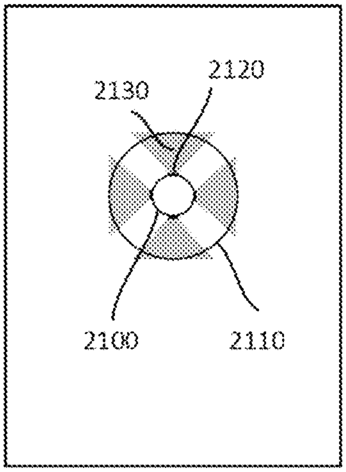
FIG. 10N and FIG. 10O illustrate examples of horizontal field of view for an imaging device such as the one illustrated in FIG. 10M.

FIG. 10N illustrates an example of an endoscope 2100 having four imaging devices 2120 (e.g., an endoscope similar to the endoscope 2000 illustrated in FIG. 10M) each with FOV 2130. Collectively, the FOVs 2130 of the four imaging devices 2120 do not provide full coverage of a lumen 2110 and the endoscope 2100 may need to be rotated to provide coverage sufficient for the purposes of the endoscopic procedure.

Figure 10O:
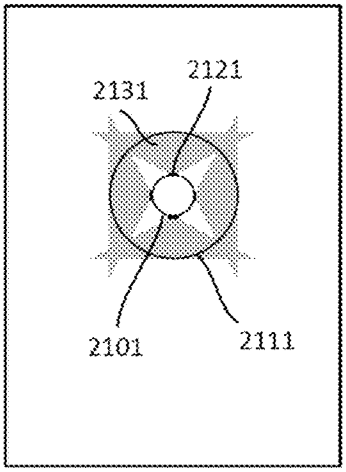

FIG. 10O illustrates an example of an endoscope 2101 having four imaging devices 2121 (e.g., an endoscope similar to the endoscope 2000 illustrated in FIG. 10M) each with FOV 2131. Collectively, the FOVs 2131 of the four imaging devices 2121 provide full coverage of a lumen 2111 and the endoscope 2101 may not need to be rotated to provide coverage sufficient for the purposes of the endoscopic procedure.

Figure 10P:
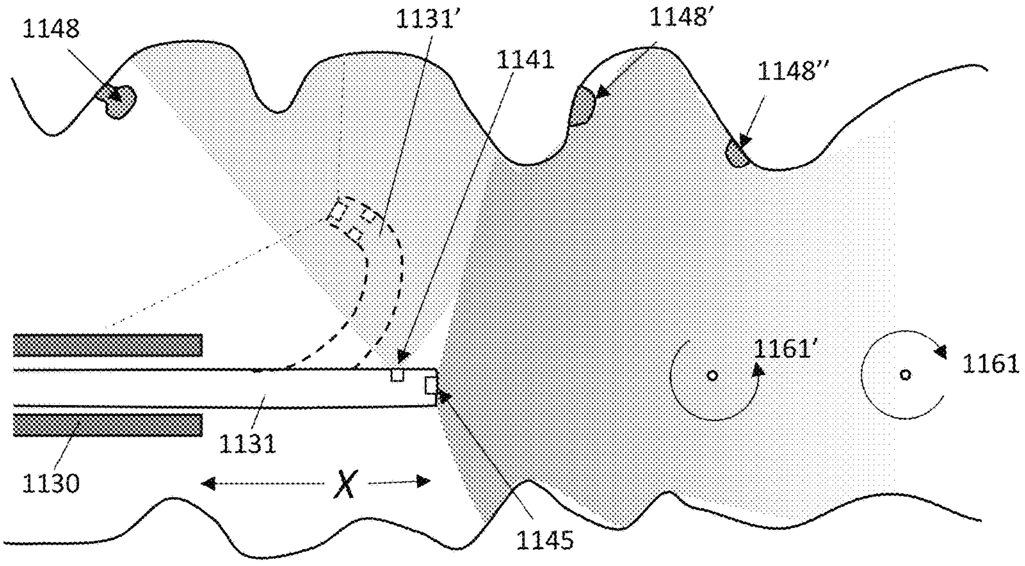
FIG. 10P illustrates examples of mapping-specific movements, including dither (including both axial or x axis motion in this figure, as well as rotational dither about a centerline), and articulation of the bending section and its torque or roll, that may be used to generate a full or nearly-full mapping of a lumen.

The tip may be steered in any appropriate manner, which may be matched to the location of the sensor(s), e.g., cameras, and the resulting fields of view. For example, FIG. 10P illustrates different tip movements of the inner elongate member 1131 (e.g., endoscope) within a lumen relative to an outer elongate member 1130 (e.g., overtube). In FIG. 10P, the outer elongate member 1130 is rigidized in the center of the vessel, and the inner elongate member (including a distal-facing camera 1145 and a side/lateral-facing camera 1141) is capable of being steered and "bent" or articulated from a linear configuration to a nearly fully retroflexed configuration. The amount of bending possible may be controlled by the distance that the second member is extended ("x") out of the lumen of the outer member. Thus, the more extended the inner (second) elongate member is, the more retroflexed it may become at maximum bending. Retroflex angles vary but can be as high as 220 degrees. The inner elongate member may also be rotated clockwise 1161 or counterclockwise 1161', either while linear or bent, allowing additional scanning of the lumen. Thus, the apparatuses described herein may control the wall angle of approach of the camera(s) on the elongate members. Thus the tip of the endoscope 1131 may be manipulated, in some cases automatically, manually or semi-automatically, to better view the lumen wall including any structures 1148, 1148', 1148" (e.g., lesions, such as polyps, etc.).

With manual endoscopes, back-end axial or rotational movements correspond poorly to distal end motions. In contrast, robotically controlled rigidizing systems may be configured so that axial and rotational movement of the endoscope is methodical, particularly for mapping, which may automate and perform multiple, rapid and repeated bending and rotating movements, and are configured to prevent or limit uncontrolled and/or undesirable motion of the endoscope, such as jumping and whipping, and the effects of looping and reductions. Torquing of an endoscope normally creates whipping of the end of the endoscope, leading to off-center movement and axial displacement that may prevent accurate mapping. The methods and apparatuses described herein may generally avoid reducing the lumen (e.g., colon) when withdrawing the endoscope by rigidizing the first elongate member and withdrawing the flexible second elongate member, the lumen proximal to the distal end is not reduced. Pulling the entire scope proximally in a typical endoscope results in reducing the lumen. Similarly, advancing a typical endoscope distally results in looping. Both looping and reducing is undesirable when mapping because they may alter the wall configuration and result in unpredictable lurching and jumping of the endoscope relative to the wall, making it difficult, if not impossible, to accurately and repeatedly and efficiently position the endoscope and therefore the camera(s) relative to the walls as is necessary for accurate and rapid mapping described herein.

In general, these methods and apparatuses may instead provide a controlled kinematic system to methodically interrogate the lumen and particularly the luminal walls. These methods may use rigidization of the overtube/endoscope pair to maintain a predictable and locked-in position between the camera(s) at the distal end region and the wall(s) of the lumen. This may enable the apparatus and method to include dithering, e.g., the purposeful commanded motion in which the cameras (e.g., the distal end region) is repeatedly moved over a range of movements, such as back and forth, typically over a relatively small distance/angle range (e.g., 1 mm to 20 mm, 1 mm to 15 mm, 1 mm to 10 mm, etc., or +/−170 degrees, +/−155 degrees, +/−140 degrees, +/−120 degrees, +/−130 degrees, +/−110 degrees, +/−90 degrees, +/−70 degrees, +/−60 degrees, etc.). This precise dither may provide repeated images that may be combined either before or during stitching to form the coverage map. It may also allow higher resolution images, and image averaging, subtraction, etc. and imaging the same regions in different wavelengths (visible light, UV, Near-IR, etc.). In general, the methods and apparatuses described herein may provide automated and precise control of positioning of the camera relative to the lumen in a manner that is not possible with traditional endoscopes. In some cases these apparatuses may use other modalities, such as Lidar, e.g., for shape recreation.

Image/Tissue Analysis

As mentioned, the apparatuses described herein may monitor and/or analyze images as they are being acquired in real- or near-real time and/or after the image have been collected (hours, days, years). This image analysis may be performed on all or some of the images, including images from the distal-facing camera(s) and/or the lateral-facing (side facing) camera(s). Image processing may identify regions of missing wall (e.g., where a region of the lumen wall is occluded). Image processing may identify regions of interest such as polyps or other lesions.

Any appropriate image analysis may be done. For example, to analyze images and identify features of interest, various techniques can be applied. Examples of techniques that may be used may include: edge detection, feature extraction, objection detection, color analysis, texture analysis, feature dimensions, and/or shape recognition. In some cases the vasculature may be identified and used for mapping, as described below. For example, edge detection may be performed using one or more algorithms such as Canny or Sobel to detect the boundaries of objects within an image by identifying sharp changes in pixel intensity. Feature Extraction may be performed including techniques like Scale-Invariant Feature Transform (SIFT) or Histogram of Oriented Gradients (HOG) identify key points, textures, or patterns that are invariant to scale and rotation. Object Detection may include machine learning (e.g., deep learning) models including but not limited Convolutional Neural Networks (CNNs) that are trained to recognize specific objects and may include the use of bounding boxes or segmentation masks to locate them in images. Color analysis may include histogram analysis or color segmentation that may be used to identify and distinguish areas based on color distribution. Texture Analysis may include techniques like Local Binary Patterns (LBP) analyze pixel patterns to capture texture details for classification or pattern recognition. Shape Recognition may include contour detection and shape matching algorithms detect the geometry of objects, useful for recognizing specific forms. In general, these techniques may help extract meaningful insights from images of the lumen.

Thus, any of these methods may be configured to detect regions of interest. Examples of regions of interest in the colon may include, but are not limited to: polyps, inflammation, ulcers, diverticula, tumors or masses, bleeding or hemorrhoids, strictures, and/or mucosal patterns (such as a "cobblestone" appearance).

In some examples a trained machine learning agent may be used. The machine learning agent may be referred to herein as a trained pattern matching agent, and this trained pattern matching agent may be an artificial intelligence agent. The machine learning agent may be a deep learning agent. In some examples, the trained pattern matching agent may be trained neural network. Any appropriate type of neural network may be used, including generative neural networks. The neural network may be one or more of: perceptron, feed forward neural network, multilayer perceptron, convolutional neural network, radial basis functional neural network, recurrent neural network, long short-term memory (LSTM), sequence to sequence model, modular neural network, etc. The trained machine learning agent may be trained using a training data set taken from mappings of 'healthy' patients.

In any of these methods and apparatuses a trained machine learning agent may be used to detect or otherwise identify one or more lesion (e.g., polyp, inflammation, etc.) from the images of the body lumen (e.g., colon). Regions of the one or more images including the detected/suspect region may be flagged (marked, etc.) for immediate or later review. Any of these methods and apparatuses may include marking, flagging or otherwise indicating in the images (or an index of the image that refers to one or more specific images), and/or a map (e.g., 2D or 3D image) an indicator of a lesion (e.g., text, symbol, code, image, etc.).

The methods and apparatuses described herein may also or alternatively provide relative locations of anatomical features and/or distance indexing.

Relative Location Within Lumen

The method and apparatuses descried herein may generally determine a relative or absolute location of the apparatus within the lumen. For example, any of these methods and apparatuses may include shape sensing and/or depth (e.g., insertion depth). One or more shape sensors may be incorporated into the apparatus (e.g., overtube, endoscope, etc., including inserted within a channel, e.g., working channel, of either the overtube or endoscope). For example, a colonoscope may include electromagnetic (EM) field detection components disposed at multiple positions along its length where the EM field detection components each detect an EM field produced by an EM field generator such that differences in the strength and/or polarity of the EM field detected at each location provides an indication of a present shape of the colonoscope. The EM field generator may be external or internal. The EM field generator may be composed of multiple generators positioned internally or externally. In one embodiment, each EM field generator is matched with an EM field detection component. Alternatively or additionally, the apparatus may include an optical shape sensor, including a fiber optic shape sensor. For example one or more optical sensors may be positioned along a length of the endoscope. One such optical sensor includes an optical fiber or fibers, where at least one optical fiber can include a Bragg grating (FBG), or multiple FBGs arranged discretely, contiguously, continuously, or in another arrangement along or within the fiber. Another example of shape sensing incorporates inertial measurement units (IMUs) along the length of the colonoscope, and shape of the colonoscope is calculated based on motion of the colonoscope.

Figure 11A:
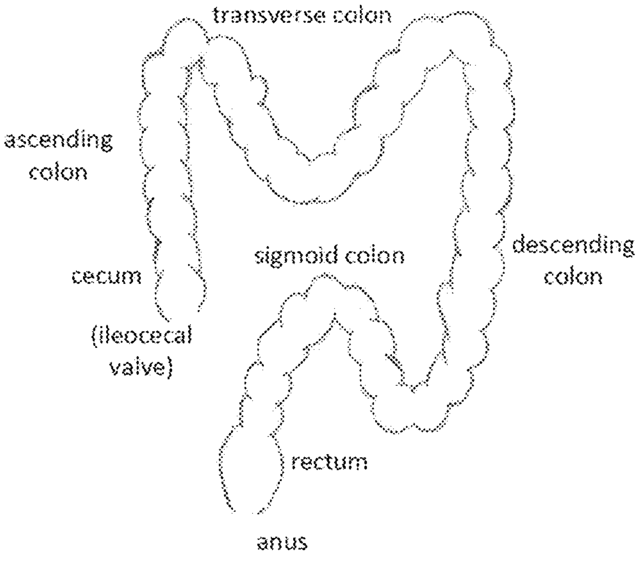
FIGS. 11A and 11B illustrates a 2D representation of a generic colon, including named regions (FIG. 11A) and zones (FIG. 11B).

FIG. 11A illustrates a simplistic outline of a colon, including the anus, rectum, sigmoid colon, descending colon, transverse colon, ascending colon, and cecum. The colon ends at the ileocecal valve (not shown) between the colon and the lower intestine. A colonoscopy using a traditional commercial manual colonoscope may be able to reach from the anus to the cecum, depending on the state and tortuosity of the colon of the individual receiving the colonoscopy. In contrast, due to the stability it provides, a DR colonoscope can consistently reach the cecum and can pass through the ileocecal valve and into the lower intestine as far as the length of the colonoscope will allow.

Figure 11B:
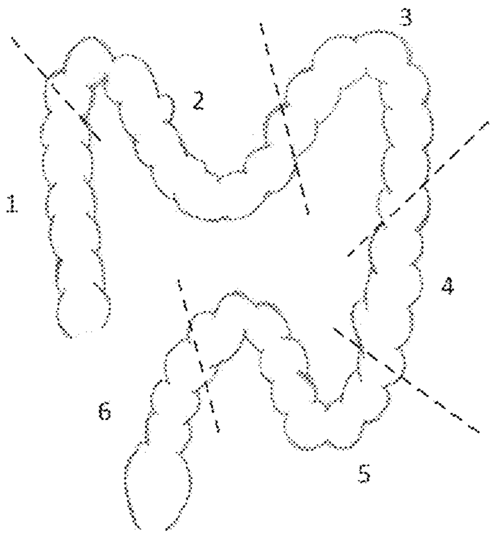

FIG. 11B illustrates labeling the colon in six zones labeled zones 1-6 (corresponding roughly to the cecum, ascending colon, transverse colon, descending colon, sigmoid colon, and rectum, respectively). Some of these portions of the colon have unique characteristics with respect to the other portions, and therefore it can be beneficial to set different parameters of automated interrogation for one or more of the six zones as compared to one or more of the other zones. Such parameters may include speed of axial movement, speed of rotation, pitch of rotation, number of images captured, imaging angles, etc. These approximate regions may be identified by landmarks or characteristics known to those of skill in interpreting colonoscopies. In some cases the apparatus or method may include identifying which region (1-6) the apparatus is positioned within. In some cases the method or apparatus may include outputting a 2D image (e.g., a 2D map) that is specific to the particular patient or that is generic (as shown in FIGS. 11A-11B). The patient-specific 2D map (which may be referred to as a customized map) may be fully customized to correspond to the sizes and distances within the patient's actual colon. Alternatively or additionally the patient-specific 2D map may be a stock (e.g., general) image selected from a library or other database of colon images that most closely corresponds to the patient. In some cases a general 2D map of the colon may be modified (by scaling portions, e.g., regions 1-6) to more closely represent the lengths and/or relative positions of the regions (e.g., 1-6) of a particular patient's colon. The 2D map in these example may be referred to as an overview map of the patient's colon. Although these examples are specific to colon mapping, similar techniques may be used for other body regions, including any portion of the gastrointestinal tract (mouth, esophagus, stomach, small intestines, large intestines, etc.) or region of the GI tract (e.g., upper GI, lower GI), airways (lungs, bronchi, trachea, etc.), biliary tract, urethera, ureters, circulatory system (e.g., arteries, veins, chambers of the heart, etc.).

FIGS. 11C-11N illustrates one example of a method of controlling a nested dynamically rigidizing apparatus with sufficient precision to interrogate the wall of the colon through the six zones labeled in FIG. 11B. FIGS. 11C-11N are laid out in a sequence to provide a visualization of the colonoscope as it traverses the colon. In an embodiment, such an illustration of the colon may be provided in real time to the physician, with the position of the colonoscope within the colon shown overlaid on the 2D map (representation) of a colon to indicate progression of the endoscope (e.g., colonoscope) through the colon. The apparatus or method may identify the present position of the colonoscope within the colon and may provide instructions to a display device to show or update the position of the colonoscope on the illustration of the colon as the colonoscope moves.

As mentioned above, in some examples the colonoscope includes position and/or shape sensing so that, along with feedback from other sensors, memory of commanded motions, and/or a kinematic model of the system, the system can know the approximate present position of the colonoscope. In an embodiment, the apparatus may include software that recognizes the zone of the colon where the colonoscope is presently positioned so that, along with feedback from sensors, memory of commanded motions, and/or a kinematic model of the system, the system can know the approximate present position of the colonoscope. For example, the position within the colon may be determined by one or more machine learning agents that may recognize the position based on images from the one or more cameras and/or based on the insertion length within the lumen and/or the shape of the colonoscope and/or overtube. In some examples the apparatus or method may recognize where the colonoscope is in the colon presently based on a comparison of presently-received image data to image data stored in a memory. In any of these methods and apparatuses, a combination of feedback from sensors, memory of commanded motions, a kinematic model of the system, recognition of the colon zone, and/or image data stored in a memory may be used to identify a present location of the colonoscope within the colon.

Figure 11C:
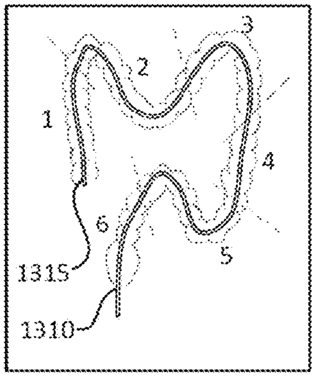
FIGS. 11C-11N schematically illustrate an example of an automated lumen wall interrogation technique that may be used during a robotic colonoscopic mapping procedure as described herein.

In panel FIG. 11C, a nested assembly of the overtube and endoscope 1310 is illustrated as having been advanced through zones 6, 5, 4, 3, 2, and 1 such that a distal tip 1315 of the apparatus 1310 is in the cecum. In some examples an automatic withdrawal interrogation may be initiated, e.g., to map (or further map) the colon, as described herein. In some cases this mapping may fill in regions that were not completely mapped during insertion. In some examples mapping is performed only (or primarily) during withdrawal. Mapping may be automatic (e.g., during a fully automated withdrawal) and/or semi-automatic (e.g., assisted by the user during operation), or manually.

Figure 11D:
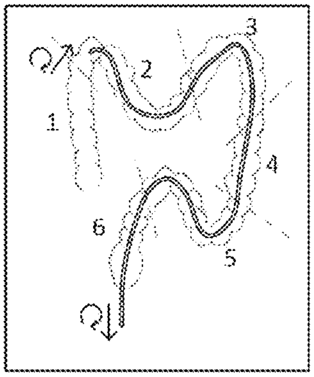

FIG. 11D shows that, as the nested assembly of the overtube and endoscope 1310 is pulled and rotated by the system from a location exterior to the anus, the distal tip 1315 (e.g., of the endoscope) of the apparatus 1310 correspondingly is controllably rotated and withdrawn into zone 2 as forces applied from the location exterior to the anus are translated to controllable forces at the distal tip 1315.

Figure 11E:
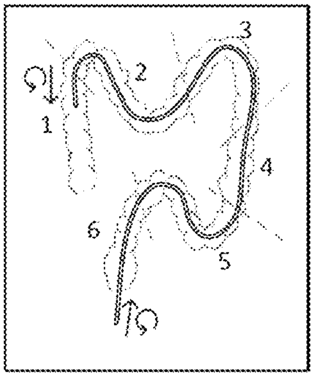

FIG. 11E provides an example of dithering during the interrogation, as described herein. Rotation direction of the nested assembly of endoscope may be reversed as the distal tip 1315 is advanced back into zone 1 by an overlap amount so that the overlap amount of the colon is imaged with both a counter-clockwise rotation and a clockwise rotation.

Figure 11F:
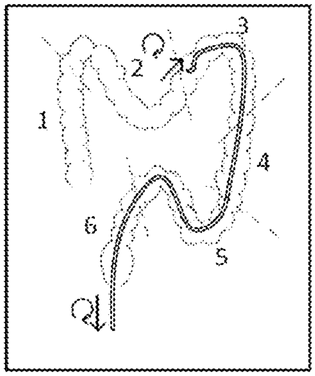

FIG. 11F illustrates continued dithering in the interrogation, with the nested assembly of the overtube and endoscope 1310 reversing axial and rotation directions and being withdrawn into zone 3.

Figure 11G:
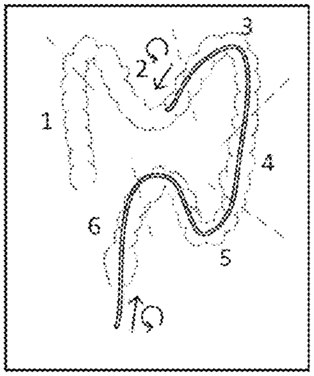
Figure 11H:
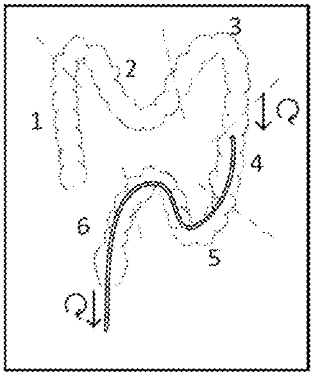
Figure 11I:
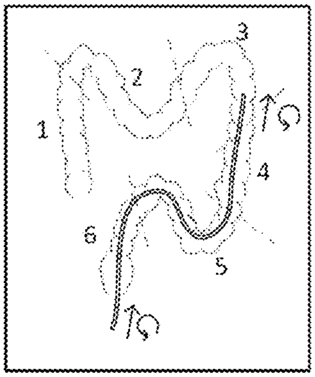
Figure 11J:
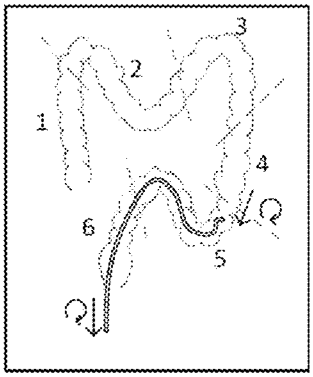
Figure 11K:
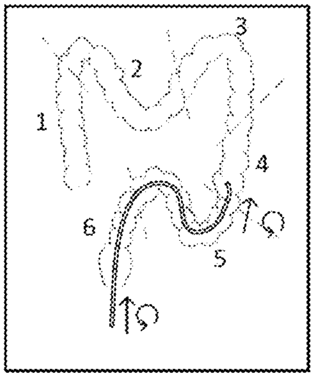
Figure 11L:
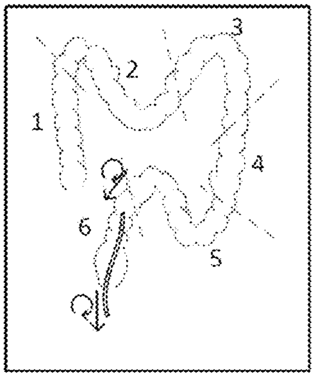
Figure 11M:
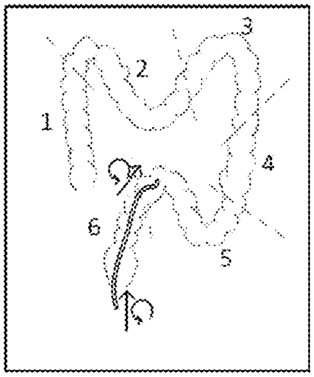

FIG. 11G illustrates continued dithering in the interrogation, with the nested assembly of the overtube and endoscope 1310 reversing axial and rotation directions and being advanced by an overlap amount back into zone 2.

Figure 11N:
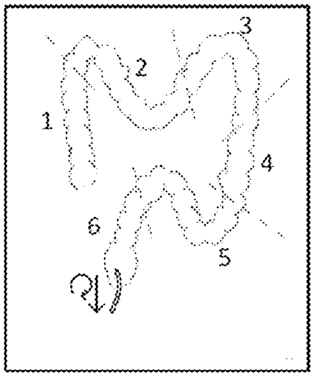

FIGS. 11H-11N illustrate continued interrogation, withdrawing the nested assembly of the overtube and endoscope 1310 into a zone not yet imaged, advancing back into the previous zone, withdrawing into a zone not yet imaged, advancing back into the previous zone, and so forth until the nested assembly of the overtube and endoscope 1310 is ready to be removed from the colon entirely (e.g., FIG. 11N). During the axial dithering, the nested assembly of the overtube and endoscope 1310 is rotationally dithered, reversing direction at every axial reversal.

In variations including a multiple side-facing cameras, rotation may not be needed.

The highly-controllable axial and rotational movement of a colonoscope (e.g., as described with respect to FIGS. 11C-11N) is not possible with a traditional commercial manual colonoscope where forces exerted from a location exterior to the anus cannot reliably be translated to controlled forces within the colon. Rather, in a traditional commercial manual colonoscope, forces exerted on the colonoscope from a location exterior to the anus translate to unpredictable motion along the length of the colonoscope, and the unpredictability increases as the colonoscope is advanced through the tortuosity of the colon. In contrast, a nested assembly of the overtube and endoscope may provide for controllable and predictable movement of the apparatus 1310 and the distal tip 1315 along the length of the tortuous colon all the way to the cecum.

Dithering

In general, the methods and apparatuses described herein may be particularly adapted to scanning by taking advantage of the nested assembly of the rigidizing overtube and endoscope. This configuration may uniquely allow advantages for smoothly and more completely imaging within a lumen, particularly a tortious lumen such as the colon, by allowing repeated, in some cases oscillating, axial and/or rotational movements of the endoscope referred to herein as dithering. Dithering of the tip of the endoscope, including the one or more cameras may be used alone or in combination with other maneuvers to image the lumen, and in particular the walls of the lumen.

For example, dithering may include axial movement (advancement) of the tip of the endoscope relative to the overtube while the overtube remains rigid and the endoscope is flexible. The axial movement may be a relatively small "inspection length" (as described below in reference to FIG. 12B), e.g., between 0.1 mm and 50 mm (e.g., between 1 mm and 50 mm, between 1 mm and 40 mm, between 1 mm and 30 mm, between 1 mm and 20 mm, between 1 mm and 15 mm, between 1 mm and 10 mm, between 1 mm and 8 mm, etc.). The tip may be cycled through distal then proximal movements. Dithering may also or alternatively include rotational movements (clockwise/counterclockwise). A full cycle of dithering may be performed so that the tip start and finishes in the same location (axial and/or rotational location) and/or dithering may be performed as the tip is advanced, e.g., so that the tip is reciprocating axially (and/or rotationally) as it is advanced over a region of the lumen.

Dithering may include rotational movement, e.g., rotating the endoscope clockwise then counterclockwise (or vice versa). The rotation may be any appropriate angle (e.g., +30°, 45°, 60°, 75°, 90°, 105°, 120°, 180°, 360°, 450°, etc.). Thus, the endoscope may be rolled within the overtube.

Figure 12A:
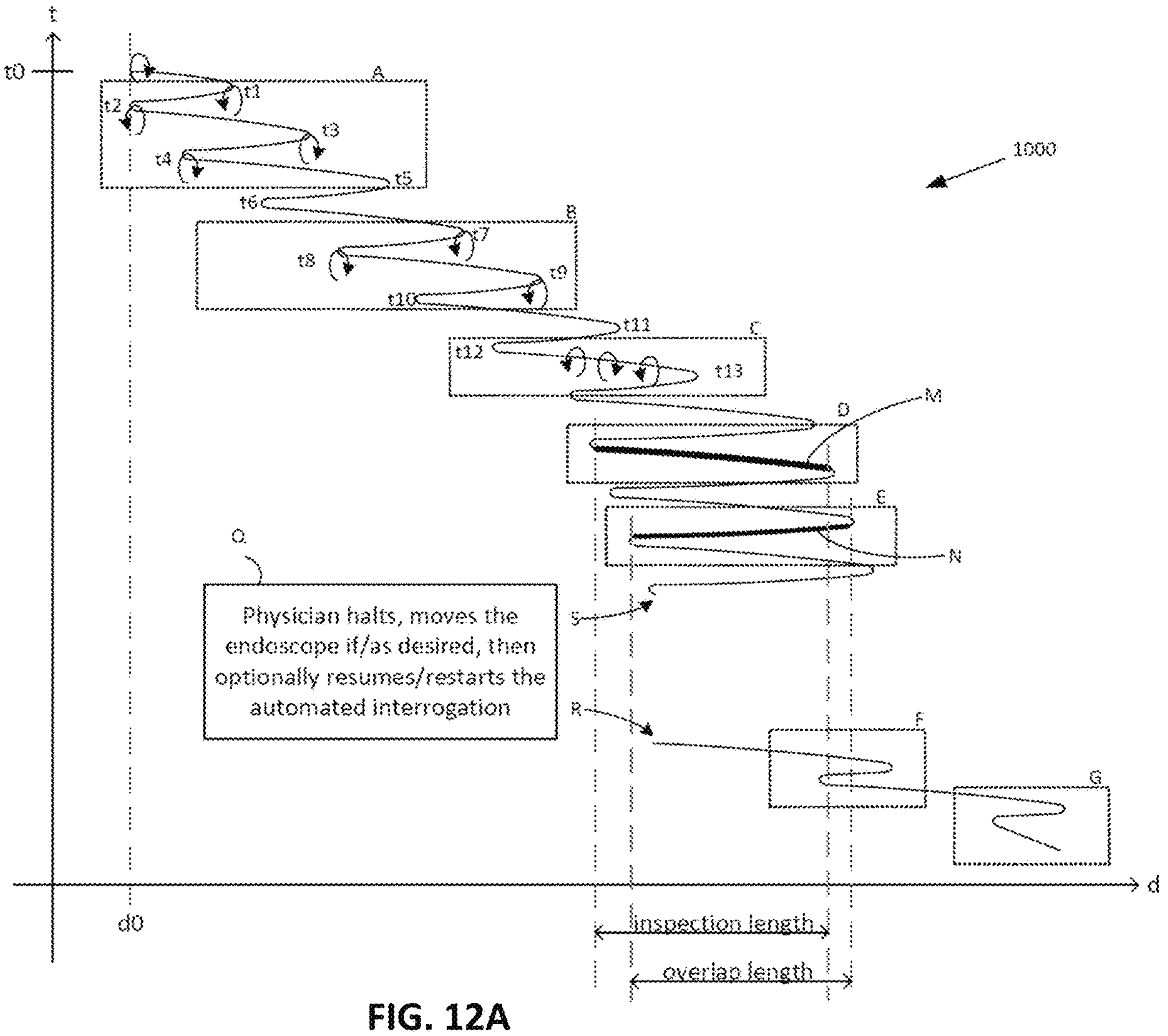
FIG. 12A illustrates a plot of an automated lumen wall interrogation technique that may be used during a robotic endoscopic procedure.

FIG. 12A illustrates an example of dithering, which may include both axial and rotational movements. In FIG. 12A, the tip of the endoscope including the one or more cameras may be controlled to provide alternating withdrawal and advancement interrogation. Dithering techniques such as illustrated in FIG. 12A or similar are not limited to colonoscopy.

FIG. 12A shows a graph 1000 that plots time 't' (vertical axis) against distance of movement 'd' (horizontal axis) of a distal tip of an endoscope starting from an initial position of the endoscope within a lumen. A time 't0' indicates when automated interrogation is initiated and a position 'd0' indicates a position of the endoscope distal tip at time 't0'. The position 'd0' may be at the endoscopic procedure entry point (e.g., anus in a colonoscopy) or at a point between the entry point and a destination point, with distance of movement 'd' referencing advancement into the lumen. Alternatively, the position 'd0' may be at a position within the lumen at any point away from the entry point of the endoscopic procedure (e.g., at a point along the large intestine or small intestine away from the anus entry point in a colonoscopy), with distance of movement 'd' referencing movement towards the entry point (e.g., anus in a colonoscopy). For purposes of the example of FIG. 12A, interrogation is described as being performed during withdrawal of the nested apparatus from the position 'd0' in the lumen towards a procedure entry point (e.g., anus in a colonoscopy). However, such automated interrogation could be performed during advancement, withdrawal, or during both advancement and withdrawal. Several interrogation techniques are illustrated in FIG. 12A by way of example without limitation, and other interrogation techniques are also within the scope of this disclosure.

The interrogation can begin by retracting the overtube to expose a full reciprocation distance of the endoscope, or the interrogation can begin at the present extension of the endoscope with respect to the overtube. While interrogating, the overtube is rigidized and the endoscope is relaxed (e.g., in a flexible state). As needed during the interrogation, such as when the endoscope is not sufficiently extended from the overtube to allow movement as required for the automated interrogation, the overtube may be retracted to expose the reciprocation distance of the endoscope. Shape copy techniques may be used to advance and/or withdrawal the nested apparatus within the lumen.

A first interrogation technique is shown in FIG. 12A between times t1-t5 in the dashed-line box labeled 'A' where the endoscope is moved in the advancement direction (forward) between t1 and t2 with rotation shown by an arced arrow in a first direction (e.g., counterclockwise), then the endoscope is moved in the withdrawal direction (backward) between t2 and t3 by an amount approximately equal to the inspection distance and with no change in the rotation direction. The endoscope is then moved in the forward direction between t3 and t4 by an amount approximately equal to a defined overlap distance with rotation direction switched to the opposite direction (e.g., clockwise). At t4, rotation direction is maintained and axial direction is reversed. At t5, both rotation direction and axial direction are reversed. In this technique, each length of the lumen is inspected at least three times and in both clockwise and counter-clockwise directions. In this technique, a length of the lumen around the axial reversal points (e.g., at t3) is inspected four times.

A second interrogation technique is shown in FIG. 12A between times t7-t9 in the dashed-line box labeled 'B' in which axial dithering is similar to the first interrogation technique. In this second interrogation technique, rotation direction is reversed at every axial direction reversal (e.g., at t7, t8, and t9).

A third interrogation technique is shown in FIG. 12A between times t12-t13 in the dashed-line box labeled 'C' where rotational direction is varied (rotational dithering) as the endoscope is moved in an axial direction (e.g., backward or forward).

A dashed-line box labeled D in FIG. 12A highlights, using a thickened line 'M', an example of movement in amount approximately equal to a defined inspection length; a dashed-line box labeled E highlights, using a thickened line 'N', an example of movement in amount approximately equal to a defined overlap length. As can be seen by comparing boxes A-E in FIG. 12A, inspection length and/or overlap length may be varied during an automated interrogation, in accordance with system programming and/or in accordance with user input.

Figure 12B:
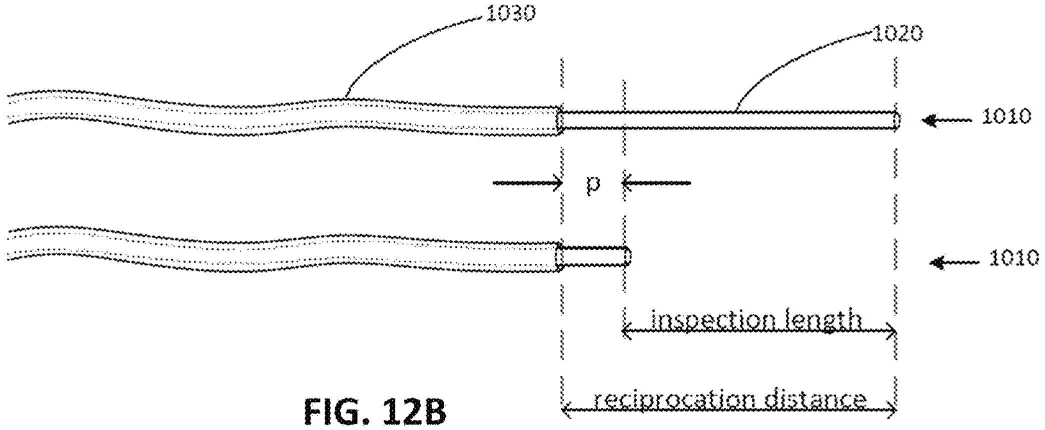
FIG. 12B illustrates an example of an endoscope and overtube that may be used for the technique illustrated in FIG. 12A.

FIG. 12B illustrates an example of an endoscopic system 1010 that may be used for the technique illustrated in FIG. 12A. The nested assembly 1010 includes an endoscope 1020 and an overtube 1030. The endoscope 1020 is shown extended out of the overtube 1030 to its reciprocation distance and is also shown withdrawn within the overtube 1030 so that only a length 'p' of the endoscope 1020 extends from the overtube 1030. The length 'p' represents approximately a length where the overtube 1030 begins to hamper bending of the endoscope 1020. Although interrogation can occur if the endoscope 1020 extends less than the length 'p' from the overtube 1030, for the example of FIG. 12B the inspection length is defined to be less than the reciprocation distance by the amount 'p'. In some embodiments, the inspection length may be equal to the reciprocation distance.

As noted in text box 'Q' in FIG. 12A, at any time during an automated interrogation, the physician may temporarily suspend or permanently stop the ongoing interrogation, as illustrated by way of example by an 'S' indicating a stop/suspend. If suspended, the physician may subsequently resume the interrogation at the point in the lumen that the interrogation was suspended as illustrated by way of example by an 'R' indicating a resume/restart. For resume, the endoscope and overtube are moved to their last positions prior to the suspending of the interrogation and continue to complete the interrogation approximately as it would have been completed if not suspended. Alternatively, for restart, the initial position do would be reset to the position at which the interrogation was restarted.

Any of these methods and apparatuses may include a rewind feature, such that commanded movements are stored in memory for a time, such as 5 seconds (secs), 10 secs, 30 secs, 1 minute (min), 5 minutes, 30 minutes, or other time period. When a rewind input is received from the system or a user, the sequence of movements that was stored in the memory is retrieved and the sequence reversed.

A dashed-line box labeled F in FIG. 12A illustrates that the overlap length may be much smaller than the inspection length. A dashed-line box labeled G in FIG. 12A illustrates that pitch of rotation may be different or varied during parts of the auto interrogation as controlled by the system or when modified by user input.

In an embodiment of the example of FIG. 12A, the apparatus has an arbitrarily-defined reciprocation distance of 40 cm, an arbitrarily-defined inspection length of 30 cm, and an arbitrarily-defined overlap length of 10 cm. The desired end point of the endoscopic procedure can be approximately 1.5 m (150 cm) or more from the entry point depending on the person. Assuming 1.5 m of lumen and the 30 cm inspection length, the length of the lumen can be interrogated in five interrogation passes (1.5 m/30 cm). In a realistic situation in an individual's body, with a 30 cm inspection length, the number of complete interrogation passes may be 5 passes with at least an additional partial interrogation pass.

Control of Movements

The methods and apparatuses described herein may be configured for automatic, manual or semi-automatic control of the mapping, including pre-setting and/or adjusting (before and/or during operation) of the movement parameters, including dithering, advancing, withdrawing, etc. In general, these methods and apparatuses may including one or more inputs, including user-controlled inputs, for controlling and/or adjusting operation of the apparatus during, before or after mapping.

For example, in some embodiments, reciprocation distance, inspection length, overlap length, and/or rotation pitch may be input or modified prior to initiating auto-interrogation, during a halt in auto-interrogation, or during auto-interrogation. In some embodiments, axial and/or rotational speed may be input or modified prior to initiating auto-interrogation, during a halt in auto-interrogation, or during auto-interrogation.

Rotation during an interrogation could occur either at discrete locations along the withdrawal path, or rotation could occur continuously or semi-continuously along the rotation path. An example of discrete locations is stopping axial movement at a position, capturing images at that position, moving to another axial position, and capturing images at the other position. An example of continuous rotation is approximately constant angular speed rotation during approximately constant linear speed motion of the endoscope such that the motion of the imaging device defines approximately a spiral path. Another example of continuous rotation is constant or variable rotation as the endoscope dithers axially (alternating forward and backward) during withdrawal. An example of semi-continuous rotation is dithering rotationally (e.g., alternating clockwise and counterclockwise) during forward motion and/or backward motion of the endoscope.

The controllability of axial and/or rotational movement (e.g., dithering) needed to provide any of the interrogation techniques described above is not possible with a traditional commercial manual endoscope.

Additionally, the precise torsional rotational capability provided by the apparatus allows for a reduced number of side imaging devices (e.g., cameras) if side imaging devices are used. In a traditional commercial manual endoscope, if a side imaging device had a 120-degree field of view (FOV), at least three side imaging devices would be required on the manual endoscope to view and image the inner circumference of the lumen because the lack of control using the manual endoscope would not permit the physician to controllably roll the endoscope for circumferential viewing and imaging. In contrast, with the controllable rotation provided by these apparatuses, only one side imaging device would be needed to image the inner circumference of the lumen. An automated interrogation such as any of the interrogation techniques described herein may have user input capability.

For example, a user may temporarily or permanently halt an automated procedure.

During a temporary halt, a user may, for example, control the robotic system to look more closely at an area under interrogation, including using axial and/or rotational movement to approach and/or inspect an area more closely, or use a zoom-in capability of the imaging system.

The system may include a user access device for adjusting an interrogation while it is ongoing. For example, a user access device may include a knob, dial, lever, slider, rocker switch, or other device (which may be physical or may be a virtual representation), or a combination of devices, to control axial motion direction, radial motion direction, speed of travel axially, pitch, and/or speed of travel radially.

A user access device may include a touchscreen with a representation of the lumen or a representation of the view provided by the imaging device, and the user can indicate on the touchscreen a location to which the user wishes the endoscope to travel, or to which the user wishes overtube/endoscope to travel using shape copy as needed. The system could then auto-navigate to the entered location.

A user access device may recognize verbal input. Verbal inputs could include simple or complex commands such as "Start", "Stop", "Forward", "Speed 6", "Reverse Speed 3", "Faster", "Slower", "Half speed", "Crawl", or other commands, or other sounds (e.g., a whistled note or sequence of notes). Verbal inputs could include phrases or sentences to be interpreted by the system, such as "reinterrogate previous zone and if an irregularity is found, direct the forward-looking imaging device to face the irregularity head-on". Intelligent software (known sometimes as artificial intelligence) may interpret such phrases or sentences based on a model trained for robotic endoscopic procedures.

In an embodiment, a radial dial may be rotated clockwise to axially move the endoscope and/or overtube one direction (forward or backward) and rotated counter-clockwise to axially move the opposite direction. A mid-position of the dial may be neutral (neither forward nor backward axial movement). Speed of movement could be controlled by rotating the dial more or less, so that dial rotation to a maximum detent would represent maximum speed with decreasing motion as the rotation approached the dial mid-position (neutral).

In some examples, a rotational potentiometer ("pot") controls both speed and direction. Such pot could be in the form of a knob or a wheel. When the pot is in a neutral position (e.g., at a middle point, or at a predefined or user selected detent position) there is no movement. As the pot is rotated in one direction (e.g., clockwise for a knob or forward for a wheel) the system progresses through its routines, and progression becomes faster as the pot is rotated farther. When the pot is rotated in the opposite direction (e.g., counterclockwise for a knob or backward for a wheel), the recent activities are performed in reverse (rewind) until the pot is returned to or through the middle position, and progression in reverse becomes faster as the pot is rotated farther away from the neutral position.

In an embodiment, a slider controls both speed and direction. When the slider is in a neutral position (e.g., at a middle point, or at a predefined or user selected detent position) there is no movement. As the slider is moved in one direction (e.g., forward, sideways, or other direction depending on placement of the slider) the system progresses through its routines, and progression becomes faster as the slider is moved farther. When the slider is moved in the opposite direction, the recent activities are performed in reverse (rewind) until the slider is returned to or through the middle position, and progression in reverse becomes faster as the slider is moved farther away from the neutral position. In an embodiment, the slider is a virtual representation on a user input device.

In an embodiment, speed and direction can be controlled using a touchpad where motion of one or more fingertips on the touchpad directs speed and movement of the endoscope axially and rotationally. When the touchpad is not being touched, there is no movement of the endoscope. Rotational direction can be controlled by moving a finger across the touchpad in an arc motion in the direction of desired rotational movement; if enabled, rotational speed can be controlled by an increase in speed of the finger movement. Axial direction can be controlled by moving a finger in approximately a line across the touchpad, the line being drawn away from the user for forward and toward the user for backward and the finger travel following a perimeter region of the touchpad and back to moving in a line to continue axial motion; if enabled, axial speed can be controlled by an increase in speed of finger movement. Two or more fingers can be moved on the touchpad to control other actions. For example, two fingers moving in a circle may control pitch of a spiral motion, two fingers moving apart from each other may control advancement of the endoscope out of the overtube and the fingers moving toward each other may control retraction of the endoscope into the overtube, tapping of three fingers may initiate performing recent activities in reverse (rewind) until the three fingers are tapped again, etc. The foregoing are a just a few examples of use of a touchpad for controlling the endoscope and/or overtube. Numerous finger and/or hand touches or movements can be mapped to defined activities, either predefined or defined by the user.

The ability to perform functions in reverse (rewind) as described above can be a useful tool in a physician's set of tools. For example, if the physician halts an automated procedure to move the endoscope for closer viewing of an area and then treats the area, it may be quite difficult to identify where the automated procedure was halted; the physician can control the system to perform the movement functions in reverse and return to where the procedure was halted or to a previous (or subsequent) point and continue with the automated procedure. Effectively performing functions in reverse is highly enabled by a robotic system, particularly one that utilizes a nested configuration.

The control represented by the examples of user input above are not possible using a traditional commercial manual endoscope. A robotically driven DR system can provide the user with lumen wall interrogation at a level not feasible with a traditional commercial manual endoscope.

Image Stitching

Figure 13A:
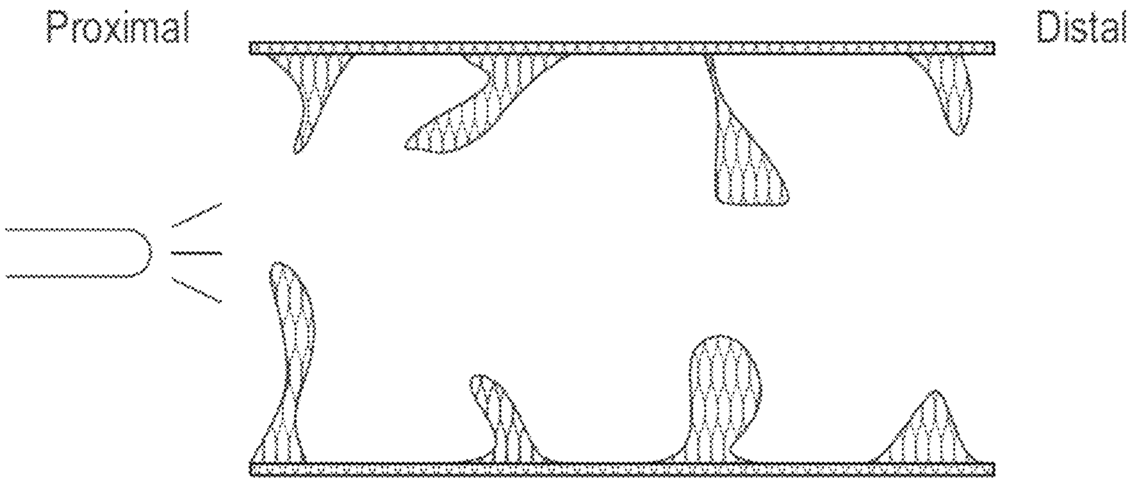
FIG. 13A shows another example of a distal end region of a rigidizing endoscope that may be used for mapping a body lumen (e.g., colon with haustral folds) as described herein.

In general, these apparatuses and methods may combine images, either raw images or processed images, from the one or more cameras in order to form the coverage map or 3D model. For example FIG. 13A shows an illustration of an apparatus as described herein within a lumen of a body (e.g., colon) showing the irregular shape of a section through the lumen, including haustral folds, and regions of interest (e.g., polyps). The camera(s) on the apparatus may take images from the posterior-directed camera and/or one or more laterally-directed cameras, as described herein. In some cases, these images may be combined to form a map of the lumen. In some cases the methods described herein may select all or some of the images (or a combined version of the images) that may be indexed and maintained with as a reference to a region of the lumen that may be provided when the region is selected, e.g., from a 2D or 3D representation of the lumen.

Figure 13B:
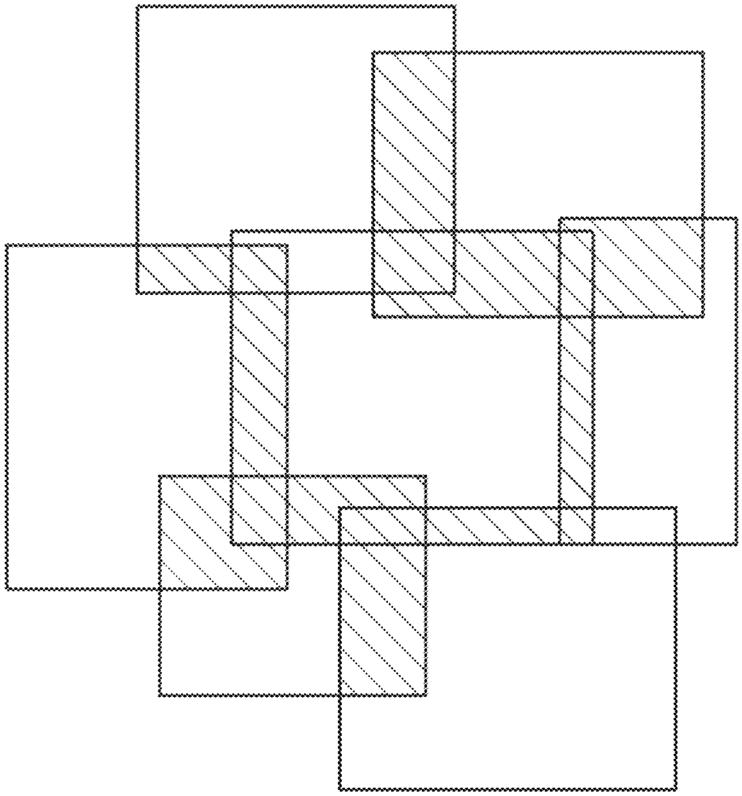
FIG. 13B schematically illustrates one example of a method of combining (e.g., stitching) a plurality of images taken with an endoscope within a body lumen. Overlapping regions may be aligned. Stitching may be enabled by a large number of pictures with significant overlap and a plethora of surface features.

Thus, in any of the methods described herein, the images (2D images) may be combined or "stitched" together to form a map. FIG. 13B schematically illustrates one example of image stitching. Image stitching may utilize relationships across images, including unique anatomical features that appear in one image and then appear in an adjacent other image. In some cases it may be beneficial to use the vascular (e.g., veins) landmarks that may be visible, particularly under certain wavelengths of light (e.g., near-IR). The images may then be aligned and aligned images are then tied together as an image map that grows with those related features as new images are added.

Figure 14A:
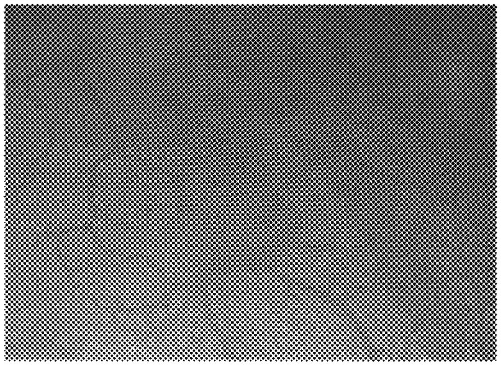
FIG. 14A, FIG. 14B, FIG. 14C and FIG. 14D illustrate creating a lumen map using techniques such as described herein.
Figure 14B:
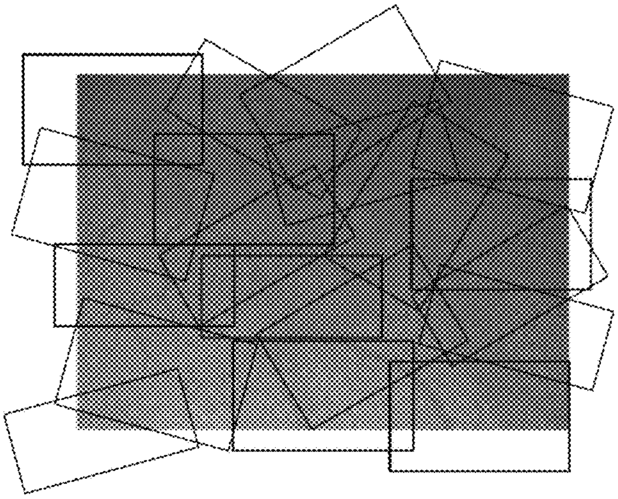
Figure 14C:
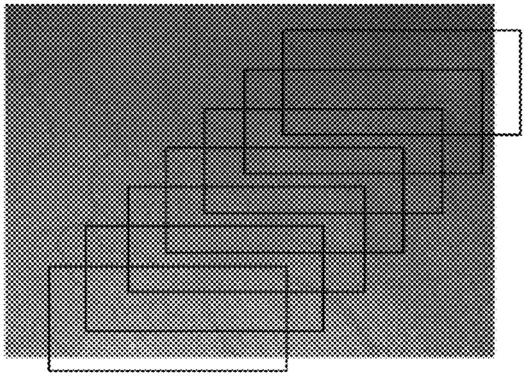
Figure 14D:
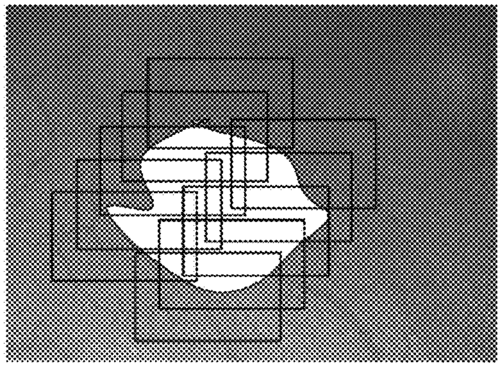

FIG. 14A-FIG. 14D illustrate examples of stitching images to create a lumen map using techniques such as described herein. FIG. 14A is a depiction of a lumen to be mapped. FIG. 14B illustrates the use of images from multiple perspectives and possibly multiple imaging devices to create a lumen map over time. For example, each time or sometimes when the endoscope is adjacent to a portion of the lumen for which an image has not been obtained, the system causes an image to be captured to stitch with other images using registration based on common recognized features. FIG. 14C illustrates how the use of one imaging device being moved in a somewhat spiral pattern at a given pitch can capture images during axial movement in one direction as the lumen wall is interrogated. If desired, by axial dithering a next sequence of images can be captured in the opposite axial direction. Additionally, the endoscope can be rotationally dithered to image more of the lumen or to obtain additional perspectives or more depth perception. FIG. 14D illustrates identifying an unimaged area in an existing lumen map and defining a pattern of endoscope movement to capture images that can be registered to the existing lumen map using recognized features of the lumen and the existing lumen map that are common to both.

In any of the images taken by the apparatus, the image may include information (e.g., metadata) with one or more camera parameters, including the relative position of the camera (e.g., the position and/or orientation of the camera based on the position and/or orientation of the tip. The position and/or orientation may include the depth of the endoscope (e.g., as encoded by the system, from one or more sensors/encoders on the proximal end of endoscope), the rotational position (e.g., roll information), sensor data on the tip of the endoscope (e.g., inertial measurements (IMUs), accelerometers, etc.), shape sensors data, timing information, etc. This data, including position and/or orientation information may be used as an index of the images. In some cases representative images may be selected and may be stored in a subset of images used to represent the lumen. For example, either during or after the procedure (e.g., colonoscopy), the patient-specific mapping data may be examined by a user (e.g., doctor, clinician, etc.), by selecting a position and/or orientation, e.g., from a two-dimensional (2D) or three-dimensional (3D) image of the lumen (e.g., colon) and displaying one or more of the representative images corresponding to the selected location and/or filed of view. For example, the user may select a position (and optionally an orientation, e.g., forward looking down the lumen, looking sideways at various angular increments (e.g., 10 degree, 15 degrees, 20 degrees, 30 degrees, 45 degrees, 90 degrees, etc.), backwards looking, etc.) and the apparatus or method may identify a representative image taken from the mapping dataset (or selected from the mapping dataset) from the point of view within the lumen of the selected position (and optionally orientation). A user interface may allow the user to change the selected location and/or orientation so that other representative images are shown.

In some cases, the representative images may be the actual collected images. In some examples the representative images may be formed by combining (e.g., stitching) multiple images. In some cases the representative images may be processed (e.g., light balanced, filtered, sharpened, etc.). The database of representative images may include an additional index of images from the actual and/or representative image indicating a lesion (e.g., polyp) is likely present.

Figure 15A:
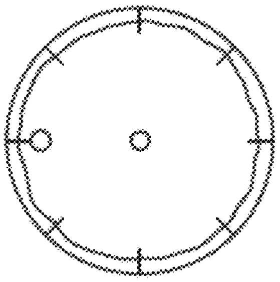
FIGS. 15A-15C illustrate a method of manipulating a coverage map generated for the tubular body lumen, such as the section shown in FIG. 15A.
Figure 15B:
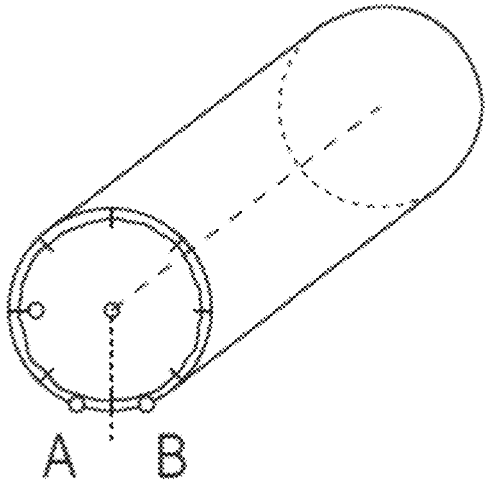
Figure 15C:
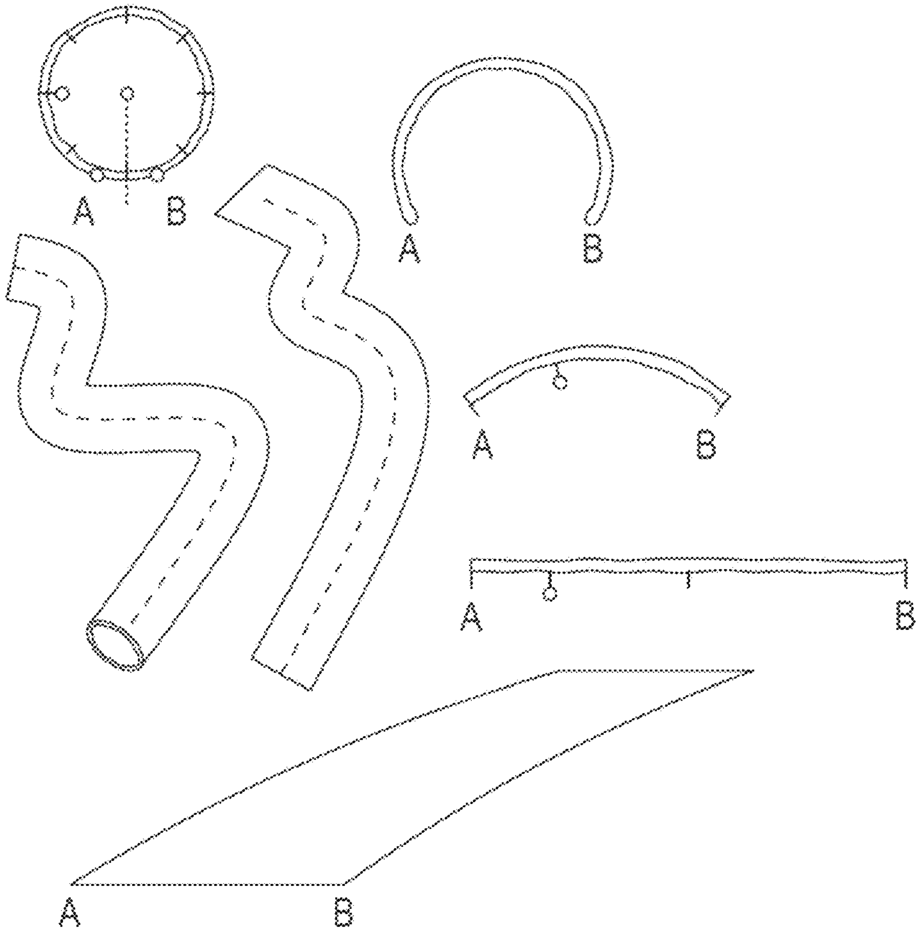

In some examples these two-dimensional images may be used to generate a three-dimensional model of the lumen, for example, a 3D mesh model. In some example the two dimensional images may be linked (stitched) so that 2D images taken during mapping may be displayed when a user selects a particular position on a 2D or 3D representation of the lumen. Thus 3D or 2D lumen representation may be derived from the images. In some examples the 2D or 3D representation may be based on a generic image (see, e.g., FIGS. 11A-11B) or a modified version of a generic or reference image that is customized to correspond to patient's lumen. In some examples the image map may be tubular, as it is imagining an approximately tubular shape (e.g., FIG. 15A), and may be used to construct a 3-D model. Data from the collected images may also be transformed into a flat 2D image, as shown in FIGS. 15B and 15C, illustrating unzipping/unwrapping and unrolling of the image. In some cases the image may be left cylindrical or as a cylinder that exhibits the tortuosity of the shape of the colon but may be displayed in an unwrapped/flat configuration. In general, any of these methods and apparatuses may include a stitched gap analysis algorithm (SLAM) tied to kinematic control, including with the benefits of rigidized and/or nested elements as described herein.

In some examples, these methods and apparatuses may form a map (e.g., a coverage map) by features detection, feature mapping, sparse reconstruction (e.g., bundle adjustment), and dense reconstruction (e.g., Mesh Generation/Surface Reconstruction). These methods and apparatuses for performing them may use images having lots of features and having enough common features across images to match. Thus, as mentioned herein multiple perspectives and/or rapid sampling may be used. For example, feature detection and matching may use one or more traditional techniques like Harris detector, SIFT, SURF, etc. or modern data-driven techniques likeDUST3R, Track-Any-Point (TAP) family of techniques.

Bundle Adjustment is the process of jointly estimating camera poses for the images used, and the 3D locations of the matched features in the image. The convergence of this process may yield a 3D structure.

Structural accuracy may be contingent on the images used, as a collective, capturing all the 3D structure from all possible angles with enough feature overlap between subsets of images to generate consistent stitching of the various sub-sections. Textural accuracy may be contingent on image resolution. Either or both sparse and dense reconstruction may be used. In sparse reconstructions, only points/pixels whose features have matched between multiple image views, are mapped from 2D to 3D (hence the name "sparse"). In dense reconstruction, the gains from sparse reconstruction are extrapolated to all the points/pixels (leading to the creation of depth maps, surface normals, and high-quality 3D meshes). This dense reconstruction is then leveraged to synthesize novel views of the scene using conventional techniques like Rasterization or Ray-tracing, or their AI-based counterparts like Gaussian Splatting (GS) or Neural Radiance Fields (NeRFs).

Structure from Motion (SfM) may generate 3D structure from a collection of 2D images. This may be particularly applicable to static scenes. This may also be a one step process and may be done on the fly (real time), locally and/or "offline". In some cases this may be somewhat computationally expensive and may not be done in real-time. In this technique, knowledge of camera poses is not necessary. Popular tools that may perform SfM may include COLMAP and OpenSFM.

As mentioned, in some cases Simultaneous Localization and Mapping (SLAM) may be used. SLAM may generate an incremental 3D map of the scene, along with the estimation of the camera location in the scene. This may be applicable to dynamic scenes, where either the camera is in motion (e.g., on a robot) and/or there are other moving entities. This may be done online and in real-time as it may be an incremental process. Popular tools that may be used to perform SMAP may include ORB-SLAM2. There are multiple different types of SLAM: (a) Monocular SLAM (using on a single camera), (b) VINS or Visual Inertial SLAM (using camera +IMU), (c) Stereo SLAM (using at least two cameras), etc. Monocular SLAM and INS may be considered vSLAM (e.g., Visual SLAM).

In any of the methods and apparatuses described herein, e.g., when reconstructing the body lumen, such as a colon, SfM may be used. For example, COLMAP may be used to generate a 3D reconstruction of the colon using just monocular video (which may be done with any endoscopy video). In examples performing lumen (e.g., colon) reconstruction with vSLAM, the method or apparatus may use Visual-Inertial SLAM to do 3D Mapping of the lumen in real-time using the robot. In some cases, reconstruction may be performed in real-time and more accurately using SLAM and the robotic components described herein (rather than with SfM).

In some cases colon reconstruction may be performed using a hybrid approach, e.g., using vSLAM for incremental and accurate map update during robot motion, and SfM for global drift corrections and realignment during robot idle-times and/or shape copy. This may generate geometrically consistent models. In this case, SfM may be seeded by more accurate 3D reconstruction coming from the vSLAM technique. This may simplify the SfM so that it only needs to correct for drift and therefore may be performed faster whilst preserving SLAM-level accuracy).

Thus, any of the methods and apparatuses described herein may use image stitching. In general, image stitching may combine multiple overlapping images to create a single, seamless panoramic (or in this case, tubular) image. The goal is to align the individual images so that the final result looks like one continuous image. As used herein, image stitching may include image capture, in which multiple images are taken from slightly different perspectives, often with overlapping regions. These images are typically captured by moving the apparatus, e.g., so that the one or more cameras acquire images that preferably overlap. The cameras, e.g., at the end region of the endoscope may be moved, and in some cases may be dithered to acquire overlapping images. Any percentage of overlap may be used. For example, overlap of about 20-30% between consecutive images may be helpful in finding common features for alignment. A higher overlap percentage may be even more beneficial. The method may further include feature detection, in which each image may be analyzed to find key points or features that are distinct and easily recognizable. Any appropriate feature detection technique may be used. For example, common feature detection algorithms include: SIFT (Scale-Invariant Feature Transform), which detects key points in different scales and orientations; SURF (Speeded-Up Robust Features); and ORB (Oriented FAST and Rotated BRIEF). Identified key points may be used to identify matching areas between overlapping images. The key points between overlapping images may be compared to find correspondences. For example, the haustral fold, pattern of blood vessels and/or a texture pattern appearing in multiple images can be matched. In some examples, RANSAC (Random Sample Consensus) may be used to remove outliers (incorrect matches) and refine the matching process.

In any of these methods, the images taken may be modified prior to stitching, for example, by filtering, enhancing, color matching, level matching, combining, subtracting, etc. In some cases images may be taken at relatively high rates (e.g., x or more frames per second, such as >10 frames per second (fps), >20 fps, >30 fps, >40 fps, >50 fps, >60 fps, >70 fps, >80 fps, >100 fps, >120 fps, etc.).

Once matching features are identified, a transformation matrix (called a homography) may be computed that aligns the images. This matrix warps the images so that they align correctly with each other in terms of perspective. Common transformations include rotation, scaling, translation, and in some cases, warping to correct distortions (especially if the camera lens introduces distortion). After the images are aligned, the overlapping regions may be blended to smooth out seams or differences in brightness, contrast, and color. Techniques like feathering, multi-band blending, or exposure compensation may be used to create a seamless transition between images. This blending helps eliminate visible lines or mismatches where the images overlap. The stitched image may have irregular edges due to the alignment and warping process. A final step may involve cropping the image to remove these irregularities, resulting in a clean, luminal (e.g., tubular) output.

In general, methods described herein may be enhanced and performed more quickly and accurately because the movement of the camera(s), e.g. on the distal end region of the second elongate member/endoscope, may be continuously and smoothly performed, preventing whipping, jumping and jitter in the images. The relative positions of the camera within the lumen may therefore smoothly transition, particularly a higher imaging rates and/or slower movement rates. This may allow stitching with higher confidence, and fewer landmarks, which may further enhance the speed. In general, the methods and apparatuses described herein may estimate the relative movement of the camera(s) using an IMU so that relative pose of the camera in sequential images is known which might prove a useful input to some of the 3D reconstruction approaches described herein. Thus, in any of these methods and apparatuses, the reconstruction process may leverage the relative position of the camera to determine depth (e.g., distance from the camera to the wall of the lumen), including using an IMU in the tip by using it to predict where the tip pose has moved between frames and then using that relative pose information in conjunction with the camera images to enhance the 3D reconstruction.

In any of these methods and apparatuses the images being acquired may be monitored, in real time, to identify one or more regions of interest as mentioned above. These regions of interest may be marked on the map, or a separate layer of the map, and/or may be maintained in a database referencing the location on the map. Thus, any of these methods and apparatuses may include luminal wall unfurling and wall analysis, as described herein.

The ongoing mapping (e.g., the coverage map) may be configured to be transformed based on where in the lumen the apparatus (e.g., the distal end region of the inner and/or outer members of the apparatus) are positioned. This is because the luminal walls may change overall shape somewhat as the apparatus is moved through the, distending and constricting, which may depend on stresses applied by the apparatus; although these changes are mitigated greatly by the use of the nested, rigidizing apparatuses described herein, the amount of insufflation and/or patient body position may change the configuration of the lumen. This effect may be addressed herein by adjusting the mapping. For example, a luminal-based coordinate system may be used in connection with the mapping (and particularly with 3D reconstructions used as part of the mapping in some cases) which may assist in handling handle bulk movement and distortion of the colon after its 3D geometry has been created. In general, the actual images will not change that much relative to distinct local features such as blood vessel patterns while the 3D surface can move significantly. Thus luminal-based coordinates can be used to relate the prior 3D surfaces to where they are now when the unique features are seen. This feature ID may also be used for machine learning.

During the acquisition of images the methods described herein may improve the imaging quality of the lumen, including imaging in difficult regions or regions having more tortious anatomy, by using one or more techniques, such as insufflation (or more likely, additional insufflation), and/or an expandable spreader such as a balloon, fingers and endocuff, etc. These techniques may also be combined with movement of the distal end region of the apparatus.

In some examples the method or apparatus may include an expandable spreader on the distal end region (near or even over the one or more cameras). For example, these methods may include inflating an optically transparent balloon through which the one or more cameras may image, and retracing the tip with the balloon therein to image the lumen walls as the balloon or other expandable spreader expands the wall, therefore allowing visualization of regions that may otherwise be occluded.

These methods and apparatuses may be used while advancing within the colon for the first time, and/or while withdrawing from the colon. As described above mapping may be done passively, e.g., as the user is steering the device within the lumen, or actively, commanding a series of movement to advantageously map the colon. For example, as the user is driving the apparatus through the lumen, the apparatus may build a partial coverage map of the lumen, noting which regions need further detail. The method and apparatus may keep track of what has and has not been seen better than a person is capable of doing so. The apparatus and method may be driven in automatic mode (or switched between manual and automatic modes) in which the apparatus may manipulate the scope to cover all areas that cannot or were not done as well by a computer, and without the ergonomic issues. Should the system still need help, it could default to manual in that area. In general, automation makes repetitive tasks easier to perform, including mapping tasks. The apparatus may be configured to be operable in a 'screening mode' in which the apparatus performs automated motions of the inner and outer to sweep the camera view over surfaces of the inside of the lumen to search.

As mentioned above, any of these methods and apparatuses may use a hierarchical understanding of geometry in the sense that while the colon can move around, there are limits as to how far it can move and that can be used to improve searching for prior local features to use for discerning the location of the camera at any given time. Thus, these methods and apparatuses may be configured to follow surface landmarks, while allowing the relative distances between the landmarks to be different, within certain parameters (e.g., elasticity parameters). In general, a coverage map may be transformed from the initial representation to a distorted configuration that tracks the current luminal configuration (which may change between the insertion and withdrawal stages, as mentioned). For example, the coverage map may be represented as a 3D model using a parametric surface (e.g., a Bezier or NURBS surface), but more likely may be described as a Mesh (comprising interconnected vertices, edges and/or faces, e.g., triangles, quadrilaterals, etc.) and/or a point cloud of discrete points representing the surface geometry.

The coverage map may be transformed by a non-rigid transformation, e.g., elastically changing the relationship between points within the surface (allowing stretching based on rules that relate to actual tissue properties). Examples of transforms may include free-form deformation (FFD). FFD controls the deformation of a surface by embedding it within a lattice. Points on the surface are displaced based on how control points in the lattice are moved. Ins some cases the technique may include elastic deformation, in which models the surface as a physically deformable object, where forces or constraints are applied. Techniques such as finite element methods (FEM) are used to simulate elasticity. In some cases as-rigid-as-possible deformation may be used. This technique minimizes distortion while allowing for local deformations, often used in shape manipulation. Other mapping techniques that may be used include the use of barycentric coordinates, particularly when working with a mesh as the coverage map. Barycentric coordinates allow the interpolation of positions within a triangle or polygon. If a triangle on the original surface is mapped to a deformed triangle, the same barycentric coordinates of a point within the original triangle can be used to find the corresponding point on the deformed triangle. In some cases the mapping may use harmonic maps Harmonic maps minimize distortion when deforming surfaces, that may minimize a smoothness energy function, ensuring that local geometric properties are preserved as much as possible. In some cases a Laplace-Beltrami Operator may be used; this operator may be used to compute harmonic maps, ensuring that the mapping between surfaces is as smooth as possible. It is often used for texture mapping and mesh deformation.

In some cases the mapping may include conformal mappings that may preserve angles, ensuring that the local shapes are preserved even though the surface might stretch. This may be useful for applications like texture mapping, where local features should not get distorted too much. Techniques such as Laplacian smoothing can be applied to enforce conformality. In some cases as-rigid-as-possible (ARAP) surface deformation techniques may be used. This technique preserves local rigidity by minimizing the deviation from rigid transformations for small regions of the surface. It's a useful method for smooth deformations and also when it is desirable to maintain the overall structure while allowing local flexibility. Alternatively or additionally, thin-plate spline (TPS) techniques may be used. TPS is a smooth interpolation technique that is often used for non-rigid deformation. It warps a surface by minimizing bending energy, allowing for smooth, gradual deformations. It can be used to deform a mesh by matching control points on the original surface to the deformed surface.

When mapping surfaces to deformed versions, you often need to minimize some energy or cost function to find the best transformation. These cost functions can depend on: stretching energy (which measures how much the surface is stretched or compressed), bending energy (which measures how much the surface is bent or twisted); and one or more correspondence constraints (which ensures that certain key points or features on the original surface map to specified points on the deformed surface.

Thus, while the colon can move around, there are limits as to how far it can move and that can be used to improve searching for prior local features to use for discerning the location of the camera at any given time.

Figure 16:
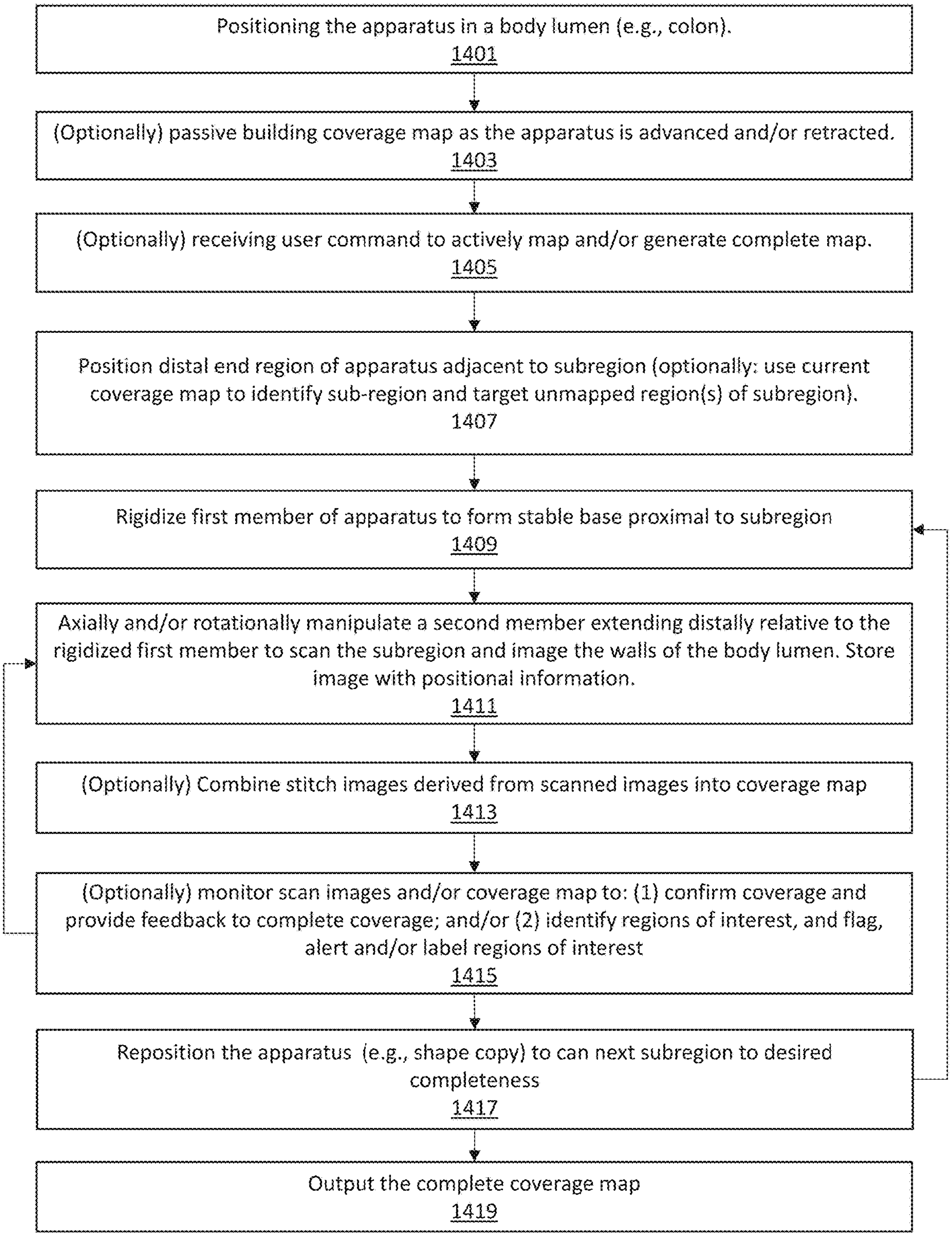
FIG. 16 schematically illustrates an example of a method of mapping a body lumen.

FIG. 16 illustrates one example of a method of mapping a patient lumen, such as but not limited to a colon. For example, in FIG. 16, the method may generally include positioning the apparatus within the body lumen (e.g., colon) 1401. The apparatus may be any of the apparatuses described herein. These methods may optionally include passively building a coverage map, as described above, while the apparatus is advanced and/or retracted 1403. The user may optionally enter a command in to actively map and/or generate a map that is x % complete (e.g., 80% or more, 85% or more, 90% or more, 95% or more, etc.) 1405 over a predefined or user defined region of the body lumen. Thereafter the method may include positioning a distal end region of apparatus adjacent to subregion (e.g., in some optional cases to use current coverage map to identify sub-region and target unmapped region(s) of subregion) 1407. As described herein the method or apparatus may include a software agent (e.g., module) that may determine how complete imaging of region is; this information may be output and/or may be used to automate scanning.

In some examples the methods and apparatuses described herein may include the use of 3D depth as part of the mapping to correct for distance-based distortion. Thus, any of these methods and apparatuses may determine a depth from the camera to the wall(s) of the lumen, and this depth may be used to generate the mapping (e.g., the coverage map), including by scaling and/or including/rejecting regions of the images being stitched. For example, depth approximations from the images may be used to reject imagery (e.g., regions of the image) that are too far away (e.g., greater than a threshold) and hence may otherwise distort the stitched images.

Any appropriate technique for approximating depth may be used, including the use of a trained machine learning agent. For example, any of these methods and apparatuses may estimate or simulate depth from one or more of the 2D images collected by the apparatus, e.g., may infer depth from a single image or a set of images, using a combination of geometry, machine learning, or both. In some cases monocular depth estimation (using a single image) may be used. Monocular depth estimation involves inferring depth information from a single image without any stereo data. It may use a trained machine learning agent that is trained on large datasets. These models extract visual cues from texture, shading, and perspective to predict depth. Similarly, one or more deep learning agents/models may be used, such as a neural network, especially convolutional neural networks (CNNs) and transformers, that is/are trained to predict depth maps directly from input images. Examples include models like DORN (Deep Ordinal Regression Network) and DenseDepth. In some cases a shape-from-shading technique may be used, in which the apparatus or method infers depth from variations in lighting and shading in an image, assuming a consistent light source. In some cases, particularly where the fields of view overlap between the multiple cameras, stereo vision may be used (e.g., using two or more images). Stereo vision relies on having two or more images of the same scene taken from different viewpoints. The difference in perspective between the images allows for triangulation to estimate depth. For example, stereo cameras may be used. By matching corresponding pixels in the left and right images, a disparity map may be computed, which directly relates to the depth of the scene. In some cases epipolar geometry may be used. This technique uses the geometric relationship between two camera views to estimate depth.

Any of the methods and apparatuses described herein may use structured light, e.g., including projecting a known pattern of light (e.g., having edges) and inferring depth from the image of the projected result. E.g., structure from motion (SfM) may be used. This technique estimates depth from a series of 2D images taken from different viewpoints (e.g., moving the camera around the scene). SfM simultaneously reconstructs 3D points and camera poses by analyzing the motion of objects between frames.

Any of these methods and apparatuses may use feature matching. Key points may be detected in the image sequence and matched between frames. These matched points are used to calculate depth via triangulation. In some cases bundle adjustment may be used to refine the 3D structure and camera positions after an initial reconstruction. In some cases a depth from defocus (DfD) technique may be used. This technique leverages the blur in an image caused by the camera's depth of field. The amount of defocus (blurriness) provides cues to the depth of objects. For example, a focusing mechanism may be used, including analyzing how the sharpness of an image varies with camera focus, one can estimate the depth of various scene elements.

Any of these methods and apparatuses may use Light-field cameras (plenoptic cameras) that capture not only intensity but also the direction of incoming light rays. This allows for post-capture depth estimation by using computational methods to refocus the image or analyze the light field. In some cases a lytro Camera may be used, that captures the full light field of a scene, enabling depth estimation after the image has been taken.

In some cases depth may be determined from Motion Parallax. This method estimates depth from the relative motion of objects in a scene as the observer or camera moves. Near objects move faster across the field of view, while distant objects move more slowly. For example, an optical flow analysis may be used in which the motion of pixels between consecutive frames is analyzed to infer depth based on how much individual pixels move.

Any of these methods and apparatuses may include the use of perspective and geometric cues; depth can be estimated using simple geometric and perspective cues, such as vanishing Points (e.g., parallel lines in the real world appear to converge in the image, and the distance to the vanishing point can provide depth information), and the relative sizes of known objects. E.g., if the size of objects in the scene are known, their size in the image can be used to estimate their distance.

Alternatively or additionally, one or more separate modes may be used to infer depth, such as LIDAR and/or RADAR Data. Thus, depth may be estimated by combining LIDAR or RADAR data with images to provide more accurate depth maps. The LIDAR or RADAR sensor directly measures distance, and this information is often fused with image data.

Alternatively or additionally, manual annotation (photogrammetry) may be used; in cases where automatic methods are insufficient, depth can be estimated by manual annotation through photogrammetry. Human operators mark points and surfaces on the image.

Thus, any of the methods and apparatuses described herein may be configured to build an initial ('rough' or incomplete) map of the surface of the lumen during an insertion phase and may leverage this map to fill-in missing regions or less-completely mapped regions during the pull back phase. But as mentioned above, stitching/mosaicking of images to form the map (coverage map) may determine and use a 3D depth, and/or may provide 3D surface reconstruction, to allow the stitching to happen with minimal distortion. In any of these methods and apparatuses, the technique may estimate a depth of the region shown in the image and may remove regions having a depth (e.g., distance from the camera) of greater than a threshold, since the further from the camera (e.g., looking down the colon tubular passage) the less accurate and/or more distorted the mapping may be.

In any of the methods and apparatuses described herein, the methods may include selectively turning on/off the light fibers to change the shadowing to generate more complex visual data from the same location. This might help with surface reconstruction. The rate at which the light may be modulated (turned on/off) may be selected so that it is not apparent to the display.

In some cases, it is possible to follow an entirely different approach to stitching where the technique start with a 3D reconstruction that is unwrapped.

In some examples, once in position, the first member of the apparatus (e.g., overtube) may be rigidized 1409, and then axially and/or rotationally manipulating a second member extending distally relative to the rigidized first member to scan the subregion and image the walls of the body lumen 1411. The images may be combined/stitched to be sufficiently clear when derived from the scanned image to form a coverage map/coverage mapping 1413. Optionally, as mentioned, the apparatus may continuously or discretely monitor scan images and/or coverage map to: (1) confirm coverage and provide feedback to complete coverage; and/or (2) identify regions of interest, and flag, alert and/or label regions of interest 1415. The steps may include reposition the apparatus (e.g., shape copy) to can next subregion to desired completeness 1417. These steps (scanning the subjection), including selecting the subregion, dividing up the lumen into subregions, etc. may be performed on the fly or calculated from an existing client. Once completed, the output the complete coverage map may be stored, and/or compared one or more counterparts 1419.

Figure 17A:
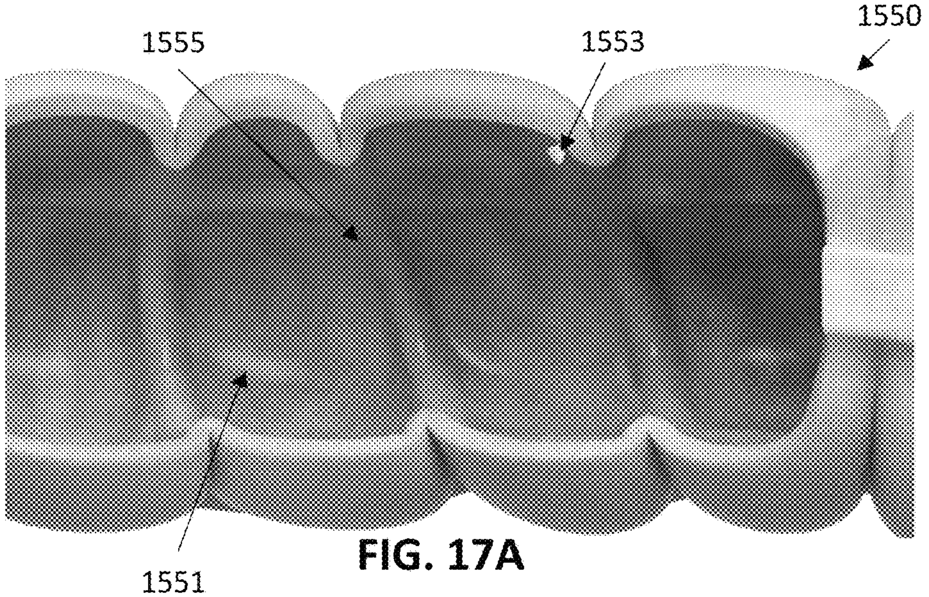
FIGS. 17A-17K illustrate an example of a method of mapping a body lumen as described herein.

For example, FIGS. 17A-17K illustrate many of these steps in another variation of a method of building a coverage map using an apparatus as described herein. In this example FIG. 17A illustrates a portion (subregion) of a colon 1550, including one or more folds 1555. The lumen 1551 has been slightly insufflated. For example using the local patterns may be useful relative to 3D reconstructions and coverage mapping. The colon is going to be distended because of the pressure so the geometry will be warped but the local patterns will stay in the same relative locations no matter how the colon changes shape. That can be used in assessing location and coverage in other parts of the body.

Figure 17B:
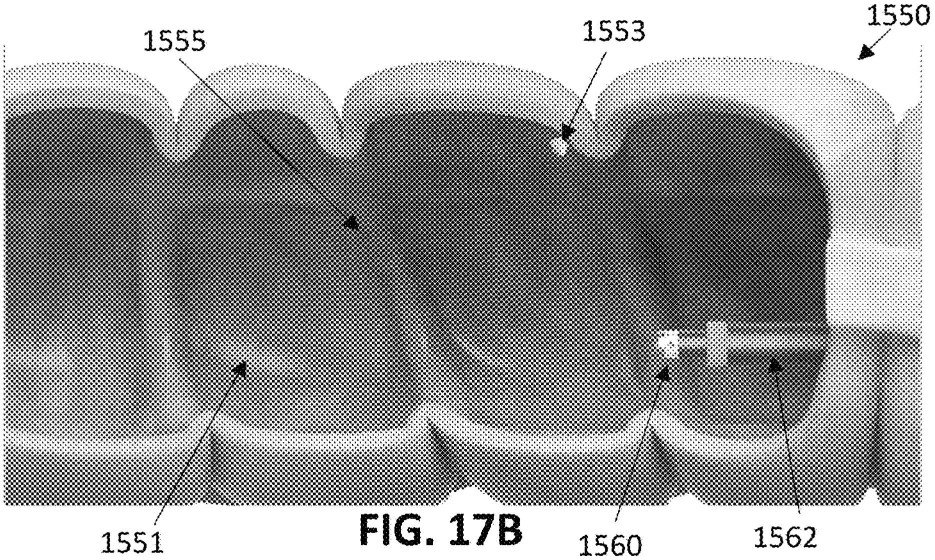
Figure 17C:
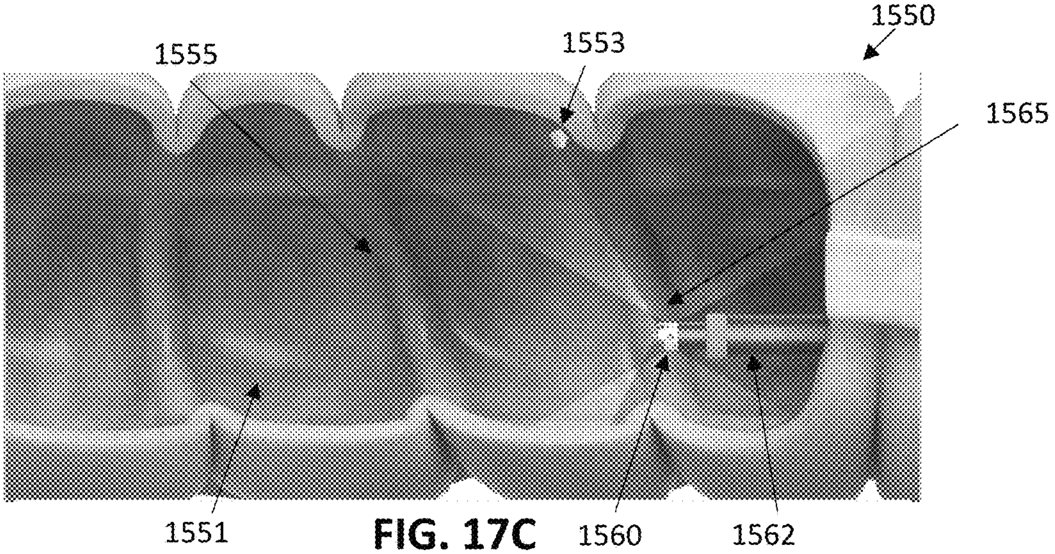
Figure 17D:
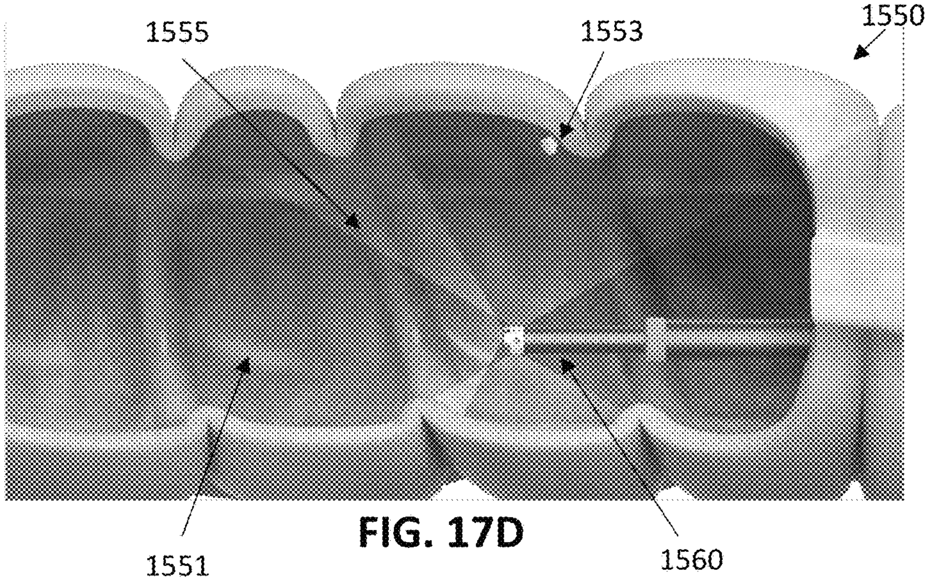
Figure 17E:
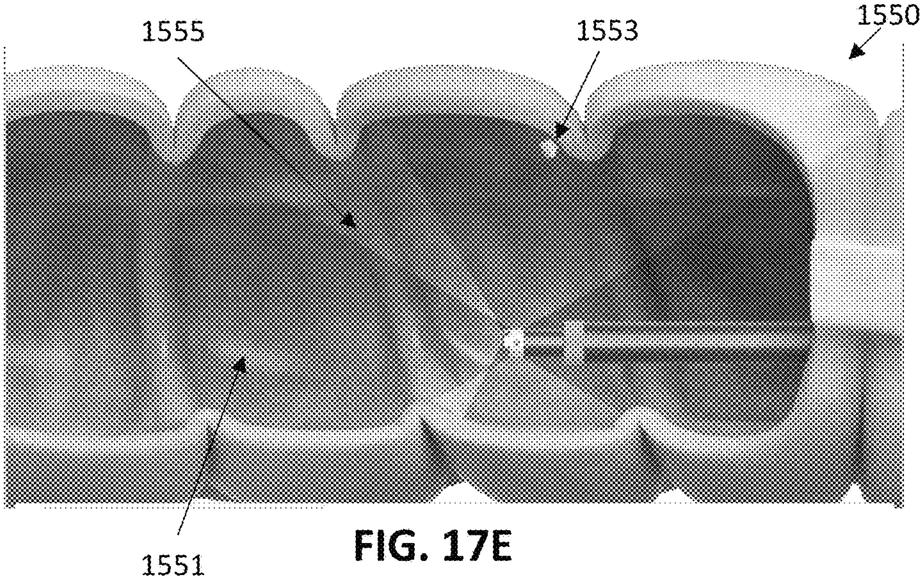
Figure 17F:
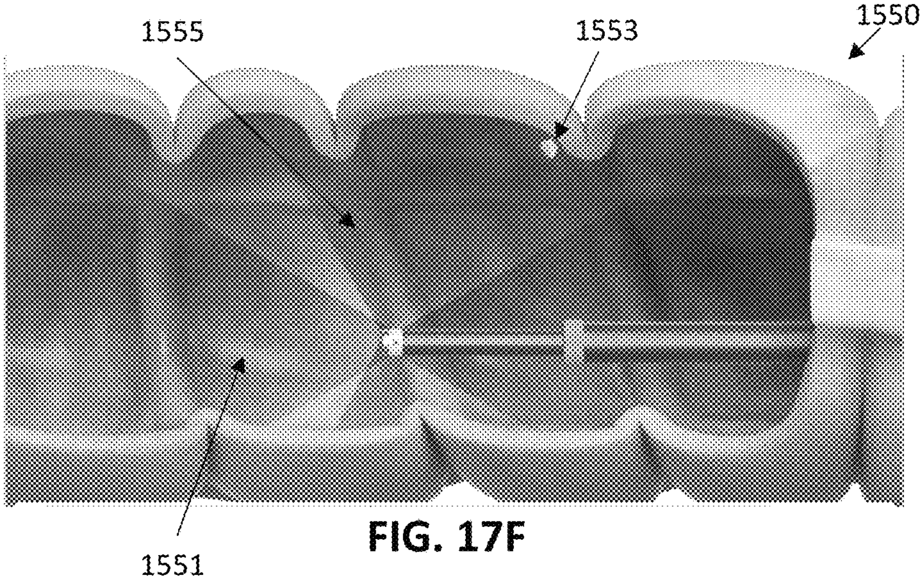
Figure 17G:
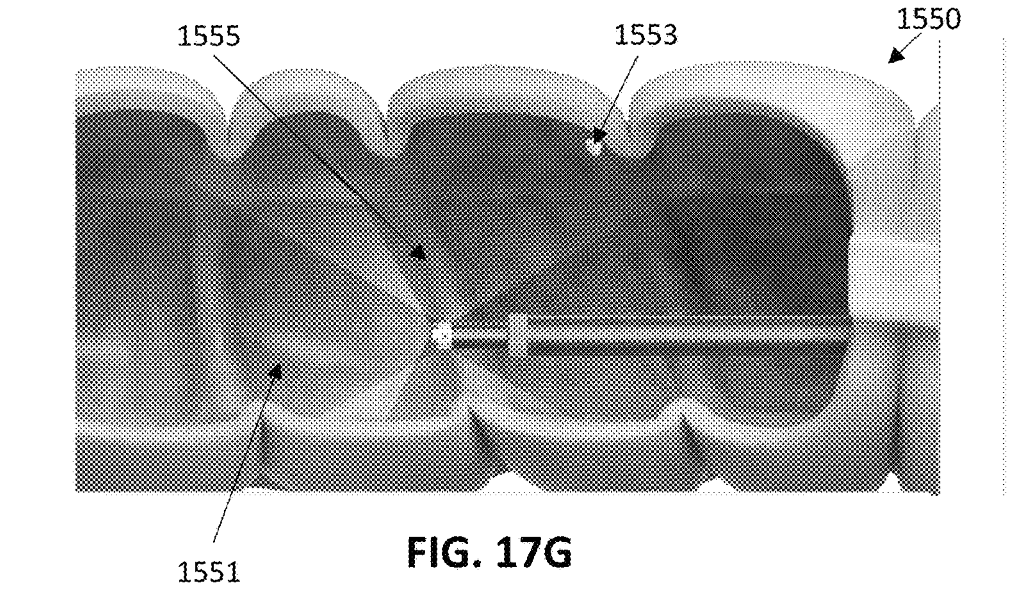
Figure 17H:
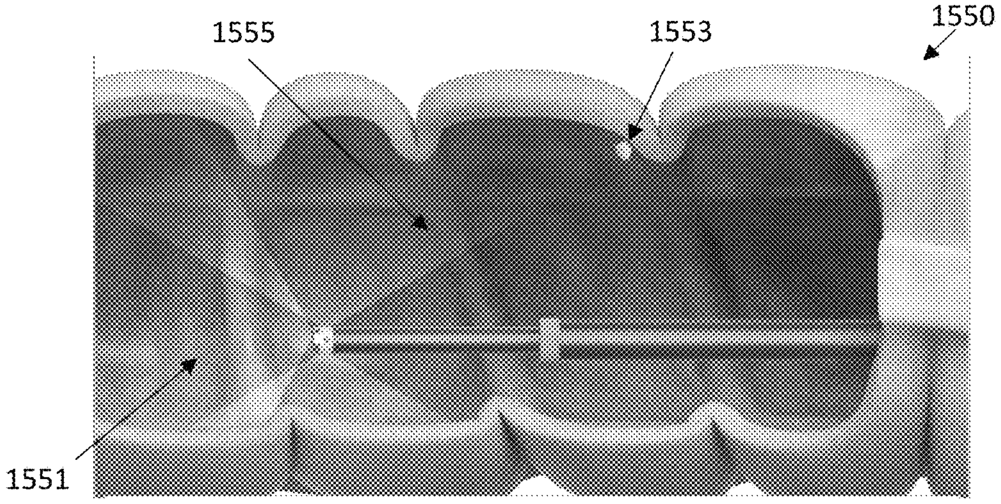
Figure 17I:
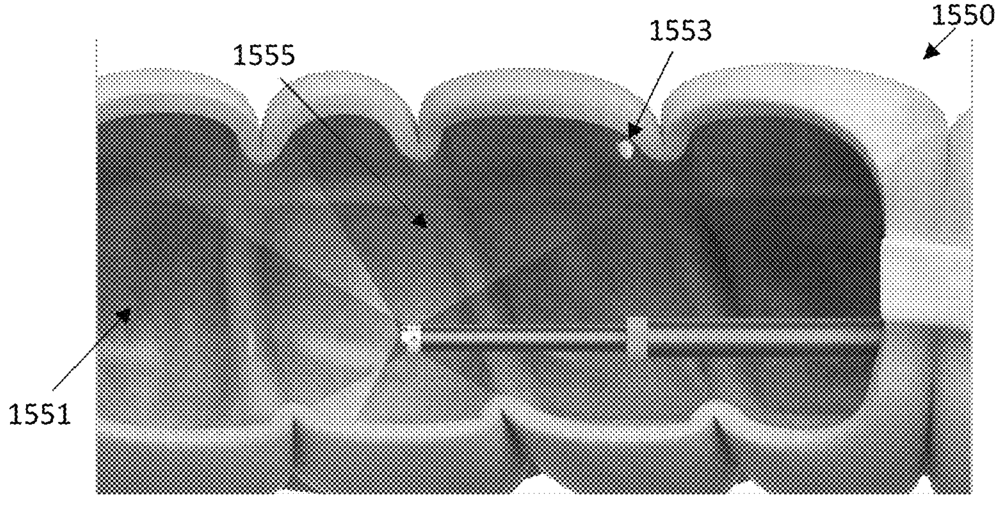
Figure 17J:
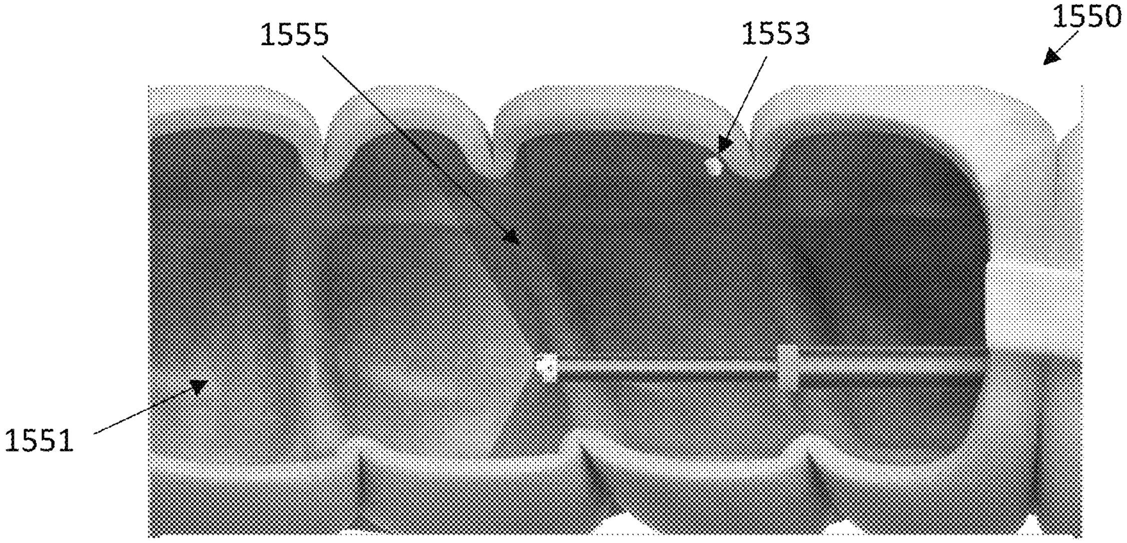

In FIG. 17B the distal end region of an apparatus, including an inner member 1560 and an outer member 1562 are shown. Once positioned adjacent to the target region (e.g., subregion), the outer member 1562 may be locked into position by rigidizing, e.g., by adding pressure (or vacuum) between the layers so that a bladder layer within the outer member is driven against the rigidizing layer. In FIG. 17C, the device is shown with the overtube member 1562 rigidized and cameras in the inner member (endoscope) 1560 imaging the side view as well as distal-facing view. In some cases a polyp 1553 on the side of the lumen wall may be missed by the distal-facing camera but may be visualized by a side-facing camera view 1565. The inner member (e.g., second flexible elongate member) may then be advanced while imaging, as shown in FIG. 17D. In some cases the inner member may be dithered (in a back and forth movement) as described above, while capturing images of the walls from multiple perspectives, including on either side of the folds/protrusions. Eventually, with the inner member 1560 steered to the position (which may be curved or bent, not shown), the inner member may be rigidized, and the outer member may be de-rigidized into a flexible state and advanced over the rigid inner member, as shown in FIG. 17E. Imaging may be paused or may be continued during this step. The inner member may then be repositioned to scan a second sub-region, as shown in FIG. 17I the apparatus is pulled proximally (retracted) while imaging. Optionally the retraction may be performed by shape copying, as described above, to prevent looping or reduction of the colon.

Figure 17K:
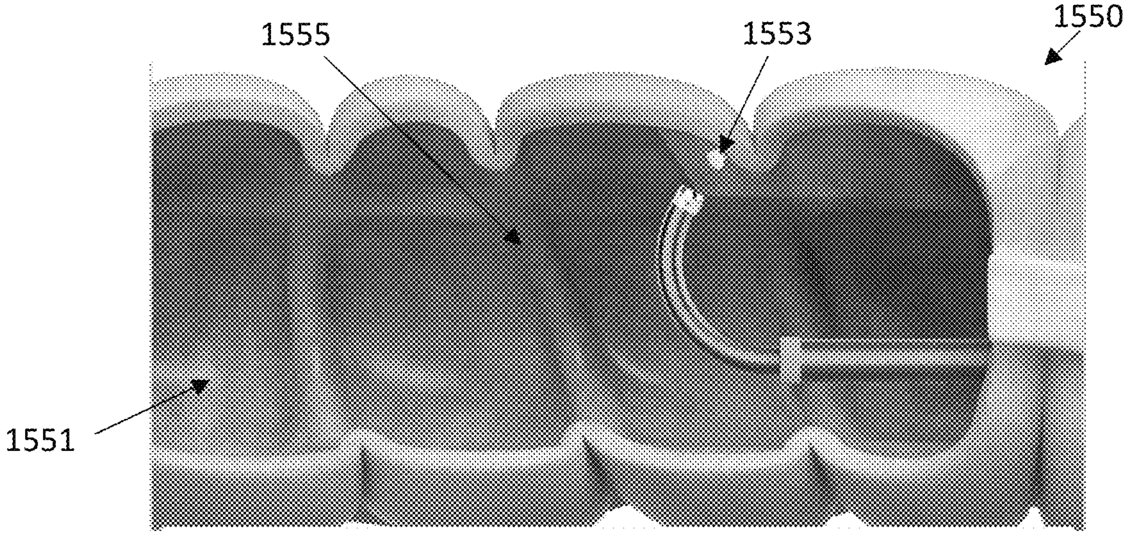
Figure 18A:
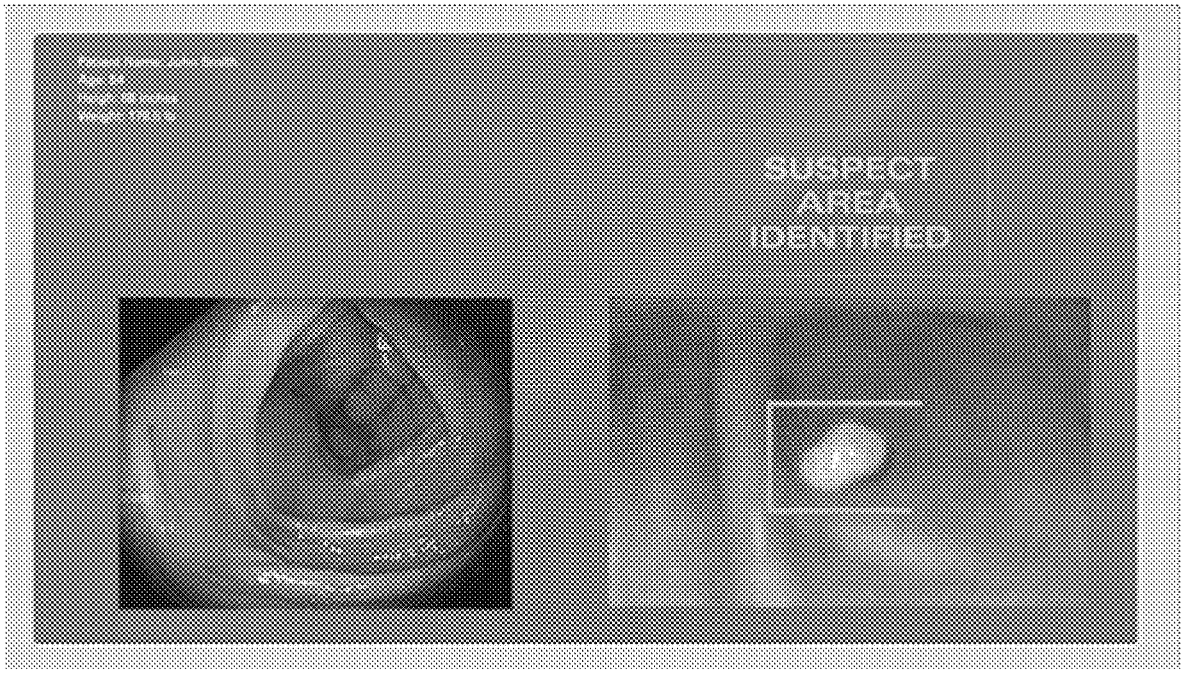
FIGS. 18A and 18B illustrate automatic monitoring to identify regions of interest from peripheral regions while navigation and/or mapping a body lumen.
Figure 18B:
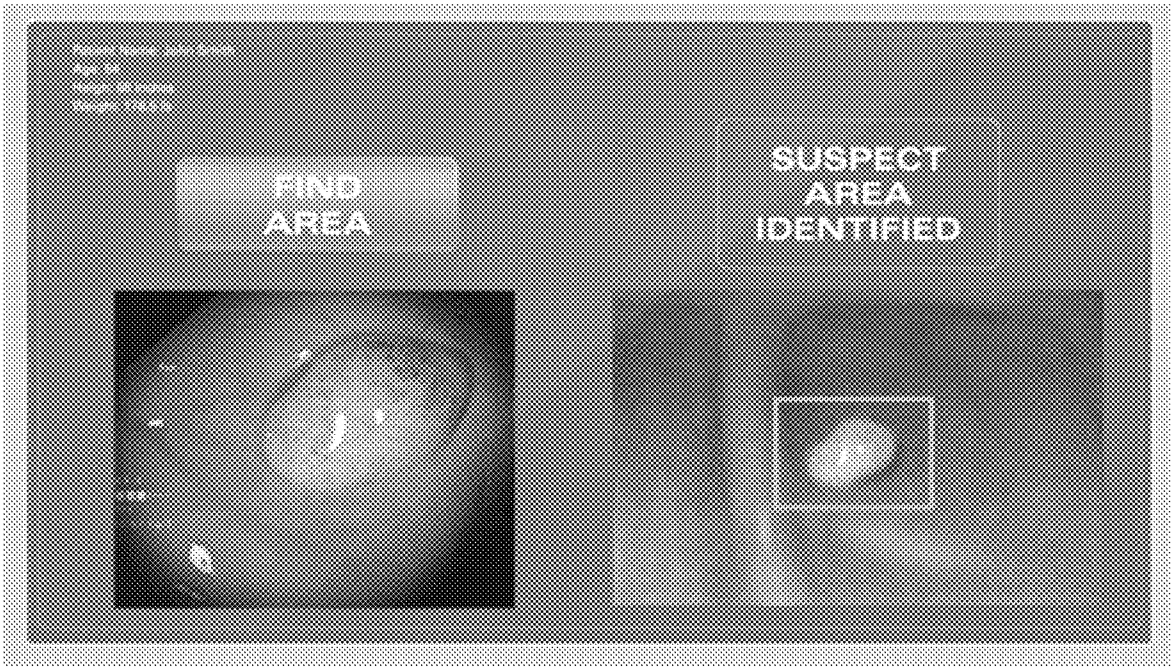

In any of these methods and apparatuses the system may monitor the images being acquired to identify when a region of interest is identified and to mark or track them. In some cases these methods may present the user with an indicator that a region of interested (e.g., polyp) has been identified and ask the user if they would like to automatically steer to the region. This is illustrated in FIGS. 18A-18B and FIGS. 17J-17K. For example, in FIG. 18A a user interface is shown, showing the image from the forward-facing camera, e.g., as the device is advanced (see, e.g., FIGS. 17A-17H). A second window on the user interface shows a putative region of interest captured in this example from a side-viewing camera and automatically identified (e.g., using a trained machine learning agent, trained to identify polyps). In this case, when the system identifies the potential region of interest, the "suspected area identified" is illuminated, and a user input ("Find Area") is presented in the user interface. If the user selects this input, the apparatus may automatically steer to the region of interest, as shown in FIG. 18B. FIGS. 17H-17K illustrate the steps for automatically retroflexing so that the distal-facing camera on the second (inner) elongate member is oriented towards the suspected region of interest, first by retracting the apparatus proximally, positioning and rigidizing the overtube (FIG. 17J) then steering the inner member until the distal-facing camera is imaging the region of interest directly (FIG. 17K). In some cases the apparatus may move the distal end of the apparatus around the region of interest (e.g., at least partially circling it) to provide images from multiple different perspectives.

Expandable Spreaders

Any of the methods and apparatuses described herein may include one or more expandable spreaders. In general, an expandable spreader is a structure that extend distally from the tip of the endoscope assembly (e.g., endoscope, shield, etc.) and/or overtube and mechanically pushes ('spreads') the wall of the body lumen to enhance imaging of the wall. For example, an expandable spreader (also referred to herein as a collapsable spreader and/or an expandable/collapsible spreader), may including a balloon (e.g., a transparent balloon), a cage, a frame, a shell, one or more probes, one or more arms, etc.

The expandable spreader may be deployed within the body lumen, e.g. by actuation of a manual, automatic and/or semi-automatic control. For example, the expandable spreader may be configured to deploy by pulling a pull-wire to extend/expand the expandable spreader from the distal end region of the endoscope assembly and/or overtube. The expandable spreader may be reversibly deployed. In general the apparatus may image through and/or around the expandable spreader. For example, the expandable spreader may push against the wall of the body lumen, holding it at a fixed distance and/or expanding the distal-facing and/or side-facing region being interrogated by the camera(s) of the scope (e.g., endoscope assembly).

Figure 21A:
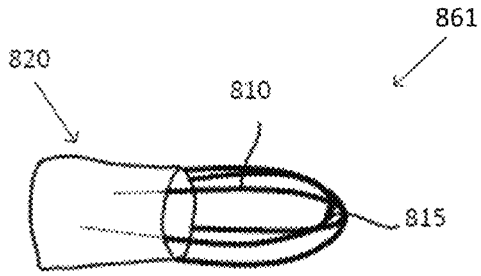
FIGS. 21A-21B schematically illustrate examples of collapsable spreaders (e.g., lumen expansion devices), each in a collapsed state.

These expandable spreaders may be used instead of or in addition to insufflation. Generally speaking, insufflation may be used to locally or globally expand the body region (e.g., by adding gas (e.g., air, nitrogen, oxygen, etc.). FIGS. A few examples of lumen expansion by mechanical augmentation are described with respect to FIGS. 21A, 21B, 22A, and 22B. For example, FIG. 21A schematically illustrates an example of mechanical augmentation using an expandable spreader that is configured as a cage 861. The cage 861 includes an expandable frame that includes multiple filaments 810. The filaments 810 may be constructed of, or include, metal, polymer, ceramic, suture, and/or any other material that can exert sufficient force against a lumen wall to expand the wall outwards for better viewing capability, while being sufficiently pliable to be collapsed until the cage 861 is deployed and return to a collapsed state after deployment. The filaments 810 (arms or bars of the cage 861) meet at an end 815; the filaments 810 may be connected together at the end 815, may cross over each other at the end 815, or may be coupled to a fixture (e.g., ring) at the end 815. The cage 861 is coupled to (e.g., permanently or removably attached to) an endoscope, overtube, or shield in a coupling area 820. In an embodiment, ends of the filaments 810 are slidably disposed in coupling area 820 so that the filaments 810 may be extended for deployment of the cage 861 and retracted for collapse of the cage 861.

Figure 21B:
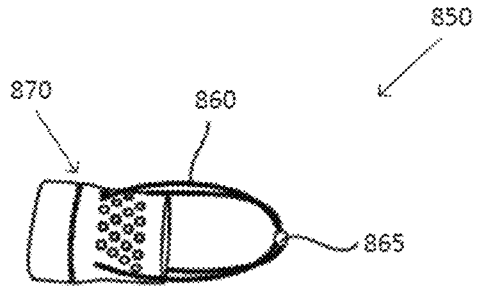

FIG. 21B illustrates another example of an expandable spreader providing mechanical augmentation in the form of a cage 850. In this example the cage 850 includes an expandable frame that includes multiple arms (e.g., bars, filaments, etc.) 860. The filaments 860 may be constructed of, or include, metal, polymer, ceramic, suture, or any other material that can exert sufficient force against a lumen wall to expand the wall outwards for better viewing capability, while being sufficiently pliable to be collapsed until the cage 850 is deployed and return to a collapsed state after deployment. The filaments 860 meet at an end 865; the filaments 850 may be connected together at the end 865, may cross over each other at the end 865, or may be coupled to a fixture (e.g., ring) at the end 865. The cage 850 is coupled to (permanently or removably attached to) an endoscope, overtube, or shield in a coupling area 870. In an embodiment, ends of the filaments 860 are slidably disposed in coupling area 870 so that the filaments 860 may be extended for deployment of the cage 850 and retracted for collapse of the cage 850.

Figure 22A:
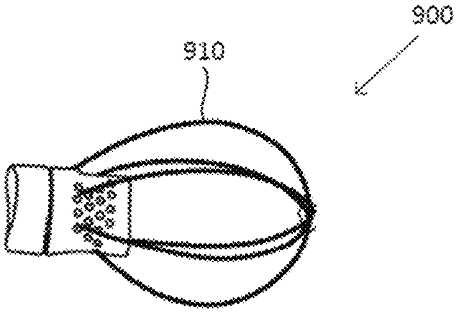
FIGS. 22A-22B schematically illustrate examples of collapsable spreaders (e.g., lumen expansion devices), each in an expanded state.
Figure 22B:
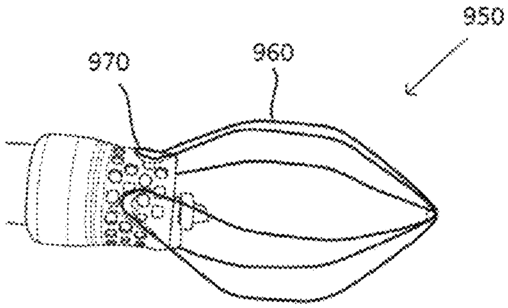

FIG. 22A illustrates an example of an expandable spreader providing mechanical augmentation in the form of a cage 900 with arms (e.g., filaments) 910 shown in an expanded state. In this example, the cage 900 expands into a somewhat spherical or elongated spherical shape. FIG. 22B illustrates an example of an expandable spreader in the form of a filament structure cage 950 with filaments 960 shown in an expanded state. In this example, the cage 950 expands into a shape similar to a prolate spheroid (e.g., similar to the shape of a football). The filaments 960 of the cage 950 are formed as loops 970. In an embodiment, the cage 950 is made of a single filament 960 that is shaped to form multiple loops.

Alternatively to, or additionally to, mechanical augmentation using an expandable spreader such as one of the cages described above, mechanical movement of the anatomy could be performed or augmented by a balloon or other inflated device, which could exist proximal to a camera, distal to a camera, both proximal and distal to a camera, or with the camera seeing through the inflated device.

Figure 23:
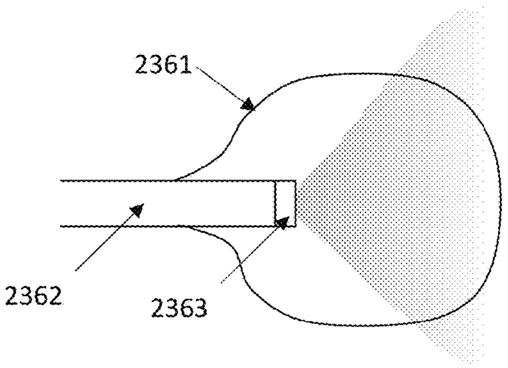
FIG. 23 shows an example of a collapsable spreader configured as transparent balloon, through which imaging may occur.

FIG. 23 illustrates an example of an expandable spreader that is configured as a transparent balloon 2361 that is configured to extend distally (when inflated) from the distal end of the endoscope 2362. The tip 2363 of the endoscope in this example resides within the balloon 2361 and may record images through the walls of the balloon, which may be transparent. In some cases the balloon may be configured to leak (e.g., 'weep') from one or more small opening through the ballon in order to help remove/clear any residue from the outer surface of the balloon. The ballon may be filled with a fluid (e.g., liquid, such as saline, gas, etc.).

As mentioned, alternatively to, or additionally to, mechanical augmentation using an expandable spreader, insufflation by liquid or gas may be used for lumen expansion. In some cases, certain oversight bodies (e.g., governmental, clinical, or procedure site bodies) provide guidelines or rules regarding limits on an amount of insufflation that can be introduced in particular lumens, such as by volume or by lumen pressure. Even without such guidelines or rules, physicians may self-impose insufflation limits in the best interests of their patients. If insufflation limits are exceeded, the lumen can be vented. One or more pressure sensors can be included on an endoscope, overtube, shield, or expandable spreader so that lumen pressure can be monitored. An insufflation supply can be monitored for a volume of fluid (liquid or gas) that has been introduced. Pressure sensing and fluid supply monitoring can both be implemented.

In some examples lumen expansion may be controlled by an automated system. For example, as the endoscope is maneuvered through the lumen, the automated system can monitor incoming data to recognize when visibility has been limited, such as when the lumen has collapsed or lumen tissue occludes the imaging device. Monitoring can include monitoring image data from one or more imaging devices and/or monitoring pressure sensor data from one or more pressure sensors to recognize a situation with limited visibility. When the automated system recognizes that visibility is limited, the system can automatically engage lumen expansion using an expandable spreader. When the automated system recognizes that lumen expansion is preferably removed (e.g., if the volume of insufflation fluid is approaching the insufflation limit, visibility is not needed for a time, or retraction of mechanical augmentation may improve maneuverability), the system can cause retraction of mechanical augmentation by the expandable spreader, halting of additional insufflation, and/or venting.

Any of these apparatuses may be configured to include the ability to controllably rotate and reciprocate, including through the use of motors, software, sensors, and DR, allows a user to methodically interrogate a region. It also allows a user to cover an area again and again, methodically, in a manner that could not be accomplished with a traditional commercial, non-rigidizing system.

Maps

In general, the methods and apparatuses described herein may be configured to provide mapping and/or to use mapping, e.g., for autonomous or semi-autonomous (e.g., assisted) navigation of the robotic apparatuses described herein and/or detection of structures (e.g., lesions, such as but not limited to polyps, inflammation, etc.). Any of the mapping methods and apparatuses described herein may include one or more of: percentage of coverage (scanned/unscanned regions), regions of coverage (scanned/unscanned regions) and/or reconstructions of regions or all of a body lumen (2D, 3D, etc.).

The methods and apparatuses for mapping may receive as input from these apparatuses at least visual input, which may include images, such as video, camera, etc. of one or more wavelength or ranges of wavelengths (visible light, near-IR, etc.). One or more other inputs may be received and used. For example any of these methods and apparatuses for mapping (e.g., percent coverage, regions of coverage, reconstructions, etc.) may include shape sensing of the imaging apparatus (e.g., endoscope assembly and/or overtube). Shape sensing may be optical shape sensing, e.g., using one or more fiber optics. Optical shape sensing may refer to the use light, typically transmitted through optical fibers, to detect and reconstruct the shape, position, and/or deformation of an object or structure in real time. Optical shape sensing may rely on the interaction of light with the physical properties of the fiber or surrounding medium, enabling precise measurements of strain, curvature, and displacement. For example, optical shape sensing may include the use of fiber Bragg gratings (FBGs) embedded along an optical fiber. These gratings reflect specific wavelengths of light, and any strain or bending in the fiber causes a shift in the reflected wavelength, which can be measured and interpreted to determine the fiber's shape. Other examples of optical shape sensing may use optical time-domain reflectometry (OTDR) or optical frequency-domain reflectometry (OFDR) to analyze backscattered light along the fiber, allowing for distributed sensing over long distances with high spatial resolution. In any of these cases, optical shape sensing may also incorporate multi-core fibers and/or helical winding patterns, enabling three-dimensional shape reconstruction by capturing strain data from multiple orientations. The optical shape sensing may be on the endoscope (e.g., integrated into the endoscope, carried in/on the scope (e.g., in an internal and/or external working channel), on and/or in the shield, or on and/or in the overtube (e.g., in an external working channel).

In the context of the invention, optical shape sensing data may be used to monitor, guide, or adapt the behavior of a system. Further, the data from the optical shape sensing may be used as an input to the mapping module(s), including in particular the machine learning agent(s) for mapping.

In any of these apparatuses shape sensing may include electromagnetic shape sensing, e.g., using an external EM field and one or more sensors in/on the endoscope assembly and/or overtube. For example an external field projector may be used outside of the robot and the one or more EM sensors may be used to detect the relative positions and/or orientation of the shape sensors and therefore the robot (e.g., overtube, endoscope assembly, etc.).

In any of these apparatuses, the methods and apparatuses for mapping may receive as input one or more endoscope and/or overtube sensors, including but not limited to: insertion sensor data, roll sensor data (for overtube and/or endoscope assembly), steering sensor data (e.g., steering of a distal end region of the endoscope), joint sensors, etc.

Insertion sensor data may include encoders (e.g., linear encoders, rotary encoders, etc.), linear variable differential transformers (LVDTs), laser or optical distance sensors, etc. Roll sensor data may include encoders, microelectromechanical (MEMs) gyroscopes, inertial measurement units (IMUs), magnetic angular sensors, etc. Steering sensor data may include shape sensors (as mentioned above), force sensors (e.g., detecting tension on one or more steering tendons, voltage used to drive actuation, etc.), encoders (encoding displacement of steering tendons, etc.

In any of these apparatuses, the methods and apparatuses for mapping may receive as input pressure sensors, e.g., pressure within the rigidizing line(s) for rigidizing the overtube and/or endoscope, which may indicate how rigid or flexible the overtube and/or endoscope is. Any of these apparatuses for mapping may receive as input data from one or more force sensors, e.g., measuring force on the overtube assembly and/or endoscope, etc.

Any of these apparatuses for mapping may receive user input(s), including inputs from one or more touchpad, keypad, controls (buttons, dials, foot pedals, etc.).

As mentioned, any of these inputs may be provided, e.g., to a trained machine learning agent used for mapping, as described herein, including mapping for percentage prediction (e.g., percentage of scan coverage), regional location of scan coverage (e.g., scanned/unscanned sub-regions within the body lumen or a region thereof), and/or reconstruction (2D and/or 3D reconstruction). Input data such as shape sensing, camera input (images, video, etc.) user input, endoscope/overtube input (insertion, roll, joint sensing, etc.), and/or force sensing may be continuous or discrete (e.g., at between about 0.01 Hz and 10 kHz or higher, e.g., between about 0.1 Hz and 1 KHz, etc.); this rate may be different for different sensing/input modalities.

Figure 24:
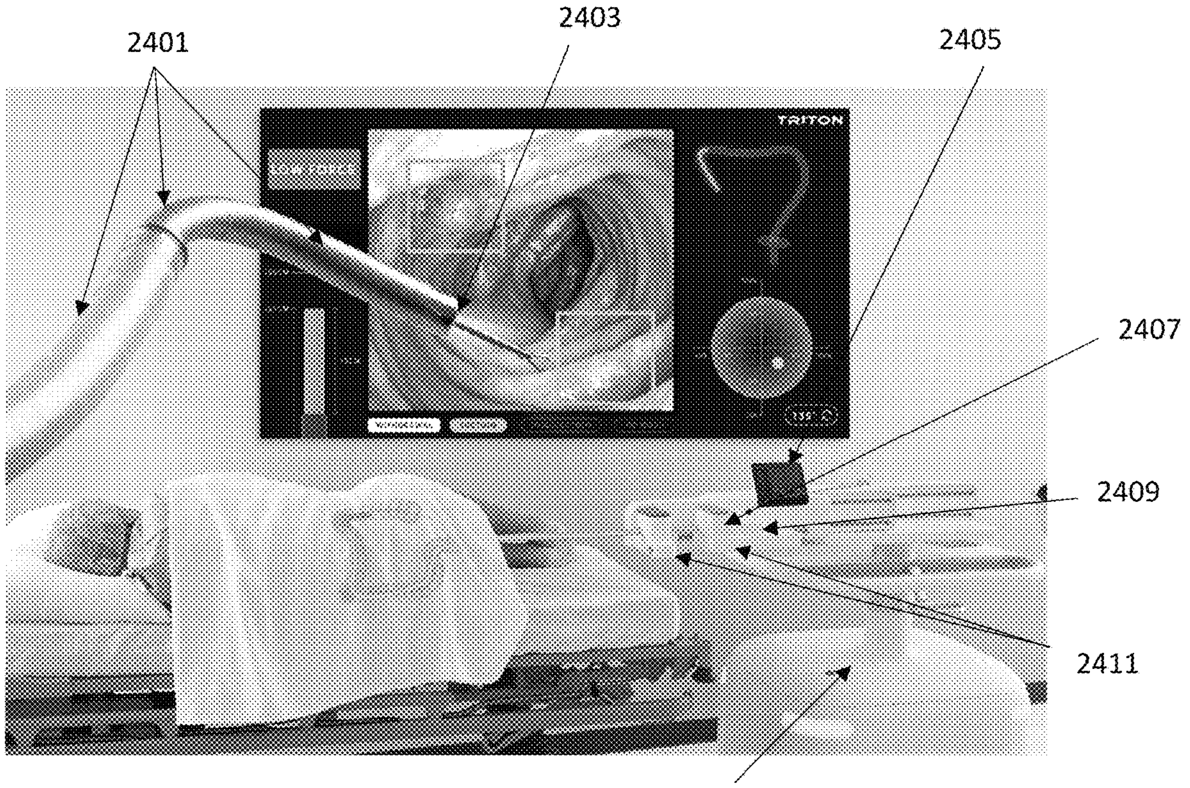
FIG. 24 illustrates an example of a medical robot apparatus, illustrating types/categories of input sources that may be used with any of the mapping methods and apparatuses described herein.

FIG. 24 schematically illustrates various sources for data input that may be used by and of these apparatuses, for display and/or for use in any of the mapping techniques including trained machine learning agents. In FIG. 24, the apparatus includes shape sensors 2401, one or more cameras 2403 (e.g., high density cameras), one or more user inputs 2405 (e.g., keypad, touch screen, button(s), etc.), one or more endoscope assembly and/or overtube sensors 2407 (e.g., insertion sensor, roll sensor, steering sensor(s), etc.), one or more working channel insertion sensors 2409, one or more force sensors 2411, and/or one or more pressure sensor(s) 2413.

Determining Completeness of Scan Region (1D Scanning)

In general, described herein are methods and apparatuses for determining how much of a region of the lumen has been scanned. In particular, these methods and apparatuses may determine how much of a region of the luminal wall at a particular position of the outer member (overtube) within the lumen, e.g., a "parked" position of the overtube within the lumen has been imaged by the apparatus. This region may be referred to as the "level" of the lumen, which may correspond to sub-regions of the length of the lumen (e.g., colon or other body region). This information may be provided to the user, particularly when manually or semi-automatically mapping, or may be used by the controller when automatically mapping. For example, any of these methods and apparatuses may include outputting the percentage of completion of a level corresponding to a particular location of the endoscope within the lumen, e.g., to a display. In some cases the output may indicate on a model or image of the lumen regions that are and/or are not fully imaged.

The percentage of coverage of a scan may be particularly important and may be part of any of these methods and apparatuses. As described herein, these methods and apparatuses may determine the percentage of coverage (e.g., how much has been scanned/imaged) for an entire body lumen (e.g., from the cecum of colon to bowel/anus), or a predefined region/sub-region and/or a user-defined or selected region/sub-region of the body lumen. The percentage of coverage may be defined slightly more granularly, e.g., as the percentage of coverage of a sub-region of the region being scanned; the body lumen being scanned may be divided up into sub-regions of any appropriate size, typically (but not exclusively) defined as regions of axial length (e.g., millimeters of insertion length, relative to the axial position). In any of these methods and apparatuses it may be assumed that the scanning is fully around the surrounding region of the endoscope, e.g., 360 degrees radially around the body lumen at the level of the sub-region being scanned.

Thus in some cases the percentage of coverage may be described as a percentage of amount scanned over each sub-region of the body lumen region being scanned. Recall that "scanning" may refer to imaging of one or more imaging modalities (e.g., visible light, near-IR, narrow wavelengths, fluorescent light, etc.). In some cases scanning may refer to just visible light scanning. In some cases percentage of coverage may be specific to each type or sub-type of imaging modality or may refer to all of the modalities being scanned.

The percentage of coverage may be based on raw scanning, and/or it may be based on a measure of the quality of scanned data. For example scans (images) of regions may be rejected if they do not meet predefined and/or user adjustable quality metrics (e.g., clarity, blurriness, illumination/lighting histogram ranges, sharpness, etc.) and not factored into the percentage of coverage estimates. Any of these apparatuses may include a module configured to apply a quality threshold when estimating the percentage of coverage from the one or more images.

Alternatively or additionally, as described in greater detail below the trained machine learning agent used to determine percentage coverage may be trained to ignore regions having images below a quality metric threshold.

The percentage of coverage may generally refer to a measure of the 'seen' (e.g., in $mm^2$) over the total sum of the surrounding region (e.g., 'seen' and 'unseen', e.g., in $mm^2$). In some cases it may be helpful to provide an estimate indicating the total percentage of coverage of the colon. For example, professional societies may recommend an adenoma detection rate (ADR) of at least 15% for women and 25% for men. It is believed that for every 1% increase in ADR, there's a 3% decrease in the risk of colorectal cancer. Thus, helping (and in some cases confirming) that the maximum amount of imaging of the body lumen (in this example, colon) has been imaged may be particularly beneficial.

Described herein are methods and apparatuses for determining the completeness of a scan (imaging and/or review) of a body lumen, and in particular body lumens in which the walls may be complex, e.g., segmented (e.g., including haustrations, folds, etc.), convoluted, etc. Such complex structures may be particularly difficult to visualize around and/or behind and may be difficult to track and recall which regions have and have not been visualized.

For example, described herein are "first degree" mapping agents (e.g., software, hardware and/or firmware) that include a trained machine learning agent that is trained on complex body lumen (e.g., colons or model colons) to determine the percentage of coverage (percent scanned/seen and/or, equivalently percent unscanned/unseen) within a body lumen that may not have been previously scanned. For example, these models may receive as input the images (e.g., video, etc.) and optionally shape sensing information and/or insertion depth for the nested endoscope assembly.

Figure 25A:
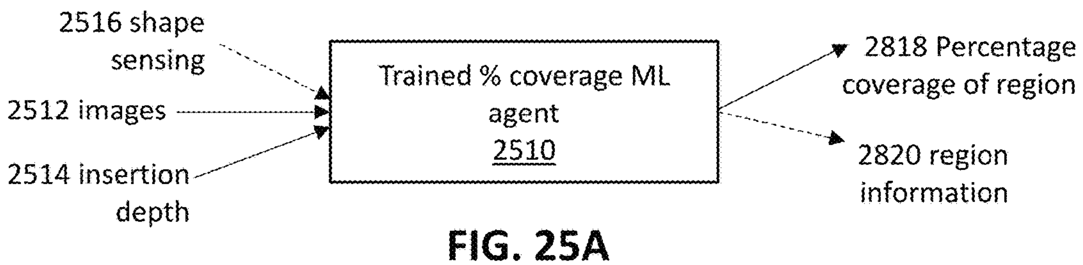
FIG. 25A schematically illustrates an apparatus (trained ML agent) configured to estimate a percentage of region (or all of) a body lumen being scanned ("% coverage").

FIG. 25A illustrates an example of a machine learning (ML) agent for estimating the percentage of coverage 2510 that is configured to receive as input the images (e.g., video) 2512 and one or both of insertion depth 2514 and/or shape sensing 2516 from the robotic apparatus, such as the nested assembly including the rigidizing overtube and endoscope assembly (e.g., shield and/or endoscope).

The percent coverage ML agent 2510 may be trained on data derived from images of real or simulated body lumen (e.g., colon) having a known geometry within which scans may be made or simulated and ray casing techniques may be used to determine (e.g., project) which regions are images and which are missed based on the known relative location of a real or simulated camera within the body lumen. For example, known body lumen geometries may be derived from CT scans of human colons (e.g., providing a digital 3D mesh model of the body lumen) and a simulated camera (e.g., endoscope) position, corresponding to insertion depth 2514 and/or shape from shape sensing data 2516 may be estimated while ray casing from the simulated camera position may be used to provide ground truth percentage coverage data. Alternatively or additionally, a percent coverage ML agent may be trained on one or more baseline colon models into which occluding elements (folds, feces, etc.) are added or modified.

Figure 25B:
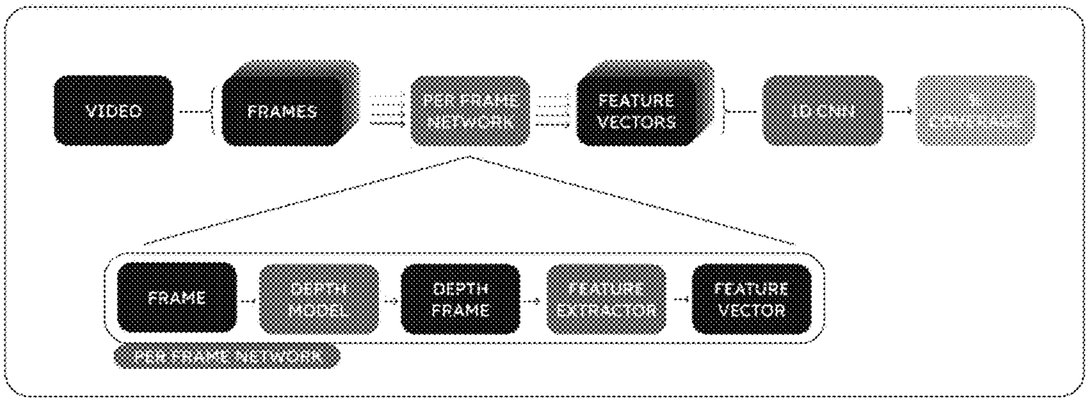
FIG. 25B illustrates one method of determining an estimate of the amount (e.g., percentage) and/or region(s) scanned ("covered") or not scanned ("uncovered") in a highly folded body region such as, but not limited to, the colon.

FIG. 25B illustrates an example of a method of determining the percentage of coverage (% coverage) from an endoscope within a body lumen. In this example video data (images) including multiple frames may be processed by the system, e.g., in the per-frame network and optionally features may be extracted (e.g., feature vectors) before passing to a trained machine learning model (percentage coverage ML agent, shown here as a "one dimension" convolutional neural network, 1D CNN) that may then output the percentage of coverage. The per frame network may optionally analyze each image ('frame') to determine a features vector, e.g., by estimating depth.

In any of these apparatuses the image data form a single camera (e.g., a forward facing camera) and/or multiple cameras may be used. For example, any of these apparatuses may determine percentage coverage from multiple cameras (forward and one or more side-facing/rear-facing cameras). The percentage coverage ML agent may be trained on same number of cameras used. As mentioned herein in additional to imaging data, any positional information on the endoscope and/or camera(s), such as shape sensing data and/or depth of insertion, etc. may be used. Other endoscope/camera positional information may be used as input to the trained percentage coverage ML agent. As mentioned, the methods and apparatuses described herein may estimate percentage of coverage as the total percentage of coverage (e.g., sum of a plurality of sub-regions) or as the percentage of coverage of one or more (e.g., current) sub-regions into which the body lumen is divided, typically by axial position.

Any of these methods and apparatuses may dynamically update the percentage of coverage of the sub-region(s) and/or total body lumen. For example, these methods and apparatuses may update in real time, e.g., every x seconds (e.g., every 10 seconds, 5 seconds, 1 second, 0.5 seconds, 0.1 seconds, etc., such as between 0.1 Hz and 10 kHz, between 0.1 Hz and 1 kHz, between 0.1 Hz and 500 Hz, etc.).

FIGS. 26A-26F illustrate examples of image showing the use of a trained percent scanned ML agent. In these figures the left side shows an image 2631 provided to the percent scanned ML agent. The right side shows an image of the shape (from shape sensing data) of the endoscope 2636, and a schematic of the tip region 2638 is shown in the middle, along with a graphical (visual) indicator of the percentage scanned for sub-regions. In FIGS. 26A-26F 10 sub-regions are shown, corresponding to an insertion depth of about 20 cm (so each subregion in this example is 5 cm, e.g., 50 mm). The sub-regions may be any appropriate depth/length, which may be based on the depth of the camera or the geometry of the body lumen. The example user interface shown in FIGS. 26A-26F also include a numerous percent scanned ML agent output 2632 showing an estimate of the percentage coverage (percent scanned) of the current region that the tip of the endoscope is positioned in, a shown by the representation of the endoscope 2638 extending from the representation of the overtube.

Figure 26A:
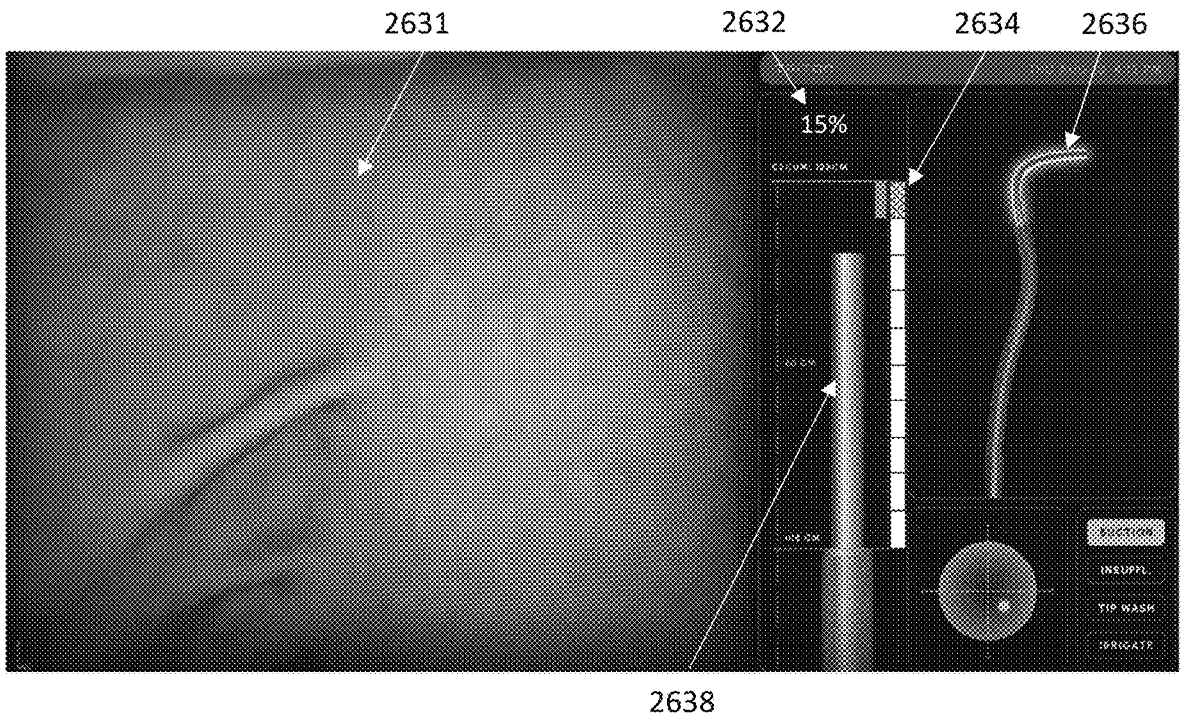
FIGS. 26A-26F illustrate an example of manual or semi-automatic mapping using an indicator of how much of a sub-region of the body lumen has been mapped.
Figure 26B:
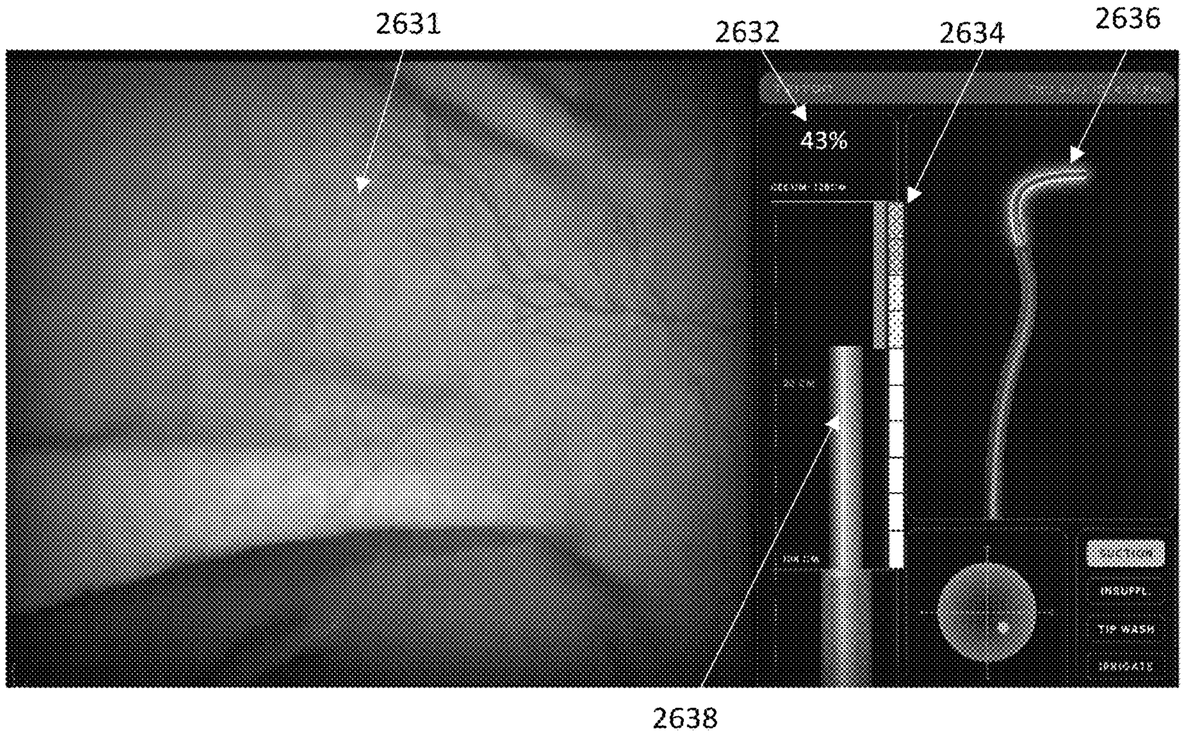
Figure 26C:
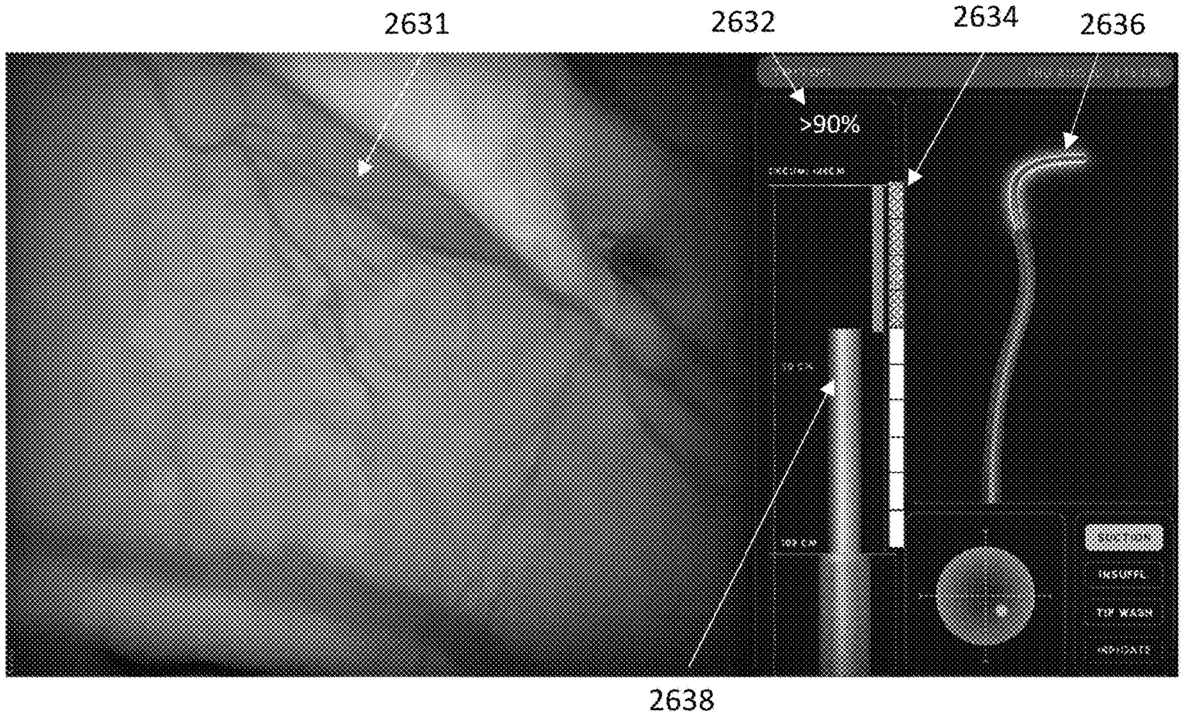
Figure 26D:
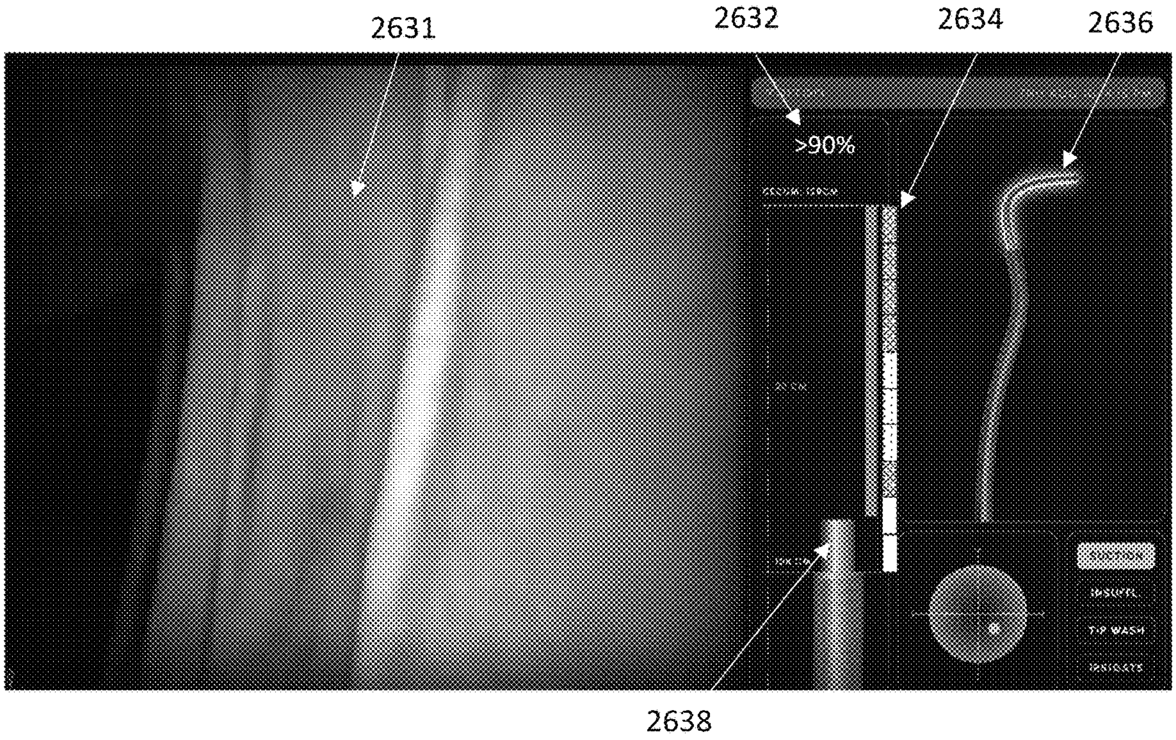
Figure 26E:
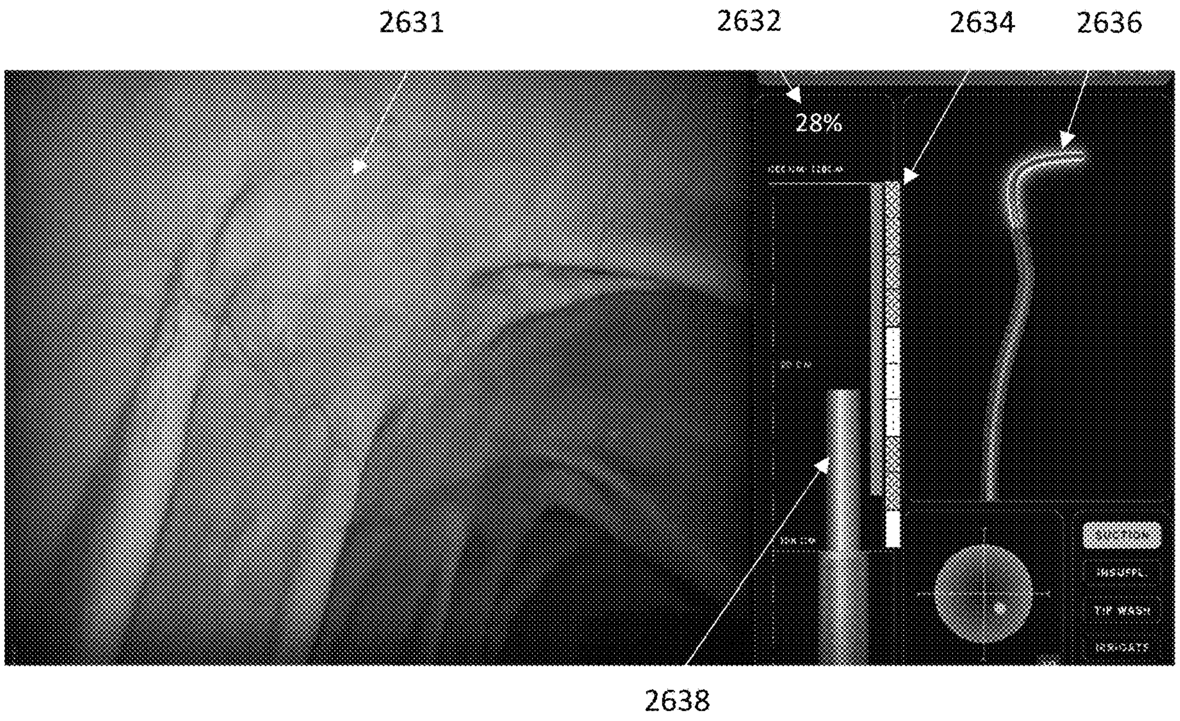
Figure 26F:
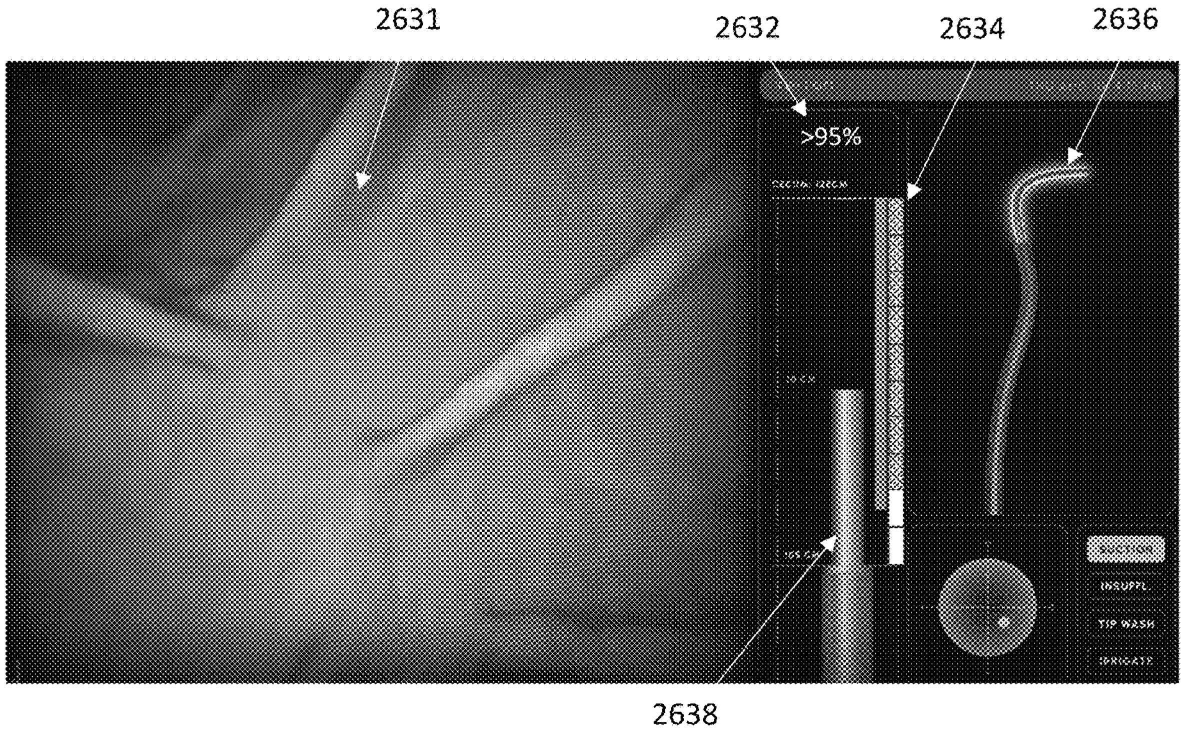

In FIG. 26A the distal most region is shown by the visual indicator 2634 as fully scanned (e.g., >90%, >95%, 100%, etc.). The numeric indicator reflects that the current region is not yet unscanned (e.g., 15% based on just the current image). In FIG. 26B the percentage scan of the next region(s) are less than complete (e.g., the current region is 43% scanned) while the distal two regions are fully scanned. In FIG. 26C the distal four regions are satisfactorily scanned (e.g., "fully" or greater than a threshold, e.g., 80%, 85%, 90%, etc.). In FIG. 26D the scope has been pulled proximally, leaving an unscanned region between the distal region and the more proximal satisfactorily scanned region. In FIG. 26E the scope is advanced distally to continue scanning the more distal region(s), until, as shown in FIG. 26F, the region has been fully scanned. Note that the tip may be bent, dithered, or otherwise moved within the lumen to more completely scan the body lumen.

Indicating Complete/Incompleteness Scan Regions (2D Scanning)

Figure 27A:
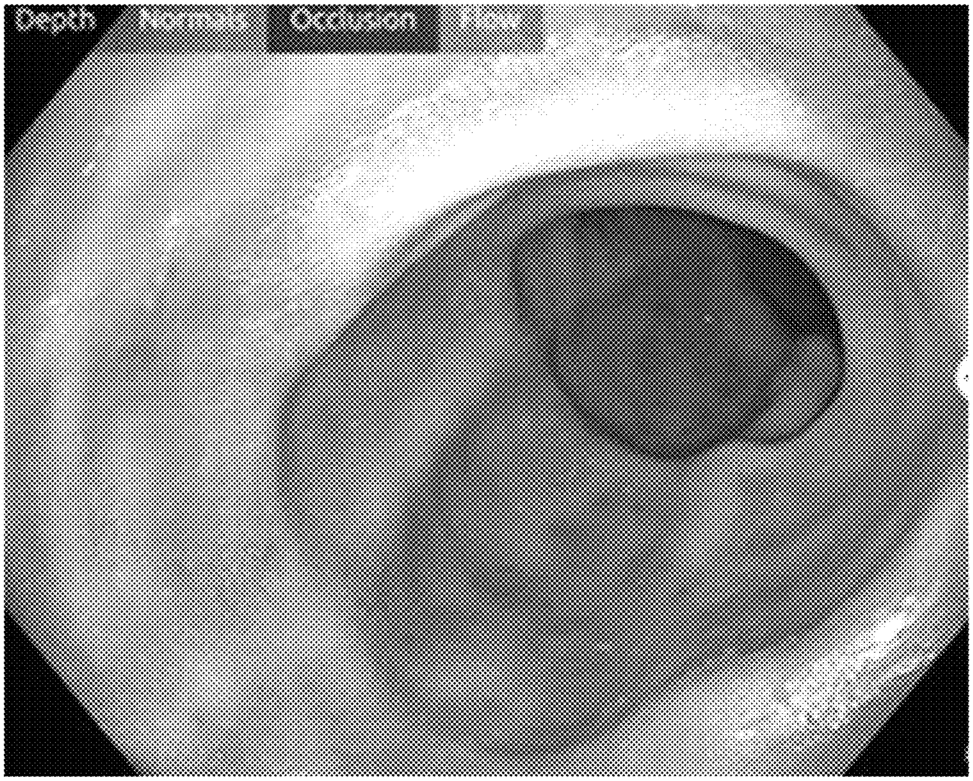
FIGS. 27A-27B illustrate an example of providing a video overlay of one or more unscanned regions.
Figure 27B:
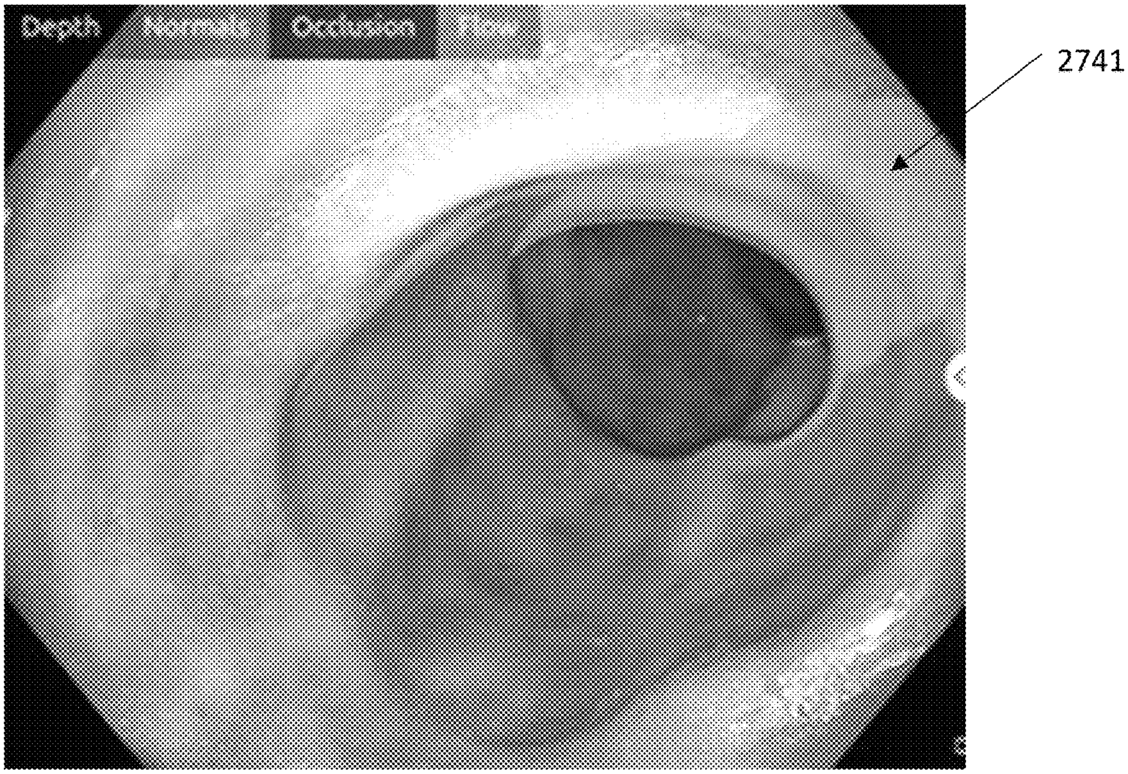

Any of these methods and apparatuses may be configured to indicate (e.g., visually, textually, etc.) regions within the body lumen that have not been scanned above a threshold level of percentage complete (or equivalently, incompleteness). For example, the same or a different trained ML agent as the percent completeness ML agent may be configured to indicate regions that are occluded to prevent full scanning. This may be referred to herein as a trained unscanned region ML agent. The ML agent may be trained as indicated above with a ground truth that further indicates which regions are not visible (e.g., by ray tracing) and may output either in addition or instead of the percentage estimate, a marker or other indicator of the unscanned region. This is illustrated, for example in FIGS. 27A-27B. In this example the trained ML agent is configured to indicate regions in which full scanning has not been made, e.g., because regions are occluded or otherwise prevented from being scanned. In FIG. 27A the image shows a portion of a body lumen; FIG. 27B shows the same image in which the trained ML agent has indicated by marked region 2741 (e.g., colored overlay) that scanning has not been completed.

Alternatively in some cases the apparatus (e.g., the trained unscanned region ML agent) may provide an indicator by region (e.g., quadrant (I, II, III, IV), clock face, etc.) of regions that are less well scanned. Thus the output of the trained unscanned region ML agent may be a graphical indicator as shown in FIG. 27B, or a text output (e.g., "quadrant I is less than 60% scanned", or simply "scanning percent 80%, quadrant I", etc.). Thus, the trained unscanned region ML agent may guide the user to scan more completely. As mentioned, this may be performed in real time.

Figure 20:
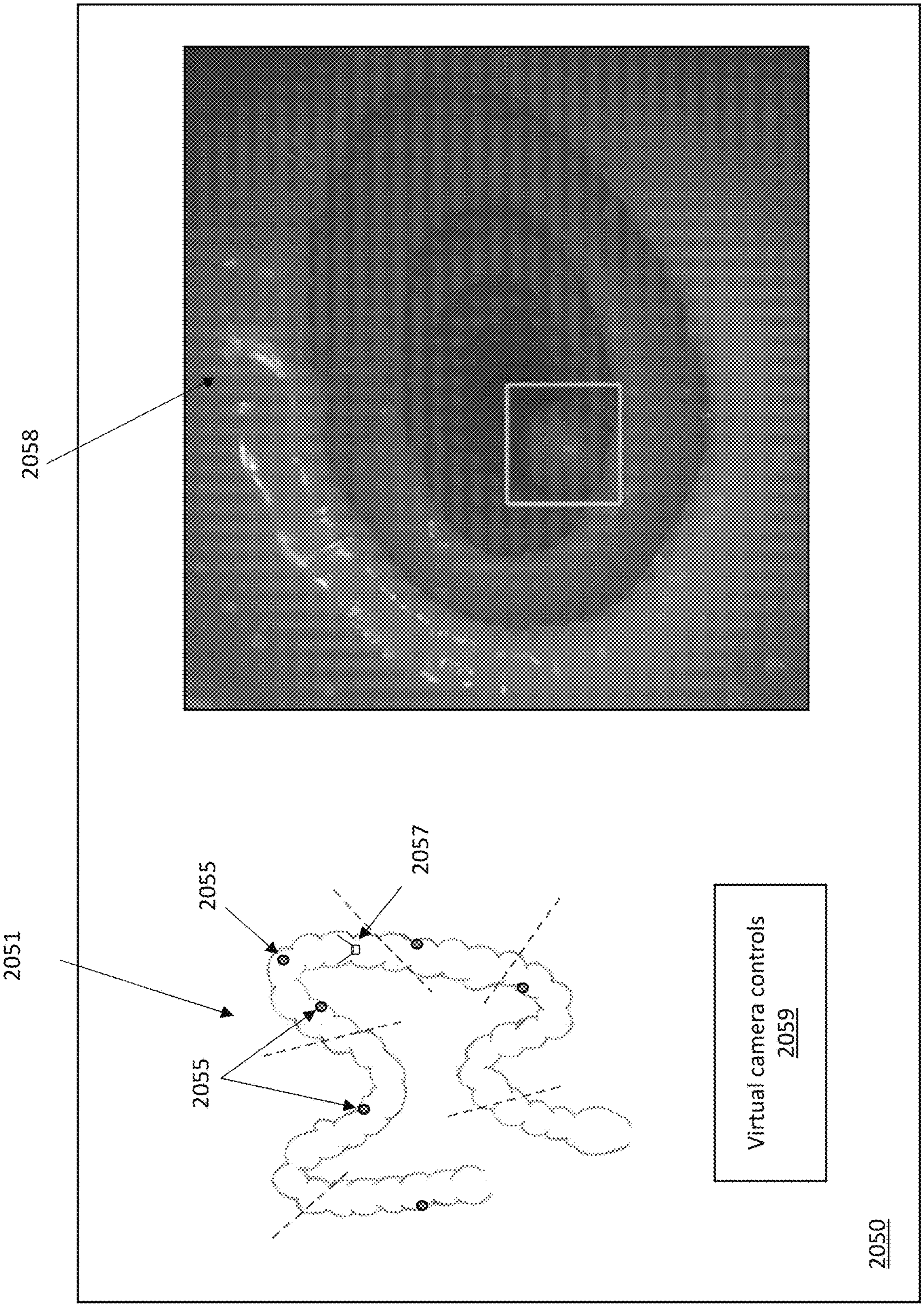
FIG. 20 illustrates an example of a 2D mapping as described herein.

Also described herein are apparatuses and methods for mapping in which a 2D map may be used to guide within a mapped/navigated body lumen, allowing a user (e.g., doctor) to virtually explore the body lumen during or after a procedure. These method or apparatuses may provide one or more stitched together images captured and processed as described herein. For example, FIG. 20 shows an example of a user interface 2050 in which a virtual image of a colon 2051, which may be generic, patient-specific or customized to a patient from a more generic image (or selected from a library of images). This representation of the colon 2051 may be a 3D image or a 2D image (e.g., an outline). This representation may include one or more markers 2055 shown on the representation. In FIG. 20 the user interface may include one or more controls 2059 which may be virtual controls, for controlling a virtual position (e.g., virtual camera, virtual window, virtual endoscope, etc.) 2057 that can be placed and/or oriented within the representation of the colon 2051. In some cases this virtual "window" 2057 may be moved though the colon by the user, e.g., via touch screen, controlling a mouse, etc. Movement of the virtual window may allow advancing/retracting, rotating left/right, forward/backwards, etc. In FIG. 20, the right side of the user interface 2050 shows an image 2058 as it would be "seen" by the virtual window 2057 in the colon. This image 2058 may include any marked region (as shown by box indicating a polyp in FIG. 20) and may be dynamically adjusted either smoothly or discretely as the position of the virtual window 2057 is moved through the colon map/model 2051.

The image 2058 shown may be a representative image corresponding to the actual or approximate position within the body lumen (e.g., colon in this example). Alternatively the image may be synthesized from images taken during the scanning and/or a 3D model (e.g., mesh model) as described herein.

2D and/or 3D Reconstruction

Figure 19A:
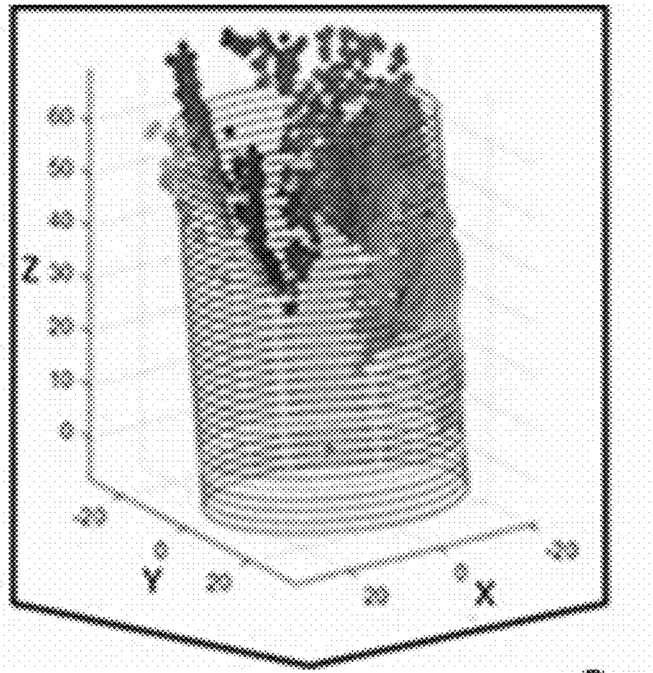
FIGS. 19A-19C illustrate examples of a 3D reconstruction, showing regions that have been and have not been mapped.
Figure 19B:
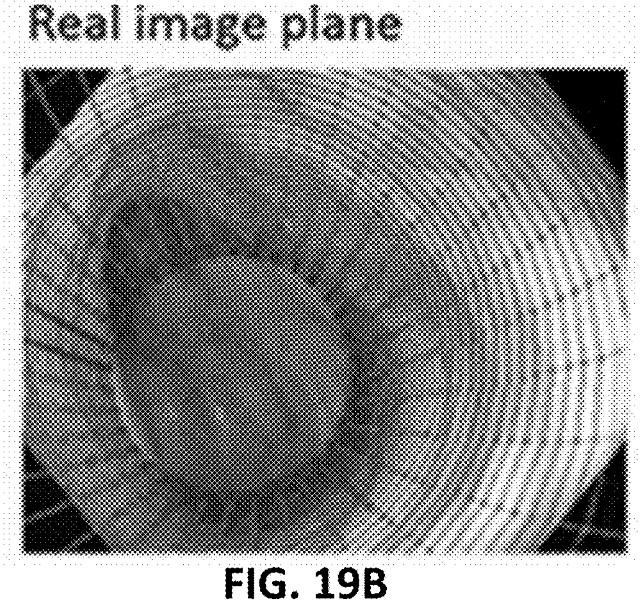
Figure 19C:
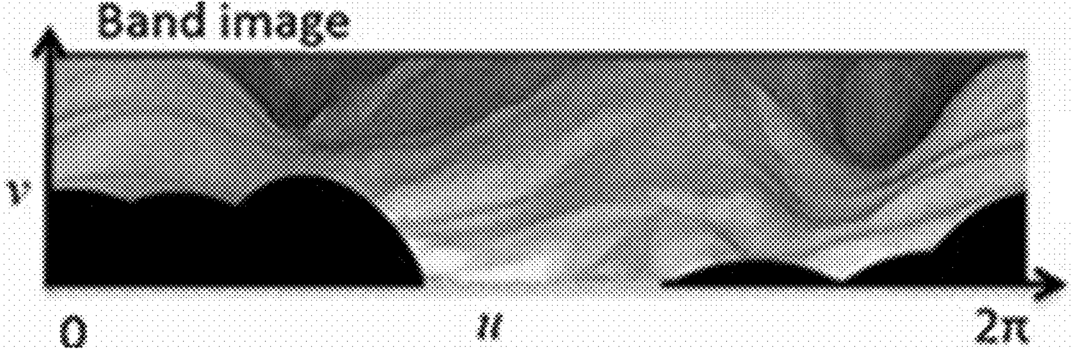

In some cases a 3D reconstruction of the lumen may be formed. For example, FIGS. 19A-19C illustrate examples of a 3D reconstruction, showing regions that have been and have not been mapped. The methods and apparatuses described herein may be particularly useful with magnetic field sensing. Once the 3D data is collected/accessed, it can be rendered and explored from any point of view. There may be utility to providing the data immersively, as in the doc is inside the colon looking about. They can be a few millimeters tall and able to naturally look about. The user could even run the scope through and build up the 3D reconstruction of the colon and then have them ride/walk through the colon annotating as they go with AI/ML notes placed there already as they move through. If you did this with high enough resolution and adequacy of coverage, you would not need to have the scope nearby unless you needed to intervene with tissue. And the scope could navigate automatically using the mapping.

In any of the methods and apparatuses described herein coverage mapping may be configured as 3D data and can be rendered and explored from any point of view. There may be utility to providing the data immersively, as in the doc is inside the colon looking about. They can be a few millimeters tall and able to naturally look about. Any of these methods may even run the scope through and build up the 3D reconstruction of the colon and then have them ride/walk through the colon annotating as they go with AI/ML notes placed there already as the user is move through. If you did this with high enough resolution and adequacy of coverage, you would not need to have the scope nearby unless you needed to intervene with tissue. And the scope could come to you automatically A method for mapping the colon during colonoscopy may begin with the manual insertion of the colonoscope. As the device moves forward, side-view cameras may focus on the walls of the lumen and may be used for mapping the colon and for detecting regions of interest, including polyps. If a region is detected, a notification may prompt the user to allow automatic navigation to the region for further analysis and/or may annotate the map to indicate a possible structure of interest (e.g. polyp). The system may display detailed information, such as the polyp's circumference, diameter, and height, while automatically recording this data in the patient's medical record. If the user selects the command to automatically move to the region of interest, the apparatus (cameras) may be moved to the correct location relative to the polyp, with automated adjustments to both the endoscope and tool position for precise operation. The procedure may include options for automated rotation around the polyp, followed by snare deployment to excise the polyp in some examples. The operator can initiate the snare's advancement, lowering, and closing via user prompts, eventually retrieving the captured polyp.

In some cases the apparatuses and methods described herein may assist the user without necessarily fully automating the driving. For example in some cases the method or apparatus may partially automate the positioning of the endoscope by actively "nudging" or assisting the user in the direction of best practices, e.g., in a guided navigation approach, for positioning the apparatus and operating a tool (e.g., snare) providing actionable tactile and/or visual feedback or even motion resistance when the user strays from the predetermined path/action.

In general, when advancing using the methods and apparatuses described herein, upon reaching the cecum, a confirmation message may appear, allowing the user to take a photograph of the cecum for the patient record. The system may facilitate the automatic withdrawal of the colonoscope. During withdrawal, the scope may perform (or continue to perform) a systematic scanning of the colon, with all cameras working together to capture full surface coverage. This is achieved through image stitching, ensuring that any missed areas are flagged for re-inspection. Additionally, the software can detect if the camera view becomes obscured, triggering an automatic tip wash to clear the lens. If problematic areas arise, the system may suggest augmentation methods or recommend manual overrides for further inspection, enhancing the thoroughness of the procedure.

As described above, in some cases mapping may be assisted by accentuating potential guideposts/landmarks within the colon, including blood vessels or other vasculature. For example, any of these apparatuses may include a dual rigidizing robotic apparatus that may, in some examples, include shape sensing, and a plurality of cameras, as described above. In some cases narrow band imaging (NBI, e.g., virtual chromoendoscopy) may be used for lighting for all or some of the cameras (e.g., side-facing cameras) which may highlight the vasculature, enhancing aligning of the images when stitching. In some cases the camera(s) may operate at a relatively high frame rate, e.g., 100 fps or higher (e.g., 120 fps or more, 150 fps or more, etc.). Lighting may vary between white light and NBI light in multiple wavelengths. In some cases different illumination wavelengths may be alternated. For example, 60 fps of white light images, with another 30 fps with one wavelength and another 30 fps with a third wavelength may be used. In some cases, only the white-light images are displayed, whereas the other wavelength image may be used by the apparatus and method to assist in mapping and/or identification of regions of interest. In some cases different wavelengths may be alternated/interleaved. In some cases the distal-facing camera may be white light, while the side/rear facing cameras may be different wavelengths (e.g., non-visible wavelengths, NBI, etc.). As described above, the controller may look for areas of interest from the images, e.g., using both white and NBI light, and by applying a trained machine learning agent to identify such suspected regions. When an area of interest is located or suspected, the apparatus may ask the user if they want to orient to that area of interest for a closer look, as described above. The apparatus may use dynamic rigidization (e.g., shape copying) to orient the endoscope automatically to view the area of interest and/or to operate on the potential lesion (e.g., polyp). This orientation may include using the endoscope only partially extended from the overtube such that the endoscope can bend around a smaller bend radius and orient to a "close-in" area of interest.

In general, areas of interest may be marked either automatically or manually. In some cases the apparatus may build a continuous image of the lumen wall by knitting together the images, e.g., image stitching, from the captured images (or modified versions of the captured images) using the vein or arterial (or other) pattern in the walls to align images. Thus, in some examples, when the user gets to the end of the colon and begins withdrawing, the apparatus may have already built a continuous image of the colon. As the user withdraws, the computer may signal to the user that there is an area that needs to be mapped in greater detail and may ask the user to manually or automatically take better images. Otherwise, it may signal that the user can rapidly withdraw. In some cases the apparatus may automatically move to capture images of regions that were missed previously. The apparatus may identify these regions automatically, in some cases with a trained machine learning agent.

On either insertion or withdrawal, the computer can also help to point or move the endoscope to previously designated areas that the user marked by following patterns on the walls of the colon. For example, the methods and apparatuses may allow the user to quickly visit and/or treat regions of interest marked on the coverage map formed.

In addition to being placed on the second or first members as described above, in any of these methods and apparatuses, cameras or other sensors may be placed either forward or side-facing on a tool (e.g., catheter) in the working channel of the second member, and may be driven and sensed, or simply sensed, by controllers in the base of system, near where the second member mounts to it. In general, images taken by the system may be placed into an automatically generated report, to be added to the patient's medical history (including into a patient's electronic record), with image locations indicated on a map that is also included in the report. Precise knowledge of image, polyp, or other feature allows for more accurate medical history documentation, including tracking over time (longitudinal tracking) as described above.

Also as described above, the maps (e.g., the coverage maps or colon maps) described herein may be configured to 'stretch' or morph as the tissue may morph. Thus the maps described herein do not need to be accurate in an absolute sense; the colon is a flexible organ and will typically not remain in a fixed same position. An accurate 3D or 2D model as described herein may instead include relative positions of locations, e.g., relative to each other. These maps may include nonlinearities, warping, etc. while minimizing or eliminating discontinuities and gaps in information. In some case the maps may not necessarily reconstruct the curves of the colon (for example, the flexures) but may reconstruct the walls a continuous "tunnel" that may be curved or bent as needed, similar to the body lumen itself.

Figure 28A:
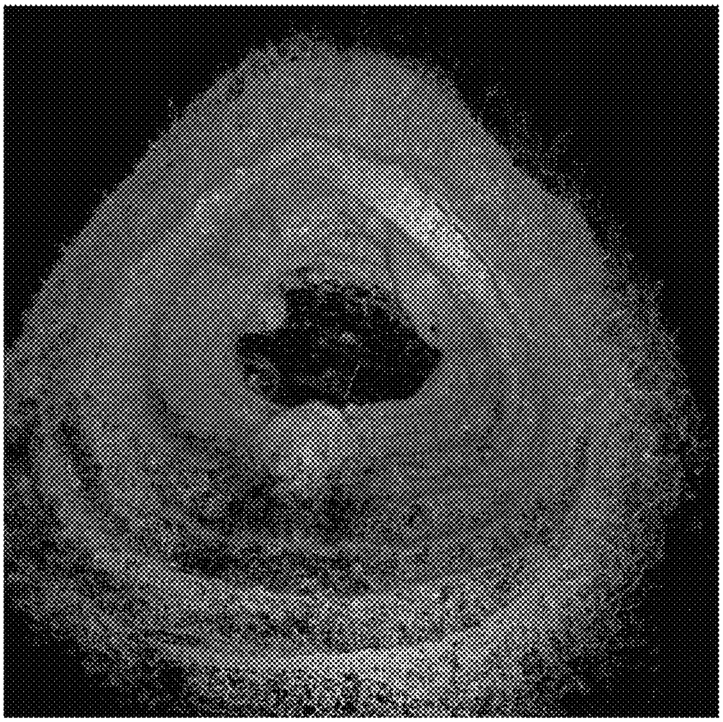
FIGS. 28A-28C illustrate an example of a 3D map of a region of a body lumen (shown as a 3D mesh model).
Figure 28B:
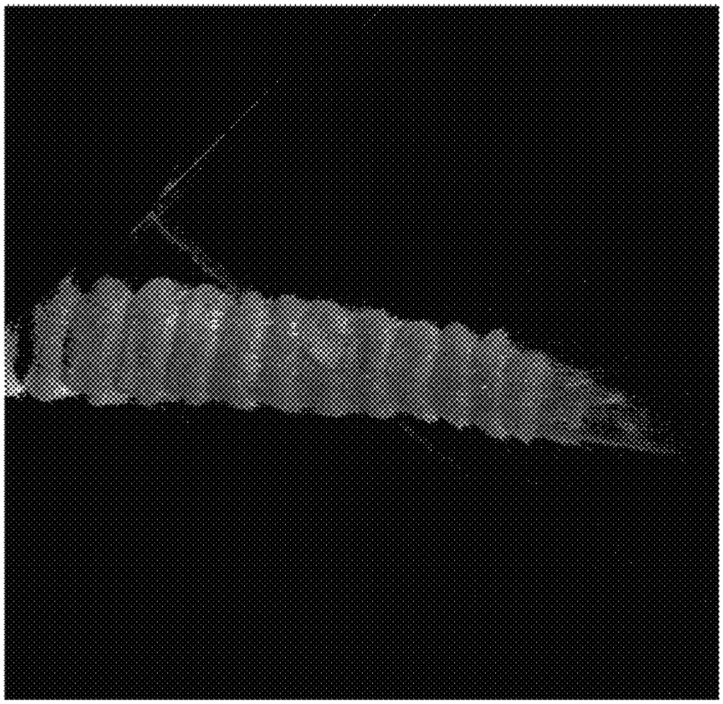
Figure 28C:
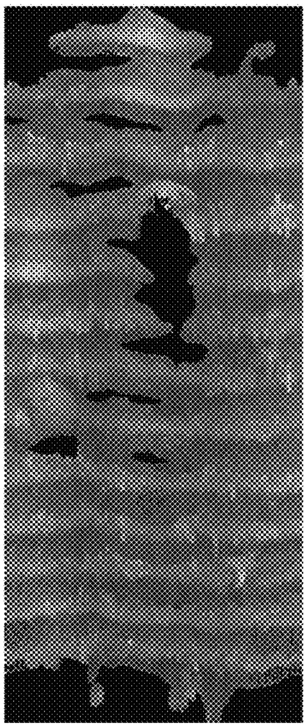

As mentioned above, any of these methods may include forming a 3D mesh model of the colon from the mapping. For example, FIGS. 28A-28C illustrates one example of a mesh 3D model of a region of a colon formed using a structure-from-motion technique as described above. As the endoscope assembly scans through the colon, the apparatus applies a structure-from-motion technique to generate a 3D mesh model of the colon. This model may be manipulated to change the view (e.g., looking down, FIG. 28A, or looking at the outside, FIG. 28B). As mentioned here, the colon may be "unrolled" to show a semi-flat (2D) model as shown in FIG. 28C. Un-imaged regions are shown as gaps. In the structure-from-motion technique shown, a monocular camera feed was used; no ML agent was used. Video was collected using an apparatus as described herein, in a GI model including polyps. Controlled motion of the camera through the colon by the robotic apparatus helps generate a denser mesh.

Figure 29A:
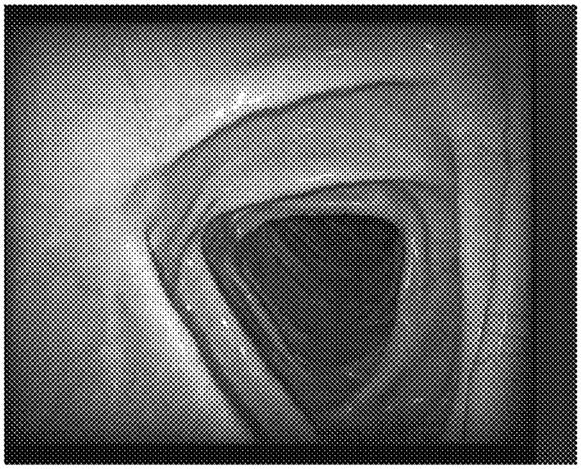
FIGS. 29A-29C illustrate an example of generating a 3D map of a region of a body lumen (shown as a 3D model).
Figure 29B:
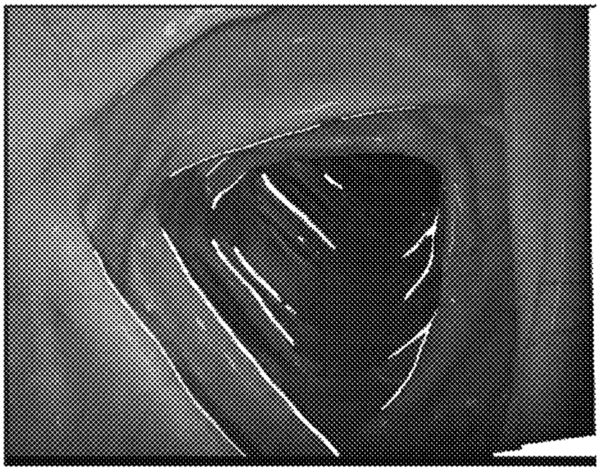
Figure 29C:
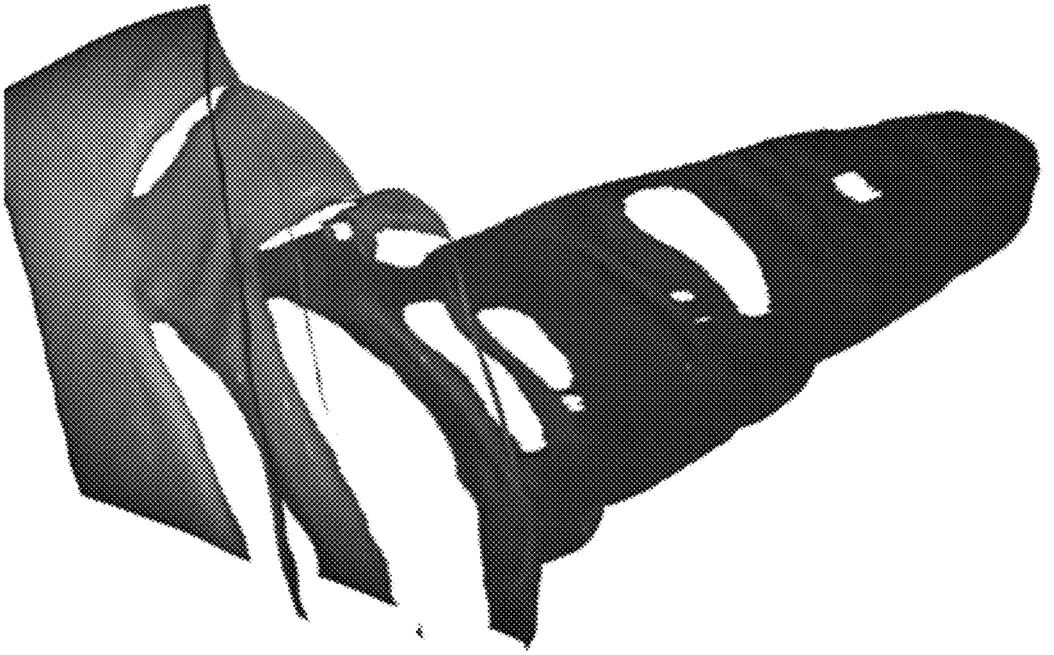
Figure 30A:
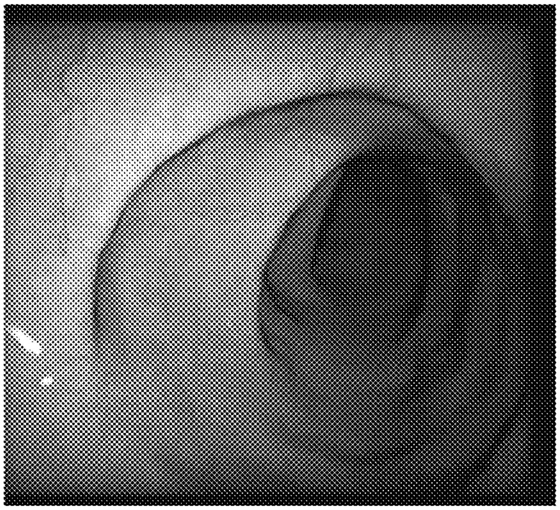
FIGS. 30A-30C illustrate an example of generating a 3D map of a region of a body lumen (shown as a 3D model).
Figure 30B:
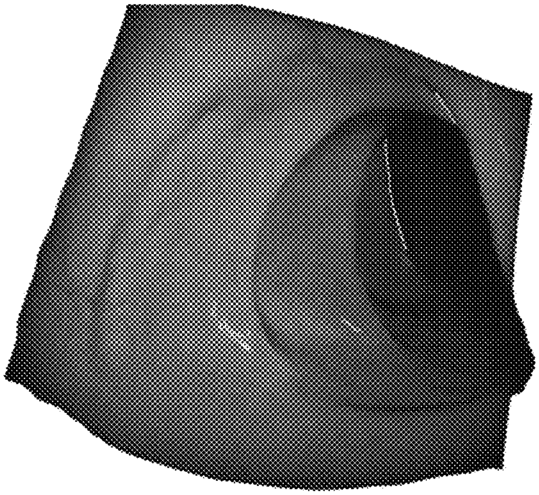
Figure 30C:
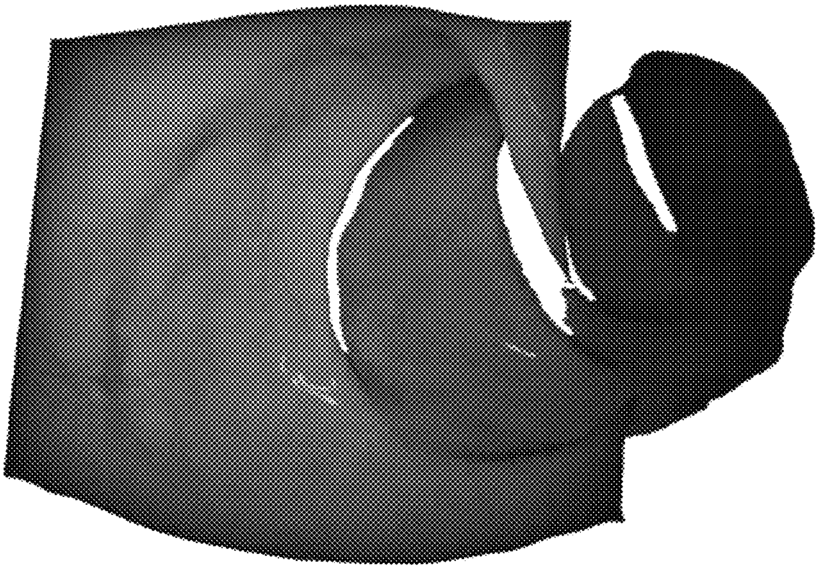

Also described herein are 3D mesh models generated using a trained ML agent (a 3D modeling ML agent) that received image and position data (shape sensing data, insertion data, etc.), as shown in FIGS. 29A-29C and 30A-30C. Any appropriate trained ML agent may be used, including but not limited to splattering-based techniques or vision transformer (ViT) based techniques. In these examples FIGS. 29A and 30A show an image captured by the endoscope, while FIGS. 29B-29C and 30B-30C show the generated models, including unscanned region showing as "gaps" or holes in the 3D model.

All publications and patent applications mentioned in this specification are herein incorporated by reference in their entirety to the same extent as if each individual publication or patent application was specifically and individually indicated to be incorporated by reference. Furthermore, it should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under", or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term “invention” merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The present disclosure contains the following clauses:

Clause 1. A method of mapping a body lumen, the method comprising: rigidizing a first member of a nested, rigidizing apparatus within the body lumen; axially and/or rotationally manipulating a second member extending distally relative to the rigidized first nested member to scan a subregion of the body lumen by imaging walls of the body lumen; combining the images of the walls of the body lumen into a coverage map of the body lumen; repositioning the nested, rigidizing apparatus within the lumen by shape copying; and repeating the steps of rigidizing, manipulating, scanning, combining and repositioning over a plurality of continuous subregions to map body lumen.

Clause 2. The method of clause 1, wherein axially and/or rotationally manipulating the second member comprises using one or more cameras on a distal end region of the second member of the nested, rigidizing apparatus to scan the subregion.

Clause 3. The method of clause 1, wherein axially and/or rotationally manipulating the second member comprises retracting and/or extending a distal end region of the second member within a first distance relative to a distal end of the first member.

Clause 4. The method of clause 1, wherein axially and/or rotationally manipulating the second member comprises retracting and/or extending a distal end region of the second member within a first distance relative to a distal end of the first member of between about 1 mm and about 300 mm.

Clause 5. The method of clause 1, wherein axially and/or rotationally manipulating the second member comprises dithering the distal end region of the second member by scanning as a distal end region of the second member is repeatedly extended and retracted along a first distance to scan the subregion.

Clause 6. The method of clause 1, wherein rigidizing the first member within the body lumen comprises rigidizing the first member within the colon.

Clause 7. The method of clause 1, wherein imaging walls of the body lumen comprises imaging using one or more distal-facing camera and one or more side and/or rear facing cameras.

Clause 8. The method of clause 1, wherein axially and/or rotationally manipulating the second member comprises maintaining the first member in a rigid configuration;

Clause 9. The method of clause 1, further comprising receiving a command to map all or a region of the body lumen.

Clause 10. The method of clause 1, wherein axially and/or rotationally manipulating the second member comprises rotating the second member relative to the first member.

Clause 11. The method of clause 1, wherein axially and/or rotationally manipulating the second member comprises articulating a distal end region of the second member.

Clause 12. The method of clause 1, wherein combining the images comprises stitching the images into the coverage map.

Clause 13. The method of clause 1, wherein axially and/or rotationally manipulating the second member comprises continuing scanning until the subregion of the body lumen has been mapped to 90% coverage or more.

Clause 14. The method of clause 1, wherein repositioning comprises advancing or withdrawing between about 1 mm and about 300 mm to an adjacent subregion.

Clause 15. The method of clause 1, wherein repeating comprises repeating until at least 80% of the body lumen has been mapped.

Clause 16. The method of clause 1, further comprising monitoring, while scanning, to detect one or more regions of interest and alerting a user if one or more regions of interest is detected.

Clause 17. The method of clause 16, further comprising stopping or pausing the method if one or more regions of interest is detected.

Clause 18. The method of clause 1, further comprising manipulating the walls of the lumen while scanning by one or more of: applying additional insufflation and/or contacting the walls with a probe.

Clause 19. The method of clause 1, wherein repositioning the nested, rigidizing apparatus within the lumen by shape copying comprises positioning and then rigidizing the second member, de-rigidizing the first member, and advancing or withdrawing the first member relative to the second member within the body lumen while the second member remains rigid.

Clause 20. A method of mapping a body lumen, the method comprising: rigidizing a first member of a nested, rigidizing apparatus within the body lumen; dithering a distal end region of a second member of the nested, rigidizing apparatus so that it extends and retracts a first distance range from a distal end of the first member; imaging the walls of the body lumen using one or more cameras on the distal end region of the second member while dithering; adding the images of the walls of the body lumen into a coverage map of the body lumen; rigidizing the second member and de-rigidizing the first member, and advancing or withdrawing the first member relative to the second member within the body lumen; and repeating the steps of rigidizing, dithering, imaging and adding the images to map the body lumen.

Clause 21. A method of mapping a long and tortuous body lumen, the method comprising: rigidizing a first member of a nested, flexible rigidizing apparatus within the body lumen; axially and/or rotationally manipulating a second member that is nested with the first member to methodically scan a subregion of the body lumen by imaging walls of the body lumen; combining the images of the walls of the body lumen into a coverage map of the body lumen; repositioning the nested, rigidizing apparatus within the lumen; and repeating the steps of rigidizing, manipulating, scanning, combining and repositioning to map body lumen.

Clause 22. A nested, rigidizing apparatus for mapping a body lumen, the apparatus comprising: a first rigidizing member, wherein the first rigidizing member is configured to be converted from a flexible configuration to a rigid configuration; a second rigidizing member, wherein the second rigidizing member is configured to be converted from a flexible configuration to a rigidizing configuration and is nested with the first rigidizing member; one or more cameras on a distal end region of the second member; and one or more processors running software configured to control the first rigidizing device and the second rigidizing device to perform a method comprising: rigidizing the first member within a body lumen; scanning a subregion of the body lumen by imaging walls of the body lumen using the one or more cameras on the distal end region of the second member as the second member is retracted and/or extended a first distance relative to a distal end of the first member; combining the images of the walls of the body lumen into a coverage map of the body lumen; repositioning the nested, rigidizing apparatus within the lumen by rigidizing the second member and de-rigidizing the first member, and advancing or withdrawing the first member relative to the second member within the body lumen while the second member remains rigid; and repeating the steps of rigidizing, scanning, combining and repositioning to map body lumen.

Clause 23. A nested, rigidizing apparatus for mapping a body lumen, the apparatus comprising: a first elongate member; a second elongate member, wherein the second elongate member is configured to rigidize; wherein the first elongate member is configured to advance relative to the second elongate member and to capture images; and a controller configured to stitch together the captured images to create a coverage map of the body lumen.

Clause 24. The apparatus of clause 23, wherein the first elongate member is configured to advance relative to the second elongate member without colon looping.

Clause 25. The apparatus of any of clauses 23-24, wherein the first elongate member is covered by a removable shield having a camera window through which the captured images are captured.

Clause 26. The apparatus of any of clauses 23-25, wherein the first elongate member is configured to advance relative to the second elongate member by sliding within a lumen of the second elongate member.

Clause 27. The apparatus of any of clauses 23-26, wherein the controller is configured to store the coverage map in a patient's medical record so that it may be compared to a second coverage map taken at a different time.

Clause 28. The apparatus of any of clauses 23-27, further comprising one or more cameras on the second elongate member configured to capture additional images, wherein the controller is configured to stitch together the captured images and the captured additional images to create the coverage map of the body lumen.

Clause 29. The apparatus of any of clauses 23-28, wherein the second elongate member is configured to rigidize in a coordinated manner to create a stable foundation enabling the first elongate member to be advanced and/or withdrawn and/or rotated without substantially moving the stable foundation within the body lumen.

Clause 30. The apparatus of clause 29, wherein controller is configured to control rigidization of the second elongate member and movement of the first elongate member to methodically capture images of the body lumen that are stitched together to create the coverage map.

Clause 31. The apparatus of clause 29, further comprising one or more cameras on the first and/or second elongate members that are configured to capture multi-band images for the captured images.

Clause 32. The apparatus of any of clauses 23-31, further comprising an expandable spreader configured to expand the lumina wall to assist in capturing images, wherein the expandable spreader is on either the first or second elongate member.

Clause 33. The apparatus of clause 31, wherein the expandable spreader comprises a transparent balloon.

Clause 34. The apparatus of clause 30, wherein the controller is configured to control deployment of the expandable spreader based on the captured images, to enhance expansion and visibility of the body lumen.

Clause 35. The apparatus of any of clauses 23-34, wherein the controller is configured to control the application of insufflation into the body lumen based on the captured images, to enhance expansion and visibility of the body lumen.

Clause 36. The apparatus of any of clauses 23-35, wherein the first elongate member is configured to rotate relative to the second elongate member without whip or axial displacement of the first elongate member.

Clause 37. The apparatus of any of clauses 23-36, wherein the controller is configured to stitch together the captured images to create the coverage map of the body lumen comprising a bowel preparation adequacy rate.

Clause 38. The apparatus of any of clauses 23-37, wherein the first and second elongate members are configured to sequentially rigidize to create repeatable axial and rotation motions, wherein the controller is further configured to control the repeatable axial and rotation motions to automate interrogation of the body lumen.

Clause 39. A method, the method comprising: advancing a nested, rigidizing apparatus in a body lumen while displaying to a user a forward-facing video image, further wherein the apparatus automatically monitors a plurality of side-facing or distal and side-facing video image to identify one or more features of interest; presenting an alert if one or more features are identified; receiving a user command to automatically direct the apparatus to the identified one or more identified features; and automatically controlling the nested rigidizing apparatus to alternate between rigidizing and de-rigidizing a first rigidizing device and a second rigidizing device to advance and/or to retract by shape copying so that a distal end of the first rigidizing device is adjacent to the one or more features of interest.

Clause 40. The method of clause 39, further comprising manually inserting the apparatus into the body lumen.

Clause 41. The method of clause 39, wherein the one or more features of interest comprises a polyp or lesion.

Clause 42. The method of clause 39, wherein presenting the alert comprises displaying a notification that one or more features of interested have been identified and requesting the user command to automatically direct the apparatus to the identified one or more identified features.

Clause 43. The method of clause 39, further comprising display, on the user interface, analytic information about the one or more features of interest.

Clause 44. The method of clause 43, wherein the analytic information comprises one or more of: circumference, diameter, and/or height.

Clause 45. The method of clause 43, wherein the analytic information comprises a diagnostic output.

Clause 46. The method of clause 43, further comprising storing the analytic information in a digital patient record.

Clause 47. The method of clause 39, wherein automatically controlling the nested rigidizing apparatus further comprises steering a distal end region of the first rigidizing device so that the one or more features of interest is displayed in the forward-facing video image.

Clause 48. The method of clause 39, wherein automatically controlling the nested rigidizing apparatus further comprises rolling the first rigidizing device to reposition a distal end of the first rigidizing device relative to the one or more features of interest.

Clause 49. The method of clause 39, wherein automatically controlling comprises controlling the nested rigidizing apparatus so that the distal end of the first rigidizing device at least partially circumnavigates the one or more features of interest.

Clause 50. The method of clause 39, further comprising receiving a user command to deploy a tool to the identified one or more features of interest.

Clause 51. The method of clause 50, further comprising automatically deploying a tool to the identified one or more features of interest.

Clause 52. The method of clause 50, further comprising presenting a user command input to automatically deploy the tool.

Clause 53. The method of clause 52, wherein the user commend input comprises one or more of: contacting the one or more features of interest with the tool, capturing the one or more features with the tool, and/or retrieving the one or more features with the tool.

Clause 54. The method of clause 39, further comprising continuing the steps of advance the nested, rigidizing apparatus in the body lumen, presenting the alert, receiving the user command and automatically controlling the nested, rigidizing apparatus, until a landmark is reached.

Clause 55. The method of clause 54, wherein the landmark is the cecum.

Clause 56. The method of clause 54, further comprising alerting the user that the landmark has been reached.

Clause 57. The method of clause 39, further comprising automatically withdrawing the nested, rigidizing apparatus out of the body lumen.

Clause 58. The method of clause 39, further controlling the automatic withdrawal so that it is completed in less than 10 minutes.

Clause 59. A method, the method comprising: advancing a nested, rigidizing apparatus in a colon while displaying to a user a forward-facing video image, further wherein the apparatus automatically monitors a plurality of side-facing or distal and side-facing video image to identify one or more features of interest; presenting an alert if one or more features are identified; receiving a user command to automatically direct the apparatus to the identified one or more identified features; and automatically controlling the nested rigidizing apparatus to alternate between rigidizing and de-rigidizing a first rigidizing device and a second rigidizing device to advance and/or to retract by shape copying so that a distal end of the first rigidizing device is adjacent to the one or more features of interest and/or steering a distal end region of the first rigidizing device so that the one or more features of interest is displayed in the forward-facing video image.

Clause 60. A nested, rigidizing apparatus for mapping a body lumen, the apparatus comprising: a first rigidizing member, wherein the first rigidizing member that is configured to be converted from a flexible configuration to a rigid configuration; a second rigidizing member, wherein the second rigidizing member is configured to be converted from a flexible configuration to a rigidizing configuration and is nested within the first rigidizing member; one or more forward-facing cameras and one or more side-facing or distal-facing cameras on a distal end region of the second member; and one or more processors running software configured to control the first rigidizing device and the second rigidizing device to perform a method comprising: advancing the nested, rigidizing apparatus in a body lumen while displaying to a user a forward-facing video image, and while automatically monitoring a plurality of side-facing or distal and side-facing video images to identify one or more features of interest; presenting an alert if one or more features are identified; receiving a user command to automatically direct the nested, rigidizing apparatus to the identified one or more identified features; and automatically controlling the nested, rigidizing apparatus to alternate between rigidizing and de-rigidizing the first rigidizing member and the second rigidizing member to advance and/or to retract by shape copying so that a distal end of the first rigidizing member is adjacent to the one or more features of interest.

Clause 61. A method of mapping a body lumen, the method comprising: rigidizing a first member of a nested, rigidizing apparatus within a region of the body lumen; axially and/or rotationally manipulating a second member extending distally relative to the rigidized first member while imaging from one or more cameras on the second member to scan the region of the body lumen by imaging walls of the body lumen; and indicating how much of the region has been scanned.

Clause 62. The method of clause 61, further comprising continuing the steps of axially and/or rotationally manipulating the second member and determining how much of the region has been scanned until the indicator exceeds a threshold.

Clause 63. The method of clause 61, wherein indicating comprises displaying an indicator of how much of the region has been scanned.

Clause 64. The method of clause 63, wherein the indicator comprises a percentage.

Clause 65. The method of clause 63, wherein the indicator comprise a graphical indicator.

Clause 66. The method of clause 61, further comprising displaying an indicator of an unscanned region or regions.

Clause 67. The method of clause 66, wherein the indicator of the unscanned region or regions comprises a marking on a representation of the body lumen including the region.

Clause 68. The method of clause 61, wherein the region of the body lumen comprises an annular length of the body lumen between 1 mm and 50 mm.

Clause 69. The method of clause 61, wherein determining how much of the region has been scanned comprises using a trained machine learning agent to determine how much of the region has been scanned.

Clause 70. The method of clause 69, further wherein the machine learning agent has been trained on colonoscopy images.

Clause 71. The method of clause 61, wherein determining how much of the region has been scanned is determined at least in part based on location and/or positional data from a distal end of the second member.

Clause 72. The method of clause 61, wherein the second member comprises a distal-facing camera and a side-facing camera.

Clause 73. The method of clause 61, further comprising repositioning the nested, rigidizing apparatus within the lumen by shape copying and repeating the steps of rigidizing, manipulating, scanning, combining and repositioning over a plurality of continuous subregions to map body lumen.

Clause 74. A method of mapping a body lumen, the method comprising: rigidizing a first member of a nested, rigidizing apparatus within a region of the body lumen; axially and/or rotationally manipulating a second member extending distally relative to the rigidized first member to scan the region of the body lumen by imaging walls of the body lumen from one or more cameras on the second member; determining how much of the region has been scanned; and continuing to scan the region by axially and/or rotationally manipulating the second member until an amount of the region being scanned exceeds a threshold.

Clause 75. A medical robot apparatus for mapping a body lumen, the apparatus comprising: a robotic drive comprising a first mount configured to engage a rigidizable outer member nested with a rigidizable inner member; a second mount configured to engage the rigidizable inner member, wherein the second mount is configured to axially move the second mount relative to the first mount to extend and/or withdraw and/or roll the rigidizable inner member relative to the rigidizable outer member; a telescoping member configured to advance and retract the first and second mount; one or more processors; and a controller configured to control operation of the rigidizable inner member and the rigidizable outer member to map a body lumen, the controller comprising instructions that, when executed cause the one or more processors to: axially and/or rotationally manipulate the rigidizing inner member while maintaining the rigidizing outer member in a rigid configuration and imaging from one or more cameras to scan a region of the body lumen by imaging walls of the body lumen from one or more cameras on the rigidizing inner member; and determine, while scanning, an indicator of how much of the region has been scanned.

Clause 76. The apparatus of clause 75, wherein the controller is configured to continue axially and/or rotationally manipulating the inner rigidizing member until the indicator exceeds a threshold.

Clause 77. The apparatus of clause 75, wherein the controller is configured to display how much of the region has been scanned.

Clause 78. The apparatus of clause 75, wherein the controller is further configured to display an indicator of an unscanned region or regions.

Clause 79. The apparatus of clause 78, wherein the indicator of the unscanned region or regions comprises a marking on a display of a representation of the body lumen including the region.

Clause 80. The apparatus of clause 75, further comprising a trained machine learning agent configured to determine how much of the region has been scanned.

Clause 81. The apparatus of clause 80, further wherein the machine learning agent has been trained on colonoscopy images.

Clause 82. The apparatus of clause 75, wherein the rigidizing inner member comprises a distal-facing camera and a side-facing camera.

Clause 83. The apparatus of clause 75, wherein the controller is further configured to reposition the nested, rigidizing apparatus within the lumen by shape copying and repeat the steps of rigidizing, manipulating, scanning, combining and repositioning over a plurality of continuous subregions to map body lumen.

Clause 84. A method, the method comprising: displaying a representation of a colon for a subject; receiving a user input indicating a position within the representation of the colon; identifying one or more images corresponding to a visualization from a point of view within the subject's colon at the indicated position; and displaying the one or more images.

Clause 85. The method of clause 84, wherein identifying comprises identifying the one or more images from a dataset of mapping colonoscopy images taken from the patient's colon.

Clause 86. The method of clause 85, wherein the mapping colonoscopy images include camera location and orientation information.

Clause 87. The method of clause 84, wherein identifying comprises synthesizing an image corresponding to the position from a dataset of mapping colonoscopy images taken from the patient's colon.

Clause 88. The method of clause 84, wherein identifying comprises identifying the one or more images from a subset of representative images taken from a set of mapping colonoscopy images taken from the patient's colon.

Clause 89. The method of clause 84, wherein the user input comprises axial position and directional information within the colon.

Clause 90. The method of clause 84, further comprising receiving, from the user, a change in the position within the representation of the colon and repeating the steps of identifying and displaying from the updated position.

Clause 91. The method of clause 84, wherein the representation of the colon comprises a two-dimensional (2D) image of the colon.

Clause 92. The method of clause 84, wherein the representation of the colon comprises a three-dimensional (3D) image of the colon.

Clause 93. The method of clause 84, wherein the representation of the colon comprises a representation of the subject's colon.

Clause 94. The method of clause 84, wherein receiving the user input comprises an indicator of location and orientation.

Clause 95. The method of clause 84, wherein the user input comprises input from a graphical user interface indicating the position selected within the colon.

Clause 96. The method of clause 84, further comprising indicating one or more regions of interest on the representation of the colon, wherein the one or more regions of interest comprises a potential polyp, tumor and/or region of inflammation.

Clause 97. A robotic system for fully mapping a body lumen, the system comprising: a first rigidizing device that is configured to be converted from a flexible configuration to a more rigid configuration; a second rigidizing device nested within the first rigidizing device that is configured to be converted from a flexible configuration to a more rigid configuration, wherein a distal end region of the second rigidizing device is steerable; one or more processors running software configured to control the first rigidizing device and the second rigidizing device to rigidize the first rigidizing device while the second rigidizing device is flexible and is steered to image the body lumen to create a stitched image of the body lumen, and to alternate between rigidizing and de-rigidizing the first and second rigidizing devices to advance and/or to retract the first and second rigidizing devices to traverse the body lumen to create a coverage map of the body lumen, wherein the software identifies one or more regions of the body lumen that have not been mapped and controls the first and second rigidizing devices to capture images of the identified regions and add them to the stitched image.

Clause 98. The system of clause 97, wherein the software is a kinematic algorithm that controls the first and second rigidizing devices to interrogate the anatomy to generate the stitched image to create a full coverage mapping of the body lumen.

Clause 99. The system of clause 97, wherein the software is configured to detect polyps.

Clause 100. The system of clause 97, wherein the software is configured to control movement of the first and second rigidizing devices without the need for manual control.

Clause 101. The system of clause 97, wherein the software is configured to assist manual control of the first and second rigidizing devices by flagging regions to be imaged.

Clause 102. The system of clause 97, wherein the software is configured to perform preprogrammed series of movements to robotically circumnavigate a selected region or polyp.

Clause 103. The system of clause 102, wherein the preprogrammed series of movements include controlling rigidization, steering of the endoscope and advancing/withdrawing the endoscope.

Clause 104. The system of clause 97, wherein the robotic system is configured for mapping a colon.

Clause 105. The system of clause 97, wherein the first rigidizing device comprises a rigidizing overtube.

Clause 106. The system of clause 97 wherein the first rigidizing device is configured to rigidize by the application of pressure within a layered structure forming a wall of the first rigidizing device.

Clause 107. The system of clause 97, wherein the second rigidizing device comprises an endoscope.

Clause 108. The system of clause 97, wherein the second rigidizing device is configured to be converted from the flexible configuration to the more rigid configuration by the application of pressure within a layered structure forming a wall of the second rigidizing device.

Clause 109. A method for mapping a body lumen, the method comprising: advancing and/or retracting a nested apparatus within the body lumen, wherein the nested apparatus includes a first rigidizing device that is configured to be converted from a flexible configuration to a more rigid configuration and a second rigidizing device that is configured to be converted from a flexible configuration to a more rigid configuration, wherein the first second rigidizing device is nested in the second rigidizing device and wherein the nested apparatus is configured to be advance and/or retracted by alternately rigidizing and de-rigidizing the first rigidizing device and the second rigidizing device and advancing or retracting the rigidizing device that is in its flexible configuration; creating a coverage map of the body lumen as the nested apparatus is advanced and/or retracted by continuously stitching together images of the body lumen taken with one or more cameras on a distal end region of the second rigidizing device to form the coverage map; and automatically controlling the first and second rigidizing devices to rigidize the first rigidizing device while steering the distal end region of the second rigidizing device to capture images and updating the coverage map with the captured images.

Clause 110. The method of clause 109, wherein automatically controlling comprises identifying regions of the body lumen that have not been mapped.

Clause 111. The method of clause 109, wherein inserting comprises inserting into a colon.

Clause 112. The method of clause 109, further comprising inserting the nested apparatus into the body lumen.

Clause 113. The method of clause 109, wherein automatically capturing comprise retroflexing the second rigidizing map.

Clause 114. The method of clause 109, wherein advancing and/or retracting the nested apparatus comprises alternating between: advancing or retracting the first rigidizing member relative to the second rigidizing member, while the first rigidizing member is in the flexible configuration and the second rigidizing member is held in the more rigid configuration, and holding the first rigidizing member in the more rigid configuration while advancing the second rigidizing member over the first rigidizing member while the second rigidizing member is in the flexible configuration.

Clause 115. A device, the device comprising: an elongate body configured to rigidize, the elongate body comprising a rigidizing layer, a support layer, and a bladder layer, wherein the bladder layer is configured to be driven against the support layer by the application of positive and/or negative pressure to rigidize the elongate body; a distal tip at a distal end of the elongate body; a distal tip region comprising one or more cameras on a distal face of the distal tip; and a plurality of lateral cameras circumferentially arranged around the distal tip configured to image completely around the circumference.

Clause 116. The device of clause 115, wherein the distal tip region comprises one or more wash channels configured to apply wash fluid to the plurality of cameras.

Clause 117. The device of clause 115, further comprising a controller configured to detect, from an image collected by the plurality of lateral cameras if at least one of the lateral cameras is obscured, and to automatically apply wash fluid to the at least one of the lateral cameras Clause 118. A method of mapping a body lumen, the method comprising: advancing and/or retracting a nested, rigidizing apparatus through the body lumen by alternately rigidizing and de-rigidizing a first rigidizing member and a second rigidizing member to so that the first rigidizing member moves over the second rigidizing member when the first rigidizing member is in a flexible configuration and the second rigidizing member is in a rigid configuration and the second rigidizing member moves within the first rigidizing member when the second rigidizing member is in the flexible configuration and the first rigidizing member is in the rigid configuration; scanning using one or more cameras on a distal end region of the second rigidizing member to capture images of the walls of the body lumen when the second rigidizing member is in the flexile configuration; adding the images into a coverage map of the body lumen; and displaying, in real time or near-real time, an extent map comprising a model of the body lumen indicating regions that have been scanned.

What is claimed is:

1. A method of mapping a body lumen, the method comprising:

rigidizing a first member of a nested, rigidizing apparatus within a region of the body lumen;

oscillating a second member of the nested, rigidizing apparatus relative to the rigidized first member by bending the second member, moving the second member axially, and/or moving the second member rotationally as the second member extends distally from the rigidized first member while imaging from one or more cameras on the second member to scan the region of the body lumen by imaging a wall of the body lumen having a plurality of folds;

estimating how much of the wall of the body lumen having the plurality of folds is obscured and using the estimate to determine an indicator of how much of the wall of the body lumen within the region has been scanned; and outputting the indicator of how much of the wall of the body lumen within the region has been scanned and/or has not been scanned.

2. The method of claim 1, further comprising continuing to oscillate the second member, estimate how much of the wall of the body lumen is obscured, and determine the indicator of how much of the wall of the body lumen within the region has been scanned until the indicator exceeds a threshold, after which the first member of the nested, rigidizing apparatus is advanced or withdrawn within the body lumen.

3. The method of claim 1, wherein outputting the indicator comprises displaying the indicator.

4. The method of claim 1, wherein the indicator comprises a percentage.

5. The method of claim 1, wherein the indicator comprise a graphical indicator.

6. The method of claim 1, further comprising displaying the indicator.

7. The method of claim 6, wherein the indicator of how much of the wall of the body lumen within the region has been scanned or has not been scanned comprises a marking on a representation of the body lumen including the region.

8. The method of claim 1, wherein the region of the body lumen comprises an annular length of the body lumen between 1 mm and 50 mm.

9. The method of claim 1, wherein determining how much of the wall of the body lumen within the region has been scanned comprises using a trained machine learning agent to determine how much of the wall of the body lumen withing the region has been scanned.

10. The method of claim 9, further wherein the trained machine learning agent has been trained on colonoscopy images.

11. The method of claim 1, wherein determining how much of the wall of the body lumen within the region has been scanned is determined at least in part based on location and/or positional data from a distal end of the second member.

12. The method of claim 1, wherein the second member comprises a distal-facing camera and a side-facing camera.

13. The method of claim 1, further comprising repositioning the nested, rigidizing apparatus within the body lumen by shape copying and repeating the steps of rigidizing, oscillating, estimating, and outputting over a plurality of continuous subregions to map the body lumen.

14. A method of mapping a body lumen, the method comprising:

(a) rigidizing an outer member of a nested, rigidizing apparatus within a region of the body lumen;

(b) oscillating an inner member of the nested rigidizing apparatus relative to the rigidized outer member by bending the inner member, moving the inner member axially, and/or moving the inner member rotationally as the inner member extends distally relative to the rigidized outer member while imaging from one or more cameras on the inner member to scan the region of the body lumen by imaging a wall of the body lumen, wherein the wall has a plurality of folds;

(c) estimating how much of the wall of the body lumen is obscured and using the estimate to determine an indicator of how much of the wall of the body lumen has been scanned;

(d) rigidizing the inner member, de-rigidizing the outer member, moving the outer member over the rigid inner member; and (d) iteratively repeating steps (a) to (d) while outputting the indicator of how much of the wall of the body lumen has been scanned and/or has not been scanned.

15. The method of claim 14, further comprising continuing performing steps (b)-(c) until the indicator exceeds a threshold value.

16. The method of claim 14, wherein the indicator comprises a marking on a representation of the body lumen including the region that has been scanned and/or has not been scanned.

17. The method of claim 14, wherein the region of the body lumen comprises an annular length of the body lumen between 1 mm and 50 mm.

18. The method of claim 14, wherein determining the indicator of how much of the wall of the body lumen within the region has been scanned comprises using a trained machine learning agent to determine the indicator of how much of the wall of the body lumen within the region has been scanned.

19. The method of claim 18, further wherein the trained machine learning agent has been trained on colonoscopy images.

20. The method of claim 14, wherein determining the indicator of how much of the wall of the body lumen within the region has been scanned is determined at least in part based on location and/or positional data from a distal end of the inner member.

21. The method of claim 14, wherein the inner member comprises a distal-facing camera and a side-facing camera.

22. The method of claim 14, further comprising generating a map of the body lumen from the scans.

* * * * *